United States Patent
Sethuraman et al.

(10) Patent No.: US 11,987,821 B2
(45) Date of Patent: May 21, 2024

(54) COMPOSITIONS AND METHODS FOR TREATING MITOCHONDRIAL NEUROGASTROINTESTINAL ENCEPHALOPATHY

(71) Applicant: Entrada Therapeutics, Inc., Boston, MA (US)

(72) Inventors: Natarajan Sethuraman, Boston, MA (US); Jason Ruth, Boston, MA (US); Louis A. Tartaglia, Boston, MA (US); Dehua Pei, Columbus, OH (US); Ziqing Qian, Boston, MA (US)

(73) Assignee: Entrada Therapeutics, Inc., Boston, MA (US)

( * ) Notice: Subject to any disclaimer, the term of this patent is extended or adjusted under 35 U.S.C. 154(b) by 189 days.

(21) Appl. No.: 17/495,238

(22) Filed: Oct. 6, 2021

(65) Prior Publication Data
US 2022/0033787 A1 Feb. 3, 2022

Related U.S. Application Data

(60) Division of application No. 16/821,018, filed on Mar. 17, 2020, now Pat. No. 11,168,310, which is a continuation of application No. PCT/US2019/019117, filed on Feb. 22, 2019.

(60) Provisional application No. 62/796,823, filed on Jan. 25, 2019, provisional application No. 62/633,933, filed on Feb. 22, 2018.

(51) Int. Cl.
| | | |
|---|---|---|
| C12N 9/00 | (2006.01) | |
| A61K 38/45 | (2006.01) | |
| A61K 47/60 | (2017.01) | |
| C07K 7/64 | (2006.01) | |
| C12N 9/10 | (2006.01) | |

(52) U.S. Cl.
CPC ............ C12N 9/1077 (2013.01); A61K 38/45 (2013.01); A61K 47/60 (2017.08); C07K 7/64 (2013.01); C12Y 204/02004 (2013.01); C07K 2319/00 (2013.01)

(58) Field of Classification Search
CPC .......... C12N 9/88; C12N 9/6424; C12N 9/78; C12N 9/14; C12Y 204/02004; C07K 7/64; C07K 2319/33
USPC ........................................ 435/69.7, 215, 219
See application file for complete search history.

(56) References Cited

U.S. PATENT DOCUMENTS

| | | | |
|---|---|---|---|
| 5,965,536 A | 10/1999 | Cohen et al. | |
| 6,110,889 A | 8/2000 | Miller et al. | |
| 6,251,854 B1 | 6/2001 | Montal et al. | |
| 6,355,619 B1 | 3/2002 | Miller et al. | |
| 6,593,292 B1 | 7/2003 | Rothbard et al. | |
| 6,605,115 B1 | 8/2003 | Cooke et al. | |
| 6,649,587 B1 | 11/2003 | Frydman et al. | |
| 6,669,951 B2 | 12/2003 | Rothbard et al. | |
| 6,730,293 B1 | 5/2004 | Rothbard et al. | |
| 6,759,387 B2 | 7/2004 | Rothbard et al. | |
| 6,794,545 B1 | 9/2004 | Frydman et al. | |
| 6,809,176 B2 | 10/2004 | Blokhin et al. | |
| 6,960,648 B2 | 11/2005 | Bonny | |
| 6,982,351 B2 | 1/2006 | Frydman et al. | |
| 7,026,347 B2 | 4/2006 | Frydman et al. | |
| 7,169,814 B2 | 1/2007 | Rothbard et al. | |
| 7,186,825 B2 | 3/2007 | Frydman et al. | |
| 7,229,961 B2 | 6/2007 | Rothbard et al. | |
| 7,253,207 B2 | 8/2007 | Blokhin et al. | |
| 7,279,502 B2 | 10/2007 | Clifford et al. | |
| 7,312,244 B2 | 12/2007 | Clifford et al. | |
| 7,585,834 B2 | 9/2009 | Wender et al. | |
| 8,614,290 B2 | 12/2013 | Wester et al. | |
| 8,628,750 B2 | 1/2014 | Wester et al. | |
| 8,629,112 B2 | 1/2014 | Gombert et al. | |
| 9,169,290 B2 | 10/2015 | O'Neil | |
| 10,626,147 B2 | 4/2020 | Pei et al. | |
| 10,815,276 B2 | 10/2020 | Pei et al. | |
| 11,168,310 B2 | 11/2021 | Sethuraman et al. | |
| 2002/0009491 A1 | 1/2002 | Rothbard et al. | |
| 2002/0035243 A1 | 3/2002 | Imfeld et al. | |
| 2002/0120100 A1 | 8/2002 | Bonny | |
| 2002/0127198 A1 | 9/2002 | Rothbard et al. | |

(Continued)

FOREIGN PATENT DOCUMENTS

| | | |
|---|---|---|
| CA | 2417064 A1 | 2/2002 |
| CA | 2455951 A1 | 2/2003 |

(Continued)

OTHER PUBLICATIONS

Devos et al., (Proteins: Structure, Function and Genetics, 2000, vol. 41: 98-107.*

(Continued)

*Primary Examiner* — Robert B Mondesi
*Assistant Examiner* — Mohammad Y Meah
(74) *Attorney, Agent, or Firm* — Fenwick & West LLP; Carl A. Morales; Cara A. Mosley

(57) ABSTRACT

Disclosed herein are compositions and methods of treating disclosure provides for compounds for use in treating Mitochondrial Neurogastrointestinal Encephalopathy Syndrome (MNGIE). In some embodiments, the compounds have cell penetrating activity and thymidine phosphorylase activity. In certain embodiments, the compounds disclosed herein comprise: a) at least one cell-penetrating peptide (CPP) moiety; and b) a thymidine phosphorylase, or an active fragment or analog thereof (TP), wherein the CPP is coupled, directly or indirectly, to TP.

18 Claims, 32 Drawing Sheets

Specification includes a Sequence Listing.

(56) References Cited

U.S. PATENT DOCUMENTS

| | | |
|---|---|---|
| 2003/0022831 A1 | 1/2003 | Rothbard et al. |
| 2003/0032593 A1 | 2/2003 | Wender et al. |
| 2003/0032594 A1 | 2/2003 | Bonny |
| 2003/0072715 A1 | 4/2003 | Frydman et al. |
| 2003/0130356 A1 | 7/2003 | Frydman et al. |
| 2003/0167129 A1 | 9/2003 | Nestor et al. |
| 2004/0152687 A1 | 8/2004 | Frydman et al. |
| 2004/0192665 A1 | 9/2004 | Frydman et al. |
| 2004/0248783 A1 | 12/2004 | Kawabe et al. |
| 2005/0192210 A1 | 9/2005 | Rothbard et al. |
| 2006/0128614 A1 | 6/2006 | Cheng et al. |
| 2006/0141514 A1 | 6/2006 | Rozzelle et al. |
| 2012/0045393 A1 | 2/2012 | Linder et al. |
| 2014/0303071 A1 | 1/2014 | O'Neil |
| 2014/0235557 A1 | 8/2014 | De Waard |
| 2015/0038671 A1 | 2/2015 | Parang et al. |
| 2016/0031941 A1 | 2/2016 | Eckert et al. |
| 2017/0020926 A1 | 1/2017 | Mata-Fink et al. |
| 2017/0112896 A1 | 4/2017 | Briesewitz |
| 2017/0190743 A1 | 7/2017 | Pei et al. |
| 2017/0304383 A1 | 10/2017 | Briesewitz et al. |
| 2017/0355730 A1 | 12/2017 | Pei et al. |
| 2018/0030411 A1 | 2/2018 | Kahvejian et al. |
| 2020/0354697 A1 | 11/2020 | Sethuraman et al. |
| 2020/0385427 A1 | 12/2020 | Pei et al. |

FOREIGN PATENT DOCUMENTS

| | | |
|---|---|---|
| CA | 3092062 | 8/2019 |
| CN | 105440105 A | 3/2016 |
| EP | 1185493 B1 | 7/2005 |
| EP | 1574507 A2 | 9/2005 |
| EP | 1797901 A1 | 6/2007 |
| JP | 3791981 | 6/2006 |
| JP | 3791981 B2 | 6/2006 |
| JP | 2016-065018 A | 4/2016 |
| TW | 201945014 | 12/2019 |
| WO | WO 1999/021877 A1 | 5/1999 |
| WO | WO 2000/011022 A1 | 3/2000 |
| WO | WO 2001/013957 A2 | 3/2001 |
| WO | WO 2002/057313 A2 | 7/2002 |
| WO | WO 2002/064091 A2 | 8/2002 |
| WO | WO 2002/067917 A1 | 9/2002 |
| WO | WO 2002/090503 A2 | 11/2002 |
| WO | WO 2003/059942 A2 | 7/2003 |
| WO | WO 2003/070755 | 8/2003 |
| WO | WO 2003/092631 A2 | 11/2003 |
| WO | WO 2003/092632 A2 | 11/2003 |
| WO | WO 2004/050685 A2 | 6/2004 |
| WO | WO 2006/041805 A1 | 4/2006 |
| WO | WO 2006/058436 A2 | 6/2006 |
| WO | WO 2006/086773 A2 | 8/2006 |
| WO | WO 2007/040535 A1 | 4/2007 |
| WO | WO 2007/055578 A1 | 5/2007 |
| WO | WO 2007/070372 A2 | 6/2007 |
| WO | WO 2007/072037 A1 | 6/2007 |
| WO | WO 2007/096662 A2 | 8/2007 |
| WO | WO 2007/106554 A2 | 9/2007 |
| WO | WO 2007/108749 A1 | 9/2007 |
| WO | WO 2007/111993 A2 | 10/2007 |
| WO | WO 2008/077194 A1 | 7/2008 |
| WO | WO 2009/027706 A2 | 3/2009 |
| WO | WO 2009/092062 A2 | 7/2009 |
| WO | WO 2010/045335 A1 | 4/2010 |
| WO | WO 2010/107832 A2 | 9/2010 |
| WO | WO 2011/095218 A1 | 8/2011 |
| WO | WO 2011/095607 A1 | 8/2011 |
| WO | WO 2013/142184 A1 | 9/2013 |
| WO | WO 2014/053629 A1 | 4/2014 |
| WO | WO 2015/179691 A2 | 11/2015 |
| WO | WO 2016/033368 A1 | 3/2016 |
| WO | WO 2016/044683 A1 | 3/2016 |
| WO | 2019165183 | 8/2019 |

OTHER PUBLICATIONS

Whisstock et al., (Quarterly Reviews of Biophysics 2003, vol. 36 (3): 307-340, in IDS.*
Witkowski et al., (Biochemistry 38:11643-11650, 1999.*
Kisselev L., (Structure, 2002, vol. 10: 8-9.*
International Search Report and Written Opinion for International Application No. PCT/US2015/032043, dated Jan. 14, 2016, 11 pages.
International Preliminary Report on Patentability for International Application No. PCT/US2015/032043, dated Nov. 22, 2016, 8 pages.
International Search Report and Written Opinion for International Application No. PCT/US2019/019117, dated May 13, 2019, 9 pages.
Alonso, A. et al., Protein tyrosine phosphatases in the human genome, Cell, Jun. 2004, 117(6):699-711.
Andaloussi, S. E. L. et al., "Design of a peptide-based vector, PepFect6, for efficient delivery of siRNA in cell culture and systemically in vivo," Nucleic Acids Res., May 2011, 39(9):3972-3987.
Anderl, J. et al., "Chemical modification allows phallotoxins and amatoxins to be used as tools in cell biology," Beilstein Journal of Organic Chemistry, 2012, 8(233):2072-2084.
Appelbaum, J. S. et al., "Arginine Topology Controls Escape of Minimally Cationic Proteins from Early Endosomes to the Cytoplasm," Chemistry & Biology, Jul. 2012, 19:819-830.
Birts, C. N. et al., "A cyclic peptide inhibitor of C-terminal binding protein dimerization links metabolism with mitotic fidelity in breast cancer cells," Chem. Sci. 2013, 4, 3046-3057.
Bolte, S. et al., "A guided tour into subcellular colocalization analysis in light microscopy," J. Microsc., Dec. 2006, 224(Pt. 3), 213-232.
Burke, T.R. Jr. et al., "Potent Inhibition of Insulin Receptor Dephosphorylation by a Hexamer Peptide Containing the Phosphotyrosyl Mimetic F2Pmp," Biochem. Biophys. Res. Commun., Oct. 1994, 204(1):129-134.
Carpenter, A. E. et al., "CellProfiler: image analysis software for identifying and quantifying cell phenotypes," Genome Biology, 2006, 7:R100.
Cascales, L. et al., "Identification and Characterization of a New Family of Cell-Penetrating Peptides," J. Biol. Chem., Oct. 2011, 286(42):36932-36943.
Chatterjee, J. et al., "N-Methylation of Peptides: A New Perspective in Medicinal Chemistry," Acc. Chem. Res., 2008, 41(10):1331-1342.
Chen, X. et al., "On-Bead Screening of Combinatorial Libraries: Reduction of Nonspecific Binding by Decreasing Surface Ligand Density," J. Comb. Chem. 2009, 11(4):604-611.
Cheng, S. H. et al., "Defective intracellular transport and processing of CFTR is the molecular basis of most cystic fibrosis," Cell, Nov. 1990, 63(4):827-834.
Cooley, C. B. et al., "Oligocarbonate Molecular Transporters: Oligomerization-Based Syntheses and Cell-Penetrating Studies," J. Am. Chem. Soc., 2009, 131(45):16401-16403.
Cushing, P. R. et al., "The Relative Binding Affinities of PDZ Partners for CFTR: A Biochemical Basis for Efficient Endocytic Recycling," Biochemistry, 2008, 47(38):10084-10098.
Cushing, P. R. et al., "A Stabilizing Influence: CAL PDZ Inhibition Extends the Half-Life of ΔF508-CFTR," Angew. Chem. Int. Ed., Dec. 2010, 49(51):9907-9911.
Deshayes, S. et al., "Cell-penetrating peptides: tools for intracellular delivery of therapeutics," Cell. Mol. Life Sci., Aug. 2005, 62(16):1839-1849.
Dewan, V. et al., "Cyclic Peptide Inhibitors of HIV-1 Capsid-Human Lysyl-tRNA Synthetase Interaction," ACS Chem. Biol., 2012, 7(4):761-769.
Doyle, D. A. et al., "Crystal Structures of a Complexed and Peptide-Free Membrane Protein-Binding Domain: Molecular Basis of Peptide Recognition by PDZ," Cell, Jun. 1996, 85(7):1067-1076.
Driggers, E. M. et al., "The exploration of macrocycles for drug discovery—an underexploited structural class," Nat. Rev. Drug Discov., Jul. 2008, 7:608-624.

(56) References Cited

OTHER PUBLICATIONS

Duchardt, F. et al., "A Comprehensive Model for the Cellular Uptake of Cationic Cell-penetrating Peptides," Traffic, Jul. 2007, 8(7):848-866.
Duchardt, F. et al., "A Cell-penetrating Peptide Derived from Human Lactoferrin with Conformation-dependent Uptake Efficiency," J. Biol. Chem., Dec. 2009, 284(52):36099-36108.
Eguchi, A. et al., "Protein Transduction Domain of HIV-1 Tat Protein Promotes Efficient Delivery of DNA into Mammalian Cells," J. Biol. Chem., Jul. 2001, 276:26204-26210.
Eichler, J. et al., "Novel α-glucosidase inhibitors identified using multiple cyclic peptide combinatorial libraries," Molecular Diversity, Aug. 1996, 1(4):233-240.
Elchelby, M. et al., "Increased insulin sensitivity and obesity resistance in mice lacking the protein tyrosine phosphatase-1B gene," Science, Mar. 1999, 283(5407):1544-1548.
El-Sayed, A. et al., "Delivery of Macromolecules Using Arginine-Rich Cell-Penetrating Peptides: Ways to Overcome Endosomal Entrapment," The AAPS Journal, Mar. 2009, 11(1):13-22.
Extended European Search Report in European Patent Application No. 15796259.8, dated Jan. 22, 2018, 6 pages.
Fernandez-Lopez, S. et al., "Antibacterial agents based on the cyclic D,L-α-peptide architecture," Nature, Jul. 2001, 412:452-456.
Ferrari, A. et al., "Caveolae-Mediated Internalization of Extracellular HIV-1 Tat Fusion Proteins Visualized in Real Time," Molecular Therapy, 2003, 8:284-294.
Fittipaldi, A. et al., "Cell Membrane Lipid Rafts Mediate Caveolar Endocytosis of HIV-1 Tat Fusion Proteins," J. Biol. Chem., Sep. 2003, 278:34141-34149.
Frackenpohl, J. et al., "The Outstanding Biological Stability of β- and γ-Peptides toward Proteolytic Enzymes: An In Vitro Investigation with Fifteen Peptidases," Chembiochem, Jun. 2001, 2(6):445-455.
Frankel, A. D. et al., "Cellular uptake of the tat protein from human immunodeficiency virus," Cell, Dec. 1988, 55(6):1189-1193.
Frost, J. R. et al., "Macrocyclization of Organo-Peptide Hybrids through a Dual Bio-orthogonal Ligation: Insights from Structure-Reactivity Studies," ChemBioChem, Jan. 2013, 14(1):147-160.
Futaki, S., "Membrane-permeable arginine-rich peptides and the translocation mechanisms," Advanced Drug Delivery Reviews, Feb. 2005, 57(4): 547-558.
Futaki, S. et al., "Arginine-rich peptides. An abundant source of membrane-permeable peptides having potential as carriers for intracellular protein delivery." The Journal of Biological Chemistry, 2001, 276(8):5836-5840.
Giebel, L. B. et al., "Screening of cyclic peptide phage libraries identifies ligands that bind streptavidin with high affinities," Biochemistry, 1995, 34(47):15430-15435.
Gobbo, M. et al., "Synthesis and biological activity of some linear and cyclic kinin analogs," Chemical Biology & Drug Design, Jul. 1994, 44(1):1-9.
Goncalves, E. et al., "Binding of Oligoarginine to Membrane Lipids and Heparan Sulfate: Structural and Thermodynamic Characterization of a Cell-Penetrating Peptide," Biochemistry, 2005, 44(7):2692-2702.
Goun, E. A. et al., "Molecular Transporters: Synthesis of Oligoguanidinium Transporters and Their Application to Drug Delivery and Real-Time Imaging," ChemBioChem, Oct. 2006, 7(10):1497-1515.
Green, M. et al., "Autonomous functional domains of chemically synthesized human immunodeficiency virus tat trans-activator protein," Cell, Dec. 1988, 55(6):1179-1188.
Gupta, B. et al., "Intracellular delivery of large molecules and small particles by cell-penetrating proteins and peptides," Advanced Drug Delivery Reviews, Feb. 2005, 57(4):637-651.
Hamill, K. M. et al., "Polymyxins facilitate entry into mammalian cells," Chem. Sci., 2016, 7:5059-5068.
Hariton-Gazal, E. et al., "Functional Analysis of Backbone Cyclic Peptides Bearing the Arm Domain of the HIV-1 Rev Protein: Characterization of the Karyophilic Properties and Inhibition of Rev-Induced Gene Expression," Biochemistry, 2005, 44(34):11555-11566.
He, R et al., "Recent Advances in PTP1B Inhibitor Development for the Treatment of Type 2 Diabetes and Obesity," Chapter 6 In: New Therapeutic Strategies for Type 2 Diabetes: Small Molecule Approaches, Jones, R. M. (ed.), RSC Drug Discovery Series No. 27, The Royal Society of Chemistry, 2012, pp. 142-176.
Heinis, C. et al., "Phage-encoded combinatorial chemical libraries based on bicyclic peptides," Nat. Chem. Biol., 2009, 5:502-507.
Herce, H. D. et al., "Molecular dynamics simulations suggest a mechanism for translocation of the HIV-1 TAT peptide across lipid membranes," Proc. Natl. Acad. Sci. U. S. A., Dec. 2007, 104(52):20805-20810.
Herce, H. D. et al., "Arginine-Rich Peptides Destabilize the Plasma Membrane, Consistent with a Pore Formation Translocation Mechanism of Cell-Penetrating Peptides," Biophys. J., Oct. 2009, 97(7):1917-1925.
Hili, R. et al., "Macrocyclization of Linear Peptides Enabled by Amphoteric Molecules," J. Am. Chem. Soc., 2010, 132(9):2889-2891.
Hirose, H. et al., "Transient Focal Membrane Deformation Induced by Arginine-rich Peptides Leads to Their Direct Penetration into Cells," Mol. Ther., 2012, 20(5):984-993.
Holub, J. M. et al., "Improved assays for determining the cytosolic access of peptides, proteins, and their mimetics," Biochemistry, Dec. 2013, 52(50):9036-6046.
Horn, M. et al., "Tuning the properties of a novel short cell-penetrating peptide by intramolecular cyclization with a triazole bridge," Chem. Commun. 2016, 52:2261-2264.
Hoyer, J. et al., "Peptide Vectors for the Nonviral Delivery of Nucleic Acids," Acc. Chem. Res., 2012, 45(7):1048-1056.
Illsley, N. P. et al., "Membrane chloride transport measured using a chloride-sensitive fluorescent probe," Biochemistry, 1987, 26(5):1215-1219.
Jang, S. et al., "Cell-Penetrating, Dimeric a-Helical Peptides: Nanomolar Inhibitors of HIV-1 Transcription," Angew. Chem. Int. Ed. 2014, 53, 10086-10089.
Jeong, J. H. et al., "siRNA Conjugate Delivery Systems," Bioconjugate Chem., 2009, 20(1):5-14.
Jha, D. et al., "CyLoP-1: A Novel Cysteine-Rich Cell-Penetrating Peptide for Cytosolic Delivery of Cargoes," Bioconj. Chem., 2011, 22(3):319-328.
Jiang, B. et al., "A Selective, Cell-Permeable Nonphosphorylated Bicyclic Peptidyl Inhibitor against Peptidyl-Prolyl Isomerase Pin1," J. Med. Chem., 58:6306-6312 (2015). Published Online: Jul. 21, 2015.
Joo, S. H. et al., "High-Throughput Sequence Determination of Cyclic Peptide Library Members by Partial Edman Degradation/Mass Spectrometry," J. Am. Chem. Soc., 2006, 128(39):13000-13009.
Josephson, L. et al., "High-Efficiency Intracellular Magnetic Labeling with Novel Superparamagnetic-Tat Peptide Conjugates," Bioconjugate Chem., 1999, 10(2):186-191.
Junkes, C. et al., "Cyclic antimicrobial R-, W-rich peptides: the role of peptide structure and E. coli outer and inner membranes in activity and the mode of action," European Biophysics Journal, 2011, 40(4):515-528.
Kaplan, I. M. et al., "Cationic TAT peptide transduction domain enters cells by macropinocytosis," Journal of Controlled Release, Jan. 2005, 102(1):247-253.
Karpurapu, M. et al., "Inhibition of nuclear factor of activated T cells (NFAT) c3 activation attenuates acute lung injury and pulmonary edema in murine models of sepsis," Oncotarget. Jan. 25, 2018;9(12):10606-10620.
Kawakami, T. et al., "In Vitro Selection of Multiple Libraries Created by Genetic Code Reprogramming to Discover Macrocyclic Peptides That Antagonize VEGFR2 Activity in Living Cells," ACS Chem. Biol., Apr. 2013, 8(6):1205-1214.
Kessler, "Conformation and Biological Activity of Cyclic Peptides," Angew. Chem. Int. Ed. Engl. 21 (1982) pp. 512-523.
Kerem, B. et al., "Identification of the cystic fibrosis gene: genetic analysis," Science, Sep. 1989, 245(4922):1073-1080.

(56) References Cited

OTHER PUBLICATIONS

Kohli, R. M. et al., "Biomimetic synthesis and optimization of cyclic peptide antibiotics," Nature, Aug. 2002, 418:658-661.

Kritzer, J. A. et al., "Rapid selection of cyclic peptides that reduce α-synuclein toxicity in yeast and animal models," Nature Chemical Biology, Sep. 2009, 5(9):655-663.

Kundu, R. et al., "Hybrid Organic-Inorganic Inhibitors of a PDZ Interaction that Regulates the Endocytic Fate of CFTR," Angew. Chem. Int. Ed., Jul. 2012, 51(29):7217-7220.

Kwon, Y-U et al., "Quantitative Comparison of the Relative Cell Permeability of Cyclic and Linear Peptides," Chemistry & Biology, Jun. 2007, 14(6):671-677.

Lalonde, M. S. et al., "Inhibition of Both HIV-1 Reverse Transcription and Gene Expression by a Cyclic Peptide that Binds the Tat-Transactivating Response Element (TAR) RNA," (2011) PLoS Pathog 7(5): e1002038. doi:10.1371/journal.ppat.1002038.

LaMontagne, K. R. Jr. et al., "Protein tyrosine phosphatase PTP1B suppresses p210 bcr-abl-induced transformation of Rat-1 fibroblasts and promotes differentiation of K562 cells," Proc. Natl. Acad. Sci. U. S. A., Nov. 1998, 95(24):14094-14099.

LaRochelle, J. R. et al., "Fluorescence Correlation Spectroscopy Reveals Highly Efficient Cytosolic Delivery of Certain Penta-Arg Proteins and Stapled Peptides," Journal of the American Chemical Society, 2015, 137:2536-2541.

Lattig-Tunnemann, G. et al., "Backbone rigidity and static presentation of guanidinium groups increases cellular uptake of arginine-rich cell-penetrating peptides," Nature Communications, 2011, 2:453. DOI:10.1038/ncomms1459.

Leduc, A-M et al., "Helix-stabilized cyclic peptides as selective inhibitors of steroid receptor-coactivator interactions," Proc. Natl. Acad. Sci. USA, Sep. 2003, 100(20):11273-11278.

Lee, H. J. et al., "PDZ domains and their binding partners: structure, specificity, and modification," Cell Communication and Signaling, 2010, 8: 8.

Lee, J. et al., "Using marine natural products to discover a protease that catalyzes peptide macrocyclization of diverse substrates," J. Am. Chem. Soc., Feb. 2009, 131(6):2122-2124.

Lee et al., "Effects of single D-amino acid substitutions on disruption of β-sheet structure and hydrophobicity in cyclic 14-residue antimicrobial peptide analogs related to gramicidin S," J. Peptide Res. 63, 2004, pp. 69-84.

Lessard, L. et al., "The two faces of PTP1B in cancer," Biochim. Biophys. Acta, Mar. 2010, 1804(3):613-619. doi: 10.1016/j.bbapap.2009.09.018. Epub Sep. 24, 2009.

Li, S. et al., "Photolithographic synthesis of cyclic peptide arrays using a differential deprotection strategy," Chem. Commun., 2005, 5:581-583.

Li, S. et al., "Fluoride enhances the activity of fungicides that destabilize cell membranes," Bioorganic & Medicinal Chemistry Letters, 2012, 22(9):3317-3322.

Lian, W. et al., "Cell-permeable bicyclic peptide inhibitors against intracellular proteins," J. Am. Chem. Soc., Jul. 2014, 136(28):9830-9833. Published Online: Jun. 27, 2014.

Lian, W. et al., "Screening Bicyclic Peptide Libraries for Protein-Protein Interaction Inhibitors:Discovery of a Tumor Necrosis Factor-α Antagonist," J. Am. Chem. Soc., 2013, 135(32):11990-11995.

Liao, H. et al., "Cell-permeable bicyclic peptidyl inhibitors against T-cell protein tyrosine phosphatase from a combinatorial library," Org Biomol Chem. Nov. 22, 2017;15(45):9595-9598.

Lin, K-J, et al., "QSAR studies of antimicrobial α, β-polypeptides," Pharmaceutical Biotechnology, 2003, 10(5):299-303 (with English Abstract).

Lindgren M. et al., "Classes and Prediction of Cell-Penetrating Peptides," Chapter 1 In: Cell-Penetrating Peptides: Methods and Protocols, Methods in Molecular Biology, vol. 683, pp. 3-19, Springer Science+Business Media, LLC 2011.

Liu, J. et al., "Nanostructured Materials Designed for Cell Binding and Transduction," Biomacromolecules, 2001, 2(2):362-368. Published Online: Apr. 19, 2001.

Liu, R. et al., "A Novel Peptide-Based Encoding System for "One-Bead One-Compound" Peptidomimetic and Small Molecule Combinatorial Libraries," J. Am. Chem. Soc., 2002, 124(26):7678-7680. Published Online: Jun. 6, 2002.

Liu, T. et al., "High-Throughput Screening of One-Bead-One-Compound Libraries: Identification of Cyclic Peptidyl Inhibitors against Calcineurin/NFAT Interaction," ACS Comb. Sci., 2011, 13(5):537-546. Published Online: Aug. 16, 2011.

Liu, T. et al., "Membrane Permeable Cyclic Peptidyl Inhibitors against Human Peptidylprolyl Isomerase Pin1," J. Med. Chem., 2010, 53(6):2494-2501.

Liu, Y. et al., "Multifunctional Tandem Peptide Modified Paclitaxel-Loaded Liposomes for the Treatment of Vasculogenic Mimicry and Cancer Stem Cells in Malignant Glioma," ACS Applied Materials & Interfaces, 2015, 7(30):16792-16801.

Lu, K. P. et al., "The prolyl isomerase PIN1: a pivotal new twist in phosphorylation signalling and disease," Nat. Rev. Mol. Cell Biol., Nov. 2007, 8:904-916.

Magzoub, M. et al., "Conformational states of the cell-penetrating peptide penetratin when interacting with phospholipid vesicles: effects of surface charge and peptide concentration," Biochim. Biophys. Acta, Jun. 2002, 1563(1-2):53-63.

Maiolo, J. R. et al., "Effects of cargo molecules on the cellular uptake of arginine-rich cell-penetrating peptides," Biochim. Biophys. Acta., Jul. 2005, 1712(2):161-172.

Maly, D. J. et al., "Combinatorial Strategies for Targeting Protein Families: Application to the Proteases," Chembiochem, Jan. 2002, 3(1):16-37.

Maly, D. J. et al., "Expedient Solid-Phase Synthesis of Fluorogenic Protease Substrates Using the 7-Amino-4-carbamoylmethylcoumarin (ACC) Fluorophore," J. Org. Chem., 2002, 67(3):910-915. Published Online: Jan. 12, 2002.

Mandal, D. et al., "Cell-Penetrating Homochiral Cyclic Peptides as Nuclear-Targeting Molecular Transporters," Angew. Chem. Int. Ed., 2011, 50:9633-9637.

Marsault, E. et al., "Macrocycles Are Great Cycles: Applications, Opportunities, and Challenges of Synthetic Macrocycles in Drug Discovery," J. Med. Chem., 2011, 54(7):1961-2004. Published Online: Mar. 7, 2011.

Martinez-Rodriguez et al., "Natural Occurrence and Industrial Applications of D-Amino Acids: An Overview," Chemistry & Biodiversity, vol. 7, 2010, 18 pages.

Meutermans, W. D. F. et al., "Synthesis of Difficult Cyclic Peptides by Inclusion of a Novel Photolabile Auxiliary in a Ring Contraction Strategy," J. Am. Chem. Soc., 1999, 121(42):9790-9796. Published Online: Oct. 8, 1999.

Millward, S. W. et al., "Design of Cyclic Peptides That Bind Protein Surfaces with Antibody-Like Affinity," ACS Chem Biol., 2007, 2(9):625-634. Published Online: Sep. 21, 2007.

Millward, S. W. et al., "A General Route for Post-Translational Cyclization of mRNA Display Libraries," J. Am. Chem. Soc., 2005, 127(41):14142-14143. Published Online: Sep. 27, 2005.

Ming, Z. et al., "Synthesis of RGD containing peptides and their vasodilation effect," Preparative Biochemistry & Biotechnology, 2000, 30(3):247-256.

Miranda, E. et al., "A Cyclic Peptide Inhibitor of HIF-1 Heterodimerization That Inhibits Hypoxia Signaling in Cancer Cells," Journal of the American Chemical Society, 2013, 135(28):10418-10425.

Miskolzie, M. et al., "An NMR conformational analysis of cyclic bradykinin mimics. Evidence for a β-turn," Journal of Biomolecular Structure & Dynamics, 2000, 17(6):947-955.

Mitra, S. et al., "Highly sensitive peptide-based probes for protein tyrosine phosphatase activity utilizing a fluorogenic mimic of phosphotyrosine," Bioorg. Med. Chem. Lett., Dec. 2005, 15(23):5142-5145.

Morais Cabral, J. H. et al., "Crystal structure of a PDZ domain," Nature, Aug. 1996, 382:649-652.

Moore, J. D. et al., "Pin1 inhibitors: Pitfalls, progress and cellular pharmacology," Bioorg. Med. Chem. Lett., Aug. 2013, 23(15):4283-4291. doi: 10.1016/j.bmcl.2013.05.088. Epub Jun. 6, 2013.

Mosmann, T., "Rapid colorimetric assay for cellular growth and survival: Application to proliferation and cytotoxicity assays," J. Immunol. Methods, Dec. 1983, 65(1-2):55-63.

(56) References Cited

OTHER PUBLICATIONS

Mueller, J. et al., "Comparison of Cellular Uptake Using 22 CPPs in 4 Different Cell Lines," Bioconjugate Chem., 2008, 19(12):2363-2374.
Muratovska, A. et al., "Conjugate for efficient delivery of short interfering RNA (siRNA) into mammalian cells," FEBS Lett., Jan. 2004, 558(1-3):63-68.
Nakase, I. et al., "Efficient Intracellular Delivery of Nucleic Acid Pharmaceuticals Using Cell-Penetrating Peptides," Acc. Chem. Res., 2012, 45(7):1132-1139.
Nakase, I. et al., "Interaction of arginine-rich peptides with membrane-associated proteoglycansis crucial for induction of actin organization and macropinocytosis," Biochemistry, 2007, 46:492-501.
Ngu-Schwemlein, M. et al., "In vitro synergy between some cationic amphipathic cyclooctapeptides and antibiotics," Australian Journal of Chemistry, 2015, 68(2):218-223.
Nguyen, L. T. et al., "Serum Stabilities of Short Tryptophan- and Arginine-Rich Antimicrobial Peptide Analogs," PLoS One 5(9): e12684. doi: 10.1371/journal.pone.0012684, 2010, 8 pages.
Nischan, N. et al., "Covalent Attachment of Cyclic TAT Peptides to GFP Results in Protein Delivery into Live Cells with Immediate Bioavailability," Angew. Chem. Int. Ed., 2015, 54:1950-1953, with Supporting Information pp. S1-S26.
Nori, A. et al., "Tat-conjugated synthetic macromolecules facilitate cytoplasmic drug delivery to human ovarian carcinoma cells," Bioconjugate Chem., Jan.-Feb. 2003, 14(1):44-50.
Ocampo-Garcia, B. E. et al., "Design and biological evaluation of 99mTc-N2S2-Tat(49-57)-c(RGDyK): A hybrid radiopharmaceutical for tumors expressing $\alpha(v)\beta(3)$ integrins," Nuclear Medicine and Biology (2013), 40(4):481-487.
Oh, D. et al., "Enhanced Cellular Uptake of Short Polyarginine Peptides through Fatty Acylation and Cyclization," Molecular Pharmaceutics, 2014, 11(8):2845-2854.
Oh, D. et al., "Amphiphilic Bicyclic Peptides as Cellular Delivery Agents," ChemMedChem, 2014, 9(11):2449-2453.
Oh, D. et al., "Antibacterial activities of amphiphilic cyclic cell-penetrating peptides against multidrug-resistant pathogens," Molecular Pharmaceutics, 2014, 11(10):3528-3536.
Okamoto, H. et al., "Conformational transitions of cyclic D,L-peptides," Journal of Computational Chemistry, 2009, 30(6):962-973.
Palm-Apergi, C. et al., "The membrane repair response masks membrane disturbances caused by cell-penetrating peptide uptake," FASEB J., Jan. 2009, 23(1):214-223.
Pawson, T. et al., "Assembly of Cell Regulatory Systems Through Protein Interaction Domains," Science, Apr. 2003, 300(5618):445-452.
Pham, W. et al., "Enhancing Membrane Permeability by Fatty Acylation of Oligoarginine Peptides," Chembiochem, Aug. 2004, 5(8):1148-1151.
Pomilio, A. B. et al., "Naturally-Occurring Cyclopeptides: Structures and Bioactivity," Current Organic Chemistry, Nov. 2006, 10(16):2075-2121.
Pooga, M. et al., "Cellular translocation of proteins by transportation," FASEB J., 2001, 15:1451-1453.
Pritz, S. et al., "Synthesis of Biologically Active Peptide Nucleic Acid-Peptide Conjugates by Sortase-Mediated Ligation," Journal of Organic Chemistry, 2007, 72(10):3909-3912.
Qian, Z. et al., "Efficient delivery of cyclic peptides into mammalian cells with short sequence motifs," ACS Chem. Biol., 2013, 8:423-431. Published Online: Nov. 6, 2012.
Qian, Z. et al., "Discovery and Mechanism of Highly Efficient Cyclic Cell-Penetrating Peptides," Biochemistry, 2016, 55:2601-2612. Published Online: Apr. 18, 2016.
Qian, Z. et al., "Early endosomal escape of a cyclic cell-penetrating peptide allows effective cytosolic cargo delivery," Biochemistry, 2014, 53:4034-4046. Published Online: Jun. 4, 2014.
Qian, Z. et al., "Intracellular Delivery of Peptidyl Ligands by Reversible Cyclization: Discovery of a PDZ Domain Inhibitor that Rescues CFTR Activity," Angew. Chem. Int. Ed., 2015, 54:5874-5878. Published Online: Mar. 17, 2015.
Qian, Z. et al., "Monitoring the cytosolic entry of cell-penetrating peptides using a pH-sensitive fluorophore," Chem. Commun., 2015, 51:2162-2165. Published Online: Dec. 17, 2014.
Qian, Z. et al., "Enhancing the Cell Permeability and Metabolic Stability of Peptidyl Drugs by Reversible Bicyclization," Angew Chem Int Ed Engl. Feb. 1, 2017;56(6):1525-1529.
Qin, C. et al., "Optimization of Antibacterial Cyclic Decapeptides," J. Comb. Chem., 2004, 6(3):398-406.
Ren, L. et al., "Substrate Specificity of Protein Tyrosine Phosphatases 1B, RPTPα, SHP-1, and SHP-2," Biochemistry, 2011, 50(12):2339-2356.
Rezai, T. et al., "Testing the Conformational Hypothesis of Passive Membrane Permeability Using Synthetic Cyclic Peptide Diastereomers," J. Am. Chem. Soc., 2006, 128(8):2510-2511.
Rezai, T. et al., "Conformational Flexibility, Internal Hydrogen Bonding, and Passive Membrane Permeability: Successful in Silico Prediction of the Relative Permeabilities of Cyclic Peptides," J. Am. Chem. Soc., 2006, 128(43):14073-14080.
Rhodes, C.A. et al., "Cell-Permeable Bicyclic Peptidyl Inhibitors against NEMO-IκB Kinase Interaction Directly from a Combinatorial Library," J Am Chem Soc. Sep. 26, 2018;140(38):12102-12110.
Richard, J. P. et al., "Cellular uptake of unconjugated TAT peptide involves clathrin-dependent endocytosis and heparan sulfate receptors," J. Biol. Chem., 2005, 280:15300-15306.
Ricouart, A. et al., "Design of potent protein kinases inhibitors using the bisubstrate approach," Journal of Medicinal Chemistry, 1991, 34(1):73-78.
Riedl, S. J. et al., "Molecular mechanisms of caspase regulation during apoptosis," Nat. Rev. Mol. Cell Biol., Nov. 2004, 5:897-907.
Roberts, K. D. et al., "Efficient synthesis of thioether-based cyclic peptide libraries," Tetrahedron Letters, Nov. 1998, 39(45):8357-8360.
Roberts, K. E. et al., "Computational Design of a PDZ Domain Peptide Inhibitor that Rescues CFTR Activity," PLos Computational Biology, Apr. 2012, 8(4):e1002477. doi:10.1371/journal.pcbi.1002477.
Rothbard, J. B. et al., "Conjugation of arginine oligomers to cyclosporin A facilitates topical delivery and inhibition of inflammation," Nature Medicine, 2000, 6:1253-1257.
Rotstein, B. H. et al., "Solvatochromic Reagents for Multicomponent Reactions and their Utility in the Development of Cell-Permeable Macrocyclic Peptide Vectors," 2011, Chem. Eur. J., 17:12257-12261.
Rueping, M. et al., "Cellular Uptake Studies with β-Peptides," ChemBioChem, Mar. 2002, 3(2-3):257-259.
Rusnati, M. et al., "Multiple Interactions of HIV-I Tat Protein with Size-defined Heparin Oligosaccharides," J. Biol. Chem., Oct. 1999, 274(40):28198-28205.
Saar, K. et al., "Cell-penetrating peptides: A comparative membrane toxicity study," Anal. Biochem., 2005, 345:55-65.
Sako, Y. et al., "Ribosomal synthesis of bicyclic peptides via two orthogonal inter-side-chain reactions," J. Am. Chem. Soc., Jun. 2008, 130(23):7232-7234. doi: 10.1021/ja800953c. Epub May 14, 2008.
Salvado, I. et al., "Membrane-disrupting iridium(III) oligocationic organometallopeptides," Chemical Communications, 2016, 52(73):11008-11011.
Schafmeister, C. E. et al., "An All-Hydrocarbon Cross-Linking System for Enhancing the Helicity and Metabolic Stability of Peptides," J. Am. Chem. Soc., 2000, 122(24):5891-5892.
Schmidt, N. et al., "Arginine-rich cell-penetrating peptides," FEBS Lett., 2010, 584:1806-1813.
Schwarze, S. R. et al., "In vivo protein transduction: delivery of a biologically active protein into the mouse," Science, Sep. 1999, 285(5433):1569-1572.
Scott, C. P. et al., "Production of cyclic peptides and proteins in vivo," PNAS USA, Nov. 1999, 96(24):13638-13643.
Sela et al., "Different roles of D-amino acids in immune phenomena," The FASEB Journal, vol. 11, May 1997, 449-456.
Shirazi, A. N. et al., "Cysteine and arginine-rich peptides as molecular carriers," Bioorg. Med. Chem. Lett., 2016, 26:656-661.

(56) References Cited

OTHER PUBLICATIONS

Shirazi, A. N. et al., "Cyclic Peptide-Capped Gold Nanoparticles as Drug Delivery Systems," Mol. Pharmaceutics, 2013, 11:500-511.

Shirazi, A. N. et al., "Design and Biological Evaluation of Cell-Penetrating Peptide-Doxorubicin Conjugates as Prodrugs," Mol. Pharmaceutics (2013); 10:488-499.

Shirazi, A. N. et al., "Cyclic peptides containing tryptophan and arginine as Src kinase inhibitors," Bioorganic & Medicinal Chemistry Letters (2013); 23: 3230-3234.

Slee, E. A. et al., "Benzyloxycarbonyl-Val-Ala-Asp (OMe) fluoromethylketone (Z-VAD.FMK) inhibits apoptosis by blocking the processing of CPP32," Biochemical Journal, Apr. 1996, 315(1):21-24.

Songyang, Z. et al., "Recognition of Unique Carboxyl-Terminal Motifs by Distinct PDZ Domains," Science, Jan. 1997, 275(5296):73-77.

Stanford, S. M. et al., "High-throughput screen using a single-cell tyrosine phosphatase assay reveals biologically active inhibitors of tyrosine phosphatase CD45," Proc. Natl. Acad. Sci. U. S. A., Aug. 2012, 109(35):13972-13977.

Stewart, J. M. et al., "Bradykinin antagonists: Anti-cancer drugs for the new millennium?" Peptides for the New Millennium, Proceedings of the American Peptide Symposium, 16th, Minneapolis, MN, United States, Jun. 26-Jul. 1, 1999 (2000), Meeting Date 1999, 219-221. Fields, G. B. et al., (eds.), Kluwer Academic Publishers, Dordrecht, Neth.

Stewart, K. M. et al., "Cell-penetrating peptides as delivery vehicles for biology and medicine," Org. Biomol. Chem., Jul. 2008, 6(13):2242-2255. doi: 10.1039/b719950c. Epub Apr. 15, 2008.

Suhorutsenko, J. et al., "Cell-penetrating peptides, PepFects, show no evidence of toxicity and immunogenicity in vitro and in vivo," Bioconjugate Chem., Nov. 2011, 22(11):2255-2262. doi: 10.1021/bc200293d. Epub Oct. 10, 2011.

Sun, Y. et al., "A thioester ligation approach to amphipathic bicyclic peptide library," Org. Lett., May 2001, 3(11):1681-1684.

Tam, J. P. et al., "Disulfide bond formation in peptides by dimethyl sulfoxide. Scope and applications," J. Am. Chem. Soc., 1991, 113(17):6657-6662.

Tavassoli, A. et al., "Inhibition of HIV Budding by a Genetically Selected Cyclic Peptide Targeting the Gag-TSG101 Interaction," ACS Chemical Biology, 2008, 3(12):757-764.

Thakkar, A. et al., "Traceless Capping Agent for Peptide Sequencing by Partial Edman Degradation and Mass Spectrometry," Anal. Chem., 2006, 78(16):5935-5939.

Thornberry, N. A. et al., "A Combinatorial Approach Defines Specificities of Members of the Caspase Family and Granzyme B. Functional Relationships Established For Key Mediators Of Apoptosis," J. Biol. Chem., Jul. 1997, 272:17907-17911.

Traboulsi, H. et al., "Macrocyclic Cell Penetrating Peptides: A Study of Structure-Penetration Properties," Bioconjugate Chemistry, 2015, 26:405-411.

Trinh, T. B. et al., "Discovery of a Direct Ras Inhibitor by Screening a Combinatorial Library of Cell-Permeable Bicyclic Peptides," ACS Comb Sci., 2016, 18:75-85. Published Online: Dec. 8, 2015.

Tse, B. N. et al., "Translation of DNA into a Library of 13 000 Synthetic Small-Molecule Macrocycles Suitable for in Vitro Selection," J. Am. Chem. Soc., 2008, 130(46):15611-15626.

Turner, R. A. et al., "Click chemistry as a macrocyclization tool in the solid-phase synthesis of small cyclic peptides," Org. Lett., Nov. 2007, 9(24): 5011-5014. Epub Oct. 23, 2007.

Tyagi, M. et al., "Internalization of HIV-1 tat requires cell surface heparan sulfate proteoglycans," J. Biol. Chem., Feb. 2001, 276(5):3254-3261. Epub Oct. 6, 2000.

Upadhyaya, P. et al., "Inhibition of Ras signaling by blocking Ras-effector interactions with cyclic peptide," Angew. Chem. Int. Ed., May 2015, 54:7602-7606. Published Online: May 7, 2015.

Van Goor, F. et al., "Correction of the F508del-CFTR protein processing defect in vitro by the investigational drug VX-809," PNAS USA, Nov. 2011, 108(46):18843-18848.

Varkouhi, A. K. et al., "Endosomal escape pathways for delivery of biologicals," J. Controlled Release, May 2011, 151(3):220-228. Epub Nov. 13, 2010.

Verdurmen et al., "Preferential Uptake of L- versus D-Amino Acid Cell-Penetrating Peptides in a Cell Type-Dependent Manner," Chemistry & Biology, 2011, vol. 18, p. 1000-1010.

Wadia, J. S. et al., "Transmembrane delivery of protein and peptide drugs by TAT-mediated transduction in the treatment of cancer," Adv. Drug Delivery Rev., Feb. 2005, 57(4):579-596. Epub Dec. 19, 2004.

Wallbrecher, R. et al., "Exploration of the Design Principles of a Cell-Penetrating Bicylic Peptide Scaffold," Bioconjugate Chemistry, 2014, 25(5):955-964. Published Online: Apr. 3, 2014.

Wang, C-W. et al., "Increased potency of a novel D-β-naphthylalanine-substituted antimicrobial peptide against fluconazole-resistant fungal pathogens," FEMS Yeast Research, 2009, 9(6):967-970.

Wender, P. A. et al., "The design, synthesis, and evaluation of molecules that enable or enhance cellular uptake: Peptoid molecular transporters," PNAS, Nov. 2000, 97(24):13003-13008.

White, T. R. et al., "On-resin N-methylation of cyclic peptides for discovery of orally bioavailable scaffolds," Nat. Chem. Biol., Sep. 2011, 7(11): 810-817.

Wolde, M. et al., "Targeting CAL as a negative regulator of DeltaF508-CFTR cell-surface expression: an RNA interference and structure-based mutagenetic approach," J. Biol. Chem., Mar. 2007, 282(11):8099-8109. Epub Dec. 11, 2006.

Wu, G. et al., "Structural basis of IAP recognition by Smac/DIABLO," Nature, Dec. 2000, 408(6815):1008-1012.

Wu, X. et al., "Inhibition of Ras-effector interactions by cyclic peptides," Med. Chem. Commun., 2013, 4:378-382. Published Online: Nov. 27, 2012.

Xie, L. et al., "Cellular Effects of Small Molecule PTP1B Inhibitors on Insulin Signaling," Biochemistry, 2003, 42(44):12792-12804.

Yin, J. et al., "Genetically encoded short peptide tag for versatile protein labeling by Sfp phosphopantetheinyl transferase," PNAS USA, Nov. 2005, 102(44):15815-15820.

Zabolotny, J. M. et al., "PTP1B regulates leptin signal transduction in vivo," Dev. Cell, Apr. 2002, 2(4):489-495.

Zhao, K. et al., "Enhanced activity of cyclic transporter sequences driven by phase behavior of peptide-liquid complexes," Soft Matter, 2012, 8(24): 6430-6433.

Ziegler, A. et al., "Interaction of the protein transduction domain of HIV-1 TAT with heparan sulfate: binding mechanism and thermodynamic parameters," Biophys. J., Jan. 2004, 86(1):254-263.

Ziegler, A., "Thermodynamic studies and binding mechanisms of cell-penetrating peptides with lipids and glycosaminoglycans," Adv. Drug Delivery Rev., Mar. 2008, 60(4-5):580-597. Epub Oct. 22, 2007.

Devos et al., "Practical Limits of Function Prediction," Proteins: Structure, Function and Genetics, 2000, vol. 41: 98-107.

Kisselev, "Polypeptide Release Factors in Prokaryotes and Eukaryotes: Same Function, Different Structure," Structure, 2002, vol. 10: 8-9.

Nguyen, L. T. et al., "Serum Stabilities of Short Tryptophan- and Arginine-Rich Antimicrobial Peptide Analogs," PLoS One, Sep. 10, 2010, 5(9): e12684. doi:10.1371/journal.pone.0012684, 2010, 8 pages.

Whisstock et al., "Prediction of protein function from protein sequence and structure," Quarterly Reviews of Biophysics, 2003, vol. 36 (3): 307-340.

Witkowski et al., "Conversion of a β-Ketoacyl Synthase to a Malonyl Decarboxylase by Replacement of the Active-Site Cysteine with Glutamine," Biochemistry 38:11643-11650, 1999.

"International Application Serial No. PCT/US2015/032043, International Preliminary Report on Patentability dated Dec. 1, 2016", 8 pgs.

"International Application Serial No. PCT/US2019/019117, International Preliminary Report on Patentability dated Sep. 3, 2020", 7 pgs.

"U.S. Appl. No. 16/821,018, Preliminary Amendment filed Jun. 18, 2020", 14 pgs.

"U.S. Appl. No. 16/821,018, Restriction Requirement dated Sep. 1, 2020", 11 pgs.

(56) References Cited

OTHER PUBLICATIONS

"U.S. Appl. No. 16/821,018, Response filed Nov. 2, 2020 to Restriction Requirement dated Sep. 1, 2020", 2 pgs.
"U.S. Appl. No. 16/821,018, Non Final Office Action dated Nov. 20, 2020", 9 pgs.
"U.S. Appl. No. 16/821,018, Response filed Feb. 22, 2021 to Non Final Office Action dated Nov. 20, 2020", 13 pgs.
"U.S. Appl. No. 16/821,018, Non Final Office Action dated Mar. 12, 2021", 4 pgs.
"U.S. Appl. No. 16/821,018, Response filed Jun. 14, 2021 to Non Final Office Action dated Mar. 12, 2021", 16 pgs.
"U.S. Appl. No. 16/821,018, Examiner Interview Summary dated Jun. 28, 2021", 2 pgs.
"U.S. Appl. No. 16/821,018, Notice of Allowance dated Jul. 6, 2021", 12 pgs.
"U.S. Appl. No. 16/821,018, Applicant's Summary of Examiner Interview filed Jul. 19, 2021", 1 pg.
"English translation of WO2016173214", [Online] Retrieved from the Internet: <URL: https://patents.google.com/patent/WO2016173214A1/en>, (2016), 11 pgs.
"Taiwanese Application Serial No. 108106055, Office Action dated May 19, 2023", w/ English Translation, 12 pgs.
Kalafatovic, Daniela, "Cell-Penetrating Peptides: Design Strategies beyond Primary Structure and Amphipathicity", Molecules, vol. 22, No. 11, (Nov. 8, 2017), 38 pgs.
Extended European Search Report for EP Appl. No. 19758042.6 dated Oct. 27, 2021, 7 pages.

\* cited by examiner

1. Before protease cleavage
2. After protease cleavage
3. Flow-through from HisTrap column
4. Elution from HisTrap column
5. Concentrated TP after dialysis 1. Unconjugated TP
2. Conjugated cCPP12-N-TP cCPP12-N-TP Lanes:
1. TP-Alexa568 0 hr
2. TP-Alexa568 2 hr
3. TP-Alexa568 12 hr
4. TP-Alexa568 24 hr
5. CP-N-TP-Alexa568 0 hr
6. CP-N-TP-Alexa568 2 hr
7. CP-N-TP-Alexa568 12 hr
8. CP-N-TP-Alexa568 24 hr Lanes:
1. Media treated (negative control).
2. Incubated with 1 uM TP
3. Incubated with 0.1 uM CP12-N-TP
4. Incubated with 0.5 uM CP12-N-TP
5. Incubated with 1 uM CP12-N-TP
6. Protein ladder
7. Liver homogenate, positive control
8. 5 ng fresh TP 1. Media treated (negative control)
2. Incubated with 1 uM TP11
3. Incubated with 0.1 uM cCPP12-N-TP11
4. Incubated with 0.5 uM cCPP12-N-TP11
5. Incubated with 1 uM cCPP12-N-TP11
6. Incubated with 1 uM cCPP12-N-TP11 but lysed with cytosolic lysis buffer
7. 20 nM of fresh cCPP12-N-TP11

1, Supernatant
2, Flow
3, 50%B elution
4, 75%B elution
5, 100%B elution

1. TP11
2. cCPP12-N-TP11
3. TP16
4. cCPP12-N-TP16

1. Fc-TP16
2. cCPP12-N-Fc-TP16

L: ladder
1. Dissolved inclusion body
2. Refolded protein after rapid dilution

Elution profile after Q sepharase

SEQUENCE LISTING

```
<160> NUMBER OF SEQ ID NOS: 127

<210> SEQ ID NO 1
<211> LENGTH: 482
<212> TYPE: PRT
<213> ORGANISM: Homo sapiens

<400> SEQUENCE: 1

Met Ala Ala Leu Met Thr Pro Gly Thr Gly Ala Pro Pro Ala Pro Gly
1               5                   10                  15

Asp Phe Ser Gly Glu Gly Ser Gln Gly Leu Pro Asp Pro Ser Pro Glu
            20                  25                  30

Pro Lys Gln Leu Pro Glu Leu Ile Arg Met Lys Arg Asp Gly Gly Arg
        35                  40                  45

Leu Ser Glu Ala Asp Ile Arg Gly Phe Val Ala Ala Val Val Asn Gly
    50                  55                  60

Ser Ala Gln Gly Ala Gln Ile Gly Ala Met Leu Met Ala Ile Arg Leu
65                  70                  75                  80

Arg Gly Met Asp Leu Glu Glu Thr Ser Val Leu Thr Gln Ala Leu Ala
                85                  90                  95
```

Gln Ser Gly Gln Gln Leu Glu Trp Pro Glu Ala Trp Arg Gln Leu
                100                 105                 110

Val Asp Lys His Ser Thr Gly Val Gly Asp Lys Val Ser Leu Val
                115                 120                 125

Leu Ala Pro Ala Leu Ala Ala Cys Gly Cys Lys Val Pro Met Ile Ser
130                 135                 140

Gly Arg Gly Leu Gly His Thr Gly Gly Thr Leu Asp Lys Leu Glu Ser
145                 150                 155                 160

Ile Pro Gly Phe Asn Val Ile Gln Ser Pro Glu Gln Met Gln Val Leu
                165                 170                 175

Leu Asp Gln Ala Gly Cys Cys Ile Val Gly Gln Ser Glu Gln Leu Val
                180                 185                 190

Pro Ala Asp Gly Ile Leu Tyr Ala Ala Arg Asp Val Thr Ala Thr Val
                195                 200                 205

Asp Ser Leu Pro Leu Ile Thr Ala Ser Ile Leu Ser Lys Lys Leu Val
210                 215                 220

Glu Gly Leu Ser Ala Leu Val Val Asp Val Lys Phe Gly Gly Ala Ala
225                 230                 235                 240

Val Phe Pro Asn Gln Glu Gln Ala Arg Glu Leu Ala Lys Thr Leu Val
                245                 250                 255

Gly Val Gly Ala Ser Leu Gly Leu Arg Val Ala Ala Leu Thr Ala
                260                 265                 270

Met Asp Lys Pro Leu Gly Arg Cys Val Gly His Ala Leu Glu Val Glu
                275                 280                 285

Glu Ala Leu Leu Cys Met Asp Gly Ala Gly Pro Pro Asp Leu Arg Asp
290                 295                 300

Leu Val Thr Thr Leu Gly Gly Ala Leu Leu Trp Leu Ser Gly His Ala
305                 310                 315                 320

Gly Thr Gln Ala Gln Gly Ala Ala Arg Val Ala Ala Ala Leu Asp Asp
                325                 330                 335

Gly Ser Ala Leu Gly Arg Phe Glu Arg Met Leu Ala Ala Gln Gly Val
                340                 345                 350

Asp Pro Gly Leu Ala Arg Ala Leu Cys Ser Gly Ser Pro Ala Glu Arg
                355                 360                 365

Arg Gln Leu Leu Pro Arg Ala Arg Glu Gln Glu Leu Leu Ala Pro
370                 375                 380

Ala Asp Gly Thr Val Glu Leu Val Arg Ala Leu Pro Leu Ala Leu Val
385                 390                 395                 400

Leu His Glu Leu Gly Ala Gly Arg Ser Arg Ala Gly Glu Pro Leu Arg
                405                 410                 415

Leu Gly Val Gly Ala Glu Leu Leu Val Asp Val Gly Gln Arg Leu Arg
                420                 425                 430

Arg Gly Thr Pro Trp Leu Arg Val His Arg Asp Gly Pro Ala Leu Ser
                435                 440                 445

Gly Pro Gln Ser Arg Ala Leu Gln Glu Ala Leu Val Leu Ser Asp Arg
                450                 455                 460

Ala Pro Phe Ala Ala Pro Ser Pro Phe Ala Glu Leu Val Leu Pro Pro
465                 470                 475                 480

Gln Gln

<210> SEQ ID NO 2
<211> LENGTH: 331
<212> TYPE: PRT

<213> ORGANISM: Homo sapiens

<400> SEQUENCE: 2

Gly Gly Thr Leu Asp Lys Leu Glu Ser Ile Pro Gly Phe Asn Val Ile
1               5                   10                  15

Gln Ser Pro Glu Gln Met Gln Val Leu Leu Asp Gln Ala Gly Cys Cys
            20                  25                  30

Ile Val Gly Gln Ser Glu Gln Leu Val Pro Ala Asp Gly Ile Leu Tyr
        35                  40                  45

Ala Ala Arg Asp Val Thr Ala Thr Val Asp Ser Leu Pro Leu Ile Thr
    50                  55                  60

Ala Ser Ile Leu Ser Lys Lys Leu Val Glu Gly Leu Ser Ala Leu Val
65                  70                  75                  80

Val Asp Val Lys Phe Gly Gly Ala Ala Val Phe Pro Asn Gln Glu Gln
                85                  90                  95

Ala Arg Glu Leu Ala Lys Thr Leu Val Gly Val Gly Ala Ser Leu Gly
            100                 105                 110

Leu Arg Val Ala Ala Ala Leu Thr Ala Met Asp Lys Pro Leu Gly Arg
        115                 120                 125

Cys Val Gly His Ala Leu Glu Val Glu Glu Ala Leu Leu Cys Met Asp
    130                 135                 140

Gly Ala Gly Pro Pro Asp Leu Arg Asp Leu Val Thr Thr Leu Gly Gly
145                 150                 155                 160

Ala Leu Leu Trp Leu Ser Gly His Ala Gly Thr Gln Ala Gln Gly Ala
                165                 170                 175

Ala Arg Val Ala Ala Ala Leu Asp Asp Gly Ser Ala Leu Gly Arg Phe
            180                 185                 190

Glu Arg Met Leu Ala Ala Gln Gly Val Asp Pro Gly Leu Ala Arg Ala
        195                 200                 205

Leu Cys Ser Gly Ser Pro Ala Glu Arg Arg Gln Leu Leu Pro Arg Ala
    210                 215                 220

Arg Glu Gln Glu Glu Leu Leu Ala Pro Ala Asp Gly Thr Val Glu Leu
225                 230                 235                 240

Val Arg Ala Leu Pro Leu Ala Leu Val Leu His Glu Leu Gly Ala Gly
                245                 250                 255

Arg Ser Arg Ala Gly Glu Pro Leu Arg Leu Gly Val Gly Ala Glu Leu
            260                 265                 270

Leu Val Asp Val Gly Gln Arg Leu Arg Gly Thr Pro Trp Leu Arg
        275                 280                 285

Val His Arg Asp Gly Pro Ala Leu Ser Gly Pro Gln Ser Arg Ala Leu
    290                 295                 300

Gln Glu Ala Leu Val Leu Ser Asp Arg Ala Pro Phe Ala Ala Pro Ser
305                 310                 315                 320

Pro Phe Ala Glu Leu Val Leu Pro Pro Gln Gln
                325                 330

<210> SEQ ID NO 3
<211> LENGTH: 467
<212> TYPE: PRT
<213> ORGANISM: Homo sapiens

<400> SEQUENCE: 3

Gly Asp Phe Ser Gly Glu Gly Ser Gln Gly Leu Pro Asp Pro Ser Pro
1               5                   10                  15

Glu Pro Lys Gln Leu Pro Glu Leu Ile Arg Met Lys Arg Asp Gly Gly

```
                    20                  25                  30
Arg Leu Ser Glu Ala Asp Ile Arg Gly Phe Val Ala Ala Val Val Asn
            35                  40                  45
Gly Ser Ala Gln Gly Ala Gln Ile Gly Ala Met Leu Met Ala Ile Arg
        50                  55                  60
Leu Arg Gly Met Asp Leu Glu Thr Ser Val Leu Thr Gln Ala Leu
65                  70                  75                  80
Ala Gln Ser Gly Gln Gln Leu Glu Trp Pro Glu Ala Trp Arg Gln Gln
                85                  90                  95
Leu Val Asp Lys His Ser Thr Gly Gly Val Gly Asp Lys Val Ser Leu
            100                 105                 110
Val Leu Ala Pro Ala Leu Ala Ala Cys Gly Cys Lys Val Pro Met Ile
            115                 120                 125
Ser Gly Arg Gly Leu Gly His Thr Gly Gly Thr Leu Asp Lys Leu Glu
        130                 135                 140
Ser Ile Pro Gly Phe Asn Val Ile Gln Ser Pro Glu Gln Met Gln Val
145                 150                 155                 160
Leu Leu Asp Gln Ala Gly Cys Cys Ile Val Gly Gln Ser Glu Gln Leu
                165                 170                 175
Val Pro Ala Asp Gly Ile Leu Tyr Ala Ala Arg Asp Val Thr Ala Thr
            180                 185                 190
Val Asp Ser Leu Pro Leu Ile Thr Ala Ser Ile Leu Ser Lys Lys Leu
            195                 200                 205
Val Glu Gly Leu Ser Ala Leu Val Val Asp Val Lys Phe Gly Gly Ala
        210                 215                 220
Ala Val Phe Pro Asn Gln Glu Gln Ala Arg Glu Leu Ala Lys Thr Leu
225                 230                 235                 240
Val Gly Val Gly Ala Ser Leu Gly Leu Arg Val Ala Ala Ala Leu Thr
                245                 250                 255
Ala Met Asp Lys Pro Leu Gly Arg Cys Val Gly His Ala Leu Glu Val
            260                 265                 270
Glu Glu Ala Leu Leu Cys Met Asp Gly Ala Gly Pro Pro Asp Leu Arg
        275                 280                 285
Asp Leu Val Thr Thr Leu Gly Gly Ala Leu Leu Trp Leu Ser Gly His
        290                 295                 300
Ala Gly Thr Gln Ala Gln Gly Ala Ala Arg Val Ala Ala Ala Leu Asp
305                 310                 315                 320
Asp Gly Ser Ala Leu Gly Arg Phe Glu Arg Met Leu Ala Ala Gln Gly
                325                 330                 335
Val Asp Pro Gly Leu Ala Arg Ala Leu Cys Ser Gly Ser Pro Ala Glu
            340                 345                 350
Arg Arg Gln Leu Leu Pro Arg Ala Arg Glu Gln Glu Leu Leu Ala
            355                 360                 365
Pro Ala Asp Gly Thr Val Glu Leu Val Arg Ala Leu Pro Leu Ala Leu
        370                 375                 380
Val Leu His Glu Leu Gly Ala Gly Arg Ser Arg Ala Gly Glu Pro Leu
385                 390                 395                 400
Arg Leu Gly Val Gly Ala Glu Leu Leu Val Asp Val Gly Gln Arg Leu
                405                 410                 415
Arg Arg Gly Thr Pro Trp Leu Arg Val His Arg Asp Gly Pro Ala Leu
            420                 425                 430
Ser Gly Pro Gln Ser Arg Ala Leu Gln Glu Ala Leu Val Leu Ser Asp
            435                 440                 445
```

```
Arg Ala Pro Phe Ala Ala Pro Ser Pro Phe Ala Glu Leu Val Leu Pro
            450                 455                 460
Pro Gln Gln
465

<210> SEQ ID NO 4
<211> LENGTH: 461
<212> TYPE: PRT
<213> ORGANISM: Homo sapiens

<400> SEQUENCE: 4

Gly Ser Gln Gly Leu Pro Asp Pro Ser Pro Glu Pro Lys Gln Leu Pro
1               5                   10                  15

Glu Leu Ile Arg Met Lys Arg Asp Gly Gly Arg Leu Ser Glu Ala Asp
            20                  25                  30

Ile Arg Gly Phe Val Ala Ala Val Asn Gly Ser Ala Gln Gly Ala
        35                  40                  45

Gln Ile Gly Ala Met Leu Met Ala Ile Arg Leu Arg Gly Met Asp Leu
    50                  55                  60

Glu Glu Thr Ser Val Leu Thr Gln Ala Leu Ala Gln Ser Gly Gln Gln
65                  70                  75                  80

Leu Glu Trp Pro Glu Ala Trp Arg Gln Gln Leu Val Asp Lys His Ser
                85                  90                  95

Thr Gly Gly Val Gly Asp Lys Val Ser Leu Val Leu Ala Pro Ala Leu
            100                 105                 110

Ala Ala Cys Gly Cys Lys Val Pro Met Ile Ser Gly Arg Gly Leu Gly
        115                 120                 125

His Thr Gly Gly Thr Leu Asp Lys Leu Glu Ser Ile Pro Gly Phe Asn
    130                 135                 140

Val Ile Gln Ser Pro Glu Gln Met Gln Val Leu Leu Asp Gln Ala Gly
145                 150                 155                 160

Cys Cys Ile Val Gly Gln Ser Glu Gln Leu Val Pro Ala Asp Gly Ile
                165                 170                 175

Leu Tyr Ala Ala Arg Asp Val Thr Ala Thr Val Asp Ser Leu Pro Leu
            180                 185                 190

Ile Thr Ala Ser Ile Leu Ser Lys Lys Leu Val Glu Gly Leu Ser Ala
        195                 200                 205

Leu Val Val Asp Val Lys Phe Gly Gly Ala Ala Val Phe Pro Asn Gln
    210                 215                 220

Glu Gln Ala Arg Glu Leu Ala Lys Thr Leu Val Gly Val Gly Ala Ser
225                 230                 235                 240

Leu Gly Leu Arg Val Ala Ala Ala Leu Thr Ala Met Asp Lys Pro Leu
                245                 250                 255

Gly Arg Cys Val Gly His Ala Leu Glu Val Glu Glu Ala Leu Leu Cys
            260                 265                 270

Met Asp Gly Ala Gly Pro Pro Asp Leu Arg Asp Leu Val Thr Thr Leu
        275                 280                 285

Gly Gly Ala Leu Leu Trp Leu Ser Gly His Ala Gly Thr Gln Ala Gln
    290                 295                 300

Gly Ala Ala Arg Val Ala Ala Ala Leu Asp Asp Gly Ser Ala Leu Gly
305                 310                 315                 320

Arg Phe Glu Arg Met Leu Ala Ala Gln Gly Val Asp Pro Gly Leu Ala
                325                 330                 335

Arg Ala Leu Cys Ser Gly Ser Pro Ala Glu Arg Arg Gln Leu Leu Pro
```

```
            340                 345                 350
Arg Ala Arg Glu Gln Glu Leu Leu Ala Pro Ala Asp Gly Thr Val
            355                 360                 365
Glu Leu Val Arg Ala Leu Pro Leu Ala Leu Val Leu His Glu Leu Gly
    370                 375                 380
Ala Gly Arg Ser Arg Ala Gly Glu Pro Leu Arg Leu Gly Val Gly Ala
385                 390                 395                 400
Glu Leu Leu Val Asp Val Gly Gln Arg Leu Arg Gly Thr Pro Trp
                405                 410                 415
Leu Arg Val His Arg Asp Gly Pro Ala Leu Ser Gly Pro Gln Ser Arg
                420                 425                 430
Ala Leu Gln Glu Ala Leu Val Leu Ser Asp Arg Ala Pro Phe Ala Ala
            435                 440                 445
Pro Ser Pro Phe Ala Glu Leu Val Leu Pro Pro Gln Gln
    450                 455                 460

<210> SEQ ID NO 5
<211> LENGTH: 448
<212> TYPE: PRT
<213> ORGANISM: Homo sapiens

<400> SEQUENCE: 5

Gln Leu Pro Glu Leu Ile Arg Met Lys Arg Asp Gly Gly Arg Leu Ser
1               5                   10                  15
Glu Ala Asp Ile Arg Gly Phe Val Ala Ala Val Asn Gly Ser Ala
            20                  25                  30
Gln Gly Ala Gln Ile Gly Ala Met Leu Met Ala Ile Arg Leu Arg Gly
        35                  40                  45
Met Asp Leu Glu Glu Thr Ser Val Leu Thr Gln Ala Leu Ala Gln Ser
50                  55                  60
Gly Gln Gln Leu Glu Trp Pro Glu Ala Trp Arg Gln Leu Val Asp
65                  70                  75                  80
Lys His Ser Thr Gly Gly Val Gly Asp Lys Val Ser Leu Val Leu Ala
                85                  90                  95
Pro Ala Leu Ala Ala Cys Gly Cys Lys Val Pro Met Ile Ser Gly Arg
            100                 105                 110
Gly Leu Gly His Thr Gly Gly Thr Leu Asp Lys Leu Glu Ser Ile Pro
        115                 120                 125
Gly Phe Asn Val Ile Gln Ser Pro Glu Gln Met Gln Val Leu Leu Asp
130                 135                 140
Gln Ala Gly Cys Cys Ile Val Gly Gln Ser Glu Gln Leu Val Pro Ala
145                 150                 155                 160
Asp Gly Ile Leu Tyr Ala Ala Arg Asp Val Thr Ala Thr Val Asp Ser
                165                 170                 175
Leu Pro Leu Ile Thr Ala Ser Ile Leu Ser Lys Lys Leu Val Glu Gly
            180                 185                 190
Leu Ser Ala Leu Val Val Asp Val Lys Phe Gly Gly Ala Ala Val Phe
        195                 200                 205
Pro Asn Gln Glu Gln Ala Arg Glu Leu Ala Lys Thr Leu Val Gly Val
210                 215                 220
Gly Ala Ser Leu Gly Leu Arg Val Ala Ala Ala Leu Thr Ala Met Asp
225                 230                 235                 240
Lys Pro Leu Gly Arg Cys Val Gly His Ala Leu Glu Val Glu Glu Ala
                245                 250                 255
```

-continued

```
Leu Leu Cys Met Asp Gly Ala Gly Pro Pro Asp Leu Arg Asp Leu Val
            260                 265                 270

Thr Thr Leu Gly Gly Ala Leu Leu Trp Leu Ser Gly His Ala Gly Thr
        275                 280                 285

Gln Ala Gln Gly Ala Ala Arg Val Ala Ala Ala Leu Asp Asp Gly Ser
    290                 295                 300

Ala Leu Gly Arg Phe Glu Arg Met Leu Ala Ala Gln Gly Val Asp Pro
305                 310                 315                 320

Gly Leu Ala Arg Ala Leu Cys Ser Gly Ser Pro Ala Glu Arg Arg Gln
                325                 330                 335

Leu Leu Pro Arg Ala Arg Glu Gln Glu Glu Leu Leu Ala Pro Ala Asp
            340                 345                 350

Gly Thr Val Glu Leu Val Arg Ala Leu Pro Leu Ala Leu Val Leu His
        355                 360                 365

Glu Leu Gly Ala Gly Arg Ser Arg Ala Gly Glu Pro Leu Arg Leu Gly
    370                 375                 380

Val Gly Ala Glu Leu Leu Val Asp Val Gly Gln Arg Leu Arg Arg Gly
385                 390                 395                 400

Thr Pro Trp Leu Arg Val His Arg Asp Gly Pro Ala Leu Ser Gly Pro
                405                 410                 415

Gln Ser Arg Ala Leu Gln Glu Ala Leu Val Leu Ser Asp Arg Ala Pro
            420                 425                 430

Phe Ala Ala Pro Ser Pro Phe Ala Glu Leu Val Leu Pro Pro Gln Gln
        435                 440                 445

<210> SEQ ID NO 6
<211> LENGTH: 699
<212> TYPE: PRT
<213> ORGANISM: Artificial Sequence
<220> FEATURE:
<223> OTHER INFORMATION: IgG1Fc-TP (16-482) N-terminal fusion

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

-continued

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Asp Phe Ser Gly Glu Gly Ser
225                 230                 235                 240

Gln Gly Leu Pro Asp Pro Ser Pro Glu Pro Lys Gln Leu Pro Glu Leu
                245                 250                 255

Ile Arg Met Lys Arg Asp Gly Arg Leu Ser Glu Ala Asp Ile Arg
            260                 265                 270

Gly Phe Val Ala Ala Val Val Asn Gly Ser Ala Gln Gly Ala Gln Ile
        275                 280                 285

Gly Ala Met Leu Met Ala Ile Arg Leu Arg Gly Met Asp Leu Glu Glu
    290                 295                 300

Thr Ser Val Leu Thr Gln Ala Leu Ala Gln Ser Gly Gln Gln Leu Glu
305                 310                 315                 320

Trp Pro Glu Ala Trp Arg Gln Gln Leu Val Asp Lys His Ser Thr Gly
                325                 330                 335

Gly Val Gly Asp Lys Val Ser Leu Val Leu Ala Pro Ala Leu Ala Ala
            340                 345                 350

Cys Gly Cys Lys Val Pro Met Ile Ser Gly Arg Gly Leu Gly His Thr
        355                 360                 365

Gly Gly Thr Leu Asp Lys Leu Glu Ser Ile Pro Gly Phe Asn Val Ile
    370                 375                 380

Gln Ser Pro Glu Gln Met Gln Val Leu Leu Asp Gln Ala Gly Cys Cys
385                 390                 395                 400

Ile Val Gly Gln Ser Glu Gln Leu Val Pro Ala Asp Gly Ile Leu Tyr
                405                 410                 415

Ala Ala Arg Asp Val Thr Ala Thr Val Asp Ser Leu Pro Leu Ile Thr
            420                 425                 430

Ala Ser Ile Leu Ser Lys Lys Leu Val Glu Gly Leu Ser Ala Leu Val
        435                 440                 445

Val Asp Val Lys Phe Gly Gly Ala Ala Val Phe Pro Asn Gln Glu Gln
450                 455                 460

Ala Arg Glu Leu Ala Lys Thr Leu Val Gly Val Gly Ala Ser Leu Gly
465                 470                 475                 480

Leu Arg Val Ala Ala Ala Leu Thr Ala Met Asp Lys Pro Leu Gly Arg
                485                 490                 495

Cys Val Gly His Ala Leu Glu Val Glu Glu Ala Leu Leu Cys Met Asp
            500                 505                 510

Gly Ala Gly Pro Pro Asp Leu Arg Asp Leu Val Thr Thr Leu Gly Gly
        515                 520                 525

Ala Leu Leu Trp Leu Ser Gly His Ala Gly Thr Gln Ala Gln Gly Ala
    530                 535                 540

Ala Arg Val Ala Ala Ala Leu Asp Asp Gly Ser Ala Leu Gly Arg Phe
545                 550                 555                 560

Glu Arg Met Leu Ala Ala Gln Gly Val Asp Pro Gly Leu Ala Arg Ala
                565                 570                 575

Leu Cys Ser Gly Ser Pro Ala Glu Arg Arg Gln Leu Leu Pro Arg Ala
            580                 585                 590

Arg Glu Gln Glu Glu Leu Leu Ala Pro Ala Asp Gly Thr Val Glu Leu

-continued

```
                595                 600                 605
Val Arg Ala Leu Pro Leu Ala Leu Val Leu His Glu Leu Gly Ala Gly
        610                 615                 620

Arg Ser Arg Ala Gly Glu Pro Leu Arg Leu Gly Val Gly Ala Glu Leu
625                 630                 635                 640

Leu Val Asp Val Gly Gln Arg Leu Arg Arg Gly Thr Pro Trp Leu Arg
                645                 650                 655

Val His Arg Asp Gly Pro Ala Leu Ser Gly Pro Gln Ser Arg Ala Leu
        660                 665                 670

Gln Glu Ala Leu Val Leu Ser Asp Arg Ala Pro Phe Ala Ala Pro Ser
        675                 680                 685

Pro Phe Ala Glu Leu Val Leu Pro Pro Gln Gln
        690                 695

<210> SEQ ID NO 7
<211> LENGTH: 704
<212> TYPE: PRT
<213> ORGANISM: Artificial Sequence
<220> FEATURE:
<223> OTHER INFORMATION: IgG1Fc-TP (16-482) N-terminal fusion with GGGGS
      linker

<400> SEQUENCE: 7

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Gly Ser Gly Asp Phe
225                 230                 235                 240

Ser Gly Glu Gly Ser Gln Gly Leu Pro Asp Pro Ser Pro Glu Pro Lys
                245                 250                 255
```

```
Gln Leu Pro Glu Leu Ile Arg Met Lys Arg Asp Gly Gly Arg Leu Ser
                260                 265                 270

Glu Ala Asp Ile Arg Gly Phe Val Ala Val Val Asn Gly Ser Ala
            275                 280                 285

Gln Gly Ala Gln Ile Gly Ala Met Leu Met Ala Ile Arg Leu Arg Gly
        290                 295                 300

Met Asp Leu Glu Glu Thr Ser Val Leu Thr Gln Ala Leu Ala Gln Ser
305                 310                 315                 320

Gly Gln Gln Leu Glu Trp Pro Glu Ala Trp Arg Gln Gln Leu Val Asp
                325                 330                 335

Lys His Ser Thr Gly Val Gly Asp Lys Val Ser Leu Val Leu Ala
            340                 345                 350

Pro Ala Leu Ala Ala Cys Gly Cys Lys Val Pro Met Ile Ser Gly Arg
                355                 360                 365

Gly Leu Gly His Thr Gly Gly Thr Leu Asp Lys Leu Glu Ser Ile Pro
            370                 375                 380

Gly Phe Asn Val Ile Gln Ser Pro Glu Gln Met Gln Val Leu Leu Asp
385                 390                 395                 400

Gln Ala Gly Cys Cys Ile Val Gly Gln Ser Glu Gln Leu Val Pro Ala
                405                 410                 415

Asp Gly Ile Leu Tyr Ala Ala Arg Asp Val Thr Ala Thr Val Asp Ser
            420                 425                 430

Leu Pro Leu Ile Thr Ala Ser Ile Leu Ser Lys Lys Leu Val Glu Gly
                435                 440                 445

Leu Ser Ala Leu Val Val Asp Val Lys Phe Gly Gly Ala Ala Val Phe
450                 455                 460

Pro Asn Gln Glu Gln Ala Arg Glu Leu Ala Lys Thr Leu Val Gly Val
465                 470                 475                 480

Gly Ala Ser Leu Gly Leu Arg Val Ala Ala Leu Thr Ala Met Asp
            485                 490                 495

Lys Pro Leu Gly Arg Cys Val Gly His Ala Leu Glu Val Glu Glu Ala
                500                 505                 510

Leu Leu Cys Met Asp Gly Ala Gly Pro Pro Asp Leu Arg Asp Leu Val
            515                 520                 525

Thr Thr Leu Gly Gly Ala Leu Leu Trp Leu Ser Gly His Ala Gly Thr
530                 535                 540

Gln Ala Gln Gly Ala Ala Arg Val Ala Ala Ala Leu Asp Asp Gly Ser
545                 550                 555                 560

Ala Leu Gly Arg Phe Glu Arg Met Leu Ala Ala Gln Gly Val Asp Pro
                565                 570                 575

Gly Leu Ala Arg Ala Leu Cys Ser Gly Ser Pro Ala Glu Arg Arg Gln
            580                 585                 590

Leu Leu Pro Arg Ala Arg Glu Gln Glu Glu Leu Leu Ala Pro Ala Asp
                595                 600                 605

Gly Thr Val Glu Leu Val Arg Ala Leu Pro Leu Ala Leu Val Leu His
610                 615                 620

Glu Leu Gly Ala Gly Arg Ser Arg Ala Gly Glu Pro Leu Arg Leu Gly
625                 630                 635                 640

Val Gly Ala Glu Leu Val Asp Val Gly Gln Arg Leu Arg Arg Gly
            645                 650                 655

Thr Pro Trp Leu Arg Val His Arg Asp Gly Pro Ala Leu Ser Gly Pro
                660                 665                 670

Gln Ser Arg Ala Leu Gln Glu Ala Leu Val Leu Ser Asp Arg Ala Pro
```

-continued

```
               675                 680                 685
Phe Ala Ala Pro Ser Pro Phe Ala Glu Leu Val Leu Pro Pro Gln Gln
           690                 695                 700

<210> SEQ ID NO 8
<211> LENGTH: 699
<212> TYPE: PRT
<213> ORGANISM: Artificial Sequence
<220> FEATURE:
<223> OTHER INFORMATION: TP (16-482)- IgG1Fc C-terminal fusion

<400> SEQUENCE: 8

Gly Asp Phe Ser Gly Glu Gly Ser Gln Gly Leu Pro Asp Pro Ser Pro
1               5                   10                  15

Glu Pro Lys Gln Leu Pro Glu Leu Ile Arg Met Lys Arg Asp Gly Gly
            20                  25                  30

Arg Leu Ser Glu Ala Asp Ile Arg Gly Phe Val Ala Ala Val Val Asn
        35                  40                  45

Gly Ser Ala Gln Gly Ala Gln Ile Gly Ala Met Leu Met Ala Ile Arg
    50                  55                  60

Leu Arg Gly Met Asp Leu Glu Glu Thr Ser Val Leu Thr Gln Ala Leu
65                  70                  75                  80

Ala Gln Ser Gly Gln Gln Leu Glu Trp Pro Glu Ala Trp Arg Gln Gln
                85                  90                  95

Leu Val Asp Lys His Ser Thr Gly Gly Val Gly Asp Lys Val Ser Leu
            100                 105                 110

Val Leu Ala Pro Ala Leu Ala Ala Cys Gly Cys Lys Val Pro Met Ile
        115                 120                 125

Ser Gly Arg Gly Leu Gly His Thr Gly Gly Thr Leu Asp Lys Leu Glu
    130                 135                 140

Ser Ile Pro Gly Phe Asn Val Ile Gln Ser Pro Glu Gln Met Gln Val
145                 150                 155                 160

Leu Leu Asp Gln Ala Gly Cys Cys Ile Val Gly Gln Ser Glu Gln Leu
                165                 170                 175

Val Pro Ala Asp Gly Ile Leu Tyr Ala Ala Arg Asp Val Thr Ala Thr
            180                 185                 190

Val Asp Ser Leu Pro Leu Ile Thr Ala Ser Ile Leu Ser Lys Lys Leu
        195                 200                 205

Val Glu Gly Leu Ser Ala Leu Val Val Asp Val Lys Phe Gly Gly Ala
    210                 215                 220

Ala Val Phe Pro Asn Gln Glu Gln Ala Arg Glu Leu Ala Lys Thr Leu
225                 230                 235                 240

Val Gly Val Gly Ala Ser Leu Gly Leu Arg Val Ala Ala Ala Leu Thr
                245                 250                 255

Ala Met Asp Lys Pro Leu Gly Arg Cys Val Gly His Ala Leu Glu Val
            260                 265                 270

Glu Glu Ala Leu Leu Cys Met Asp Gly Ala Gly Pro Pro Asp Leu Arg
        275                 280                 285

Asp Leu Val Thr Thr Leu Gly Gly Ala Leu Leu Trp Leu Ser Gly His
    290                 295                 300

Ala Gly Thr Gln Ala Gln Gly Ala Ala Arg Val Ala Ala Ala Leu Asp
305                 310                 315                 320

Asp Gly Ser Ala Leu Gly Arg Phe Glu Arg Met Leu Ala Ala Gln Gly
                325                 330                 335

Val Asp Pro Gly Leu Ala Arg Ala Leu Cys Ser Gly Ser Pro Ala Glu
```

```
                340                 345                 350
Arg Arg Gln Leu Leu Pro Arg Ala Arg Glu Gln Glu Glu Leu Leu Ala
            355                 360                 365

Pro Ala Asp Gly Thr Val Glu Leu Val Arg Ala Leu Pro Leu Ala Leu
        370                 375                 380

Val Leu His Glu Leu Gly Ala Gly Arg Ser Arg Ala Gly Glu Pro Leu
385                 390                 395                 400

Arg Leu Gly Val Gly Ala Glu Leu Leu Asp Val Gly Gln Arg Leu
                405                 410                 415

Arg Arg Gly Thr Pro Trp Leu Arg Val His Arg Asp Gly Pro Ala Leu
            420                 425                 430

Ser Gly Pro Gln Ser Arg Ala Leu Gln Glu Ala Leu Val Leu Ser Asp
        435                 440                 445

Arg Ala Pro Phe Ala Ala Pro Ser Pro Phe Ala Glu Leu Val Leu Pro
    450                 455                 460

Pro Gln Gln Glu Pro Lys Ser Cys Asp Lys Thr His Thr Cys Pro Pro
465                 470                 475                 480

Cys Pro Ala Pro Glu Leu Leu Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Thr Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly Lys
    690                 695

<210> SEQ ID NO 9
<211> LENGTH: 704
<212> TYPE: PRT
<213> ORGANISM: Artificial Sequence
<220> FEATURE:
<223> OTHER INFORMATION: TP (16-482)- IgG1Fc C-terminal fusion with
      GGGGS linker

<400> SEQUENCE: 9
```

```
Gly Asp Phe Ser Gly Glu Gly Ser Gln Gly Leu Pro Asp Pro Ser Pro
1               5                   10                  15

Glu Pro Lys Gln Leu Pro Glu Leu Ile Arg Met Lys Arg Asp Gly Gly
            20                  25                  30

Arg Leu Ser Glu Ala Asp Ile Arg Gly Phe Val Ala Ala Val Val Asn
        35                  40                  45

Gly Ser Ala Gln Gly Ala Gln Ile Gly Ala Met Leu Met Ala Ile Arg
    50                  55                  60

Leu Arg Gly Met Asp Leu Glu Glu Thr Ser Val Leu Thr Gln Ala Leu
65                  70                  75                  80

Ala Gln Ser Gly Gln Gln Leu Glu Trp Pro Glu Ala Trp Arg Gln Gln
                85                  90                  95

Leu Val Asp Lys His Ser Thr Gly Val Gly Asp Lys Val Ser Leu
                100                 105                 110

Val Leu Ala Pro Ala Leu Ala Ala Cys Gly Cys Lys Val Pro Met Ile
            115                 120                 125

Ser Gly Arg Gly Leu Gly His Thr Gly Gly Thr Leu Asp Lys Leu Glu
        130                 135                 140

Ser Ile Pro Gly Phe Asn Val Ile Gln Ser Pro Glu Gln Met Gln Val
145                 150                 155                 160

Leu Leu Asp Gln Ala Gly Cys Cys Ile Val Gly Gln Ser Glu Gln Leu
                165                 170                 175

Val Pro Ala Asp Gly Ile Leu Tyr Ala Ala Arg Asp Val Thr Ala Thr
            180                 185                 190

Val Asp Ser Leu Pro Leu Ile Thr Ala Ser Ile Leu Ser Lys Lys Leu
            195                 200                 205

Val Glu Gly Leu Ser Ala Leu Val Val Asp Val Lys Phe Gly Gly Ala
    210                 215                 220

Ala Val Phe Pro Asn Gln Glu Gln Ala Arg Glu Leu Ala Lys Thr Leu
225                 230                 235                 240

Val Gly Val Gly Ala Ser Leu Gly Leu Arg Val Ala Ala Ala Leu Thr
            245                 250                 255

Ala Met Asp Lys Pro Leu Gly Arg Cys Val Gly His Ala Leu Glu Val
            260                 265                 270

Glu Glu Ala Leu Leu Cys Met Asp Gly Ala Gly Pro Pro Asp Leu Arg
        275                 280                 285

Asp Leu Val Thr Thr Leu Gly Gly Ala Leu Leu Trp Leu Ser Gly His
        290                 295                 300

Ala Gly Thr Gln Ala Gln Gly Ala Ala Arg Val Ala Ala Ala Leu Asp
305                 310                 315                 320

Asp Gly Ser Ala Leu Gly Arg Phe Glu Arg Met Leu Ala Ala Gln Gly
            325                 330                 335

Val Asp Pro Gly Leu Ala Arg Ala Leu Cys Ser Gly Ser Pro Ala Glu
            340                 345                 350

Arg Arg Gln Leu Leu Pro Arg Ala Arg Glu Gln Glu Leu Leu Ala
        355                 360                 365

Pro Ala Asp Gly Thr Val Glu Leu Val Arg Ala Leu Pro Leu Ala Leu
        370                 375                 380

Val Leu His Glu Leu Gly Ala Gly Arg Ser Arg Ala Gly Glu Pro Leu
385                 390                 395                 400

Arg Leu Gly Val Gly Ala Glu Leu Leu Val Asp Val Gly Gln Arg Leu
            405                 410                 415

Arg Arg Gly Thr Pro Trp Leu Arg Val His Arg Asp Gly Pro Ala Leu
```

```
            420                 425                 430
Ser Gly Pro Gln Ser Arg Ala Leu Gln Glu Ala Leu Val Leu Ser Asp
        435                 440                 445

Arg Ala Pro Phe Ala Ala Pro Ser Pro Phe Ala Glu Leu Val Leu Pro
    450                 455                 460

Pro Gln Gln Gly Gly Gly Ser Glu Pro Lys Ser Cys Asp Lys Thr
465                 470                 475                 480

His Thr Cys Pro Pro Cys Pro Ala Pro Glu Leu Leu Gly Gly Pro Ser
                485                 490                 495

Val Phe Leu Phe Pro Pro Lys Pro Lys Asp Thr Leu Met Ile Ser Arg
            500                 505                 510

Thr Pro Glu Val Thr Cys Val Val Val Asp Val Ser His Glu Asp Pro
        515                 520                 525

Glu Val Lys Phe Asn Trp Tyr Val Asp Gly Val Glu Val His Asn Ala
    530                 535                 540

Lys Thr Lys Pro Arg Glu Glu Gln Tyr Asn Ser Thr Tyr Arg Val Val
545                 550                 555                 560

Ser Val Leu Thr Val Leu His Gln Asp Trp Leu Asn Gly Lys Glu Tyr
                565                 570                 575

Lys Cys Lys Val Ser Asn Lys Ala Leu Pro Ala Pro Ile Glu Lys Thr
            580                 585                 590

Ile Ser Lys Ala Lys Gly Gln Pro Arg Glu Pro Gln Val Tyr Thr Leu
        595                 600                 605

Pro Pro Ser Arg Glu Glu Met Thr Lys Asn Gln Val Ser Leu Thr Cys
    610                 615                 620

Leu Val Lys Gly Phe Tyr Pro Ser Asp Ile Ala Val Glu Trp Glu Ser
625                 630                 635                 640

Asn Gly Gln Pro Glu Asn Asn Tyr Lys Thr Thr Pro Pro Val Leu Asp
                645                 650                 655

Ser Asp Gly Ser Phe Phe Leu Tyr Ser Lys Leu Thr Val Asp Lys Ser
            660                 665                 670

Arg Trp Gln Gln Gly Asn Val Phe Ser Cys Ser Val Met His Glu Ala
        675                 680                 685

Leu His Asn His Tyr Thr Gln Lys Ser Leu Ser Leu Ser Pro Gly Lys
    690                 695                 700

<210> SEQ ID NO 10
<211> LENGTH: 704
<212> TYPE: PRT
<213> ORGANISM: Artificial Sequence
<220> FEATURE:
<223> OTHER INFORMATION: TP (16-482)- IgG1Fc_R435 C-terminal fusion with
      GGGGS linker

<400> SEQUENCE: 10

Gly Asp Phe Ser Gly Glu Gly Ser Gln Gly Leu Pro Asp Pro Ser Pro
1               5                   10                  15

Glu Pro Lys Gln Leu Pro Glu Leu Ile Arg Met Lys Arg Asp Gly Gly
            20                  25                  30

Arg Leu Ser Glu Ala Asp Ile Arg Gly Phe Val Ala Ala Val Val Asn
        35                  40                  45

Gly Ser Ala Gln Gly Ala Gln Ile Gly Ala Met Leu Met Ala Ile Arg
    50                  55                  60

Leu Arg Gly Met Asp Leu Glu Glu Thr Ser Val Leu Thr Gln Ala Leu
65                  70                  75                  80
```

-continued

```
Ala Gln Ser Gly Gln Gln Leu Glu Trp Pro Glu Ala Trp Arg Gln Gln
                85                  90                  95

Leu Val Asp Lys His Ser Thr Gly Gly Val Gly Asp Lys Val Ser Leu
            100                 105                 110

Val Leu Ala Pro Ala Leu Ala Ala Cys Gly Cys Lys Val Pro Met Ile
        115                 120                 125

Ser Gly Arg Gly Leu Gly His Thr Gly Gly Thr Leu Asp Lys Leu Glu
    130                 135                 140

Ser Ile Pro Gly Phe Asn Val Ile Gln Ser Pro Glu Gln Met Gln Val
145                 150                 155                 160

Leu Leu Asp Gln Ala Gly Cys Cys Ile Val Gly Gln Ser Glu Gln Leu
                165                 170                 175

Val Pro Ala Asp Gly Ile Leu Tyr Ala Ala Arg Asp Val Thr Ala Thr
            180                 185                 190

Val Asp Ser Leu Pro Leu Ile Thr Ala Ser Ile Leu Ser Lys Lys Leu
        195                 200                 205

Val Glu Gly Leu Ser Ala Leu Val Val Asp Val Lys Phe Gly Gly Ala
    210                 215                 220

Ala Val Phe Pro Asn Gln Glu Gln Ala Arg Glu Leu Ala Lys Thr Leu
225                 230                 235                 240

Val Gly Val Gly Ala Ser Leu Gly Leu Arg Val Ala Ala Ala Leu Thr
                245                 250                 255

Ala Met Asp Lys Pro Leu Gly Arg Cys Val Gly His Ala Leu Glu Val
            260                 265                 270

Glu Glu Ala Leu Leu Cys Met Asp Gly Ala Gly Pro Pro Asp Leu Arg
        275                 280                 285

Asp Leu Val Thr Thr Leu Gly Gly Ala Leu Leu Trp Leu Ser Gly His
    290                 295                 300

Ala Gly Thr Gln Ala Gln Gly Ala Ala Arg Val Ala Ala Ala Leu Asp
305                 310                 315                 320

Asp Gly Ser Ala Leu Gly Arg Phe Glu Arg Met Leu Ala Ala Gln Gly
                325                 330                 335

Val Asp Pro Gly Leu Ala Arg Ala Leu Cys Ser Gly Ser Pro Ala Glu
            340                 345                 350

Arg Arg Gln Leu Leu Pro Arg Ala Arg Glu Gln Glu Leu Leu Ala
        355                 360                 365

Pro Ala Asp Gly Thr Val Glu Leu Val Arg Ala Leu Pro Leu Ala Leu
370                 375                 380

Val Leu His Glu Leu Gly Ala Gly Arg Ser Arg Ala Gly Glu Pro Leu
385                 390                 395                 400

Arg Leu Gly Val Gly Ala Glu Leu Leu Val Asp Val Gly Gln Arg Leu
                405                 410                 415

Arg Arg Gly Thr Pro Trp Leu Arg Val His Arg Asp Gly Pro Ala Leu
            420                 425                 430

Ser Gly Pro Gln Ser Arg Ala Leu Gln Glu Ala Leu Val Leu Ser Asp
        435                 440                 445

Arg Ala Pro Phe Ala Ala Pro Ser Pro Phe Ala Glu Leu Val Leu Pro
450                 455                 460

Pro Gln Gln Gly Gly Gly Gly Ser Glu Pro Lys Ser Cys Asp Lys Thr
465                 470                 475                 480

His Thr Cys Pro Pro Cys Pro Ala Pro Glu Leu Leu Gly Gly Pro Ser
                485                 490                 495

Val Phe Leu Phe Pro Pro Lys Pro Lys Asp Thr Leu Met Ile Ser Arg
```

```
                  500                 505                 510
Thr Pro Glu Val Thr Cys Val Val Asp Val Ser His Glu Asp Pro
            515                 520                 525

Glu Val Lys Phe Asn Trp Tyr Val Asp Gly Val Glu Val His Asn Ala
530                 535                 540

Lys Thr Lys Pro Arg Glu Glu Gln Tyr Asn Ser Thr Tyr Arg Val Val
545                 550                 555                 560

Ser Val Leu Thr Val Leu His Gln Asp Trp Leu Asn Gly Lys Glu Tyr
            565                 570                 575

Lys Cys Lys Val Ser Asn Lys Ala Leu Pro Ala Pro Ile Glu Lys Thr
            580                 585                 590

Ile Ser Lys Ala Lys Gly Gln Pro Arg Glu Pro Gln Val Tyr Thr Leu
            595                 600                 605

Pro Pro Ser Arg Glu Glu Met Thr Lys Asn Gln Val Ser Leu Thr Cys
            610                 615                 620

Leu Val Lys Gly Phe Tyr Pro Ser Asp Ile Ala Val Glu Trp Glu Ser
625                 630                 635                 640

Asn Gly Gln Pro Glu Asn Asn Tyr Lys Thr Thr Pro Pro Val Leu Asp
                    645                 650                 655

Ser Asp Gly Ser Phe Phe Leu Tyr Ser Lys Leu Thr Val Asp Lys Ser
            660                 665                 670

Arg Trp Gln Gln Gly Asn Val Phe Ser Cys Ser Val Met His Glu Ala
            675                 680                 685

Leu His Asn Arg Tyr Thr Gln Lys Ser Leu Ser Leu Ser Pro Gly Lys
            690                 695                 700

<210> SEQ ID NO 11
<211> LENGTH: 704
<212> TYPE: PRT
<213> ORGANISM: Artificial Sequence
<220> FEATURE:
<223> OTHER INFORMATION: IgG1Fc(R435)-TP (16-482) N-terminal fusion with
      GGGGS linker

<400> SEQUENCE: 11

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                    85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
            130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
            165                 170                 175
Lys Thr Thr Pro Pro Val Leu Asp Ser Asp Gly Ser Phe Phe Leu Tyr
        180                 185                 190
Ser Lys Leu Thr Val Asp Lys Ser Arg Trp Gln Gln Gly Asn Val Phe
    195                 200                 205
Ser Cys Ser Val Met His Glu Ala Leu His Asn Arg Tyr Thr Gln Lys
210                 215                 220
Ser Leu Ser Leu Ser Pro Gly Lys Gly Gly Gly Ser Gly Asp Phe
225                 230                 235                 240
Ser Gly Glu Gly Ser Gln Gly Leu Pro Asp Pro Ser Pro Glu Pro Lys
        245                 250                 255
Gln Leu Pro Glu Leu Ile Arg Met Lys Arg Asp Gly Gly Arg Leu Ser
        260                 265                 270
Glu Ala Asp Ile Arg Gly Phe Val Ala Val Val Asn Gly Ser Ala
        275                 280                 285
Gln Gly Ala Gln Ile Gly Ala Met Leu Met Ala Ile Arg Leu Arg Gly
        290                 295                 300
Met Asp Leu Glu Glu Thr Ser Val Leu Thr Gln Ala Leu Ala Gln Ser
305                 310                 315                 320
Gly Gln Gln Leu Glu Trp Pro Glu Ala Trp Arg Gln Leu Val Asp
        325                 330                 335
Lys His Ser Thr Gly Gly Val Gly Asp Lys Val Ser Leu Val Leu Ala
            340                 345                 350
Pro Ala Leu Ala Ala Cys Gly Cys Lys Val Pro Met Ile Ser Gly Arg
        355                 360                 365
Gly Leu Gly His Thr Gly Gly Thr Leu Asp Lys Leu Glu Ser Ile Pro
    370                 375                 380
Gly Phe Asn Val Ile Gln Ser Pro Glu Gln Met Gln Val Leu Leu Asp
385                 390                 395                 400
Gln Ala Gly Cys Cys Ile Val Gly Gln Ser Glu Gln Leu Val Pro Ala
            405                 410                 415
Asp Gly Ile Leu Tyr Ala Ala Arg Asp Val Thr Ala Thr Val Asp Ser
        420                 425                 430
Leu Pro Leu Ile Thr Ala Ser Ile Leu Ser Lys Lys Leu Val Glu Gly
    435                 440                 445
Leu Ser Ala Leu Val Val Asp Val Lys Phe Gly Gly Ala Ala Val Phe
    450                 455                 460
Pro Asn Gln Glu Gln Ala Arg Glu Leu Ala Lys Thr Leu Val Gly Val
465                 470                 475                 480
Gly Ala Ser Leu Gly Leu Arg Val Ala Ala Leu Thr Ala Met Asp
            485                 490                 495
Lys Pro Leu Gly Arg Cys Val Gly His Ala Leu Glu Val Glu Ala
        500                 505                 510
Leu Leu Cys Met Asp Gly Ala Gly Pro Pro Asp Leu Arg Asp Leu Val
    515                 520                 525
Thr Thr Leu Gly Gly Ala Leu Leu Trp Leu Ser Gly His Ala Gly Thr
530                 535                 540
Gln Ala Gln Gly Ala Ala Arg Val Ala Ala Leu Asp Asp Gly Ser
545                 550                 555                 560
Ala Leu Gly Arg Phe Glu Arg Met Leu Ala Ala Gln Gly Val Asp Pro
            565                 570                 575
Gly Leu Ala Arg Ala Leu Cys Ser Gly Ser Pro Ala Glu Arg Arg Gln
```

```
                580                 585                 590
Leu Leu Pro Arg Ala Glu Gln Glu Leu Leu Ala Pro Ala Asp
            595                 600                 605

Gly Thr Val Glu Leu Val Arg Ala Leu Pro Leu Ala Leu Val Leu His
            610                 615                 620

Glu Leu Gly Ala Gly Arg Ser Arg Ala Gly Glu Pro Leu Arg Leu Gly
625                 630                 635                 640

Val Gly Ala Glu Leu Leu Val Asp Val Gly Gln Arg Leu Arg Arg Gly
                645                 650                 655

Thr Pro Trp Leu Arg Val His Arg Asp Gly Pro Ala Leu Ser Gly Pro
            660                 665                 670

Gln Ser Arg Ala Leu Gln Glu Ala Leu Val Leu Ser Asp Arg Ala Pro
            675                 680                 685

Phe Ala Ala Pro Ser Pro Phe Ala Glu Leu Val Leu Pro Pro Gln Gln
            690                 695                 700

<210> SEQ ID NO 12
<211> LENGTH: 699
<212> TYPE: PRT
<213> ORGANISM: Artificial Sequence
<220> FEATURE:
<223> OTHER INFORMATION: IgG1Fc-TP_R435 (16-482) N-terminal fusion

<400> SEQUENCE: 12

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Arg Tyr Thr Gln Lys
    210                 215                 220

Ser Leu Ser Leu Ser Pro Gly Lys Gly Asp Phe Ser Gly Glu Gly Ser
225                 230                 235                 240

Gln Gly Leu Pro Asp Pro Ser Pro Glu Pro Lys Gln Leu Pro Glu Leu
```

```
                245                 250                 255
Ile Arg Met Lys Arg Asp Gly Gly Arg Leu Ser Glu Ala Asp Ile Arg
            260                 265                 270

Gly Phe Val Ala Ala Val Val Asn Gly Ser Ala Gln Gly Ala Gln Ile
            275                 280                 285

Gly Ala Met Leu Met Ala Ile Arg Leu Arg Gly Met Asp Leu Glu Glu
            290                 295                 300

Thr Ser Val Leu Thr Gln Ala Leu Ala Gln Ser Gly Gln Gln Leu Glu
305                 310                 315                 320

Trp Pro Glu Ala Trp Arg Gln Gln Leu Val Asp Lys His Ser Thr Gly
                325                 330                 335

Gly Val Gly Asp Lys Val Ser Leu Val Leu Ala Pro Ala Leu Ala Ala
                340                 345                 350

Cys Gly Cys Lys Val Pro Met Ile Ser Gly Arg Gly Leu Gly His Thr
                355                 360                 365

Gly Gly Thr Leu Asp Lys Leu Glu Ser Ile Pro Gly Phe Asn Val Ile
            370                 375                 380

Gln Ser Pro Glu Gln Met Gln Val Leu Leu Asp Gln Ala Gly Cys Cys
385                 390                 395                 400

Ile Val Gly Gln Ser Glu Gln Leu Val Pro Ala Asp Gly Ile Leu Tyr
                405                 410                 415

Ala Ala Arg Asp Val Thr Ala Thr Val Asp Ser Leu Pro Leu Ile Thr
            420                 425                 430

Ala Ser Ile Leu Ser Lys Lys Leu Val Glu Gly Leu Ser Ala Leu Val
            435                 440                 445

Val Asp Val Lys Phe Gly Gly Ala Ala Val Phe Pro Asn Gln Glu Gln
450                 455                 460

Ala Arg Glu Leu Ala Lys Thr Leu Val Gly Val Gly Ala Ser Leu Gly
465                 470                 475                 480

Leu Arg Val Ala Ala Ala Leu Thr Ala Met Asp Lys Pro Leu Gly Arg
                485                 490                 495

Cys Val Gly His Ala Leu Glu Val Glu Glu Ala Leu Leu Cys Met Asp
                500                 505                 510

Gly Ala Gly Pro Pro Asp Leu Arg Asp Leu Val Thr Thr Leu Gly Gly
            515                 520                 525

Ala Leu Leu Trp Leu Ser Gly His Ala Gly Thr Gln Ala Gln Gly Ala
530                 535                 540

Ala Arg Val Ala Ala Ala Leu Asp Asp Gly Ser Ala Leu Gly Arg Phe
545                 550                 555                 560

Glu Arg Met Leu Ala Ala Gln Gly Val Asp Pro Gly Leu Ala Arg Ala
                565                 570                 575

Leu Cys Ser Gly Ser Pro Ala Glu Arg Arg Gln Leu Leu Pro Arg Ala
            580                 585                 590

Arg Glu Gln Glu Glu Leu Leu Ala Pro Ala Asp Gly Thr Val Glu Leu
            595                 600                 605

Val Arg Ala Leu Pro Leu Ala Leu Val Leu His Glu Leu Gly Ala Gly
            610                 615                 620

Arg Ser Arg Ala Gly Glu Pro Leu Arg Leu Gly Val Gly Ala Glu Leu
625                 630                 635                 640

Leu Val Asp Val Gly Gln Arg Leu Arg Arg Gly Thr Pro Trp Leu Arg
                645                 650                 655

Val His Arg Asp Gly Pro Ala Leu Ser Gly Pro Gln Ser Arg Ala Leu
                660                 665                 670
```

-continued

Gln Glu Ala Leu Val Leu Ser Asp Arg Ala Pro Phe Ala Ala Pro Ser
              675                 680                 685

Pro Phe Ala Glu Leu Val Leu Pro Pro Gln Gln
    690                 695

<210> SEQ ID NO 13
<211> LENGTH: 699
<212> TYPE: PRT
<213> ORGANISM: Artificial Sequence
<220> FEATURE:
<223> OTHER INFORMATION: TP (16-482) - IgG1Fc_R435 C-terminal fusion

<400> SEQUENCE: 13

Gly Asp Phe Ser Gly Glu Gly Ser Gln Gly Leu Pro Asp Pro Ser Pro
1               5                   10                  15

Glu Pro Lys Gln Leu Pro Glu Leu Ile Arg Met Lys Arg Asp Gly Gly
                20                  25                  30

Arg Leu Ser Glu Ala Asp Ile Arg Gly Phe Val Ala Ala Val Val Asn
            35                  40                  45

Gly Ser Ala Gln Gly Ala Gln Ile Gly Ala Met Leu Met Ala Ile Arg
    50                  55                  60

Leu Arg Gly Met Asp Leu Glu Glu Thr Ser Val Leu Thr Gln Ala Leu
65                  70                  75                  80

Ala Gln Ser Gly Gln Gln Leu Glu Trp Pro Glu Ala Trp Arg Gln Gln
                85                  90                  95

Leu Val Asp Lys His Ser Thr Gly Gly Val Gly Asp Lys Val Ser Leu
                100                 105                 110

Val Leu Ala Pro Ala Leu Ala Ala Cys Gly Cys Lys Val Pro Met Ile
            115                 120                 125

Ser Gly Arg Gly Leu Gly His Thr Gly Gly Thr Leu Asp Lys Leu Glu
    130                 135                 140

Ser Ile Pro Gly Phe Asn Val Ile Gln Ser Pro Glu Gln Met Gln Val
145                 150                 155                 160

Leu Leu Asp Gln Ala Gly Cys Cys Ile Val Gly Gln Ser Glu Gln Leu
                165                 170                 175

Val Pro Ala Asp Gly Ile Leu Tyr Ala Ala Arg Asp Val Thr Ala Thr
                180                 185                 190

Val Asp Ser Leu Pro Leu Ile Thr Ala Ser Ile Leu Ser Lys Lys Leu
            195                 200                 205

Val Glu Gly Leu Ser Ala Leu Val Val Asp Val Lys Phe Gly Gly Ala
    210                 215                 220

Ala Val Phe Pro Asn Gln Glu Gln Ala Arg Glu Leu Ala Lys Thr Leu
225                 230                 235                 240

Val Gly Val Gly Ala Ser Leu Gly Leu Arg Val Ala Ala Ala Leu Thr
                245                 250                 255

Ala Met Asp Lys Pro Leu Gly Arg Cys Val Gly His Ala Leu Glu Val
                260                 265                 270

Glu Glu Ala Leu Leu Cys Met Asp Gly Ala Gly Pro Pro Asp Leu Arg
            275                 280                 285

Asp Leu Val Thr Thr Leu Gly Gly Ala Leu Leu Trp Leu Ser Gly His
    290                 295                 300

Ala Gly Thr Gln Ala Gln Gly Ala Ala Arg Val Ala Ala Ala Leu Asp
305                 310                 315                 320

Asp Gly Ser Ala Leu Gly Arg Phe Glu Arg Met Leu Ala Ala Gln Gly
                325                 330                 335

```
Val Asp Pro Gly Leu Ala Arg Ala Leu Cys Ser Gly Ser Pro Ala Glu
            340                 345                 350

Arg Arg Gln Leu Leu Pro Arg Ala Arg Glu Gln Glu Leu Leu Ala
        355                 360                 365

Pro Ala Asp Gly Thr Val Glu Leu Val Arg Ala Leu Pro Leu Ala Leu
        370                 375                 380

Val Leu His Glu Leu Gly Ala Gly Arg Ser Arg Ala Gly Glu Pro Leu
385                 390                 395                 400

Arg Leu Gly Val Gly Ala Glu Leu Leu Val Asp Val Gly Gln Arg Leu
                405                 410                 415

Arg Arg Gly Thr Pro Trp Leu Arg Val His Arg Asp Gly Pro Ala Leu
            420                 425                 430

Ser Gly Pro Gln Ser Arg Ala Leu Gln Glu Ala Leu Val Leu Ser Asp
            435                 440                 445

Arg Ala Pro Phe Ala Ala Pro Ser Pro Phe Ala Glu Leu Val Leu Pro
    450                 455                 460

Pro Gln Gln Glu Pro Lys Ser Cys Asp Lys Thr His Thr Cys Pro Pro
465                 470                 475                 480

Cys Pro Ala Pro Glu Leu Leu Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
        530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
            595                 600                 605

Glu Met Thr Lys Asn Gln Val Ser Leu Thr Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn Arg Tyr
        675                 680                 685

Thr Gln Lys Ser Leu Ser Leu Ser Pro Gly Lys
    690                 695

<210> SEQ ID NO 14
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
```

```
<222> LOCATION: (2)..(2)
<223> OTHER INFORMATION: Xaa is L-2-naphthylalanine

<400> SEQUENCE: 14

Phe Xaa Arg Arg Arg
1               5

<210> SEQ ID NO 15
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is L-2-naphthylalanine

<400> SEQUENCE: 15

Phe Xaa Arg Arg Arg Cys
1               5

<210> SEQ ID NO 16
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is L-2-naphthylalanine
<220> FEATURE:
<221> NAME/KEY: misc_feature
<222> LOCATION: (6)..(6)
<223> OTHER INFORMATION: Xaa is selenocysteine

<400> SEQUENCE: 16

Phe Xaa Arg Arg Arg Xaa
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (4)..(4)
<223> OTHER INFORMATION: Xaa is L-2-naphthylalanine

<400> SEQUENCE: 17

Arg Arg Arg Xaa Phe
1               5

<210> SEQ ID NO 18
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (5)..(5)
<223> OTHER INFORMATION: Xaa is L-2-naphthylalanine

<400> SEQUENCE: 18

Arg Arg Arg Arg Xaa Phe
1               5
```

<210> SEQ ID NO 19
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is L-2-naphthylalanine

<400> SEQUENCE: 19

Phe Xaa Arg Arg Arg Arg
1               5

<210> SEQ ID NO 20
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is D-2-naphthylalanine
<220> FEATURE:
<221> NAME/KEY: misc_feature
<222> LOCATION: (3)..(3)
<223> OTHER INFORMATION: Xaa is D-arginine
<220> FEATURE:
<221> NAME/KEY: misc_feature
<222> LOCATION: (5)..(5)
<223> OTHER INFORMATION: Xaa is D-arginine

<400> SEQUENCE: 20

Phe Xaa Xaa Arg Xaa Arg
1               5

<210> SEQ ID NO 21
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is D-phenylalanine
<220> FEATURE:
<221> NAME/KEY: misc_feature
<222> LOCATION: (2)..(2)
<223> OTHER INFORMATION: Xaa is L-2-naphthylalanine
<220> FEATURE:
<221> NAME/KEY: misc_feature
<222> LOCATION: (4)..(4)
<223> OTHER INFORMATION: Xaa is D-arginine
<220> FEATURE:
<221> NAME/KEY: misc_feature
<222> LOCATION: (6)..(6)
<223> OTHER INFORMATION: Xaa is D-arginine

<400> SEQUENCE: 21

Xaa Xaa Arg Xaa Arg Xaa
1               5

<210> SEQ ID NO 22
<211> LENGTH: 6
<212> TYPE: PRT
<213> ORGANISM: Artificial Sequence
<220> FEATURE:
<223> OTHER INFORMATION: synthetic construct

```
<220> FEATURE:
<221> NAME/KEY: misc_feature
<222> LOCATION: (5)..(5)
<223> OTHER INFORMATION: Xaa is L-2-naphthylalanine

<400> SEQUENCE: 22

Arg Arg Phe Arg Xaa Arg
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa is L-2-naphthylalanine

<400> SEQUENCE: 23

Phe Arg Arg Arg Arg Xaa
1               5

<210> SEQ ID NO 24
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is D-arginine
<220> FEATURE:
<221> NAME/KEY: misc_feature
<222> LOCATION: (5)..(5)
<223> OTHER INFORMATION: Xaa is L-2-naphthylalanine

<400> SEQUENCE: 24

Xaa Arg Phe Arg Xaa Arg
1               5

<210> SEQ ID NO 25
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa is L-2-naphthylalanine

<400> SEQUENCE: 25

Arg Arg Xaa Phe Arg Arg
1               5

<210> SEQ ID NO 26
<211> LENGTH: 7
<212> TYPE: PRT
<213> ORGANISM: Artificial Sequence
<220> FEATURE:
<223> OTHER INFORMATION: synthetic construct

<400> SEQUENCE: 26

Cys Arg Arg Arg Arg Phe Trp
1               5
```

```
<210> SEQ ID NO 27
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is D-phenylalanine
<220> FEATURE:
<221> NAME/KEY: misc_feature
<222> LOCATION: (3)..(3)
<223> OTHER INFORMATION: Xaa is L-2-naphthylalanine
<220> FEATURE:
<221> NAME/KEY: misc_feature
<222> LOCATION: (5)..(5)
<223> OTHER INFORMATION: Xaa is D-arginine
<220> FEATURE:
<221> NAME/KEY: misc_feature
<222> LOCATION: (7)..(7)
<223> OTHER INFORMATION: Xaa is D-arginine

<400> SEQUENCE: 27

Phe Xaa Xaa Arg Xaa Arg Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa is L-2-naphthylalanine

<400> SEQUENCE: 28

Phe Phe Xaa Arg Arg Arg Arg
1               5

<210> SEQ ID NO 29
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa is L-2-naphthylalanine

<400> SEQUENCE: 29

Arg Phe Arg Phe Arg Xaa Arg
1               5

<210> SEQ ID NO 30
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is selenocysteine

<400> SEQUENCE: 30

Xaa Arg Arg Arg Arg Phe Trp
1               5
```

```
<210> SEQ ID NO 31
<211> LENGTH: 7
<212> TYPE: PRT
<213> ORGANISM: Artificial Sequence
<220> FEATURE:
<223> OTHER INFORMATION: synthetic construct

<400> SEQUENCE: 31

Cys Arg Arg Arg Arg Phe Trp
1               5

<210> SEQ ID NO 32
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is L-2-naphthylalanine

<400> SEQUENCE: 32

Phe Xaa Arg Arg Arg Arg Gln Lys
1               5

<210> SEQ ID NO 33
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is L-2-naphthylalanine

<400> SEQUENCE: 33

Phe Xaa Arg Arg Arg Arg Gln Cys
1               5

<210> SEQ ID NO 34
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is D-phenylalanine
<220> FEATURE:
<221> NAME/KEY: misc_feature
<222> LOCATION: (2)..(2)
<223> OTHER INFORMATION: Xaa is L-2-naphthylalanine
<220> FEATURE:
<221> NAME/KEY: misc_feature
<222> LOCATION: (4)..(4)
<223> OTHER INFORMATION: Xaa is D-arginine
<220> FEATURE:
<221> NAME/KEY: misc_feature
<222> LOCATION: (6)..(6)
<223> OTHER INFORMATION: Xaa is D-arginine

<400> SEQUENCE: 34

Xaa Xaa Arg Xaa Arg Xaa Arg Gln
1               5

<210> SEQ ID NO 35
<211> LENGTH: 8
```

-continued

<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is L-2-naphthylalanine

<400> SEQUENCE: 35

Phe Xaa Arg Arg Arg Arg Gln
1               5

<210> SEQ ID NO 36
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (5)..(5)
<223> OTHER INFORMATION: Xaa is L-2-naphthylalanine
<220> FEATURE:
<221> NAME/KEY: misc_feature
<222> LOCATION: (8)..(8)
<223> OTHER INFORMATION: Xaa is L-norleucine

<400> SEQUENCE: 36

Arg Arg Arg Arg Xaa Phe Asp Xaa Cys
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic construct

<400> SEQUENCE: 37

Phe Trp Arg Arg Arg
1               5

<210> SEQ ID NO 38
<211> LENGTH: 5
<212> TYPE: PRT
<213> ORGANISM: Artificial Sequence
<220> FEATURE:
<223> OTHER INFORMATION: synthetic construct

<400> SEQUENCE: 38

Arg Arg Arg Trp Phe
1               5

<210> SEQ ID NO 39
<211> LENGTH: 5
<212> TYPE: PRT
<213> ORGANISM: Artificial Sequence
<220> FEATURE:
<223> OTHER INFORMATION: synthetic construct

<400> SEQUENCE: 39

Phe Phe Arg Arg Arg
1               5

<210> SEQ ID NO 40
<211> LENGTH: 5
<212> TYPE: PRT
<213> ORGANISM: Artificial Sequence

```
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa is D-arginine
<220> FEATURE:
<221> NAME/KEY: misc_feature
<222> LOCATION: (5)..(5)
<223> OTHER INFORMATION: Xaa is D-arginine

<400> SEQUENCE: 40

Phe Phe Xaa Arg Xaa
1               5

<210> SEQ ID NO 41
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (4)..(4)
<223> OTHER INFORMATION: Xaa is D-arginine

<400> SEQUENCE: 41

Phe Phe Arg Xaa Arg
1               5

<210> SEQ ID NO 42
<211> LENGTH: 5
<212> TYPE: PRT
<213> ORGANISM: Artificial Sequence
<220> FEATURE:
<223> OTHER INFORMATION: synthetic construct

<400> SEQUENCE: 42

Phe Arg Phe Arg Arg
1               5

<210> SEQ ID NO 43
<211> LENGTH: 5
<212> TYPE: PRT
<213> ORGANISM: Artificial Sequence
<220> FEATURE:
<223> OTHER INFORMATION: synthetic construct

<400> SEQUENCE: 43

Phe Arg Arg Phe Arg
1               5

<210> SEQ ID NO 44
<211> LENGTH: 5
<212> TYPE: PRT
<213> ORGANISM: Artificial Sequence
<220> FEATURE:
<223> OTHER INFORMATION: synthetic construct

<400> SEQUENCE: 44

Phe Arg Arg Arg Phe
1               5

<210> SEQ ID NO 45
<211> LENGTH: 5
<212> TYPE: PRT
<213> ORGANISM: Artificial Sequence
<220> FEATURE:
<223> OTHER INFORMATION: synthetic construct
```

```
<220> FEATURE:
<221> NAME/KEY: misc_feature
<222> LOCATION: (2)..(2)
<223> OTHER INFORMATION: Xaa is L-2-naphthylalanine

<400> SEQUENCE: 45

Gly Xaa Arg Arg Arg
1               5

<210> SEQ ID NO 46
<211> LENGTH: 5
<212> TYPE: PRT
<213> ORGANISM: Artificial Sequence
<220> FEATURE:
<223> OTHER INFORMATION: synthetic construct

<400> SEQUENCE: 46

Phe Phe Phe Arg Ala
1               5

<210> SEQ ID NO 47
<211> LENGTH: 5
<212> TYPE: PRT
<213> ORGANISM: Artificial Sequence
<220> FEATURE:
<223> OTHER INFORMATION: synthetic construct

<400> SEQUENCE: 47

Phe Phe Phe Arg Arg
1               5

<210> SEQ ID NO 48
<211> LENGTH: 6
<212> TYPE: PRT
<213> ORGANISM: Artificial Sequence
<220> FEATURE:
<223> OTHER INFORMATION: synthetic construct

<400> SEQUENCE: 48

Phe Phe Arg Arg Arg Arg
1               5

<210> SEQ ID NO 49
<211> LENGTH: 6
<212> TYPE: PRT
<213> ORGANISM: Artificial Sequence
<220> FEATURE:
<223> OTHER INFORMATION: synthetic construct

<400> SEQUENCE: 49

Phe Arg Arg Phe Arg Arg
1               5

<210> SEQ ID NO 50
<211> LENGTH: 6
<212> TYPE: PRT
<213> ORGANISM: Artificial Sequence
<220> FEATURE:
<223> OTHER INFORMATION: synthetic construct

<400> SEQUENCE: 50

Phe Arg Arg Arg Phe Arg
1               5

<210> SEQ ID NO 51
<211> LENGTH: 6
<212> TYPE: PRT
```

```
<213> ORGANISM: Artificial Sequence
<220> FEATURE:
<223> OTHER INFORMATION: synthetic construct

<400> SEQUENCE: 51

Arg Phe Phe Arg Arg Arg
1               5

<210> SEQ ID NO 52
<211> LENGTH: 6
<212> TYPE: PRT
<213> ORGANISM: Artificial Sequence
<220> FEATURE:
<223> OTHER INFORMATION: synthetic construct

<400> SEQUENCE: 52

Arg Phe Arg Arg Phe Arg
1               5

<210> SEQ ID NO 53
<211> LENGTH: 6
<212> TYPE: PRT
<213> ORGANISM: Artificial Sequence
<220> FEATURE:
<223> OTHER INFORMATION: synthetic construct

<400> SEQUENCE: 53

Phe Arg Phe Arg Arg Arg
1               5

<210> SEQ ID NO 54
<211> LENGTH: 6
<212> TYPE: PRT
<213> ORGANISM: Artificial Sequence
<220> FEATURE:
<223> OTHER INFORMATION: synthetic construct

<400> SEQUENCE: 54

Phe Phe Phe Arg Arg Arg
1               5

<210> SEQ ID NO 55
<211> LENGTH: 6
<212> TYPE: PRT
<213> ORGANISM: Artificial Sequence
<220> FEATURE:
<223> OTHER INFORMATION: synthetic construct

<400> SEQUENCE: 55

Phe Phe Arg Arg Arg Phe
1               5

<210> SEQ ID NO 56
<211> LENGTH: 6
<212> TYPE: PRT
<213> ORGANISM: Artificial Sequence
<220> FEATURE:
<223> OTHER INFORMATION: synthetic construct

<400> SEQUENCE: 56

Phe Arg Phe Phe Arg Arg
1               5

<210> SEQ ID NO 57
<211> LENGTH: 6
<212> TYPE: PRT
<213> ORGANISM: Artificial Sequence
```

```
<220> FEATURE:
<223> OTHER INFORMATION: synthetic construct

<400> SEQUENCE: 57

Arg Arg Phe Phe Phe Arg
1               5

<210> SEQ ID NO 58
<211> LENGTH: 6
<212> TYPE: PRT
<213> ORGANISM: Artificial Sequence
<220> FEATURE:
<223> OTHER INFORMATION: synthetic construct

<400> SEQUENCE: 58

Phe Phe Arg Phe Arg Arg
1               5

<210> SEQ ID NO 59
<211> LENGTH: 6
<212> TYPE: PRT
<213> ORGANISM: Artificial Sequence
<220> FEATURE:
<223> OTHER INFORMATION: synthetic construct

<400> SEQUENCE: 59

Phe Phe Arg Arg Phe Arg
1               5

<210> SEQ ID NO 60
<211> LENGTH: 6
<212> TYPE: PRT
<213> ORGANISM: Artificial Sequence
<220> FEATURE:
<223> OTHER INFORMATION: synthetic construct

<400> SEQUENCE: 60

Phe Arg Arg Phe Phe Arg
1               5

<210> SEQ ID NO 61
<211> LENGTH: 6
<212> TYPE: PRT
<213> ORGANISM: Artificial Sequence
<220> FEATURE:
<223> OTHER INFORMATION: synthetic construct

<400> SEQUENCE: 61

Phe Arg Arg Phe Arg Phe
1               5

<210> SEQ ID NO 62
<211> LENGTH: 6
<212> TYPE: PRT
<213> ORGANISM: Artificial Sequence
<220> FEATURE:
<223> OTHER INFORMATION: synthetic construct

<400> SEQUENCE: 62

Phe Arg Phe Arg Phe Arg
1               5

<210> SEQ ID NO 63
<211> LENGTH: 6
<212> TYPE: PRT
<213> ORGANISM: Artificial Sequence
<220> FEATURE:
```

<223> OTHER INFORMATION: synthetic construct

<400> SEQUENCE: 63

Arg Phe Phe Arg Phe Arg
1               5

<210> SEQ ID NO 64
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is L-2-naphthylalanine

<400> SEQUENCE: 64

Gly Xaa Arg Arg Arg Arg
1               5

<210> SEQ ID NO 65
<211> LENGTH: 7
<212> TYPE: PRT
<213> ORGANISM: Artificial Sequence
<220> FEATURE:
<223> OTHER INFORMATION: synthetic construct

<400> SEQUENCE: 65

Phe Phe Phe Arg Arg Arg Arg
1               5

<210> SEQ ID NO 66
<211> LENGTH: 7
<212> TYPE: PRT
<213> ORGANISM: Artificial Sequence
<220> FEATURE:
<223> OTHER INFORMATION: synthetic construct

<400> SEQUENCE: 66

Arg Phe Phe Arg Arg Arg Arg
1               5

<210> SEQ ID NO 67
<211> LENGTH: 7
<212> TYPE: PRT
<213> ORGANISM: Artificial Sequence
<220> FEATURE:
<223> OTHER INFORMATION: synthetic construct

<400> SEQUENCE: 67

Arg Arg Phe Phe Arg Arg Arg
1               5

<210> SEQ ID NO 68
<211> LENGTH: 7
<212> TYPE: PRT
<213> ORGANISM: Artificial Sequence
<220> FEATURE:
<223> OTHER INFORMATION: synthetic construct

<400> SEQUENCE: 68

Arg Phe Phe Phe Arg Arg Arg
1               5

<210> SEQ ID NO 69
<211> LENGTH: 7

```
<212> TYPE: PRT
<213> ORGANISM: Artificial Sequence
<220> FEATURE:
<223> OTHER INFORMATION: synthetic construct

<400> SEQUENCE: 69

Arg Arg Phe Phe Phe Arg Arg
1               5

<210> SEQ ID NO 70
<211> LENGTH: 7
<212> TYPE: PRT
<213> ORGANISM: Artificial Sequence
<220> FEATURE:
<223> OTHER INFORMATION: synthetic construct

<400> SEQUENCE: 70

Phe Phe Arg Arg Phe Arg Arg
1               5

<210> SEQ ID NO 71
<211> LENGTH: 7
<212> TYPE: PRT
<213> ORGANISM: Artificial Sequence
<220> FEATURE:
<223> OTHER INFORMATION: synthetic construct

<400> SEQUENCE: 71

Phe Phe Arg Arg Arg Arg Phe
1               5

<210> SEQ ID NO 72
<211> LENGTH: 7
<212> TYPE: PRT
<213> ORGANISM: Artificial Sequence
<220> FEATURE:
<223> OTHER INFORMATION: synthetic construct

<400> SEQUENCE: 72

Phe Arg Arg Phe Phe Arg Arg
1               5

<210> SEQ ID NO 73
<211> LENGTH: 8
<212> TYPE: PRT
<213> ORGANISM: Artificial Sequence
<220> FEATURE:
<223> OTHER INFORMATION: synthetic construct

<400> SEQUENCE: 73

Phe Phe Phe Arg Arg Arg Arg
1               5

<210> SEQ ID NO 74
<211> LENGTH: 9
<212> TYPE: PRT
<213> ORGANISM: Artificial Sequence
<220> FEATURE:
<223> OTHER INFORMATION: synthetic construct

<400> SEQUENCE: 74

Phe Phe Phe Arg Arg Arg Arg Arg Arg
1               5

<210> SEQ ID NO 75
<211> LENGTH: 6
<212> TYPE: PRT
```

```
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is L-2-naphthylalanine
<220> FEATURE:
<221> NAME/KEY: misc_feature
<222> LOCATION: (4)..(4)
<223> OTHER INFORMATION: Xaa is D-arginine
<220> FEATURE:
<221> NAME/KEY: misc_feature
<222> LOCATION: (6)..(6)
<223> OTHER INFORMATION: Xaa is D-arginine

<400> SEQUENCE: 75

Phe Xaa Arg Xaa Arg Xaa
1               5

<210> SEQ ID NO 76
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(2)
<223> OTHER INFORMATION: Xaa can be any naturally occurring amino acid

<400> SEQUENCE: 76

Xaa Xaa Arg Arg Arg Arg
1               5

<210> SEQ ID NO 77
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is D-phenylalanine
<220> FEATURE:
<221> NAME/KEY: misc_feature
<222> LOCATION: (5)..(5)
<223> OTHER INFORMATION: Xaa is D-arginine

<400> SEQUENCE: 77

Phe Xaa Phe Arg Xaa Arg
1               5

<210> SEQ ID NO 78
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is D-phenylalanine
<220> FEATURE:
<221> NAME/KEY: misc_feature
<222> LOCATION: (3)..(3)
<223> OTHER INFORMATION: Xaa is D-phenylalanine
<220> FEATURE:
<221> NAME/KEY: misc_feature
<222> LOCATION: (4)..(4)
<223> OTHER INFORMATION: Xaa is D-arginine
<220> FEATURE:
```

```
<221> NAME/KEY: misc_feature
<222> LOCATION: (6)..(6)
<223> OTHER INFORMATION: Xaa is D-arginine

<400> SEQUENCE: 78

Xaa Phe Xaa Xaa Arg Xaa
1               5

<210> SEQ ID NO 79
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is D-phenylalanine
<220> FEATURE:
<221> NAME/KEY: misc_feature
<222> LOCATION: (3)..(3)
<223> OTHER INFORMATION: Xaa is D-phenylalanine
<220> FEATURE:
<221> NAME/KEY: misc_feature
<222> LOCATION: (5)..(5)
<223> OTHER INFORMATION: Xaa is D-arginine

<400> SEQUENCE: 79

Xaa Phe Xaa Arg Xaa Arg
1               5

<210> SEQ ID NO 80
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is D-phenylalanine
<220> FEATURE:
<221> NAME/KEY: misc_feature
<222> LOCATION: (4)..(4)
<223> OTHER INFORMATION: Xaa is D-arginine
<220> FEATURE:
<221> NAME/KEY: misc_feature
<222> LOCATION: (6)..(6)
<223> OTHER INFORMATION: Xaa is D-arginine

<400> SEQUENCE: 80

Phe Xaa Phe Xaa Arg Xaa
1               5

<210> SEQ ID NO 81
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is D-phenylalanine
<220> FEATURE:
<221> NAME/KEY: misc_feature
<222> LOCATION: (3)..(3)
<223> OTHER INFORMATION: Xaa is L-2-naphthylalanine
<220> FEATURE:
<221> NAME/KEY: misc_feature
<222> LOCATION: (4)..(4)
<223> OTHER INFORMATION: Xaa is D-arginine
<220> FEATURE:
```

<221> NAME/KEY: misc_feature
<222> LOCATION: (6)..(6)
<223> OTHER INFORMATION: Xaa is D-arginine

<400> SEQUENCE: 81

Xaa Phe Xaa Xaa Arg Xaa
1               5

<210> SEQ ID NO 82
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is D-phenylalanine
<220> FEATURE:
<221> NAME/KEY: misc_feature
<222> LOCATION: (2)..(2)
<223> OTHER INFORMATION: Xaa is L-2-naphthylalanine
<220> FEATURE:
<221> NAME/KEY: misc_feature
<222> LOCATION: (3)..(3)
<223> OTHER INFORMATION: Xaa is D-phenylalanine
<220> FEATURE:
<221> NAME/KEY: misc_feature
<222> LOCATION: (4)..(4)
<223> OTHER INFORMATION: Xaa is D-arginine
<220> FEATURE:
<221> NAME/KEY: misc_feature
<222> LOCATION: (6)..(6)
<223> OTHER INFORMATION: Xaa is D-arginine

<400> SEQUENCE: 82

Xaa Xaa Xaa Xaa Arg Xaa
1               5

<210> SEQ ID NO 83
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-2-naphthylalanine
<220> FEATURE:
<221> NAME/KEY: misc_feature
<222> LOCATION: (3)..(3)
<223> OTHER INFORMATION: Xaa is D-phenylalanine
<220> FEATURE:
<221> NAME/KEY: misc_feature
<222> LOCATION: (4)..(4)
<223> OTHER INFORMATION: Xaa is D-arginine
<220> FEATURE:
<221> NAME/KEY: misc_feature
<222> LOCATION: (6)..(6)
<223> OTHER INFORMATION: Xaa is D-arginine

<400> SEQUENCE: 83

Xaa Phe Xaa Xaa Arg Xaa
1               5

<210> SEQ ID NO 84
<211> LENGTH: 5
<212> TYPE: PRT
<213> ORGANISM: Artificial Sequence
<220> FEATURE:
<223> OTHER INFORMATION: synthetic construct
<220> FEATURE:

```
<221> NAME/KEY: misc_feature
<222> LOCATION: (2)..(2)
<223> OTHER INFORMATION: Xaa is L-2-naphthylalanine
<220> FEATURE:
<221> NAME/KEY: misc_feature
<222> LOCATION: (3)..(3)
<223> OTHER INFORMATION: Xaa is D-arginine
<220> FEATURE:
<221> NAME/KEY: misc_feature
<222> LOCATION: (5)..(5)
<223> OTHER INFORMATION: Xaa is D-arginine

<400> SEQUENCE: 84

Phe Xaa Xaa Arg Xaa
1               5

<210> SEQ ID NO 85
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is D-phenylalanine
<220> FEATURE:
<221> NAME/KEY: misc_feature
<222> LOCATION: (2)..(2)
<223> OTHER INFORMATION: Xaa is L-2-naphthylalanine
<220> FEATURE:
<221> NAME/KEY: misc_feature
<222> LOCATION: (3)..(3)
<223> OTHER INFORMATION: Xaa is D-arginine
<220> FEATURE:
<221> NAME/KEY: misc_feature
<222> LOCATION: (5)..(5)
<223> OTHER INFORMATION: Xaa is D-arginine

<400> SEQUENCE: 85

Xaa Xaa Xaa Arg Xaa
1               5

<210> SEQ ID NO 86
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (2)..(2)
<223> OTHER INFORMATION: Xaa is D-phenylalanine
<220> FEATURE:
<221> NAME/KEY: misc_feature
<222> LOCATION: (5)..(5)
<223> OTHER INFORMATION: Xaa is D-arginine
<220> FEATURE:
<221> NAME/KEY: misc_feature
<222> LOCATION: (7)..(7)
<223> OTHER INFORMATION: Xaa is D-arginine

<400> SEQUENCE: 86

Lys Xaa Phe Arg Xaa Arg Xaa Asp
1               5

<210> SEQ ID NO 87
<211> LENGTH: 8
<212> TYPE: PRT
```

```
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (1)..(1)
<223> OTHER INFORMATION: Xaa is L-2,3-diaminopropionic acid
<220> FEATURE:
<221> NAME/KEY: misc_feature
<222> LOCATION: (2)..(2)
<223> OTHER INFORMATION: Xaa is D-phenylalanine
<220> FEATURE:
<221> NAME/KEY: misc_feature
<222> LOCATION: (5)..(5)
<223> OTHER INFORMATION: Xaa is D-arginine
<220> FEATURE:
<221> NAME/KEY: misc_feature
<222> LOCATION: (7)..(7)
<223> OTHER INFORMATION: Xaa is D-arginine

<400> SEQUENCE: 87

Xaa Xaa Phe Arg Xaa Arg Xaa Asp
1               5

<210> SEQ ID NO 88
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 88

Cys Trp Trp Arg Arg Arg Arg Cys
1               5

<210> SEQ ID NO 89
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(9)
<223> OTHER INFORMATION: Cys residues jopined by disulfide bond

<400> SEQUENCE: 89

Cys Trp Trp Val Arg Arg Arg Arg Cys
1               5

<210> SEQ ID NO 90
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 90

Cys Phe Trp Arg Arg Arg Arg Cys
1               5
```

-continued

```
<210> SEQ ID NO 91
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 91

Cys Trp Trp Trp Arg Arg Arg Cys
1               5

<210> SEQ ID NO 92
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-homeoproline
<220> FEATURE:
<221> NAME/KEY: misc_feature
<222> LOCATION: (2)..(2)
<223> OTHER INFORMATION: Xaa is L-napthylalanine
<220> FEATURE:
<221> NAME/KEY: misc_feature
<222> LOCATION: (5)..(6)
<223> OTHER INFORMATION: Xaa is D-arginine
<220> FEATURE:
<221> NAME/KEY: misc_feature
<222> LOCATION: (7)..(7)
<223> OTHER INFORMATION: Xaa is D-glutamate

<400> SEQUENCE: 92

Xaa Xaa Arg Glu Xaa Xaa Xaa
1               5

<210> SEQ ID NO 93
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-homeoproline
<220> FEATURE:
<221> NAME/KEY: misc_feature
<222> LOCATION: (2)..(2)
<223> OTHER INFORMATION: Xaa is L-napthylalanine
<220> FEATURE:
<221> NAME/KEY: misc_feature
<222> LOCATION: (5)..(6)
<223> OTHER INFORMATION: Xaa is D-arginine
<220> FEATURE:
<221> NAME/KEY: misc_feature
<222> LOCATION: (7)..(7)
<223> OTHER INFORMATION: Xaa is D-glutamate

<400> SEQUENCE: 93

Xaa Xaa Arg Arg Xaa Xaa Xaa
1               5

<210> SEQ ID NO 94
<211> LENGTH: 7
```

```
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-homeoproline
<220> FEATURE:
<221> NAME/KEY: misc_feature
<222> LOCATION: (2)..(3)
<223> OTHER INFORMATION: Xaa is L-napthylalanine
<220> FEATURE:
<221> NAME/KEY: misc_feature
<222> LOCATION: (5)..(6)
<223> OTHER INFORMATION: Xaa is D-arginine
<220> FEATURE:
<221> NAME/KEY: misc_feature
<222> LOCATION: (7)..(7)
<223> OTHER INFORMATION: Xaa is D-glutamate

<400> SEQUENCE: 94

Xaa Xaa Xaa Arg Xaa Xaa Xaa
1               5

<210> SEQ ID NO 95
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-homeoproline
<220> FEATURE:
<221> NAME/KEY: misc_feature
<222> LOCATION: (2)..(3)
<223> OTHER INFORMATION: Xaa is L-napthylalanine
<220> FEATURE:
<221> NAME/KEY: misc_feature
<222> LOCATION: (5)..(6)
<223> OTHER INFORMATION: Xaa is D-arginine

<400> SEQUENCE: 95

Xaa Xaa Xaa Arg Xaa Xaa Glu
1               5

<210> SEQ ID NO 96
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-homeoproline
<220> FEATURE:
<221> NAME/KEY: misc_feature
<222> LOCATION: (2)..(2)
<223> OTHER INFORMATION: Xaa is L-napthylalanine
<220> FEATURE:
<221> NAME/KEY: misc_feature
<222> LOCATION: (5)..(6)
<223> OTHER INFORMATION: Xaa is D-arginine
<220> FEATURE:
<221> NAME/KEY: misc_feature
<222> LOCATION: (7)..(7)
<223> OTHER INFORMATION: Xaa is D-glutamate

<400> SEQUENCE: 96

Xaa Xaa Phe Arg Xaa Xaa Xaa
1               5
```

```
<210> SEQ ID NO 97
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-homeoproline
<220> FEATURE:
<221> NAME/KEY: misc_feature
<222> LOCATION: (2)..(2)
<223> OTHER INFORMATION: Xaa is L-napthylalanine
<220> FEATURE:
<221> NAME/KEY: misc_feature
<222> LOCATION: (5)..(6)
<223> OTHER INFORMATION: Xaa is D-arginine

<400> SEQUENCE: 97

Xaa Xaa Phe Arg Xaa Xaa Glu
1               5

<210> SEQ ID NO 98
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-homeoproline
<220> FEATURE:
<221> NAME/KEY: misc_feature
<222> LOCATION: (2)..(2)
<223> OTHER INFORMATION: Xaa is L-napthylalanine
<220> FEATURE:
<221> NAME/KEY: misc_feature
<222> LOCATION: (3)..(3)
<223> OTHER INFORMATION: Xaa is D-phenylalanine
<220> FEATURE:
<221> NAME/KEY: misc_feature
<222> LOCATION: (5)..(6)
<223> OTHER INFORMATION: Xaa is D-arginine
<220> FEATURE:
<221> NAME/KEY: misc_feature
<222> LOCATION: (7)..(7)
<223> OTHER INFORMATION: Xaa is D-glutamate

<400> SEQUENCE: 98

Xaa Xaa Xaa Arg Xaa Xaa Xaa
1               5

<210> SEQ ID NO 99
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-homeoproline
<220> FEATURE:
<221> NAME/KEY: misc_feature
<222> LOCATION: (2)..(2)
<223> OTHER INFORMATION: Xaa is L-napthylalanine
<220> FEATURE:
<221> NAME/KEY: misc_feature
<222> LOCATION: (3)..(3)
<223> OTHER INFORMATION: Xaa is D-phenylalanine
<220> FEATURE:
```

```
<221> NAME/KEY: misc_feature
<222> LOCATION: (5)..(6)
<223> OTHER INFORMATION: Xaa is D-arginine

<400> SEQUENCE: 99

Xaa Xaa Xaa Arg Xaa Xaa Glu
1               5

<210> SEQ ID NO 100
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-homeoproline
<220> FEATURE:
<221> NAME/KEY: misc_feature
<222> LOCATION: (2)..(2)
<223> OTHER INFORMATION: Xaa is L-napthylalanine
<220> FEATURE:
<221> NAME/KEY: misc_feature
<222> LOCATION: (3)..(3)
<223> OTHER INFORMATION: Xaa is D-napthylalanine
<220> FEATURE:
<221> NAME/KEY: misc_feature
<222> LOCATION: (5)..(6)
<223> OTHER INFORMATION: Xaa is D-arginine

<400> SEQUENCE: 100

Xaa Xaa Xaa Arg Xaa Xaa Glu
1               5

<210> SEQ ID NO 101
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is L-homeoproline
<220> FEATURE:
<221> NAME/KEY: misc_feature
<222> LOCATION: (2)..(2)
<223> OTHER INFORMATION: Xaa is L-napthylalanine
<220> FEATURE:
<221> NAME/KEY: misc_feature
<222> LOCATION: (3)..(3)
<223> OTHER INFORMATION: Xaa is D-napthylalanine
<220> FEATURE:
<221> NAME/KEY: misc_feature
<222> LOCATION: (5)..(6)
<223> OTHER INFORMATION: Xaa is D-arginine
<220> FEATURE:
<221> NAME/KEY: misc_feature
<222> LOCATION: (7)..(7)
<223> OTHER INFORMATION: Xaa is D-glutamate

<400> SEQUENCE: 101

Xaa Xaa Xaa Arg Xaa Xaa Xaa
1               5

<210> SEQ ID NO 102
<211> LENGTH: 8
<212> TYPE: PRT
<213> ORGANISM: Artificial Sequence
<220> FEATURE:
<223> OTHER INFORMATION: synthetic construct
<220> FEATURE:
```

```
<221> NAME/KEY: misc_feature
<222> LOCATION: (1)..(1)
<223> OTHER INFORMATION: Arg is modified with pimelic acid
<220> FEATURE:
<221> NAME/KEY: misc_feature
<222> LOCATION: (1)..(4)
<223> OTHER INFORMATION: Cyclization between Arg is modified with
      pimelic acid and Arg is modified with lysine peptoid residue
<220> FEATURE:
<221> NAME/KEY: misc_feature
<222> LOCATION: (4)..(4)
<223> OTHER INFORMATION: Arg is modified with lysine peptoid residue

<400> SEQUENCE: 102

Arg Gln Arg Arg Gly Arg Arg Arg
1               5

<210> SEQ ID NO 103
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (2)..(19)
<223> OTHER INFORMATION: Cys residues jopined by disulfide bond

<400> SEQUENCE: 103

Lys Cys Phe Gln Trp Gln Arg Asn Met Arg Lys Val Arg Gly Pro Pro
1               5                   10                  15

Val Ser Cys

<210> SEQ ID NO 104
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(11)
<223> OTHER INFORMATION: Cyclization between Lys and Glu
<220> FEATURE:
<221> NAME/KEY: misc_feature
<222> LOCATION: (2)..(2)
<223> OTHER INFORMATION: Xaa is D-arginine
<220> FEATURE:
<221> NAME/KEY: misc_feature
<222> LOCATION: (4)..(4)
<223> OTHER INFORMATION: Xaa is D-arginine
<220> FEATURE:
<221> NAME/KEY: misc_feature
<222> LOCATION: (6)..(6)
<223> OTHER INFORMATION: Xaa is D-arginine
<220> FEATURE:
<221> NAME/KEY: misc_feature
<222> LOCATION: (8)..(8)
<223> OTHER INFORMATION: Xaa is D-lysine
<220> FEATURE:
<221> NAME/KEY: misc_feature
<222> LOCATION: (10)..(10)
<223> OTHER INFORMATION: Xaa is D-arginine

<400> SEQUENCE: 104

Lys Xaa Arg Xaa Gly Xaa Lys Xaa Arg Xaa Glu
1               5                   10

<210> SEQ ID NO 105
<211> LENGTH: 12
<212> TYPE: PRT
<213> ORGANISM: Artificial Sequence
```

```
<220> FEATURE:
<223> OTHER INFORMATION: synthetic construct
<220> FEATURE:
<221> NAME/KEY: misc_feature
<222> LOCATION: (1)..(12)
<223> OTHER INFORMATION: Cyclization between Lys and Glu
<220> FEATURE:
<221> NAME/KEY: misc_feature
<222> LOCATION: (2)..(2)
<223> OTHER INFORMATION: Xaa is D-arginine
<220> FEATURE:
<221> NAME/KEY: misc_feature
<222> LOCATION: (4)..(4)
<223> OTHER INFORMATION: Xaa is D-arginine
<220> FEATURE:
<221> NAME/KEY: misc_feature
<222> LOCATION: (6)..(6)
<223> OTHER INFORMATION: Xaa is D-arginine
<220> FEATURE:
<221> NAME/KEY: misc_feature
<222> LOCATION: (8)..(8)
<223> OTHER INFORMATION: Xaa is D-arginine
<220> FEATURE:
<221> NAME/KEY: misc_feature
<222> LOCATION: (10)..(10)
<223> OTHER INFORMATION: Xaa is D-arginine

<400> SEQUENCE: 105

Lys Xaa Arg Xaa Arg Xaa Arg Xaa Arg Xaa Arg Glu
1               5                   10

<210> SEQ ID NO 106
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (13)..(13)
<223> OTHER INFORMATION: Xaa is D-proline

<400> SEQUENCE: 106

Arg Val Arg Thr Arg Gly Lys Arg Arg Ile Arg Arg Xaa Pro
1               5                   10

<210> SEQ ID NO 107
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (13)..(13)
<223> OTHER INFORMATION: Xaa is D-proline

<400> SEQUENCE: 107

Arg Thr Arg Thr Arg Gly Lys Arg Arg Ile Arg Val Xaa Pro
1               5                   10

<210> SEQ ID NO 108
<211> LENGTH: 8
<212> TYPE: PRT
<213> ORGANISM: Artificial Sequence
<220> FEATURE:
<223> OTHER INFORMATION: synthetic construct

<400> SEQUENCE: 108

Trp Arg Trp Arg Trp Arg Trp Arg
1               5
```

```
<210> SEQ ID NO 109
<211> LENGTH: 34
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (4)..(21)
<223> OTHER INFORMATION: Cys residues jopined by disulfide bond
<220> FEATURE:
<221> NAME/KEY: DISULFID
<222> LOCATION: (11)..(23)
<223> OTHER INFORMATION: Cys residues jopined by disulfide bond
<220> FEATURE:
<221> NAME/KEY: DISULFID
<222> LOCATION: (17)..(29)
<223> OTHER INFORMATION: Cys residues jopined by disulfide bond

<400> SEQUENCE: 109

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 110
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(10)
<223> OTHER INFORMATION: Macrocyclization by multicomponent reaction
      with aziridine aldehyde and isocyanide
<220> FEATURE:
<221> NAME/KEY: misc_feature
<222> LOCATION: (2)..(2)
<223> OTHER INFORMATION: Xaa is L-3-cyclohexyl-alanine
<220> FEATURE:
<221> NAME/KEY: misc_feature
<222> LOCATION: (3)..(3)
<223> OTHER INFORMATION: Xaa is D-arginine
<220> FEATURE:
<221> NAME/KEY: misc_feature
<222> LOCATION: (4)..(4)
<223> OTHER INFORMATION: Xaa is L-3-cyclohexyl-alanine
<220> FEATURE:
<221> NAME/KEY: misc_feature
<222> LOCATION: (5)..(5)
<223> OTHER INFORMATION: Xaa is D-arginine
<220> FEATURE:
<221> NAME/KEY: misc_feature
<222> LOCATION: (6)..(6)
<223> OTHER INFORMATION: Xaa is L-3-cyclohexyl-alanine
<220> FEATURE:
<221> NAME/KEY: misc_feature
<222> LOCATION: (7)..(7)
<223> OTHER INFORMATION: Xaa is D-arginine
<220> FEATURE:
<221> NAME/KEY: misc_feature
<222> LOCATION: (8)..(8)
<223> OTHER INFORMATION: Xaa is L-3-cyclohexyl-alanine
<220> FEATURE:
<221> NAME/KEY: misc_feature
<222> LOCATION: (9)..(9)
<223> OTHER INFORMATION: Xaa is D-arginine

<400> SEQUENCE: 110

Pro Xaa Xaa Xaa Xaa Xaa Xaa Xaa Xaa Gly
1               5                   10
```

```
<210> SEQ ID NO 111
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Ser is modified with trimesic acid
<220> FEATURE:
<221> NAME/KEY: misc_feature
<222> LOCATION: (1)..(13)
<223> OTHER INFORMATION: N-terminal amine and side chains of two
     L-2,3-diaminopropionic acid residues bicyclized with trimesic acid
<220> FEATURE:
<221> NAME/KEY: misc_feature
<222> LOCATION: (2)..(2)
<223> OTHER INFORMATION: Xaa is D-valine
<220> FEATURE:
<221> NAME/KEY: misc_feature
<222> LOCATION: (4)..(4)
<223> OTHER INFORMATION: Xaa is L-difluorophosphonomethyl phenylalanine
<220> FEATURE:
<221> NAME/KEY: misc_feature
<222> LOCATION: (6)..(6)
<223> OTHER INFORMATION: Xaa is L-2,3-diaminopropionic acid
<220> FEATURE:
<221> NAME/KEY: misc_feature
<222> LOCATION: (8)..(8)
<223> OTHER INFORMATION: Xaa is L-2-naphthylalanine
<220> FEATURE:
<221> NAME/KEY: misc_feature
<222> LOCATION: (13)..(13)
<223> OTHER INFORMATION: Xaa is L-2,3-diaminopropionic acid

<400> SEQUENCE: 111

Ser Xaa Pro Xaa His Xaa Phe Xaa Arg Arg Arg Arg Xaa
1               5                   10

<210> SEQ ID NO 112
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: D-alanine is modified with trimesic acid
<220> FEATURE:
<221> NAME/KEY: misc_feature
<222> LOCATION: (1)..(1)
<223> OTHER INFORMATION: Xaa is D-alanine
<220> FEATURE:
<221> NAME/KEY: misc_feature
<222> LOCATION: (1)..(16)
<223> OTHER INFORMATION: N-terminal amine and side chains of two
     L-2,3-diaminopropionic acid residues bicyclized with trimesic acid
<220> FEATURE:
<221> NAME/KEY: misc_feature
<222> LOCATION: (2)..(2)
<223> OTHER INFORMATION: Xaa is sarcosine
<220> FEATURE:
<221> NAME/KEY: misc_feature
<222> LOCATION: (3)..(3)
<223> OTHER INFORMATION: Xaa is D-phosphothreonine
<220> FEATURE:
<221> NAME/KEY: misc_feature
<222> LOCATION: (4)..(4)
<223> OTHER INFORMATION: Xaa is L-piperidine-2-carboxylic acid
<220> FEATURE:
<221> NAME/KEY: misc_feature
<222> LOCATION: (5)..(5)
<223> OTHER INFORMATION: Xaa is L-2-naphthylalanine
```

```
<220> FEATURE:
<221> NAME/KEY: misc_feature
<222> LOCATION: (8)..(8)
<223> OTHER INFORMATION: Xaa is D-alanine
<220> FEATURE:
<221> NAME/KEY: misc_feature
<222> LOCATION: (9)..(9)
<223> OTHER INFORMATION: Xaa is L-2,3-diaminopropionic acid
<220> FEATURE:
<221> NAME/KEY: misc_feature
<222> LOCATION: (11)..(11)
<223> OTHER INFORMATION: Xaa is L-2-naphthylalanine
<220> FEATURE:
<221> NAME/KEY: misc_feature
<222> LOCATION: (16)..(16)
<223> OTHER INFORMATION: Xaa is L-2,3-diaminopropionic acid

<400> SEQUENCE: 112

Xaa Xaa Xaa Xaa Xaa Arg Ala Xaa Xaa Phe Xaa Arg Arg Arg Arg Xaa
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(15)
<223> OTHER INFORMATION: Three Cys side chains bicyclized with
      tris(bromomethyl)benzene

<400> SEQUENCE: 113

Cys Arg Arg Ser Arg Arg Gly Cys Gly Arg Arg Ser Arg Arg Cys Gly
1               5                   10                  15

<210> SEQ ID NO 114
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(2)
<223> OTHER INFORMATION: linked by dodecanoyl moiety

<400> SEQUENCE: 114

Lys Arg Arg Arg Arg
1               5

<210> SEQ ID NO 115
<211> LENGTH: 16
<212> TYPE: PRT
<213> ORGANISM: Artificial Sequence
<220> FEATURE:
<223> OTHER INFORMATION: synthetic construct

<400> SEQUENCE: 115

Leu Lys Lys Leu Cys Lys Leu Leu Lys Leu Cys Lys Leu Ala Gly
1               5                   10                  15

<210> SEQ ID NO 116
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
```

```
<222> LOCATION: (5)..(9)
<223> OTHER INFORMATION: Cyclization between Lys and Glu

<400> SEQUENCE: 116

Arg Arg Arg Arg Lys Arg Arg Arg Glu
1               5

<210> SEQ ID NO 117
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (4)..(9)
<223> OTHER INFORMATION: Cyclization between Lys and Glu

<400> SEQUENCE: 117

Arg Arg Arg Lys Arg Arg Arg Arg Glu
1               5

<210> SEQ ID NO 118
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(9)
<223> OTHER INFORMATION: Cyclization between Lys and Glu

<400> SEQUENCE: 118

Arg Arg Lys Arg Arg Arg Arg Arg Glu
1               5

<210> SEQ ID NO 119
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(9)
<223> OTHER INFORMATION: Cyclization between Lys and Glu

<400> SEQUENCE: 119

Arg Lys Arg Arg Arg Arg Arg Arg Glu
1               5

<210> SEQ ID NO 120
<211> LENGTH: 8
<212> TYPE: PRT
<213> ORGANISM: Artificial Sequence
<220> FEATURE:
<223> OTHER INFORMATION: synthetic construct

<400> SEQUENCE: 120

Cys Arg Cys Arg Cys Arg Cys Arg
1               5

<210> SEQ ID NO 121
<211> LENGTH: 12
<212> TYPE: PRT
<213> ORGANISM: Artificial Sequence
<220> FEATURE:
<223> OTHER INFORMATION: synthetic construct
```

```
<220> FEATURE:
<221> NAME/KEY: misc_feature
<222> LOCATION: (1)..(1)
<223> OTHER INFORMATION: Xaa is L-propargylglycine
<220> FEATURE:
<221> NAME/KEY: misc_feature
<222> LOCATION: (1)..(12)
<223> OTHER INFORMATION: Cyclization by the click reaction between
      L-propargylglycine and L-6-Azido-2-amino-hexanoic
<220> FEATURE:
<221> NAME/KEY: misc_feature
<222> LOCATION: (12)..(12)
<223> OTHER INFORMATION: Xaa is L-6-Azido-2-amino-hexanoic

<400> SEQUENCE: 121

Xaa Leu Arg Lys Arg Leu Arg Lys Phe Arg Asn Xaa
1               5                   10

<210> SEQ ID NO 122
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(4)
<223> OTHER INFORMATION: Xaa is L-2,3-diaminopropionic acid
<220> FEATURE:
<221> NAME/KEY: misc_feature
<222> LOCATION: (5)..(5)
<223> OTHER INFORMATION: Xaa is D-phenylalanine
<220> FEATURE:
<221> NAME/KEY: misc_feature
<222> LOCATION: (7)..(8)
<223> OTHER INFORMATION: Xaa is L-2,3-diaminopropionic acid

<400> SEQUENCE: 122

Thr Xaa Xaa Xaa Xaa Leu Xaa Xaa Thr
1               5

<210> SEQ ID NO 123
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is L-2-amino-3-guanidinylpropionic acid
<220> FEATURE:
<221> NAME/KEY: misc_feature
<222> LOCATION: (3)..(3)
<223> OTHER INFORMATION: Xaa is L-2,3-diaminopropionic acid
<220> FEATURE:
<221> NAME/KEY: misc_feature
<222> LOCATION: (4)..(4)
<223> OTHER INFORMATION: Xaa is L-2-amino-3-guanidinylpropionic acid
<220> FEATURE:
<221> NAME/KEY: misc_feature
<222> LOCATION: (5)..(5)
<223> OTHER INFORMATION: Xaa is D-phenylalanine
<220> FEATURE:
<221> NAME/KEY: misc_feature
<222> LOCATION: (7)..(8)
<223> OTHER INFORMATION: Xaa is L-2-amino-3-guanidinylpropionic acid

<400> SEQUENCE: 123

Thr Xaa Xaa Xaa Xaa Leu Xaa Xaa Thr
1               5

<210> SEQ ID NO 124
```

```
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa is D-phenylalanine
<220> FEATURE:
<221> NAME/KEY: misc_feature
<222> LOCATION: (2)..(2)
<223> OTHER INFORMATION: Xaa is L-2-naphthylalanine
<220> FEATURE:
<221> NAME/KEY: misc_feature
<222> LOCATION: (4)..(4)
<223> OTHER INFORMATION: Xaa is D-arginine
<220> FEATURE:
<221> NAME/KEY: misc_feature
<222> LOCATION: (6)..(6)
<223> OTHER INFORMATION: Xaa is D-arginine

<400> SEQUENCE: 124

Xaa Xaa Arg Xaa Arg Xaa Arg
1               5

<210> SEQ ID NO 125
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa is L-2-naphthylalanine

<400> SEQUENCE: 125

Phe Xaa Arg Arg Arg Arg Arg
1               5

<210> SEQ ID NO 126
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (5)..(5)
<223> OTHER INFORMATION: Xaa is L-2-naphthylalanine

<400> SEQUENCE: 126

Arg Arg Phe Arg Xaa Arg Gln
1               5

<210> SEQ ID NO 127
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa is L-2-naphthylalanine

<400> SEQUENCE: 127

Arg Phe Arg Phe Arg Xaa Arg
1               5
```

COMPOSITIONS AND METHODS FOR TREATING MITOCHONDRIAL NEUROGASTROINTESTINAL ENCEPHALOPATHY

CROSS-REFERENCE TO RELATED APPLICATIONS

This Application is a divisional of U.S. application Ser. No. 16/821,018, filed on Mar. 17, 2020, now U.S. Pat. No. 11,168,310, which is a continuation of International Application No. PCT/US2019/019117, filed on Feb. 22, 2019, which claims the benefit of U.S. Provisional Application No. 62/633,933, filed Feb. 22, 2018, and U.S. Provisional Application No. 62/796,823, filed Jan. 25, 2019, the entire contents of each of which are hereby incorporated by reference for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CYPT_014_02US_SeqList_ST25.txt, date recorded. May 20, 2020, file size 103 kilobytes).

BACKGROUND

Mitochondrial neurogastrointestinal encephalopathy (MNGIE) disease is a rare, recessive mitochondrial disease that affects several parts of the body, particularly the digestive system and nervous system. Abnormalities of the digestive system are among the most common and severe features of MNGIE disease. Almost all affected people have a condition known as gastrointestinal dysmotility, in which the muscles and nerves of the digestive system do not move food through the digestive tract efficiently. The resulting serious digestive problems (satiety with small amounts of food, dysphagia, nausea, vomiting, abdominal pain, diarrhea, and intestinal blockage) lead to extreme weight loss and reduced muscle mass (cachexia).

MNGIE disease is also characterized by abnormalities of the nervous system. Affected individuals experience peripheral neuropathy, particularly in the hands and feet, as well as other signs and symptoms that can include ptosis, ophthalmoplegia, and hearing loss. Leukoencephalopathy, which is the deterioration of a type of brain tissue known as white matter, is a hallmark of MNGIE disease. These changes in the brain usually do not cause symptoms in people with this disorder.

Mutations in the TYMP gene are believed to cause MNGIE disease. This gene provides instructions for making the enzyme thymidine phosphorylase (TP). TP breaks down the DNA building block thymidine into smaller molecules, helping to regulate the level of nucleosides in cells. TYMP mutations greatly reduce or eliminate the activity of thymidine phosphorylase. This leads to a toxic level of nucleoside accumulation in the body, which disrupts the usual maintenance and repair of mitochondrial DNA (mDNA). The resulting genetic changes impair the normal function of mitochondria. Although mDNA abnormalities underlie the digestive and neurological problems characteristic of MNGIE disease, how defective mitochondria cause the specific features of the disorder is still under investigation.

For those afflicted with MNGIE, treatment options remain limited. Stem cell transplantation, which suffers from high mortality rates and liver transplantation have been evaluated, but neither affords a general solution. Therefore, management of the disease is primarily through supportive care of the various symptoms and associated ailments. As such, it is clear that new therapies are needed to treat this fatal condition.

SUMMARY

In various embodiments, the present disclosure provides for compounds for use in treating Mitochondrial Neurogastrointestinal Encephalopathy Syndrome (MNGIE). In embodiments, the compounds have cell penetrating activity and thymidine phosphorylase activity. In certain embodiments, the compounds disclosed herein comprise: a) at least one cell-penetrating peptide (CPP) moiety; and b) a thymidine phosphorylase, or an active fragment or analog thereof (TP), wherein the CPP is coupled, directly or indirectly, to TP.

In some embodiments of the present disclosure, the CPP is conjugated, directly or indirectly, to the TP.

In some embodiments of the present disclosure, the compounds further comprise a linker (L), which conjugates the CPP to TP In other embodiments, the linker conjugates the CPP to the N-terminus or the C-terminus of the TP. In another embodiment, the linker conjugates the CPP to the N-terminus of the TP. In other embodiments, the linker conjugates the CPP to a side chain of an amino acids in the TP.

In certain embodiments, the compounds disclosed herein have a structure according to Formula I-A:

CPP-L-TP     (I-A), wherein L is a covalently bound to the side chain of an amino acid on the CPP and to the N-terminus of the TP, a side chain of an amino acid in TP, or the C-terminus of the TP. In some embodiments, L is covalently bound to the N-terminus of TP. In other embodiments, L is covalently bound to the C-terminus of TP. In still other embodiments, L is covalently bound to a side chain of an amino acid of TP In some embodiments, the CPP is a cyclic cell-penetrating peptide (cCPP).

In various embodiments of the present disclosure, L is one or more D or L amino acids, each of which is optionally substituted; alkylene, alkenylene, alkynylene, carbocyclyl, or heterocyclyl, each of which is optionally substituted; or —$(R^1$—X—$R^2)z$-, wherein each of $R^1$ and $R^2$, at each instance, are independently selected from alkylene, alkenylene, alkynylene, carbocyclyl, and heterocyclyl, each X is independently $NR^3$, —$NR^3C(O)$—, S, and O, wherein each $R^3$ is independently selected from H, alkyl, alkenyl, alkynyl, carbocyclyl, and heterocyclyl, each of which is optionally substituted, and z is an integer from 1 to 20; or combinations thereof.

In some embodiments, L has a structure according to Formula II-A' or II-B':

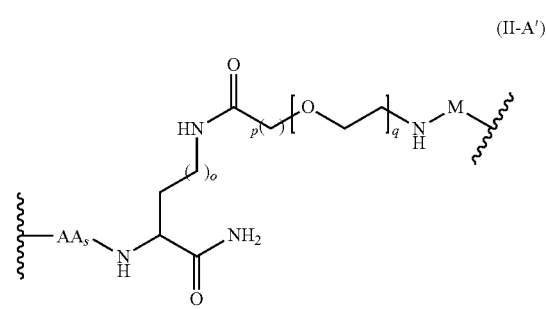

(II-A')

-continued (II-B')

[Structure: AA_s—NH—CH(C(O)NH_2)—(CH_2)_r—C(O)NH—[CH_2CH_2O]_q—(CH_2)_p—C(O)—M]

wherein
M is absent or a group that conjugates L to an amino acid on TP;
AA_s is a side chain or terminus of an amino acid on the CPP;
is an integer from 0 to 10;
p is an integer from 0 to 10;
q is an integer from 1 to 50; and
r is 0 or 1.

In certain embodiments of the present disclosure, L is Formula II-A':

(II-A')

[Structure showing AA_s—NH—CH(C(O)NH_2)—(CH_2)_o—C(O)NH—(CH_2)_p—[O—CH_2CH_2]_q—NH—M]

wherein
M is absent or a group that conjugates L to TP;
AA_s is a side chain or terminus of an amino acid on the CPP;
u is 0 or 1;
is 3;
p is 2; and
q is an integer from 10 to 15;

In various embodiments, M is present and comprises an alkylene, alkenylene, alkynylene, carbocyclyl, or heterocyclyl, each of which is optionally substituted. In some embodiments, M is present and selected from the group consisting of:

-continued wherein R is alkyl, alkenyl, alkynyl, carbocyclyl, or heterocyclyl. In a specific embodiment, M is

.

In some embodiments of the present disclosure, u is 0. In other embodiments, p is 2. In still other embodiments, q is 12. In some embodiments, u is 0, p is 2, and q is 2.

In some embodiments, L is Formula II-C':

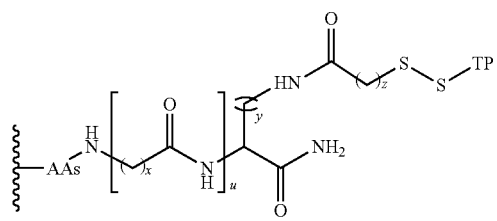

wherein:
AA$_s$ is a side chain or terminus of an amino acid on the CPP;
z is an integer from 0 to 10;
y is an integer from 0 to 10;
x is an integer from 0 to 10; and
u is an integer from 1 to 50.

In some embodiments, L is

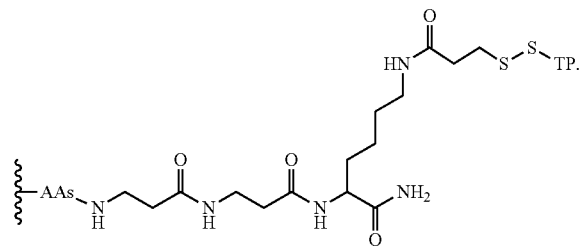

In various embodiments of the present disclosure, L or M is covalently bound to the N-terminus of TP or the C-terminus of TP. In another embodiment, L or M is covalently bound to the N-terminus of TP. In some embodiments, L or M is covalently bound to a side chain of an amino acid in TP (e.g. cysteine).

In some embodiments, the compounds disclosed herein comprise a cCPP which has a sequence comprising Formula III:

wherein:
each of AA$_1$, AA$_2$, AA$_3$, and AA$_4$, are independently selected from a D or L amino acid, each of AA$_u$ and AA$_z$, at each instance and when present, are independently selected from a D or L amino acid,
m and n are independently selected from a number from 0 to 6; and wherein:
at least two of AA$_u$, at each instance and when present, AA$_1$, AA$_2$, AA$_3$, AA$_4$, and AA$_z$,
at each instance and when present, are independently arginine, and
at least two of AA$_u$, at each instance and when present, AA$_1$, AA$_2$, AA$_3$, AA$_4$, and AA$_z$,
at each instance and when present, are independently a hydrophobic amino acid.

In some embodiments, the compound comprises cCPP which has a sequence comprising any of Formula IV-A-D:

IV-A

IV-B

IV-C

IV-D wherein:
each of AA$_{H1}$ and AA$_{H2}$ are independently a D or L hydrophobic amino acid;
at each instance and when present, each of AA$_U$ and AA$_Z$ are independently a D or L amino acid; and
m and n are independently selected from a number from 0 to 6.

In various embodiments of the present disclosure, the compound has a structure according to Formula V-A1 or V-A2:

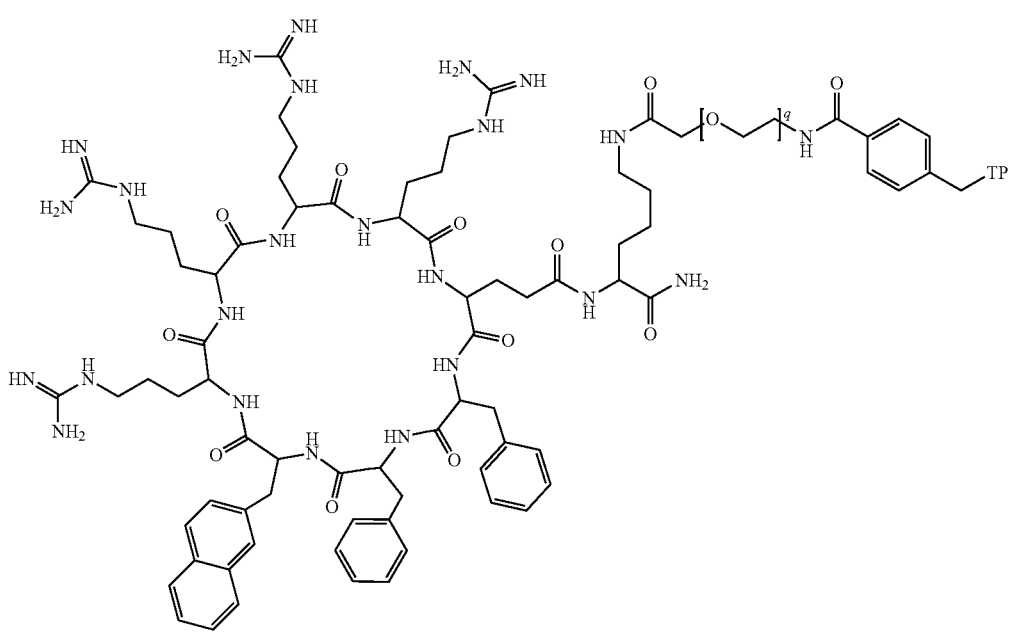
(V-A1)
or
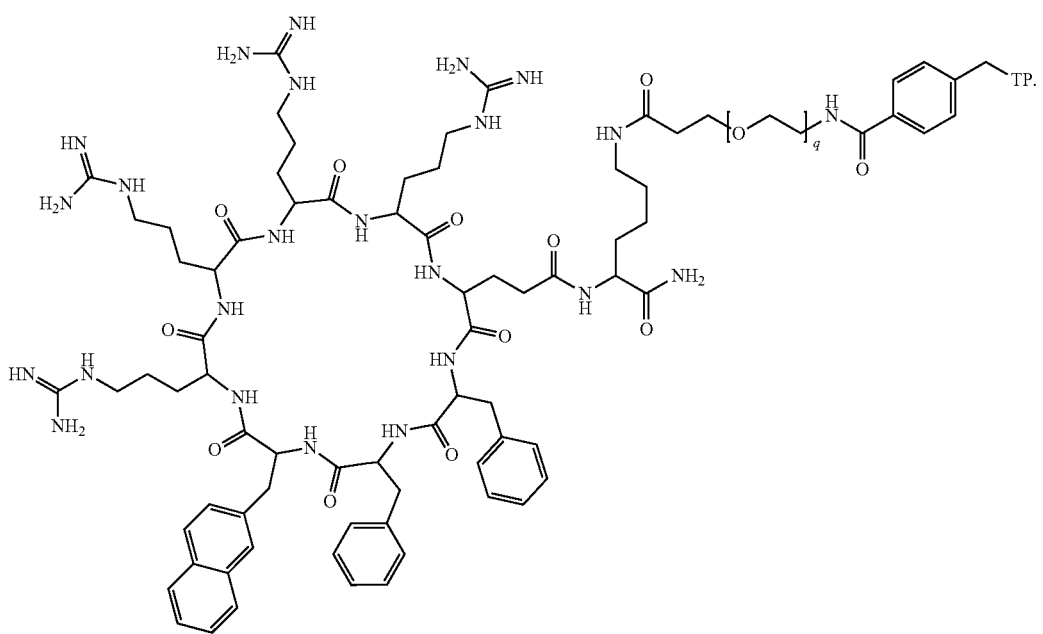
(V-A2)
In some embodiments, q is an integer from 1-50. In other embodiments, q is an integer from 10-15. In still other embodiments, q is 12.
In some embodiments, the compounds of the present disclosure have a structure according to Formula V-B1 or V-B2:

(V-B1)
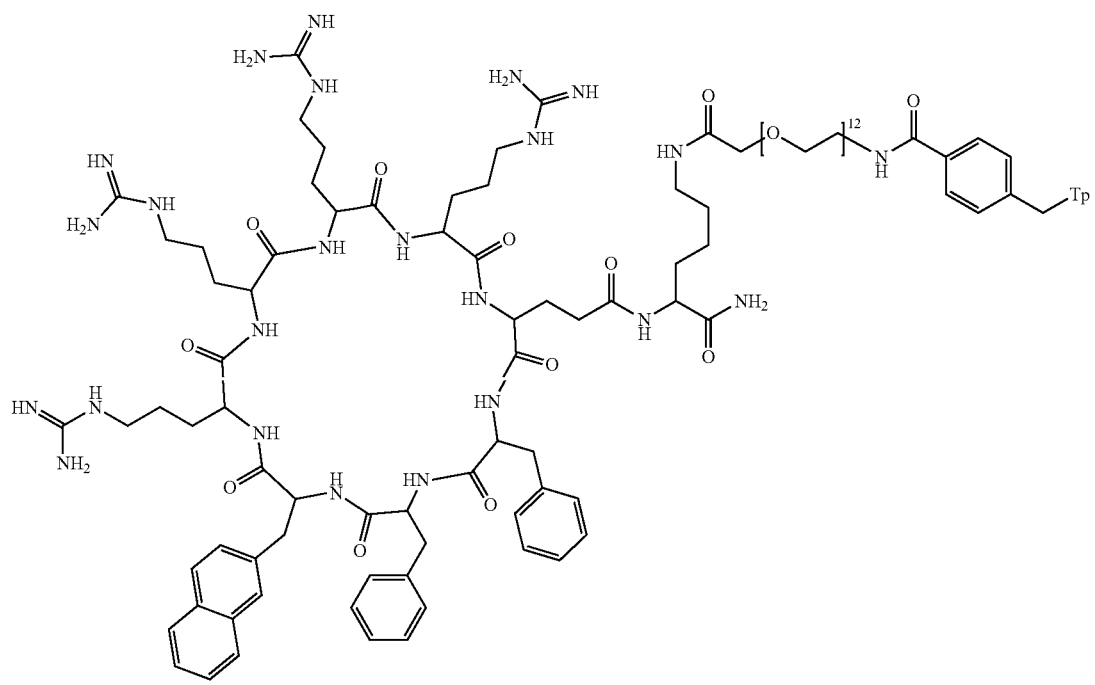
or
(V-B2)
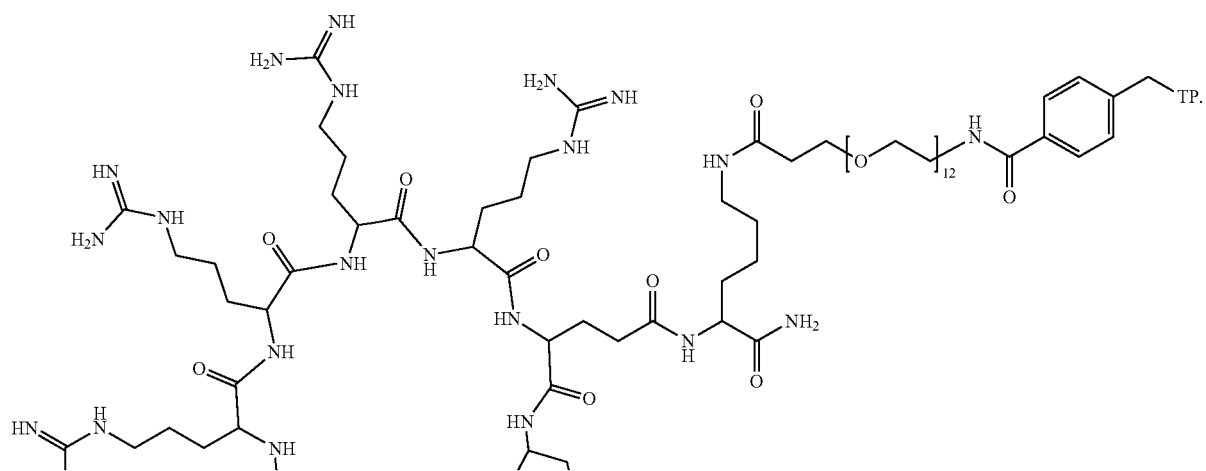
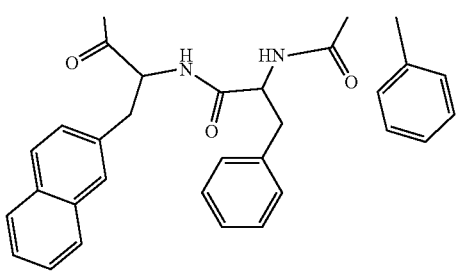

In other embodiments, the present disclosure provides a compound having the following structure of Formula V-B3 or V-B4:
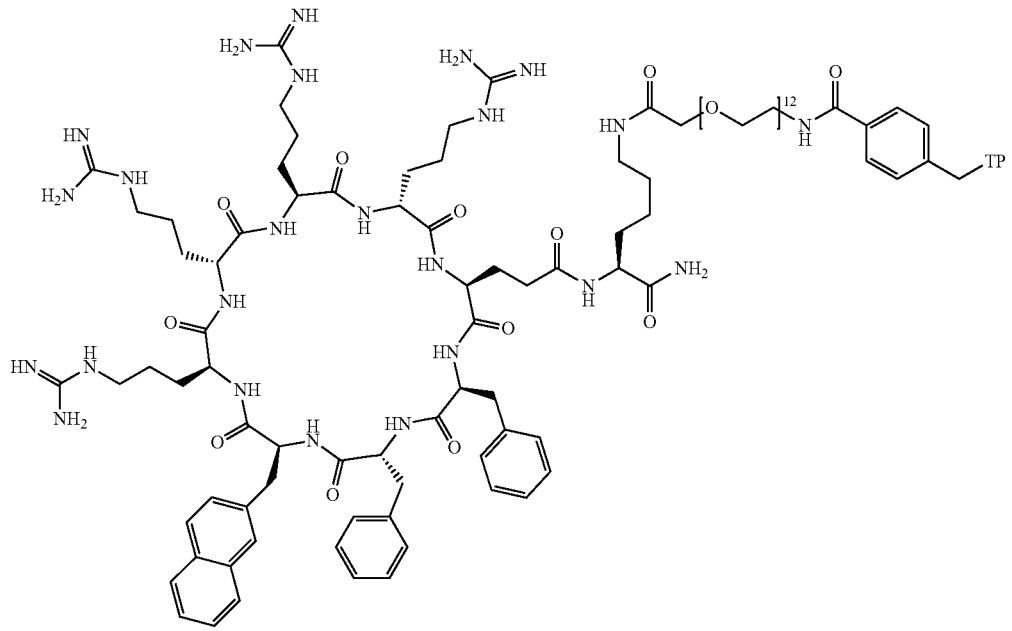
(V-B3)
or
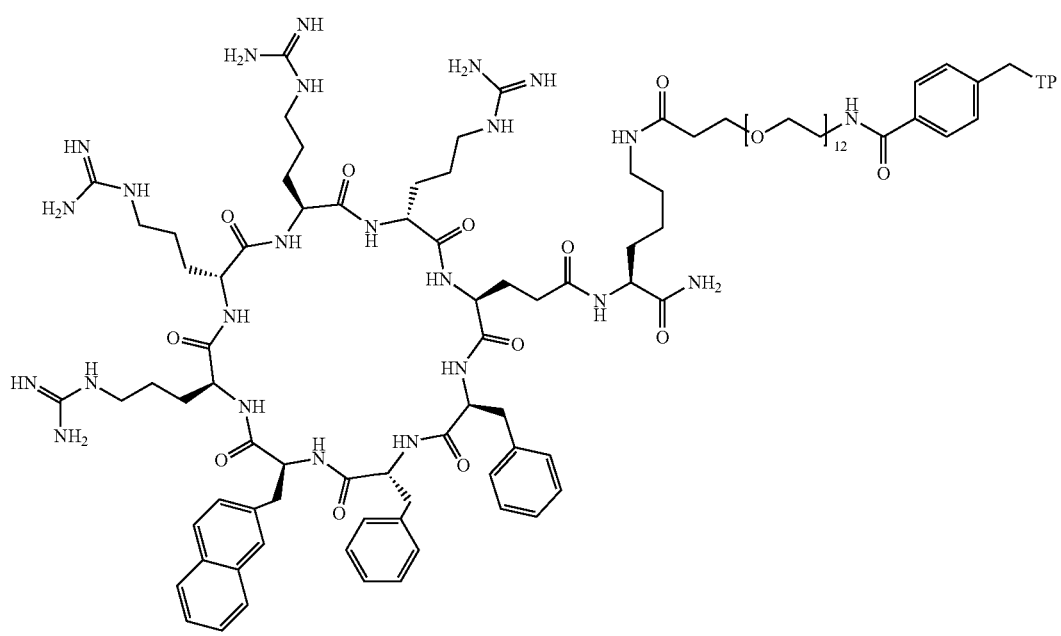
(V-B4)

In some embodiments, the present disclosure provides a compound having the following structure of Formula V-A3.

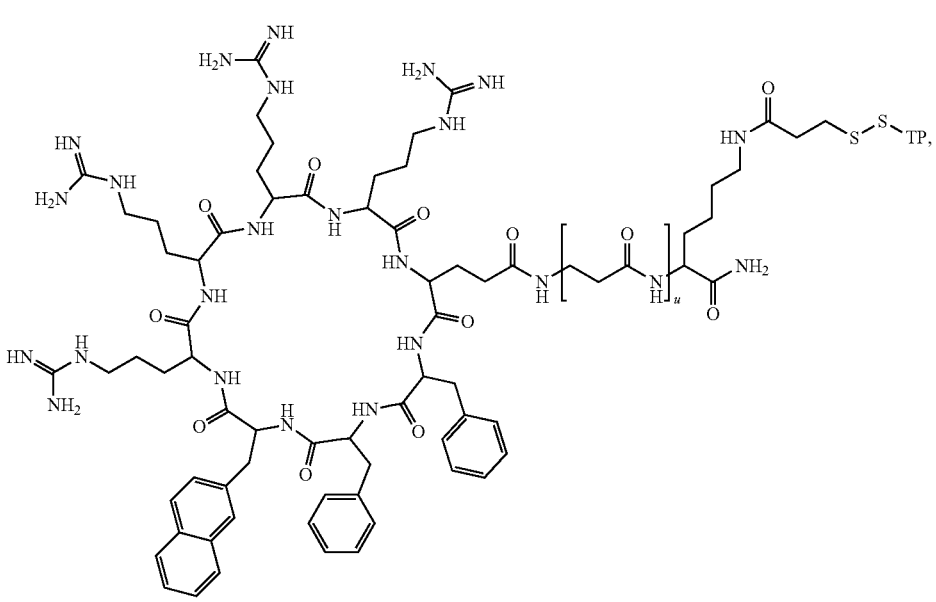

(V-A3)

In some embodiments, u is an integer from 1-50. In other embodiments, u is an integer from 1-5. In still other embodiments, u is 2.

In some embodiments, the compound of Formula V-A3 has the following structure:

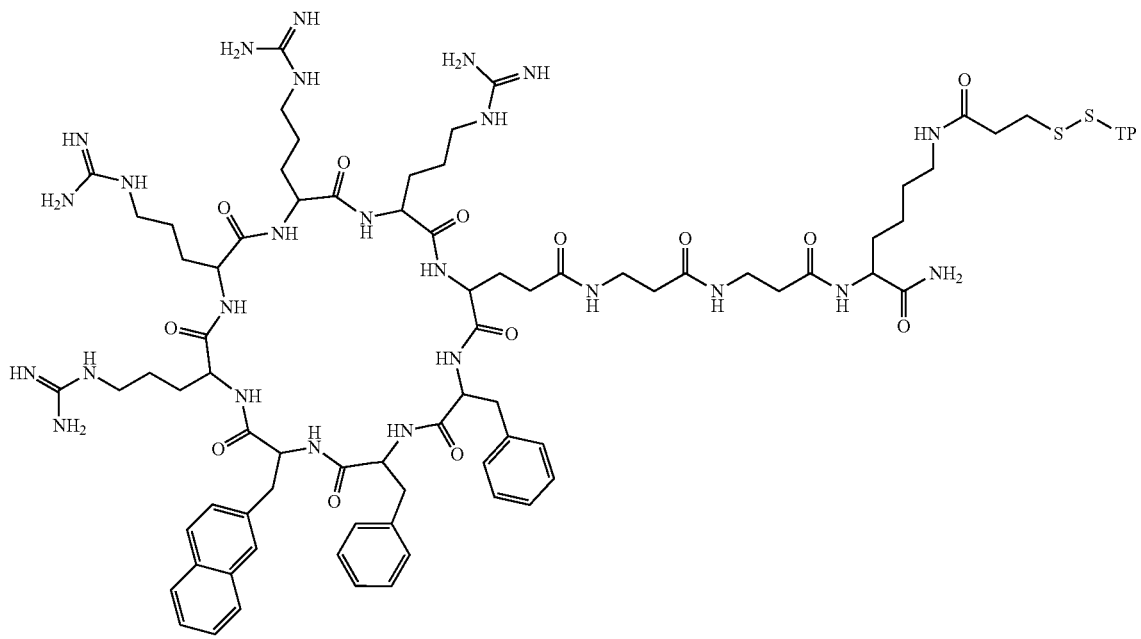

In some embodiments, the compounds disclosed herein comprise TP having an amino acid sequence which is at least 85% (e.g., 90%, 95%, or 99%) identical to SEQ ID NO. 1, 2, 3, 4, 5, 6, 7, 8, 9, 10, 11, 12, or 13.

In various embodiments, the present disclosure provides for methods of treating Mitochondrial Neurogastrointestinal Encephalopathy (MNGIE) in a patient in need thereof, comprising administering a compound disclosed herein.

In some embodiments, the present disclosure provides for methods of reducing extracellular and/or intracellular levels of thymidine in a patient in need thereof, comprising administering a compound disclosed herein. In other embodiments, the method is for treating Mitochondrial Neurogastrointestinal Encephalopathy (MNGIE).

In still other embodiments, the present disclosure provides for a cell comprising the compounds disclosed herein.

DETAILED DESCRIPTION

Definitions

Figure 1A:
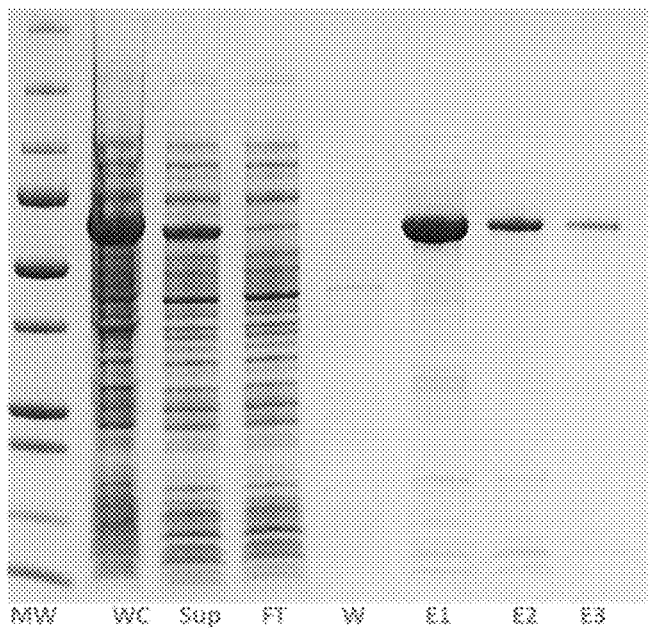
FIG. 1A is a SDS-PAGE analysis showing the expression and purification of His-tagged thymidine phosphorylase. His-tagged TP11 was expressed from E. coli culture using Terrific Broth (TB) at 25° C. overnight induced with 0.25 mM IPTG. From left to right are molecular weight marker (MW), whole cell lysate (WC), supernatant after cell lysis (Sup), flow through from His-Trap column (FT), washing (W), Elutions (E1-E3). Typically obtained 100 mg of His-TP from 1 L of E. coli. culture

The term "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

The term "pharmaceutically acceptable salts" include those obtained by reacting the active compound functioning as a base, with an inorganic or organic acid to form a salt for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods. The term "pharmaceutically acceptable salts" also includes those obtained by reacting the active compound functioning as an acid, with an inorganic or organic base to form a salt, for example salts of ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methyl amine, dimethylamine, trimethylamine, ethylamine, basic amino acids, and the like. Non limiting examples of inorganic or metal salts include lithium, sodium, calcium, potassium, magnesium salts and the like.

As used herein, "treat," "treating," "treatment" and variants thereof, refers to any administration of thymidine phosphorylase (TP) that partially or completely alleviates, ameliorates, relieves, inhibits, delays onset of, reduces severity of, and/or reduces incidence of one or more symptoms or features Mitochondrial Neurogastrointestinal Encephalopathy (MNGIE) as described herein.

As used herein, "therapeutically effective" refers to an amount of TP which confers a therapeutic effect on a patient. In some embodiments, the therapeutically effective amount is an amount sufficient to treat MNGIE.

As used herein, "cell penetrating peptide" or "CPP" refers to any peptide which is capable of penetrating a cell membrane. In some embodiments, the cyclic cell penetrating peptide is also capable of directing a protein (e.g., TP) to penetrate the membrane of a cell. In some embodiments, the cell penetrating peptide is a cyclic cell-penetrating peptide (cCPP). In some embodiments, the CPP delivers the protein to the cytosol of the cell. Without being bound by theory, the CPPs (e.g., cCPPs) deliver of the cargo to the cytosol by enabling escape of the CPP-TP conjugate from endosomes.

As used herein, "linker" or "L" refers to a moiety which that covalently bonds two or more moieties (e.g., a cCPP and TP). In some embodiments, the linker can be natural or non-natural amino acid or polypeptide. In other embodiments, the linker is a synthetic compound containing two or more appropriate functional groups suitable to bind a CPP and TP, to thereby form the compounds disclosed herein. In yet another embodiment, the linker comprises an M moiety to thereby conjugate the CPP to the TP. For example, in some embodiments, the cCPP may be covalently bound to TP via a linker.

As used herein, "polypeptide" refers to a string of at least two amino acids attached to one another by a peptide bond. There is no upper limit to the number of amino acids that can be included in a polypeptide. Further, polypeptides may include non-natural amino acids, amino acid analogs, or other synthetic molecules that are capable of integrating into a polypeptide.

As used herein, the "sequence identity" refers to the relatedness between two amino acid sequences. Those of ordinary skill in the art will appreciate that two sequences are generally considered to be "substantially identical" if they contain identical residues in corresponding positions. Amino acid sequences may be compared using any of a variety of algorithms well known in the art, including those available in commercial computer programs such as BLASTP, gapped BLAST, and PSI-BLAST, in the version in existence as of the date of filing. Exemplary programs are described in Altschul, et al., Basic local alignment search tool, *J. Mol. Biol.*, 215(3): 403-410, 1990; Altschul, et al., *Methods in Enzymology*, Altschul et al., *Nucleic Acids Res.* 25:3389-3402, 1997, Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In some embodiments, the sequence identity between two amino acid sequences may be determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), in the version that exists as of the date of filing. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows: (Identical Residues×100)/(Length of Alignment– Total Number of Gaps in Alignment)

In other embodiments, sequence identity may be determined using the Smith-Waterman algorithm, in the version that exists as of the date of filing.

As used herein, "substantial homology" refers to a comparison between amino acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains, and substitution of one amino acid for another of the same type may often be considered a "homologous" substitution.

As is well known in this art, amino acid sequences may be compared using any of a variety of algorithms, including those available in commercial computer programs such as BLASTP, gapped BLAST, and PSI-BLAST, in existence as of the date of filing. Exemplary such programs are described in Altschul, et al., Basic local alignment search tool, *J. Mol. Biol.*, 215(3): 403-410, 1990; Altschul, et al., *Methods in Enzymology*, Altschul, et al., "Gapped BLAST and PSI-BLAST: a new generation of protein database search programs", *Nucleic Acids Res.* 25:3389-3402, 1997; Baxevanis, et al., *Bioinformatics A Practical Guide to the Analysis of Gems and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. The alkylene chain is attached, directly or indirectly, to the CPP through a single bond and, directly or indirectly, to the TP through a single bond. Unless stated otherwise specifically in the specification, an alkylene chain can be optionally substituted as described herein.

"Alkenylene" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethene, propene, butene, and the like. The alkenylene chain is attached, directly or indirectly, to the CPP through a single bond and, directly or indirectly, to the TP through a single bond. Unless stated otherwise specifically in the specification, an alkenylene chain can be optionally substituted.

"Alkynyl" or "alkynyl group" refers to a straight or branched hydrocarbon chain having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain, having from two to forty carbon atoms, and having one or more carbon-carbon triple bonds. Non-limiting examples of $C_2$-$C_{40}$ alkynylene include ethynylene, propargylene and the like. The alkynylene chain is attached, directly or indirectly, to the CPP through a single bond and, directly or indirectly, to the TP through a single bond. Unless stated otherwise specifically in the specification, an alkynylene chain can be optionally substituted.

"Carbocyclyl," "carbocyclic ring" or "carbocycle" refers to a rings structure, wherein the atoms which form the ring are each carbon, and which is attached to the rest of the molecule by a single bond Carbocyclic rings can comprise from 3 to 20 carbon atoms in the ring Unless stated otherwise specifically in the specification, the carbocyclyl can be a monocyclic, bicyclic, tricyclic or tetracyclic ring system, which can include fused or bridged ring systems Carbocyclic rings include aryls and cycloalkyl, cycloalkenyl, and cycloalkynyl as defined herein. Unless stated otherwise specifically in the specification, a carbocyclyl group can be optionally substituted. In some embodiments, the carbocyclyl divalent, and is attached, directly or indirectly, to the CPP through a single bond and, directly or indirectly, to the TP through a single bond. Unless stated otherwise specifically in the specification, a heterocyclyl group can be optionally substituted.

"Cycloalkyl" refers to a stable non-aromatic monocyclic or polycyclic fully saturated hydrocarbon having from 3 to 40 carbon atoms and at least one ring, wherein the ring consists solely of carbon and hydrogen atoms, which can include fused or bridged ring systems. Monocyclic cycloalkyls include, for example, cyclopropyl, cyclobutyl, cyclopentyl, cyclohexyl, cycloheptyl, and cyclooctyl Polycyclic cycloalkyls include, for example, adamantyl, norbornyl, decalinyl, 7,7-dimethyl-bicyclo[2.2.1]heptanyl, and the like. In some embodiments, the cycloalkyl divalent and is attached, directly or indirectly, to the CPP through a single bond and, directly or indirectly, to the TP through a single bond. Unless otherwise stated specifically in the specification, a cycloalkyl group can be optionally substituted.

"Cycloalkenyl" refers to a stable non-aromatic monocyclic or polycyclic hydrocarbon having from 3 to 40 carbon atoms, at least one ring having, and one or more carbon-carbon double bonds, wherein the ring consists solely of carbon and hydrogen atoms, which can include fused or bridged ring systems. Monocyclic cycloalkenyls include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. In some embodiments, cycloalkenyl is divalent and is attached, directly or indirectly, to the CPP through a single bond and, directly or indirectly, to the TP through a single bond. Unless otherwise stated specifically in the specification, a cycloalkenyl group can be optionally substituted.

"Cycloalkynyl" refers to a stable non-aromatic monocyclic or polycyclic hydrocarbon having from 3 to 40 carbon atoms, at least one ring having, and one or more carbon-carbon triple bonds, wherein the ring consists solely of carbon and hydrogen atoms, which can include fused or bridged ring systems. Monocyclic cycloalkynyls include, for example, cycloheptynyl, cyclooctynyl, and the like. The cycloalkynyl is attached, directly or indirectly, to the CPP through a single bond and, directly or indirectly, to the TP through a single bond. Unless otherwise stated specifically in the specification, a cycloalkynyl group can be optionally substituted.

"Aryl" refers to a hydrocarbon ring system comprising hydrogen, 6 to 40 carbon atoms and at least one aromatic ring. For purposes of this disclosure, the aryl can be a monocyclic, bicyclic, tricyclic or tetracyclic ring system, which can include fused or bridged ring systems. Aryls include, but are not limited to, aryl divalent radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl divalent and is attached, directly or indirectly, to the CPP through a single bond and, directly or indirectly, to the TP through a single bond. Unless stated otherwise specifically in the specification, an aryl group can be optionally substituted.

"Heterocyclyl," "heterocyclic ring" or "heterocycle" refers to a stable 3- to 22-membered ring system which consists of two to fourteen carbon atoms and from one to eight heteroatoms selected from the group consisting of nitrogen, oxygen and sulfur. Heterocyclyl or heterocyclic rings include heteroaryls as defined below. Unless stated otherwise specifically in the specification, the heterocyclyl can be a monocyclic, bicyclic, tricyclic or tetracyclic ring system, which can include fused or bridged ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl radicals include, but are not limited to, dioxolanyl, thienyl[1,3] dithianyl, decahydroisoquinolyl, imidazolinyl, imidazolidinyl, isothiazolidinyl, isoxazdidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, succinimidyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocyclyl is divalent and is attached, directly or indirectly, to the CPP through a single bond and, directly or indirectly, to the TP through a single bond. Unless stated otherwise specifically in the specification, a heterocyclyl group can be optionally substituted.

"Heteroaryl" refers to a 5- to 22-membered aromatic ring comprising hydrogen atoms, one to fourteen carbon atoms, one to eight heteroatoms selected from the group consisting of nitrogen, oxygen and sulfur, and at least one aromatic ring. For purposes of this disclosure, the heteroaryl can be a monocyclic, bicyclic, tricyclic or tetracyclic ring system, which can include fused or bridged ring systems, and the nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). In some embodiments, the heteroaryl is divalent and is attached, directly or indirectly, to the CPP through a single bond and, directly or indirectly, to the TP through a single bond. Unless stated otherwise specifically in the specification, a heteroaryl group can be optionally substituted.

The term "ether" used herein refers to a divalent moiety having a formula $-[(R_1)_m-O-(R_2)_n]_z-$ wherein each of m, n, and z are independently selected from 1 to 40, and R1 and R2 are independently selected from an alkylene. Examples include polyethylene glycol. The ether is attached, directly or indirectly, to the CPP through a single bond and, directly or indirectly, to the TP through a single bond. Unless stated otherwise specifically in the specification, the ether can be optionally substituted.

The term "substituted" used herein means any of the above groups (i.e., alkylene, alkenylene, alkynylene, aryl, carbocyclyl, cycloalkyl, cycloalkenyl, cycloalkynyl, heterocyclyl, heteroaryl, and/or ether) wherein at least one hydrogen atom is replaced by a bond to a non-hydrogen atoms such as, but not limited to: a deuterium atom; a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyl di aryl silyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. Further, those skilled in the art will recognize that "substituted" also encompasses instances in which one or more hydrogen atoms on any of the above groups are replaced by a substituent listed in this paragraph, and the substituent then forms a covalent bond with the CPP or TP. The resulting bonding group can be considered a "substituent." For example, in certain embodiments, any of the above groups can be substituted at a first position with a carboxylic acid (i.e., $-C(=O)OH$) which forms an amide bond with an appropriate amino acid CPP (e.g., lysine), and also substituted at a second position with either an electrophilic group (e.g., $-C(=O)H$, $-CO_2R_g$, -halide, etc.) which forms a bond with the N-terminus of TP or alternatively a nucleophilic group ($-NH_2$, $-NHR_g$, $-OH$, etc.) which forms a bond with the C-terminus of TP. The resulting bond, e.g., amide bond, can be considered a "substituent." In some embodiments, the second position is substituted with a thiol group which forms a disulfide bond with a cysteine (or amino acid analog having a thiol group) in TP. The resulting disulfide is encompassed by the term substituent.

As used herein, the symbol

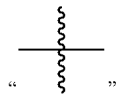

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

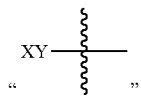

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

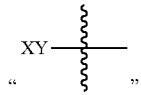

infers that when $R^3$ is "XY", the point of attachment bond is the same bond as the bond by which $R^3$ is depicted as being bonded to $CH_3$.

Compounds

Disclosed herein, in various embodiments, are compounds for treating Mitochondrial Neurogastrointestinal Encephalopathy Syndrome (MNGIE). The compounds are designed to deliver a moiety with thymidine phosphorylate activity intracellularly to MNGIE patients or patients with Mutations in the TYMP. By doing so, the compounds reduce the toxic levels of nucleosides that would otherwise accumulate in such patients. In some embodiments, the present compounds reduce toxic nucleoside levels by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100%, inclusive of all values and ranges therebetween.

In various embodiments, the compounds disclosed herein have a thymidine phosphorylase activity and cell penetrating activity, such that the compounds are able to traverse the cell membrane and reduce thymidine levels in vivo. In some embodiments, the compounds comprise: a) at least one cell-penetrating peptide (CPP) moiety; and b) at least one thymidine phosphorylase, or an active fragment or analog thereof (TP), wherein the CPP is coupled, directly or indirectly, to TP. In some embodiments, the compounds comprise 1, 2, 3, 4, 5, 6, 7, 8, 9, 10, or more TP moieties. In some embodiments, the compounds comprise one TP moiety. In some embodiments, the compounds comprise two TP moieties. As used herein, "coupled" can refer to a covalent or non-covalent association between the CPP to the TP, including fusion of the CPP to the TP and chemical conjugation of the CPP to the TP. A non-limiting example of a means to non-covalently attach the CPP to the TPP is through the streptavidin/biotin interaction, e.g., by conjugating biotin to CPP and fusing TP to streptavidin. In the resulting compound, the CPP is coupled to the TP via non-covalent association between biotin and streptavidin.

In some embodiments, the CPP is conjugated, directly or indirectly, to the TP to thereby form a CPP-TP conjugate. Conjugation of the TP to the CPP may occur at any appropriate site on these moieties. For example, in some embodiments, the N-terminus or C-terminus of the TP may be conjugated to the C-terminus, the N-terminus, or a side chain of an amino acid in the CPP In some embodiments, the CPP may be conjugated to the side change of an amino acid in TP.

In some embodiments, the TP is fused to the CPP. Fusion proteins, as used herein, refer to constructs where a linear CPP moiety is fused to the N- and/or C-terminus of the TP moiety. Such fusion protein may alternatively be described as having a cell penetrating domain and a thymidine domain. Methods of fusing polypeptides are well-known in the art. Such fusion constructs may be prepared by recombinant techniques. A recombinantly-produced TP-CPP fusion protein, in accordance with certain embodiments of the disclosure, includes the TP component and the linear CPP component associated with one another by genetic fusion. For example, the fusion protein may be generated by translation of a polynucleotide encoding the TP cloned in-frame with the linear CPP component (or vice versa). Such a fusion protein may contain one or more copies of CPP attached to the N-terminus and/or the C-terminus of the TP component. In some embodiments, a CPP component is independently attached to both the N- and C-terminus of the TP component.

In other embodiments, the TP may be chemically conjugated to the CPP through a side chain of an amino acid on TP. In still other embodiments, the TP may be conjugated to the CPP through a side chain of an amino acid on the CPP. Any amino acid side chain on the CPP and/or TP which is capable of forming a covalent bond, or which may be so modified, can be used to link TP to the CPP. The amino acid on the CPP can be a natural or non-natural amino acid. In some embodiments, the amino acid on the CPP used to conjugate the TP is aspartic acid, glutamic acid, glutamine, asparagine, lysine, ornithine, 2,3-diaminopropionic acid, or analogs thereof, wherein the side chain is substituted with a bond to the TPP or linker. In particular embodiments, the amino is lysine, or an analog thereof. In other embodiments, the amino acid is glutamic acid, or an analog thereof. In further embodiments, the amino acid is aspartic acid, or an analog thereof.

In some embodiments of the present disclosure, the compounds further comprise a linker (L), which conjugates the CPP to TP. In some embodiments, L conjugates the CPP to the N-terminus or the C-terminus of the TP. In a certain embodiment, L conjugates the CPP to the N-terminus of the TP.

In some embodiments, the CPP is conjugated to the TP through a side chain of an amino acid on the TP. Any appropriate side chain of an amino acid of TP which is capable of forming a covalent bond with the CPP, or which may be so modified, can be used to conjugate the CPP to TP. The amino acid may be a constituent of native TP or a non-native amino acid. That is, in some embodiments, TP can include a non-native amino acid which provides a handle to conjugate the CPP. In particular embodiments, the amino acid is glutamine, asparagine, lysine, cysteine, tryptophan, or analogs thereof.

In some embodiments, the CPP is cyclic (as described herein), and referred to herein as a cCPP. There are numerous possible configurations for the compounds disclosed herein. In certain embodiments, the compounds of the disclosure are exocyclic compounds wherein TP is conjugated to the side chain of an amino acid in the cCPP. In some embodiments, the compounds disclosed herein have structure (i.e., exocyclic) according to Formula I-A or Formula I-A1:

CPP-L-TP  (I-A)

or

TP-L-CPP  (I-A1), wherein L is a covalently bound to the side chain of an amino acid on the CPP and to the N-terminus of the TP, an amino acid side chain of TP, or the C-terminus of the TP.

In certain embodiments, the compounds (e.g., exocyclic compounds) disclosed herein have a structure according to Formula I-A:

CPP-L-TP  (I-A), wherein L is a covalently bound to the side chain of an amino acid on the CPP and to the N-terminus of the TP.

In some embodiments of the present disclosure, the CPP and TP together are cyclic (referred to herein as an "endocyclic compound"). In various non-limiting embodiments, the endocyclic compounds disclosed herein have a structure according to Formula I-A2, Formula I-A3, or Formula I-A4:

  I-A2

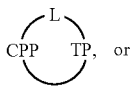  I-A3

  I-A4

In other embodiments, the TP moiety is cyclic and the CPP is a cyclic, and together they form a fused bicyclic system (referred to herein as a "bicyclic compound"). In various non-limiting embodiments, the endocyclic compounds disclosed herein have a structure according to Formula I-A5 and I-A6.

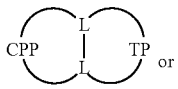  I-A5

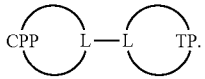  I-A6

L may be any appropriate moiety which conjugates CPP (e.g., as described herein) to a TP moiety. Thus, prior to conjugation to the CPP and TP, the linker has two or more functional groups, each of which are independently capable of forming a covalent bond to the CPP moiety and the TP moiety. In various embodiments of the present disclosure, L is covalently bound to the N-terminus of TP or the C-terminus of TP. In some embodiments, L is covalently bound to the N-terminus of TP. In other embodiments, L is covalently bound to the C-terminus of TP. In still other embodiments, L is covalently bound to the side chain of an amino acid in TP.

In various embodiments of the present disclosure, L comprises (i) one or more D or L amino acids, each of which is optionally substituted; (ii) alkylene, alkenylene, alkynylene, carbocyclyl, or heterocyclyl, each of which is optionally substituted; or (iii) —(R$^1$—X—R$^2$)z-, wherein each of R$^1$ and R$^2$, at each instance, are independently selected from alkylene, alkenylene, alkynylene, carbocyclyl, and heterocyclyl, each X is independently NR$^3$, —NR$^3$C(O)—, S, and O, wherein R$^3$ is H, alkyl, alkenyl, alkynyl, carbocyclyl, or heterocyclyl, each of which is optionally substituted, and z is an integer from 1 to 50; or (iv) combinations thereof. In some embodiments, L comprises one or more D or L amino acids, each of which is optionally substituted. In other embodiments, L comprises alkylene, alkenylene, alkynylene, carbocyclyl, or heterocyclyl, each of which is optionally substituted. In still other embodiments, L comprises —(R$^1$—X—R$^2$)z-, wherein each of R$^1$ and R$^2$, at each instance, are independently selected from alkylene, alkenylene, alkynylene, carbocyclyl, and heterocyclyl, each X is independently NR$^3$, —NR$^3$C(O)—, S, and O, wherein R$^3$ is H, alkyl, alkenyl, alkynyl, carbocyclyl, or heterocyclyl, each of which is optionally substituted, and z is an integer from 1 to 50, or combinations thereof. In certain embodiments, L is an ether, which is optionally substituted. In more specific embodiments, L comprises —(CH$_2$—O—CH$_2$)z-, wherein Z is an integer from 1-50. In more specific embodiments, L comprises —(CH$_2$—O—CH$_2$)z-, wherein Z is an integer from 1-25 (e.g., 12), and one or more D or L amino acids, such as and lysine. For example, in various embodiments, L comprises a polyethylene glycol moiety, having from 1 to 50 ethylene glycol units, and a lysine residue. In other specific embodiments, L comprises —(CH$_2$—S—CH$_2$)z-, wherein Z is an integer from 1-50. In still other specific embodiments, L comprises —(CH$_2$—NR$^3$—CH$_2$)z-, wherein R$^3$ is H, —C(O), alkyl, alkenyl, alkynyl, carbocyclyl, or heterocyclyl, each of which is optionally substituted, and z is an integer from 1-50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50, inclusive of all subranges therebetween. In some embodiments, z is an integer from 10-15. In a specific embodiment, z is 12.

As discussed above, L or M may be covalently bound to TP at any suitable location on TP. In various embodiments of the present disclosure, L or M is covalently bound to the N-terminus of TP or the C-terminus of TP. In another embodiment, L or M is covalently bound to the N-terminus of TP. In some embodiments, L or M is covalently bound to an amino acid side chain of TP.

In some embodiments, L is bound to the side chain of aspartic acid, glutamic acid, glutamine, asparagine, or lysine, or a modified side chain of glutamine or asparagine (e.g., a reduced side chain having an amino group), on the CPP or TP. In particular embodiments, the L is bound to the side chain of lysine on the CPP.

In some embodiments, L has a structure according to Formula II-A or Formula II-B:

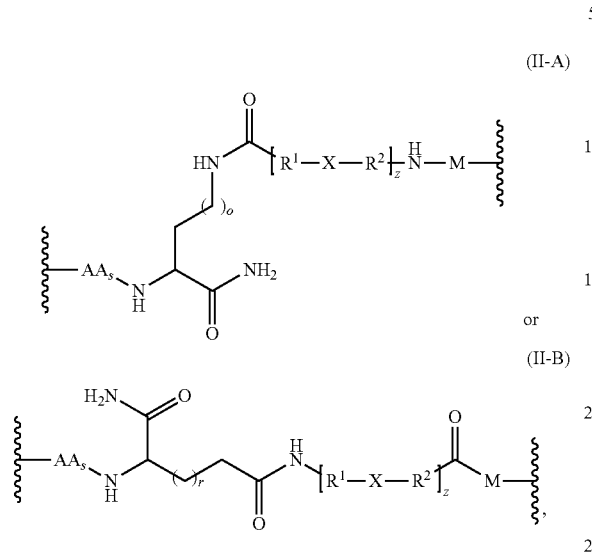

wherein each —(R$^1$—X—R$^2$)z- is defined as above.

In some embodiments, each of R$^1$ and R$^2$, at each instance, are independently selected from alkylene, alkenylene, alkynylene, carbocyclyl, and heterocyclyl, each of which is optionally substituted.

In some embodiments, each X is independently NR$^3$, —NR$^3$C(O)—, S, and O, and wherein R$^3$ is independently selected from H, alkyl, alkenyl, alkynyl, carbocyclyl, and heterocyclyl, each of which is optionally substituted.

In some embodiments, M is absent or a group bound to an amino acid on TP. In various embodiments, M is present and comprises an alkylene, alkenylene, alkynylene, carbocyclyl, or heterocyclyl, each of which is optionally substituted. In some embodiments, M is present and selected from the group consisting of:

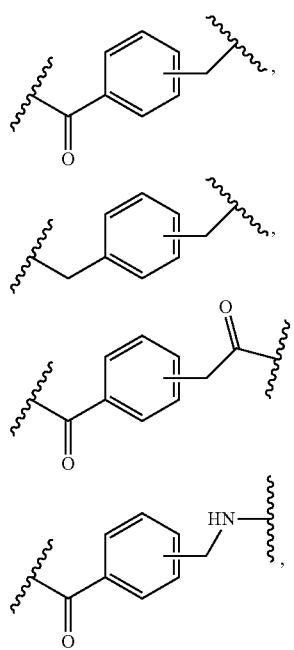

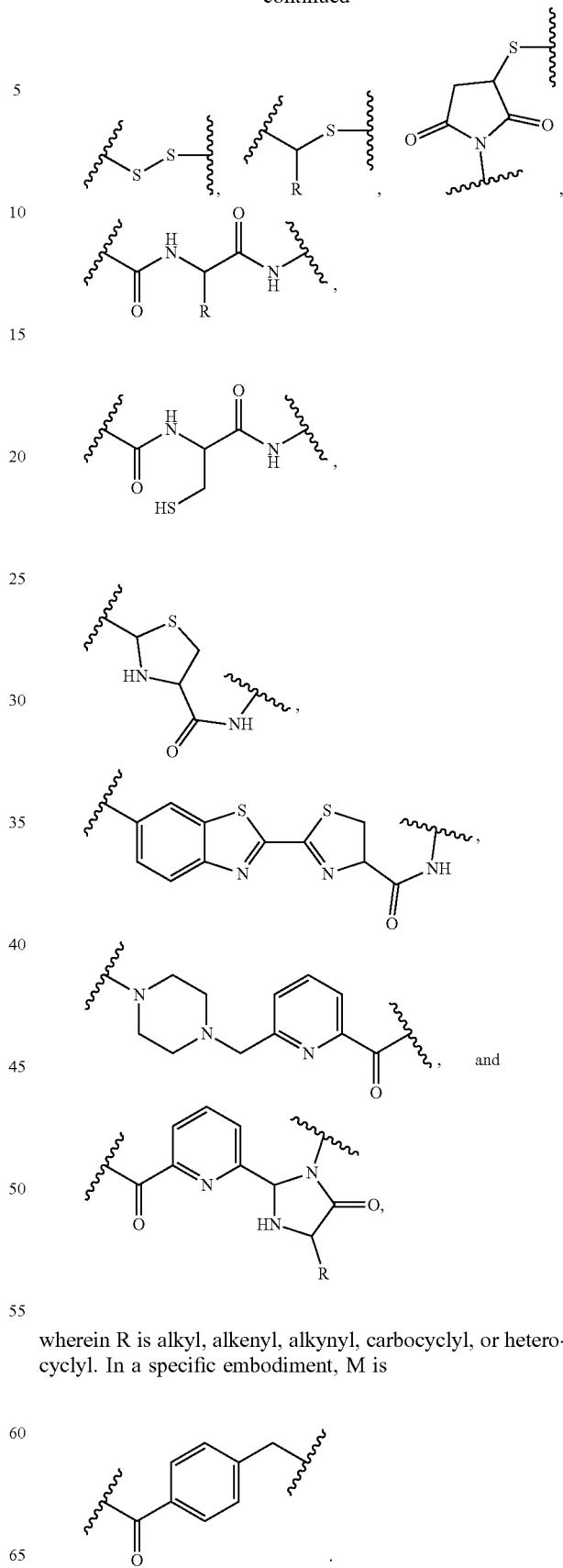

wherein R is alkyl, alkenyl, alkynyl, carbocyclyl, or heterocyclyl. In a specific embodiment, M is In another specific embodiment, M is

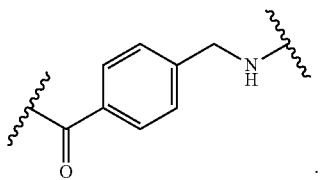 [SMILES: *NCc1ccc(C(*)=O)cc1]

In some embodiments, AA$_s$ is a side chain or terminus of an amino acid on the CPP. Non-limiting examples of AA$_s$ include aspartic acid, glutamic acid, glutamine, asparagine, or lysine, or a modified side chain of glutamine or asparagine (e.g., a reduced side chain having an amino group).

In some embodiments, o is an integer from 0 to 10, e.g., 0, 1, 2, 3, 4, 5, 6, 7, 8, 9, and 10, inclusive of all values and subranges therebetween. In other embodiments, o is 0, 1, 2, or 3.

In some embodiments, u is 0 or 1. In some embodiments, u is 0. In other embodiments u is 1.

In some embodiments p is 1 or 2. In some embodiments, p is 1 In other embodiments, p is 2.

In some embodiments, r is 0 or 1. In some embodiments, r is 0. In other embodiments, r is 1.

In some embodiments, L has a structure according to Formula II-A' or II-B':

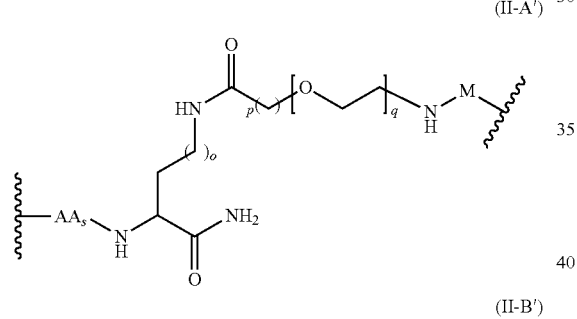

wherein each of M, AA$_s$, u, o, p, and r are defined above.

In some embodiments, q is an integer from 1 to 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50, inclusive of all ranges and values therebetween. In other embodiments, q is an integer from 5-20. In other embodiments, q is an integer from 10-15. In a specific embodiment, q is 12.

In certain embodiments, o is 0, 1, 2, or 3. In certain other embodiments, r is 0 or 1.

In certain embodiments of the present disclosure, L is Formula II-A':

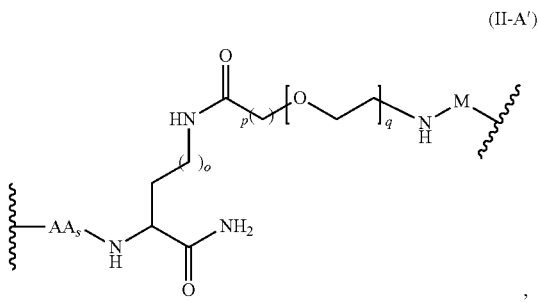

wherein

M is absent or a group bound to an amino acid on TP;

AA$_s$ is a side chain or terminus of an amino acid on the CPP;

u is 0 or 1;

is 0, 1, 2, or 3;

p is 1 or 2; and q is an integer from 10 to 15.

In some embodiments of the present disclosure, r is 0, p is 2, and q is 12. In other embodiments, r is 0. In still other embodiments, p is 2. In further embodiments, q is 12.

Other non-limiting examples of suitable L groups include:

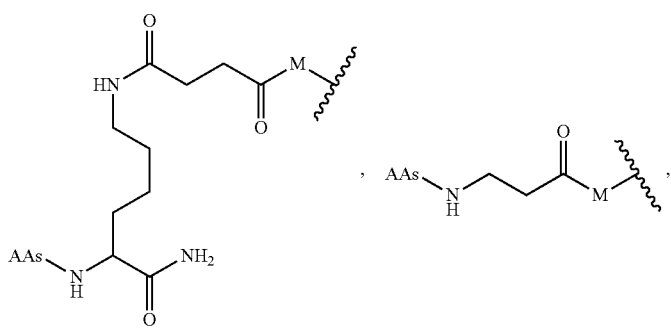

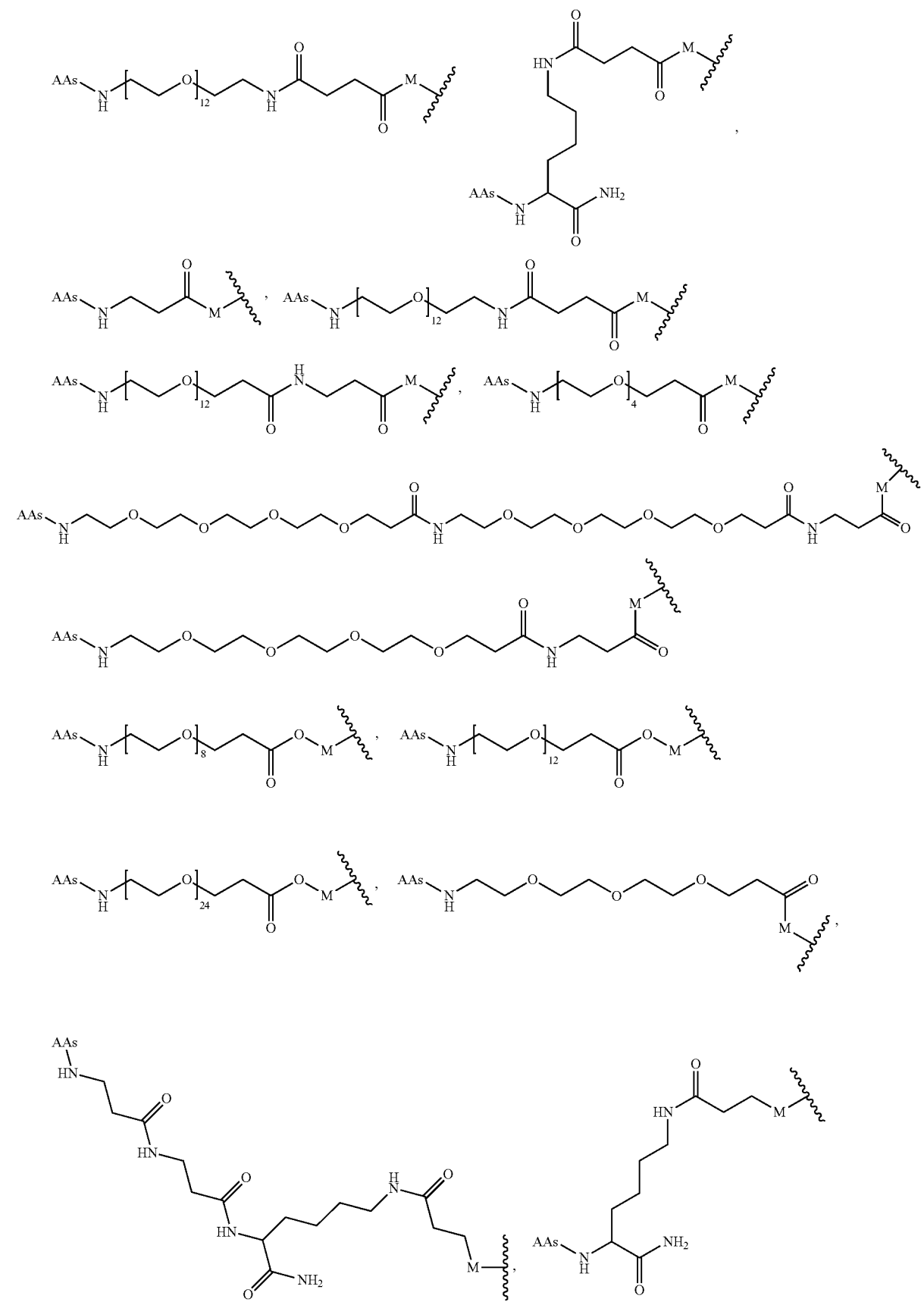

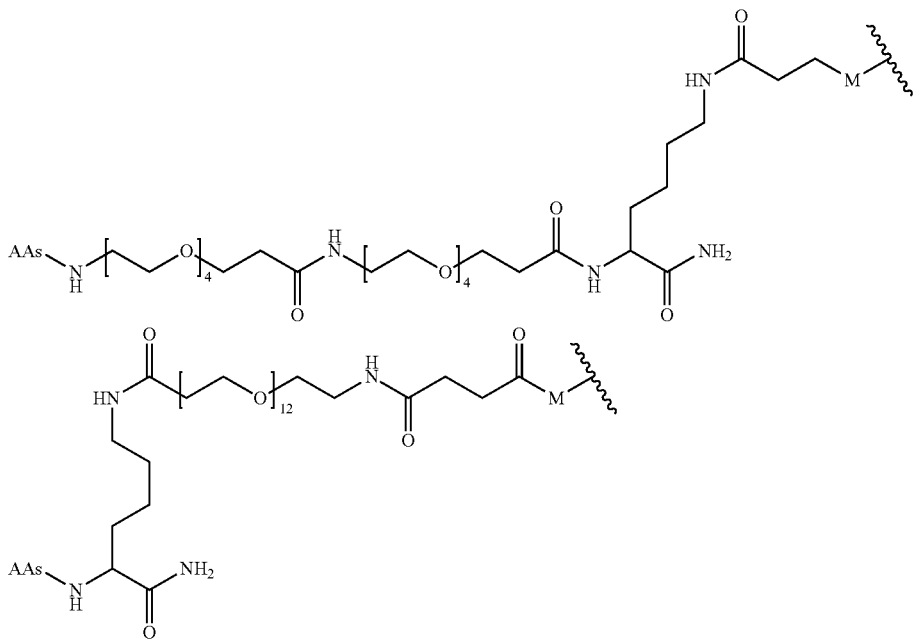

In some embodiments, the L contains a group which may be cleaved after cytosolic uptake of the compounds of the disclosure to release TP. Non-limiting examples of physiologically cleavable linking group include carbonate, thiocarbonate, thioester, disulfide, sulfoxide, hydrazine, protease-cleavable dipeptide linker, and the like.

In certain embodiments, a precursor to L also contains a thiol group, which forms a disulfide bond with the side chain of cysteine or cysteine analog located on TP.

Accordingly, in various embodiments, the compounds disclosed herein (e.g., the compounds for Formula (I-A) have the following structure:

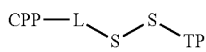

In some embodiments, the disulfide bond is formed between a thiol group on L, and the side chain of cysteine or an amino acid analog having a thiol group on TP. Such thiol containing side chains may be located on native amino acids of wild-type TP, or such thiol containing amino acids may be introduced to TP. Non-limiting examples of amino acid analogs having a thiol group which can be used with the polypeptide conjugates disclosed herein include:

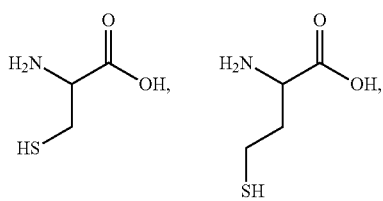

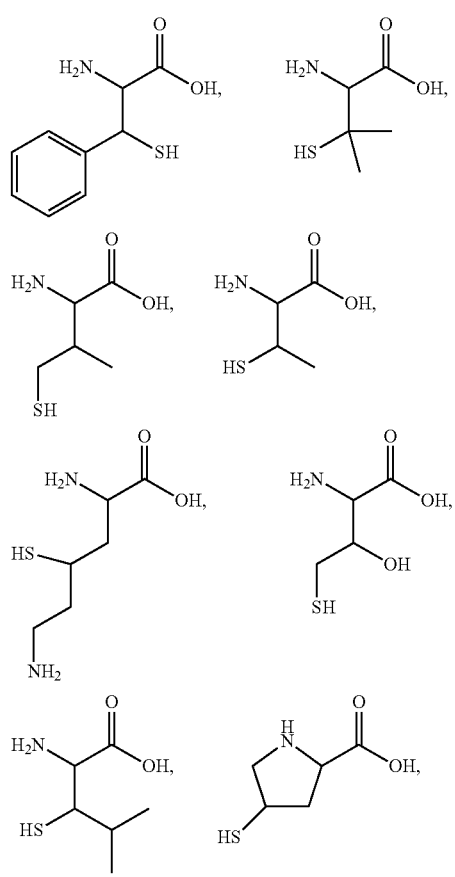

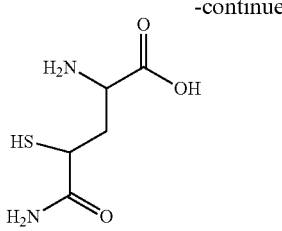

One skilled in the art will recognize that the amino acid analogs depicted above are shown as precursors, i.e., prior to incorporation into the compounds. When incorporated in the compounds of the present disclosure, the N- and C-termini are independently substituted to form peptide bonds, and the hydrogen on the thiol group is replaced with a bond to another sulfur atom to thereby form a disulfide.

In some embodiments, L is Formula II-C':

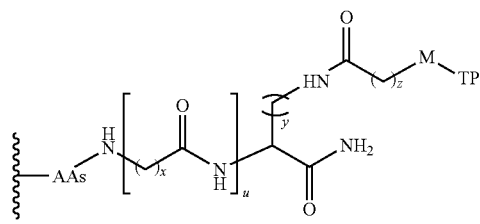

II-C' wherein:
AA$_s$ is a side chain or terminus of an amino acid on the CPP;
M is defined above;
z is an integer from 0 to 10;
y is an integer from 0 to 10;
x is an integer from 0 to 10; and
u is an integer from 1 to 50.

In some embodiments, M is a physiologically cleavable bond. In some embodiments, M is disulfide.

In some embodiments, L is

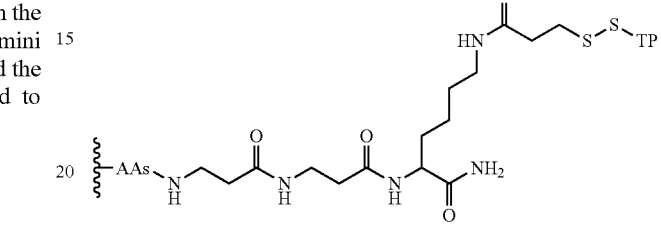

In particular embodiments, a disulfide bond is formed between a thiol group on L, and the side chain of cysteine on TP. In some embodiments, said cysteine may be a constituent of wild type TP or TP may be modified to include cysteine or an amino acid analog having a thiol group. In other embodiments, any suitable functional group of TP may be modified to form a thiol group for bonding to L.

In more specific embodiments of the present disclosure, the compound has a structure according to Formula V-A1, V-A2, or V-A3:

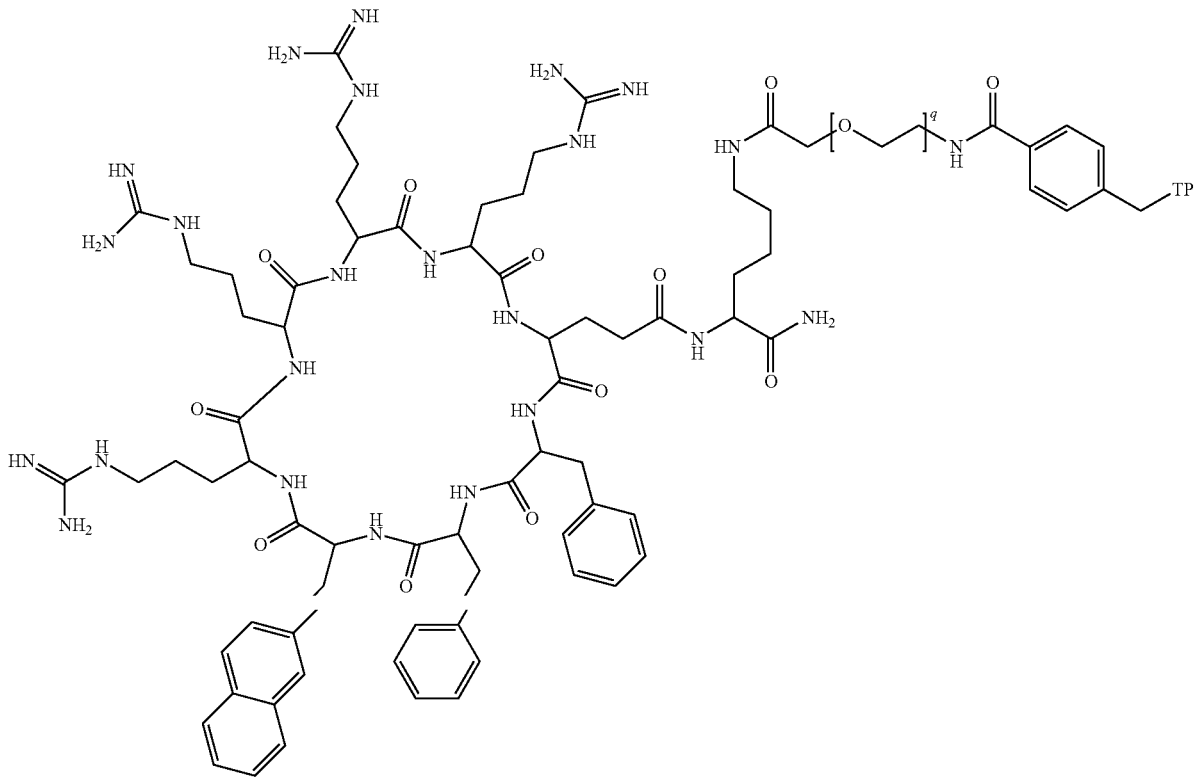

(V-A1)

(V-A2)
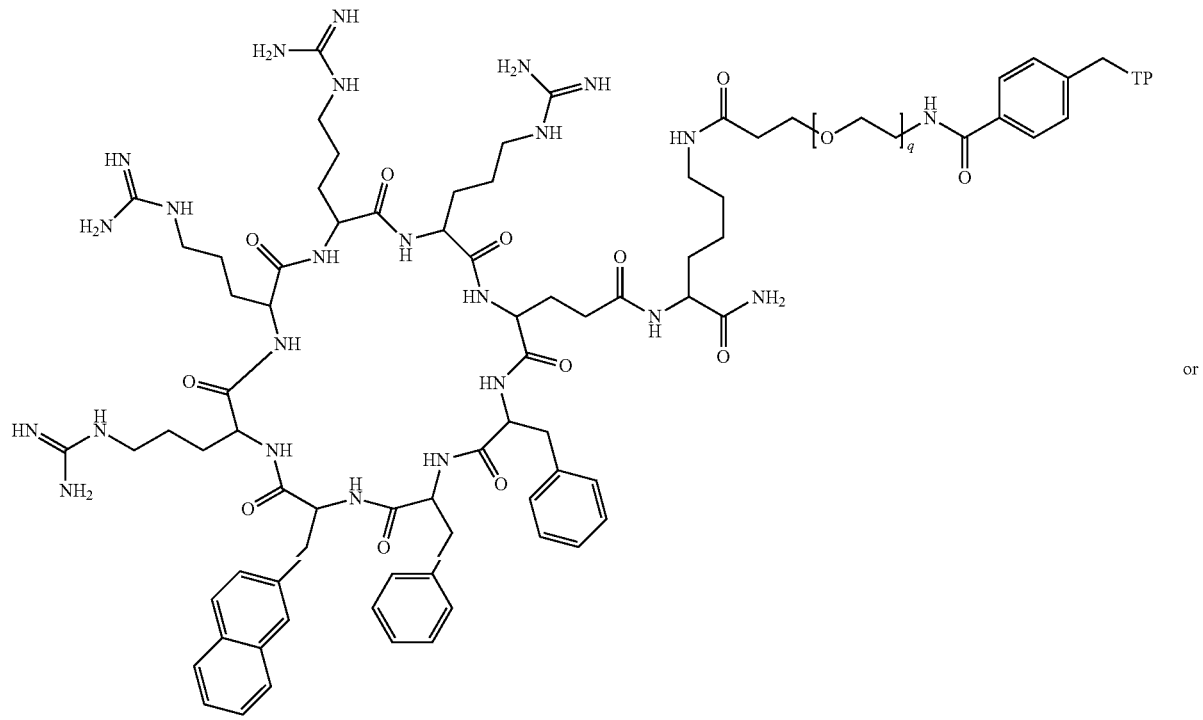
or
(V-A3)
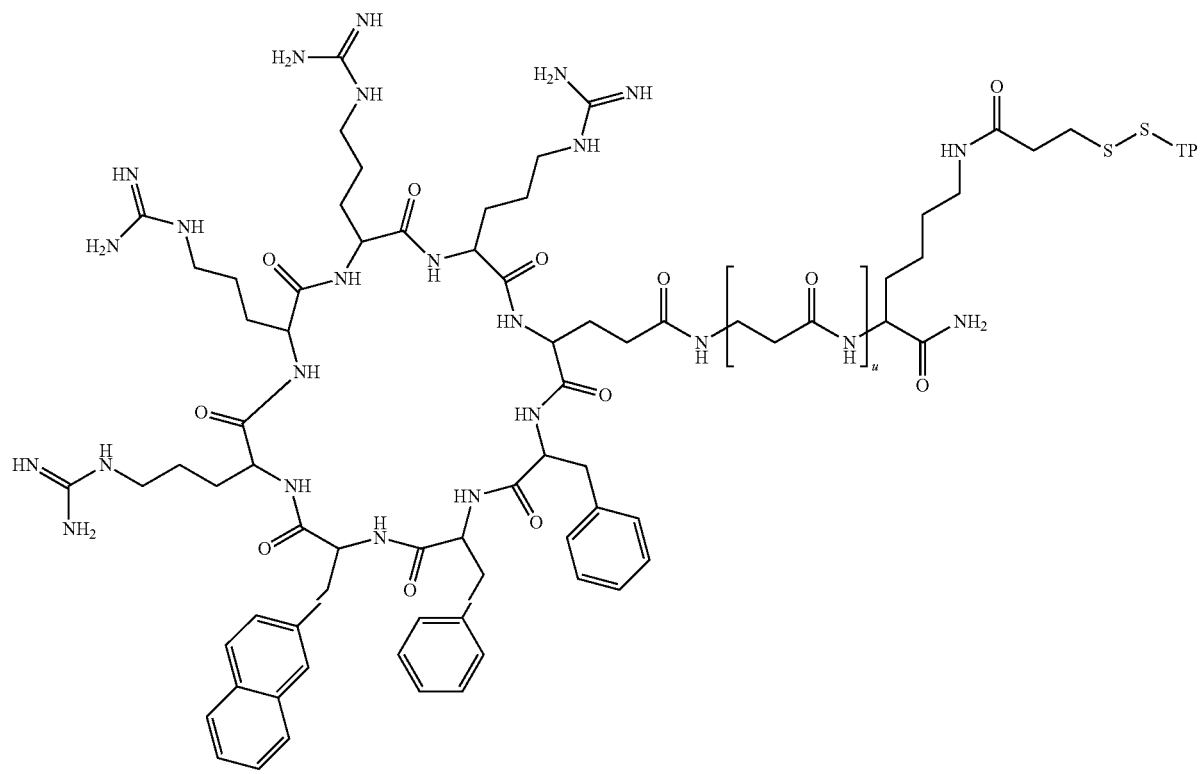
In various embodiments, q may be any integer described above, e.g., an integer in the range of from 10 to 15.
In specific embodiments the present disclosure, the compound has a structure according to Formula V-B1 or V-B2.

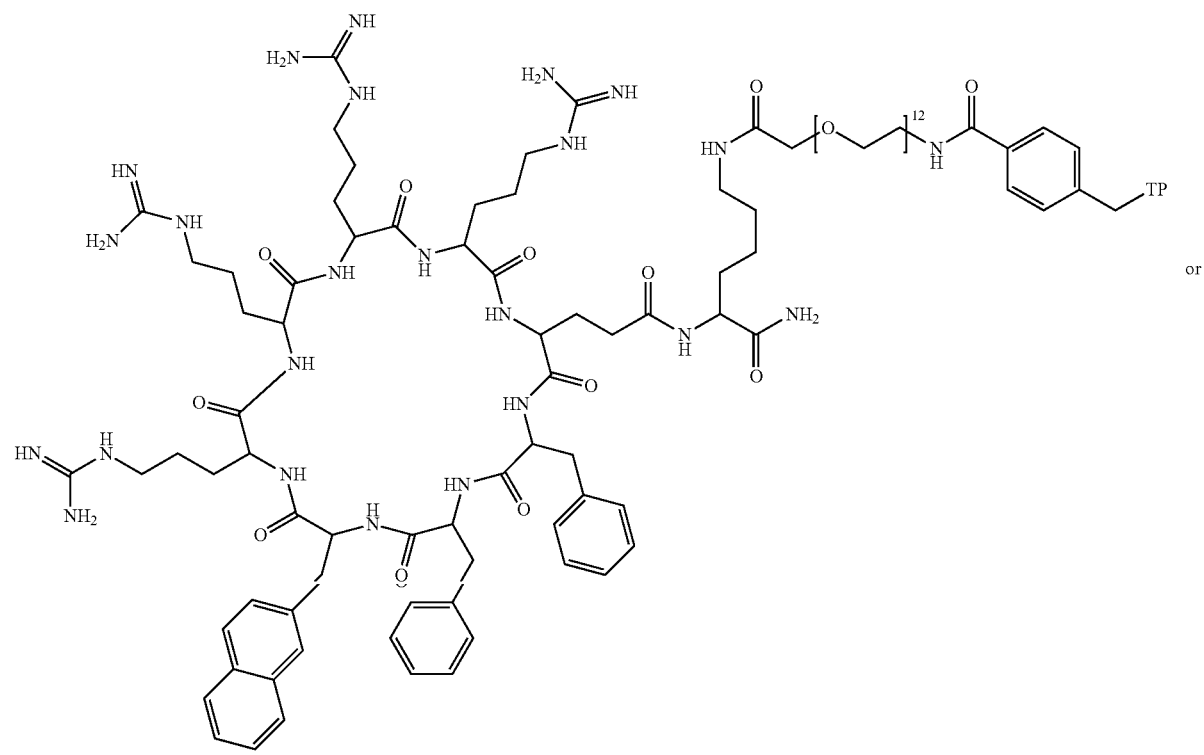
(V-B1)
or
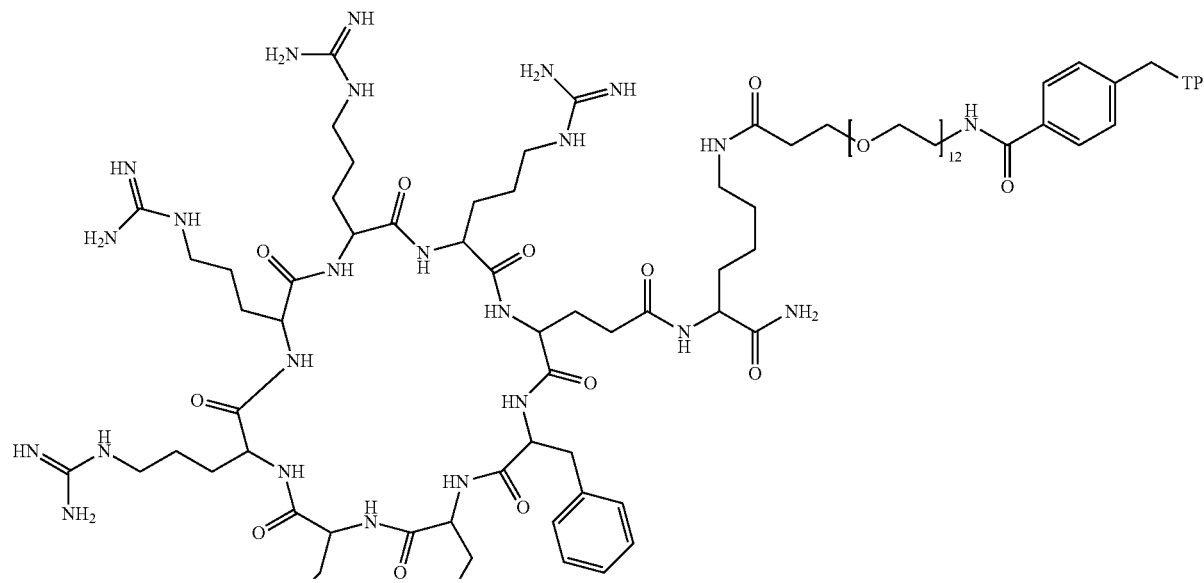
(V-B2)
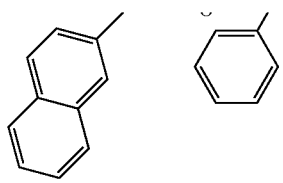

In other specific embodiments, the present disclosure provides a compound having the structure of Formula V-B3 or V-B4:
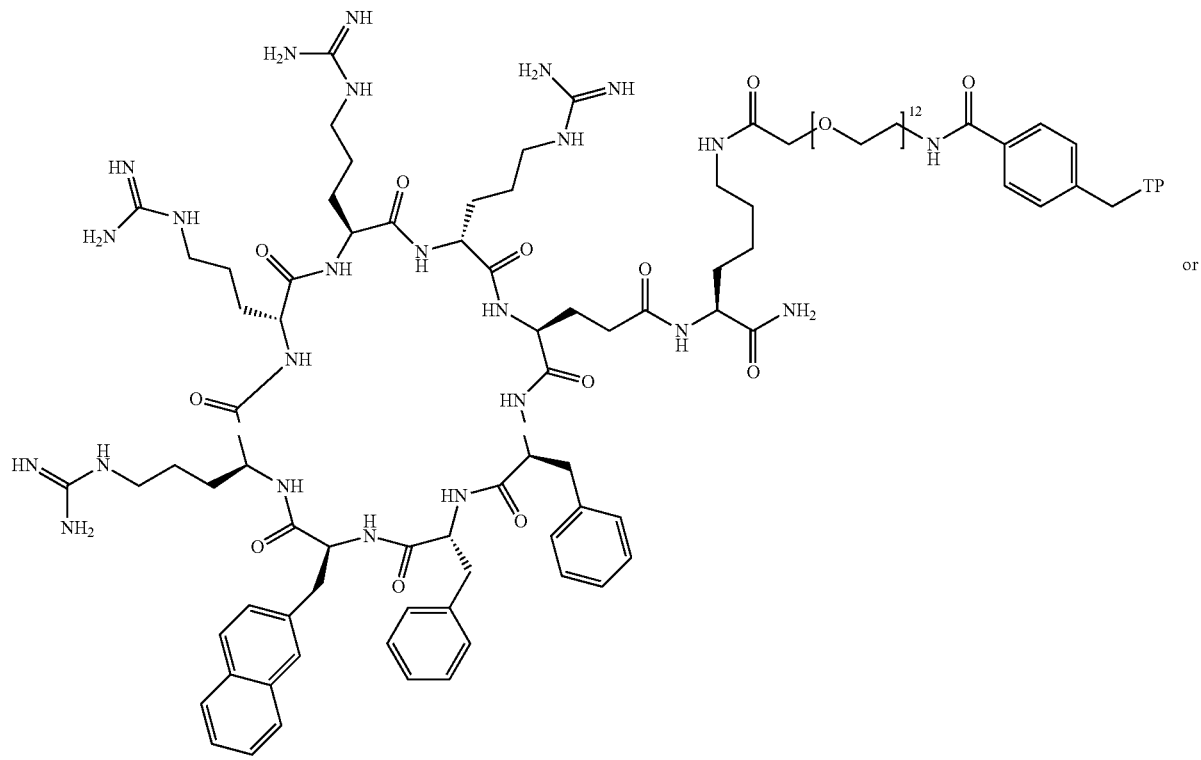
(V-B3)
or
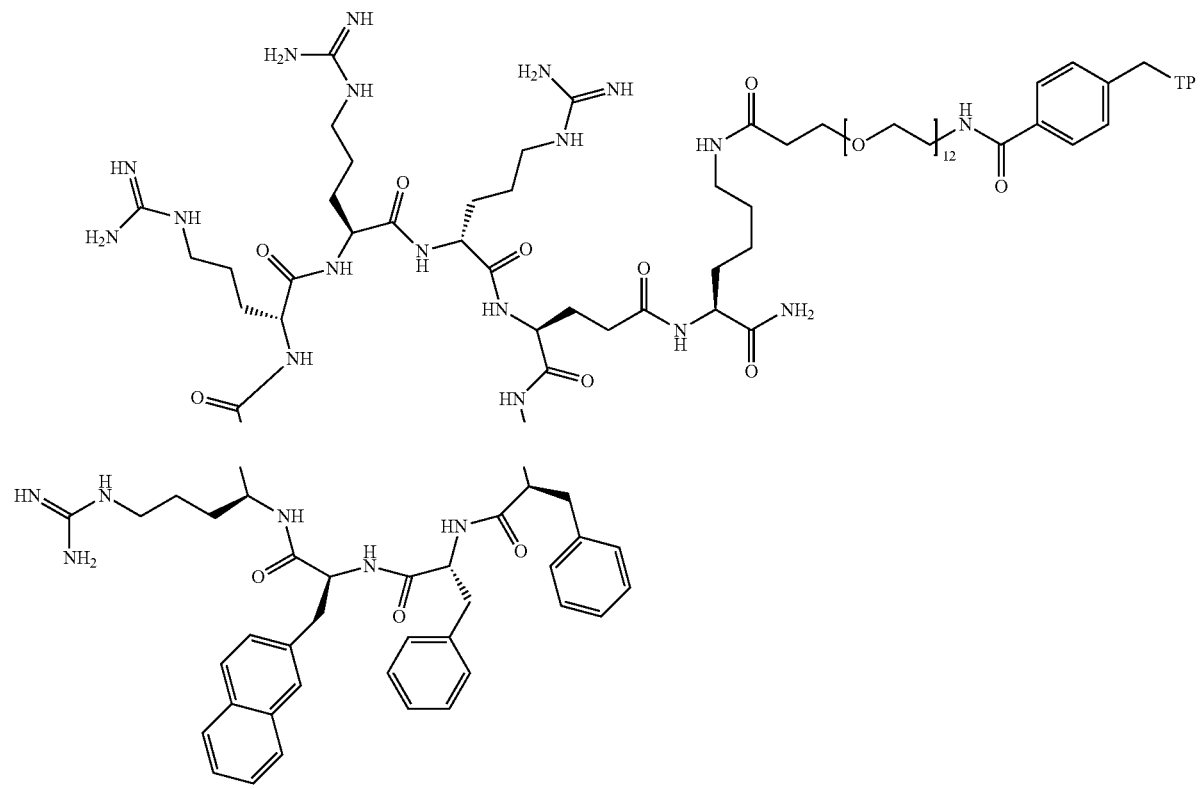
(V-B4)

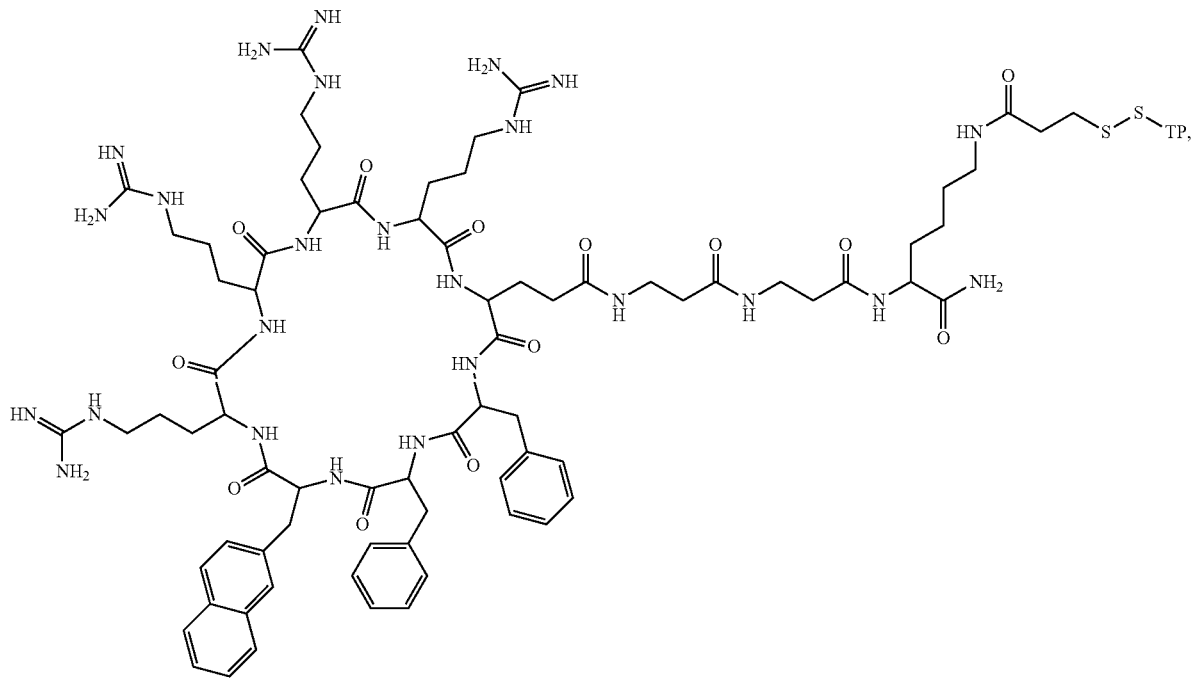

(V-B5)

The TP in any of the above structures may be any TP disclosed herein, including SEQ ID NO. 1, 2, 3, 4, 5, 6, 7, 8, 9, 10, 11, 12, and 13. Further, the TP may comprise a water-soluble polymer. In some embodiments, the water-soluble polymer comprises a PEG residue. In some embodiments, the PEG residue has a molecular weight ranging from about 1 kDa to about 100 kDa, e.g., from about 1 kDa to about 20 kDa, including about 10 kDa.

Cell-Penetrating Peptides

As discussed above, the compounds disclosed herein comprise cell-penetrating peptides (CPPs).

The CPP may be or include any amino sequence which facilitates cellular uptake of the compounds disclosed herein. Suitable CPPs for use in the compounds and methods described herein can include naturally occurring sequences, modified sequences, and synthetic sequences. In embodiments, the total number of amino acids in the CPP may be in the range of from 4 to about 20 amino acids, e.g., about 5, about 6, about 7, about 8, about 9, about 10, about 11, about 12, about 13, about 14, about 15, about 16, about 17, about 18, and about 19 amino acids, inclusive of all ranges and subranges therebetween. In some embodiments, the CPPs disclosed herein comprise about 4 to about to about 13 amino acids. In particular embodiments, the CPPs disclosed herein comprise about 6 to about 10 amino acids, or about 6 to about 8 amino acids.

Each amino acid in the CPP may be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Examples of suitable amino acids include, but are not limited to, alanine, alloisoleucine, arginine, asparagine, aspartic acid, cysteine, glutamine, glutamic acid, glycine, histidine, isoleucine, leucine, lysine, methionine, naphthylalanine, phenylalanine, proline, pyroglutamic acid, serine, threonine, tryptophan, tyrosine, valine, a derivative, or combinations thereof. These, and others, are listed in the Table 1 along with their abbreviations used herein.

TABLE 1

Amino Acid Abbreviations

| Amino Acid | Abbreviations* L-amino acid | Abbreviations* D-amino acid |
|---|---|---|
| Alanine | Ala (A) | ala (a) |
| Allo-isoleucine | AIle | aile |
| Arginine | Arg (R) | arg (r) |
| Asparagine | Asn (N) | asn (n) |
| aspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa (Σ) | pfa |
| glutamic acid | Glu (E) | glu (e) |
| glutamine | Gln (Q) | gln (q) |
| glycine | Gly (G) | gly (g) |
| histidine | His (H) | his (h) |
| Homoproline (aka pipecolic acid) | Pip (Θ) | pip (θ) |
| isoleucine | Ile (I) | ile (i) |
| leucine | Leu (L) | leu (l) |
| lysine | Lys ( K) | lys (k) |
| methionine | Met (M) | met (m) |
| napthylalanine | Nal (Φ) | nal (φ) |
| norleucine | Nle (Ω) | nle |
| phenylalanine | Phe (F) | phe (F) |
| phenylglycine | Phg (Ψ) | phg |
| 4-(phosphonodifluoromethyl) phenylalanine | F$_2$Pmp (Λ) | f$_2$pmp |
| proline | Pro (P) | pro (p) |
| sarcosine | Sar (Ξ) | sar |

TABLE 1-continued

Amino Acid Abbreviations

| Amino Acid | Abbreviations* L-amino acid | Abbreviations* D-amino acid |
|---|---|---|
| selenocysteine | Sec (U) | sec (u) |
| serine | Ser (S) | ser (s) |
| threonine | Thr (T) | thr (t) |
| tyrosine | Tyr (Y) | tyr (y) |
| tryptophan | Trp (W) | trp (w) |
| valine | Val (V) | val (v) |
| Tert-butyl-alanine | Tle | tle |
| Penicillamine | Pen | pen |
| Homoarginine | HomoArg | homoarg |
| Nicotinyl-lysine | Lys(NIC) | lys(NIC) |
| Trifluoroacetyl-lysine | Lys(TFA) | lys(TFA) |
| Methyl-leucine | MeLeu | meLeu |
| 3-(3-benzothienyl)-alanine | Bta | bta |

*single letter abbreviations: when shown in capital letters herein it indicates the L-amino acid form, when shown in lower case herein it indicates the D-amino acid form.

Non-limiting examples of linear CPPs include Polyarginine (e.g., $R_9$ or $R_{11}$), Antennapedia sequences, HIV-TAT, Penetratin, Antp-3A (Antp mutant), Buforin II. Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

In various embodiments, the cell-penetrating peptides of the present disclosure are cyclic cell-penetrating peptides (cCPPs) In some embodiment, CPPs are cyclized to form cCPP by forming a peptide bond between the N- and C-termini of two amino acids in a peptide sequence. In some embodiments, the cCPPs may include any combination of at least two arginines and at least two hydrophobic amino acids. In some embodiments, the cCPPs may include any combination of two to three arginines and at least two hydrophobic amino acids.

In some embodiments, the cCPP used in compounds described herein has a structure comprising Formula III:

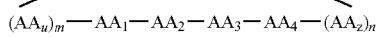

$$(AA_u)_m - AA_1 - AA_2 - AA_3 - AA_4 - (AA_z)_n$$

III wherein:
each of $AA_1$, $AA_2$, $AA_3$, and $AA_4$, are independently selected from a D or L amino acid,
each of $AA_u$ and $AA_z$, at each instance and when present, are independently selected from a D or L amino acid, and
m and n are independently selected from a number from 0 to 6; and
wherein:
at least two of $AA_u$, when present, $AA_1$, $AA_2$, $AA_3$, $AA_4$, and $AA_z$, when present, are independently arginine, and
at least two of $AA_u$, when present, $AA_1$, $AA_2$, $AA_3$, $AA_4$, and $AA_z$, when present, are independently a hydrophobic amino acid.

In some embodiments, each hydrophobic amino acid is independently selected from is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexyl alanine, norleucine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1,1'-biphenyl-4-yl)-alanine, tert-leucine, or nicotinoyl lysine, each of which is optionally substituted with one or more substituents. The structures of certain of these non-natural aromatic hydrophobic amino acids (prior to incorporation into the peptides disclosed herein) are provided below. In particular embodiments, each hydrophobic amino acid is independently a hydrophobic aromatic amino acid. In some embodiments, the aromatic hydrophobic amino acid is naphthylalanine, 3-(3-benzothienyl)-alanine, phenylglycine, homophenylalanine, phenylalanine, tryptophan, or tyrosine, each of which is optionally substituted with one or more substituents.

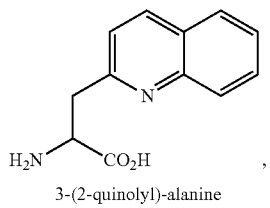

3-(2-quinolyl)-alanine

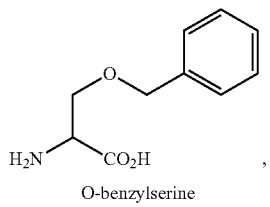

O-benzylserine

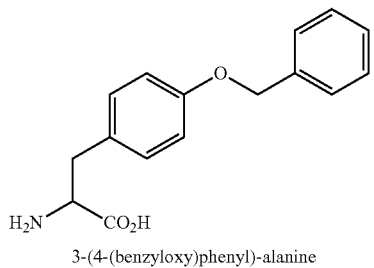

3-(4-(benzyloxy)phenyl)-alanine

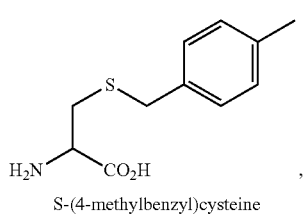

S-(4-methylbenzyl)cysteine

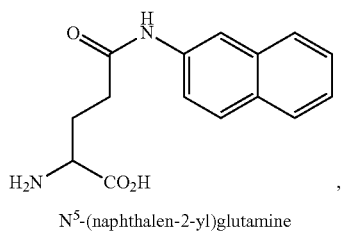

$N^5$-(naphthalen-2-yl)glutamine

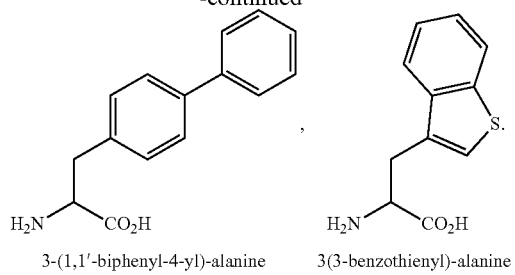

3-(1,1'-biphenyl-4-yl)-alanine    3(3-benzothienyl)-alanine

The optional substituent can be any atom or group which does not significantly reduce (e.g., by more than 50%) the cytosolic delivery efficiency of the cCPP, e.g., compared to an otherwise identical sequence which does not have the substituent. In some embodiments, the optional substituent can be a hydrophobic substituent or a hydrophilic substituent. In certain embodiments, the optional substituent is a hydrophobic substituent. In some embodiments, the substituent increases the solvent-accessible surface area (as defined herein) of the hydrophobic amino acid. In some embodiments, the substituent can be a halogen, alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio. In some embodiments, the substituent is a halogen.

Amino acids having higher hydrophobicity values can be selected to improve cytosolic delivery efficiency of a cCPP relative to amino acids having a lower hydrophobicity value. In some embodiments, each hydrophobic amino acid independently has a hydrophobicity value which is greater than that of glycine. In other embodiments, each hydrophobic amino acid independently is a hydrophobic amino acid having a hydrophobicity value which is greater than that of alanine. In still other embodiments, each hydrophobic amino acid independently has a hydrophobicity value which is greater or equal to phenylalanine. Hydrophobicity may be measured using hydrophobicity scales known in the art. Table 2 below lists hydrophobicity values for various amino acids as reported by Eisenberg and Weiss (Proc. Natl. Acad. Sci. U.S.A. 1984; 81(1): 140-144), Engleman, et al. (Ann. Rev. of Biophys. Biophys. Chem. 1986; 1986(15); 321-53), Kyte and Doolittle (J. Md. Biol. 1982; 157(1); 105-132), Hoop and Woods (Proc. Natl. Acad. Sci. U.S.A. 1981; 78(6):3824-3828), and Janin (Nature. 1979, 277(5696):491-492), the entirety of each of which is herein incorporated by reference in its entirety. In particular embodiments, hydrophobicity is measured using the hydrophobicity scale reported in Engleman, et al.

TABLE 2

| Amino Acid | Group | Eisenberg and Weiss | Englemon et al. | Kyrie and Doolittle | Hoop and Woods | Janin |
|---|---|---|---|---|---|---|
| Ile | Nonpolar | 0.73 | 3.1 | 4.5 | -1.8 | 0.7 |
| Phe | Nonpolar | 0.61 | 3.7 | 2.8 | -2.5 | 0.5 |
| Val | Nonpolar | 0.54 | 2.6 | 4.2 | -1.5 | 0.6 |
| Leu | Nonpolar | 0.53 | 2.8 | 3.8 | -1.8 | 0.5 |
| Trp | Nonpolar | 0.37 | 1.9 | -0.9 | -3.4 | 0.3 |
| Met | Nonpolar | 0.26 | 3.4 | 1.9 | -1.3 | 0.4 |
| Ala | Nonpolar | 0.25 | 1.6 | 1.8 | -0.5 | 0.3 |
| Gly | Nonpolar | 0.16 | 1.0 | -0.4 | 0.0 | 0.3 |
| Cys | Unch/Polar | 0.04 | 2.0 | 2.5 | -1.0 | 0.9 |
| Tyr | Unch/Polar | 0.02 | -0.7 | -1.3 | -2.3 | -0.4 |
| Pro | Nonpolar | -0.07 | -0.2 | -1.6 | 0.0 | -0.3 |

TABLE 2-continued

| Amino Acid | Group | Eisenberg and Weiss | Englemon et al. | Kyrie and Doolittle | Hoop and Woods | Janin |
|---|---|---|---|---|---|---|
| Thr | Unch/Polar | -0.18 | 1.2 | -0.7 | -0.4 | -0.2 |
| Ser | Unch/Polar | -0.26 | 0.6 | -0.8 | 0.3 | -0.1 |
| His | Charged | -0.40 | -3.0 | -3.2 | -0.5 | -0.1 |
| Glu | Charged | -0.62 | -8.2 | -3.5 | 3.0 | -0.7 |
| Asn | Unch/Polar | -0.64 | -4.8 | -3.5 | 0.2 | -0.5 |
| Gln | Unch/Polar | -0.69 | -4.1 | -3.5 | 0.2 | -0.7 |
| Asp | Charged | -0.72 | -9.2 | -3.5 | 3.0 | -0.6 |
| Lys | Charged | -1.10 | -8.8 | -3.9 | 3.0 | -1.8 |
| Arg | Charged | -1.80 | -12.3 | -4.5 | 3.0 | -1.4 |

The chirality of the amino acids can be selected to improve cytosolic uptake efficiency. In some embodiments, at least two of the amino acids have the opposite chirality. In some embodiments, the at least two amino acids having the opposite chirality can be adjacent to each other. In some embodiments, at least three amino acids have alternating stereochemistry relative to each other. In some embodiments, the at least three amino acids having the alternating chirality relative to each other can be adjacent to each other. In some embodiments, at least two of the amino acids have the same chirality. In some embodiments, the at least two amino acids having the same chirality can be adjacent to each other. In some embodiments, at least two amino acids have the same chirality and at least two amino acids have the opposite chirality. In some embodiments, the at least two amino acids having the opposite chirality can be adjacent to the at least two amino acids having the same chirality. Accordingly, in some embodiments, adjacent amino acids in the cCPP can have any of the following sequences: D-L; L-D; D-L-L-D; L-D-D-L; L-D-L-L-D; D-L-D-D-L; D-L-L-D-L; or L-D-D-L-D.

In some embodiments, an arginine is adjacent to a hydrophobic amino acid. In some embodiments, the arginine has the same chirality as the hydrophobic amino acid. In some embodiments, at least two arginines are adjacent to each other. In still other embodiments, three arginines are adjacent to each other. In some embodiments, at least two hydrophobic amino acids are adjacent to each other. In other embodiments, at least three hydrophobic amino acids are adjacent to each other. In other embodiments, the cCPPs described herein comprise at least two consecutive hydrophobic amino acids and at least two consecutive arginines. In further embodiments, one hydrophobic amino acid is adjacent to one of the arginines. In still other embodiments, the cCPPs described herein comprise at least three consecutive hydrophobic amino acids and there consecutive arginines. In further embodiments, one hydrophobic amino acid is adjacent to one of the arginines. These various combinations of amino acids can have any arrangement of D and L amino acids, e.g., the sequences described above.

In some embodiments, any four adjacent amino acids in the cCPPs described herein (e.g., the cCPPs according to Formula 2) can have one of the following sequences. $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$, wherein each of $AA_{H1}$ and $AA_{H2}$ are independently a hydrophobic amino acid. Accordingly, in some embodiments, the cCPPs used in the compounds described herein comprise a structure according any of Formula IV-A-D:

IV-A

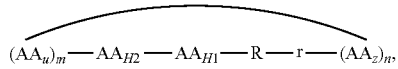

-continued

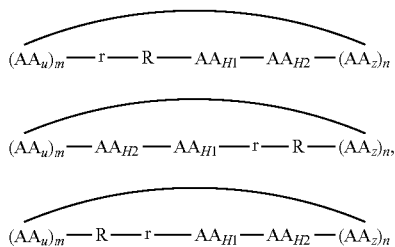

wherein:
each of $AA_{H1}$ and $AA_{H2}$ are independently a hydrophobic amino acid;
at each instance and when present, each of $AA_U$ and $AA_Z$ are independently any amino acid; and
m and n are independently selected from a number from 0 to 6.

In some embodiments, the total number of amino acids (including r, R, $AA_{H1}$, $AA_{H2}$), in the CPPs of Formula 4-A to 4-D are in the range of 6 to 10. In some embodiments, the total number of amino acids is 6. In some embodiments, the total number of amino acids is 7. In some embodiments, the total number of amino acids is 8. In some embodiments, the total number of amino acids is 9. In some embodiments, the total number of amino acids is 10.

In some embodiments, the sum of m and n is from 2 to 6. In some embodiments, the sum of m and n is 2. In some embodiments, the sum of m and n is 3. In some embodiments, the sum of m and n is 4. In some embodiments, the sum of m and n is 5. In some embodiments, the sum of m and n is 6. In some embodiments, m is 0. In some embodiments, m is 1. In some embodiments, m is 2 In some embodiments, m is 3. In some embodiments, m is 4. In some embodiments, m is 5. In some embodiments, m is 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, each hydrophobic amino acid is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, or norleucine, each of which is optionally substituted with one or more substituents. In particular embodiments, each hydrophobic amino acid is independently a hydrophobic aromatic amino acid. In some embodiments, the aromatic hydrophobic amino acid is piperidine-2-carboxylic acid, naphthylalanine, phenylglycine, homophenylalanine, phenylalanine, tryptophan, or tyrosine, each of which is optionally substituted with one or more substituents. In particular embodiments, the hydrophobic amino acid is piperidine-2-carboxylic acid, naphthylalanine, tryptophan, or phenylalanine, each of which is optionally substituted with one or more substituents.

In some embodiments, each of $AA_{H1}$ and $AA_{H2}$ are independently a hydrophobic amino acid having a hydrophobicity value which is greater than that of glycine. In other embodiments, each of $AA_{H1}$ and $AA_{H2}$ are independently a hydrophobic amino acid having a hydrophobicity value which is greater than that of alanine. In still other embodiments, each of $AA_{H1}$ and $AA_{H2}$ are independently an hydrophobic amino acid having hydrophobicity value which is greater than that of phenylalanine, e.g., as measured using the hydrophobicity scales described above, including Eisenbergand Weiss (Proc. Natl. Acad. Sci. U.S.A. 1984; 81 (1):140-144), Engleman, et al (Ann. Rev. of Biophys. Biophys. Chem. 1986(15); 321-53), Kyte and Doolittle (J. Mol. Biol. 1982; 157(1). 105-132), Hoop and Woods (Proc. Natl. Acad. Sci. U.S.A. 1981; 78(6):3824-3828), and Janin (Nature. 1979; 277(5696):491-492), (see Table 1 above). In particular embodiments, hydrophobicity is measured using the hydrophobicity scale reported in Engleman, et al.

The presence of a hydrophobic amino acid on the N- or C-terminal of a D-Arg or L-Arg, or a combination thereof, has also found to improve the cytosolic uptake of the cCPP (and the attached cargo). For example, in some embodiments, the cCPPs disclosed herein may include $AA_{H1}$-D-Arg or D-Arg-$AA_{H1}$. In other embodiments, the cCPPs disclosed herein may include $AA_{H1}$-L-Arg or L-Arg-$AA_{H1}$.

The size of the hydrophobic amino acid on the N- or C-terminal of the D-Arg or an L-Arg, or a combination thereof (i.e., $AA_{H1}$), may be selected to improve cytosolic delivery efficiency of the CPP. For example, a larger hydrophobic amino acid on the N- or C-terminal of a D-Arg or L-Arg, or a combination thereof, improves cytosolic delivery efficiency compared to an otherwise identical sequence having a smaller hydrophobic amino acid. The size of the hydrophobic amino acid can be measured in terms of molecular weight of the hydrophobic amino acid, the steric effects of the hydrophobic amino acid, the solvent-accessible surface area (SASA) of the side chain, or combinations thereof. In some embodiments, the size of the hydrophobic amino acid is measured in terms of the molecular weight of the hydrophobic amino acid, and the larger hydrophobic amino acid has a side chain with a molecular weight of at least about 90 g/mol, or at least about 130 g/mol, or at least about 141 g/mol. In other embodiments, the size of the amino acid is measured in terms of the SASA of the hydrophobic side chain, and the larger hydrophobic amino acid has a side chain with a SASA greater than alanine, or greater than glycine. In other embodiments, $AA_{H1}$ has a hydrophobic side chain with a SASA greater than or equal to about piperidine-2-carboxylic acid, greater than or equal to about tryptophan, greater than or equal to about phenylalanine, or equal to or greater than about naphthylalanine. In some embodiments, $AA_{H1}$ has a side chain side with a SASA of at least about 200 Å$^2$, at least about 210 Å2, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, AAH$_2$ has a side chain side with a SASA of at least about 200 Å$^2$, at least about 210 Å2, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the side chains of AAH$_1$ and AAH$_2$ have a combined SASA of at least about 350 Å$^2$, at least about 360 Å$^2$, at least about 370 Å$^2$, at least about 380 Å$_2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å$^2$, at least about 510 Å$^2$, at least about 520 Å$^2$, at least about 530 Å$^2$, at least about 540 Å$^2$, at least about 550 Å$^2$, at least about 560 Å$^2$, at least about 570 Å$^2$, at least about 580 Å$^2$, at least about 590 Å$^2$, at least about 600 Å$^2$, at least about 610 Å$^2$, at least about 620 Å$^2$, at least about 630 Å$^2$, at least about 640 Å$^2$, greater than about 650 Å², at least about 660 Å², at least about 670 Å², at least about 680 Å², at least about 690 Å², or at least about 700 Å². In some embodiments, $AA_{H2}$ is a hydrophobic amino acid with a side chain having a SASA that is less than or equal to the SASA of the hydrophobic side chain of $AA_{H1}$. By way of example, and not by limitation, a cCPP having a Nal-Arg motif exhibits improved cytosolic delivery efficiency compared to an otherwise identical CPP having a Phe-Arg motif; a cCPP having a Phe-Nal-Arg motif exhibits improved cytosolic delivery efficiency compared to an otherwise identical cCPP having a Nal-Phe-Arg motif; and a phe-Nal-Arg motif exhibits improved cytosolic delivery efficiency compared to an otherwise identical cCPP having a nal-Phe-Arg motif.

As used herein, "hydrophobic surface area" or "SASA" refers to the surface area (reported as square Angstroms, Å²) of an amino acid side chain that is accessible to a solvent. In particular embodiments, SASA is calculated using the 'rolling ball' algorithm developed by Shrake & Rupley (*J Mol Biol.* 79(2): 351-71), which is herein incorporated by reference in its entirety for all purposes. This algorithm uses a "sphere" of solvent of a particular radius to probe the surface of the molecule. A typical value of the sphere is 1.4 Å, which approximates to the radius of a water molecule.

SASA values for certain side chains are shown below in Table 3. In certain embodiments, the SASA values described herein are based on the theoretical values listed in Table 3 below, as reported by Tien, et al (PLOS ONE 8(11): e80635. https://doi.org/10.1371/journal.pone.0080635, which is herein incorporated by reference in its entirety for all purposes.

TABLE 3

| Residue | Theoretical | Empirical | Miller et al. (1987) | Rose et al. (1985) |
|---|---|---|---|---|
| Alanine | 129.0 | 121.0 | 113.0 | 118.1 |
| Arginine | 274.0 | 265.0 | 241.0 | 256.0 |
| Asparagine | 195.0 | 187.0 | 158.0 | 165.5 |
| Aspartate | 193.0 | 187.0 | 151.0 | 158.7 |
| Cysteine | 167.0 | 148.0 | 140.0 | 146.1 |
| Glutamate | 223.0 | 214.0 | 183.0 | 186.2 |
| Glutamine | 225.0 | 214.0 | 189.0 | 193.2 |
| Glycine | 104.0 | 97.0 | 85.0 | 88.1 |
| Histidine | 224.0 | 216.0 | 194.0 | 202.5 |
| Isoleucine | 197.0 | 195.0 | 182.0 | 181.0 |
| Leucine | 201.0 | 191.0 | 180.0 | 193.1 |
| Lysine | 236.0 | 230.0 | 211.0 | 225.8 |
| Methionine | 224.0 | 203.0 | 204.0 | 203.4 |
| Phenylalanine | 240.0 | 228.0 | 218.0 | 222.8 |
| Proline | 159.0 | 154.0 | 143.0 | 146.8 |
| Serine | 155.0 | 143.0 | 122.0 | 129.8 |
| Threonine | 172.0 | 163.0 | 146.0 | 152.5 |
| Tryptophan | 285.0 | 264.0 | 259.0 | 266.3 |
| Tyrosine | 263.0 | 255.0 | 229.0 | 236.8 |
| Valine | 174.0 | 165.0 | 160.0 | 164.5 |

In some embodiments, the cCPP does not include a hydrophobic amino acid on the N- and/or C-terminal of $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$. In alternative embodiments, the cCPP does not include a hydrophobic amino acid having a side chain which is larger (as described herein) than at least one of $AA_{H1}$ or $AA_{H2}$. In further embodiments, the cCPP does not include a hydrophobic amino acid with a side chain having a surface area greater than $AA_{H1}$. For example, in embodiments in which at least one of $AA_{H1}$ or $AA_{H2}$ is phenylalanine, the cCPP does not further include a naphthylalanine (although the cCPP may include at least one hydrophobic amino acid which is smaller than $AA_{H1}$ and $AA_{H2}$, e.g., leucine). In still other embodiments, the cCPP does not include a naphthylalanine in addition to the hydrophobic amino acids in $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$.

The chirality of the amino acids (i.e., D or L amino acids) can be selected to improve cytosolic delivery efficiency of the cCPP (and the attached cargo as described below). In some embodiments, the hydrophobic amino acid on the N- or C-terminal of an arginine (e.g., $AA_{H1}$) has the same or opposite chirality as the adjacent arginine. In some embodiments, $AA_{H1}$ has the opposite chirality as the adjacent arginine. For example, when the arginine is D-arg (i.e. "r"), $AA_{H1}$ is a D-$AA_{H1}$, and when the arginine is L-Arg (i.e., "R"), $AA_{H1}$ is a L-$AA_{H1}$. Accordingly, in some embodiments, the cCPPs disclosed herein may include at least one of the following motifs: D-$AA_{H1}$-D-arg, D-arg-D-$AA_{H1}$, L-$AA_{H1}$-L-Arg, or L-Arg-L$AA_{H1}$. In particular embodiments, when arginine is D-arg, $AA_{H1}$ can be D-nal, D-trp, or D-phe. In another non-limiting example, when arginine is L-Arg, $AA_{H1}$ can be L-Nal, L-Trp, or L-Phe.

In some embodiments, the cCPPs described herein include at least three arginines. Accordingly, in some embodiments, the cCPPs described herein include one of the following sequences: $AA_{H2}$-$AA_{H1}$-R-r-R, $AA_{H2}$-$AA_{H1}$-R-r-r, $AA_{H2}$-$AA_{H1}$-r-R-R, $AA_{H2}$-$AA_{H1}$-r-R-r, R-R-r-$AA_{H1}$-$AA_{H2}$, r-R-r-$AA_{H1}$-$AA_{H2}$, r-r-R-$AA_{H1}$-$AA_{H2}$, or, R-r-R-$AA_{H1}$-$AA_{H2}$. In particular embodiments, the cCPPs have one of the following sequences $AA_{H2}$-$AA_{H1}$-R-r-R, $AA_{H2}$-$AA_{H1}$-r-R-r, r-R-r-$AA_{H1}$-$AA_{H2}$, or R-r-R-$AA_{H1}$-$AA_{H2}$. In some embodiments, the chirality of $AA_{H1}$ and $AA_{H2}$ can be selected to improve cytosolic uptake efficiency, e.g., as described above, where $AA_{H1}$ has the same chirality as the adjacent arginine, and $AA_{H1}$ and $AA_{H2}$ have the opposite chirality.

In some embodiments, the cCPPs described herein include three hydrophobic amino acids. Accordingly, in some embodiments, the cCPPs described herein include one of the following sequences: $AA_{H3}$-$AA_{H2}$-$AA_{H1}$-R-r, $AA_{H3}$-$AA_{H2}$-$AA_{H1}$-R-r, $AA_{H3}$-$AA_{H2}$-$AA_{H1}$-r-R, $AA_{H3}$-$AA_{H2}$-$AA_{H1}$-r-R, R-r-$AA_{H1}$-$AA_{H2}$-$AA_{H3}$, R-r-$AA_{H1}$-$AA_{H2}$-$AA_{H3}$, r-R-$AA_{H1}$-$AA_{H2}$-$AA_{H3}$, or, T-R-$AA_{H1}$-$AA_{H2}$-$AA_{H3}$, wherein $AA_{H3}$ is any hydrophobic amino acid described above, e.g., piperidine-2-carboxylic acid, naphthylalanine, tryptophan, or phenylalanine. In some embodiments, the chirality of $AA_{H1}$, $AA_{H2}$, and $AA_{H3}$ can be selected to improve cytosolic uptake efficiency, e.g., as described above, where $AA_{H1}$ has the same chirality as the adjacent arginine, and $AA_{H1}$ and $AA_{H2}$ have the opposite chirality. In other embodiments, the size of $AA_{H1}$, $AA_{H2}$, and $AA_{H3}$ can be selected to improve cytosolic uptake efficiency, e.g., as described above, where $AA_{H3}$ has a SAS of less than or equal to $AA_{H1}$ and/or $AA_{H2}$.

In some embodiments, $AA_{H1}$ and $AA_{H2}$ have the same or opposite chirality. In certain embodiments, $AA_{H1}$ and $AA_{H2}$ have the opposite chirality. Accordingly, in some embodiments, the cCPPs disclosed herein include at least one of the following sequences. D-$AA_{H2}$-L-$AA_{H1}$-R-r; L-$AA_{H2}$-D-$AA_{H1}$-r-R; R-r-D-$AA_{H1}$-L-$AA_{H2}$; or r-R-L-$AA_{H1}$-D-$AA_{H1}$, wherein each of D-$AA_{H1}$ and D-$AA_{H2}$ is a hydrophobic amino acid having a D configuration, and each of L-$AA_{H1}$ and L-$AA_{H2}$ is a hydrophobic amino acid having an L configuration. In some embodiments, each of D-$AA_{H1}$ and D-$AA_{H2}$ is independently selected from the group consisting of D-pip, D-nal, D-trp, and D-phe. In particular embodiments, D-$AA_{H1}$ or D-$AA_{H2}$ is D-nal. In other particular embodiments, D-$AA_{H1}$ is D-nal. In some embodiments, each of L-$AA_{H1}$ and L-$AA_{H2}$ is independently selected from the group consisting of L-Pip, L-Nal, L-Trp, and L-Phe. In particular embodiments, each of L-AA$_{H1}$ and L-AA$_{H2}$ is L-Nal. In other particular embodiments, L-AA$_{H1}$ is L-Nal.

As discussed above, the disclosure provides for various modifications to a cCPP which may improve cytosolic delivery efficiency. In some embodiments, improved cytosolic uptake efficiency can be measured by comparing the cytosolic delivery efficiency of the CPP having the modified sequence to a proper control sequence. In some embodiments, the control sequence does not include a particular modification (e.g., matching chirality of R and AA$_{H1}$) but is otherwise identical to the modified sequence. In other embodiments, the control has the following sequence: cyclic (FΦRRRRQ).

As used herein cytosolic delivery efficiency refers to the ability of a cCPP to traverse a cell membrane and enter the cytosol. In embodiments, cytosolic delivery efficiency of the cCPP is not dependent on a receptor or a cell type. Cytosolic delivery efficiency can refer to absolute cytosolic delivery efficiency or relative cytosolic delivery efficiency.

Absolute cytosolic delivery efficiency is the ratio of cytosolic concentration of a cCPP (or a cCPP-TP conjugate) over the concentration of the CPP (or the CPP-TP conjugate) in the growth medium. Relative cytosolic delivery efficiency refers to the concentration of a cCPP in the cytosol compared to the concentration of a control cCPP in the cytosol. Quantification can be achieved by fluorescently labeling the cCPP (e.g., with a FTIC dye) and measuring the fluorescence intensity using techniques well-known in the art.

In particular embodiments, relative cytosolic delivery efficiency is determined by comparing (i) the amount of a CPP of the invention internalized by a cell type (e.g., HeLa cells) to (ii) the amount of the control CPP internalized by the same cell type. To measure relative cytosolic delivery efficiency, the cell type may be incubated in the presence of a cell-penetrating peptide of the invention for a specified period of time (e.g., 30 minutes, 1 hour, 2 hours, etc.) after which the amount of the CPP internalized by the cell is quantified using methods known in the art, e.g., fluorescence microscopy. Separately, the same concentration of the control cCPP is incubated in the presence of the cell type over the same period of time, and the amount of the control cCPP internalized by the cell is quantified.

In other embodiments, relative cytosolic delivery efficiency can be determined by measuring the IC$_{50}$ of a cCPP having a modified sequence for an intracellular target, and comparing the IC$_{50}$ of the cCPP having the modified sequence to a proper control sequence (as described herein).

In some embodiments, the relative cytosolic delivery efficiency of the cCPP-TP conjugates described herein in the range of from about 1% to about 1000% compared to cyclo(FΦRRRRQ), e.g., about 5%, about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 510%, about 520%, about 530%, about 540%, about 550%, about 560%, about 570%, about 580%, about 590%, about 600%, about 610%, about 620%, about 630%, about 640%, about 650%, about 660%, about 670%, about 680%, about 690%, about 700%, about 710%, about 720%, about 730%, about 740%, about 750%, about 760%, about 770%, about 780%, about 790%, about 800%, about 810%, about 820%, about 830%, about 840%, about 850%, about 860%, about 870%, about 880%, about 890%, about 900%, about 910%, about 920%, about 930%, about 940%, about 950%, about 960%, about 970%, about 980%, about 990%, about 1000%, inclusive of all values and subranges therebetween. cyclo(FΦRRRRQ).

In other embodiments, the absolute cytosolic delivery efficacy of from about 40% to about 100%, e.g., about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, inclusive of all values and subranges therebetween.

In some embodiments, the cCPP may be or include any of the sequences listed in Table 4. That is, the cCPPs used in the compounds disclosed herein may comprise any one of the sequences listed in Table 4, along with additional amino acids to form a cyclic sequence, or the sequences in the Table 4 may be cyclized (via a peptide bond) to form a cCPP. In some embodiments, the amino acids listed in Table 4 further include a glutamine residue or other amino acid that has a side chain that allows for conjugation of the TP.

TABLE 4

| ID | Sequence |
| --- | --- |
| PCT 1 | FΦRRR (SEQ ID NO: 14) |
| PCT 2 | FΦRRRC (SEQ ID NO: 15) |
| PCT 3 | FΦRRRU (SEQ ID NO: 16) |
| PCT 4 | RRRΦF (SEQ ID NO: 17) |
| PCT 5 | RRRRΦF (SEQ ID NO 18) |
| PCT 6 | FΦRRRR (SEQ ID NO: 19) |
| PCT 7 | FφrRrR (SEQ ID NO: 20) |
| PCT 8 | FφrRrR (SEQ ID NO: 20) |
| PCT 9 | FΦRRRR (SEQ ID NO: 19) |
| PCT 10 | fΦRrRr (SEQ ID NO: 21) |
| PCT 11 | RRFRΦR (SEQ ID NO: 22) |
| PCT 12 | FRRRRΦ (SEQ ID NO: 23) |
| PCT 13 | rRFRΦR (SEQ ID NO: 24) |
| PCT 14 | RRΦFRR (SEQ ID NO: 25) |
| PCT 15 | CRRRRFW (SEQ ID NO: 26) |
| PCT 16 | FfΦRrRr(SEQ ID NO: 27) |
| PCT 17 | FFΦRRRR (SEQ ID NO: 28) |
| PCT 18 | RFRFRΦR (SEQ ID NO: 29) |
| PCT 19 | URRRRFW (SEQ ID NO: 30) |
| PCT 20 | CRRRRFW (SEQ ID NO: 31) |
| PCT 21 | FΦRRRRQK (SEQ ID NO: 32) |
| PCT 22 | FΦRRRRQC (SEQ ID NO: 33) |
| PCT 23 | fΦRrRrRQ (SEQ ID NO: 34) |
| PCT 24 | FΦRRRRRQ (SEQ ID NO: 35) |
| PCT 25 | RRRRΦFDΩC (SEQ ID NO: 36) |
| PCT 26 | FΦRRR (SEQ ID NO: 14) |
| PCT 27 | FWRRR (SEQ ID NO: 37) |
| PCT 28 | RRRΦF (SEQ ID NO: 17) |
| PCT 29 | RRRWF (SEQ ID) NO: 38) |
| SAR 1 | FΦRRRR (SEQ ID NO: 19) |
| SAR 19 | FFRRR (SEQ ID NO: 39) |
| SAR 20 | FFrRr (SEQ ID NO: 40) |
| SAR 21 | FFRrR (SEQ ID NO: 41) |
| SAR 22 | FRFRR (SEQ ID NO: 42) |
| SAR 23 | FRRFR (SEQ ID NO: 43) |
| SAR 24 | FRRRF (SEQ ID NO: 44) |
| SAR 25 | GΦRRR (SEQ ID NO: 45) |
| SAR 26 | FFFRA (SEQ ID NO: 46) |
| SAR 27 | FFFRR (SEQ ID NO: 47) |
| SAR 28 | FFRRRR (SEQ ID NO: 48) |
| SAR 29 | FRRFRR (SEQ ID NO: 49) |
| SAR 30 | FRRRFR (SEQ ID NO: 50) |
| SAR 31 | RFFRRR (SEQ ID NO: 51) |
| SAR 32 | RFRRFR (SEQ ID NO: 52) |
| SAR 33 | FRFRRR (SEQ ID NO: 53) |
| SAR 34 | FFFRRR (SEQ ID NO: 54) |
| SAR 35 | FFRRRF (SEQ ID NO: 55) |

TABLE 4-continued

| ID | Sequence |
|---|---|
| SAR 36 | FRFFRR (SEQ ID NO: 56) |
| SAR 37 | RRFFFR (SEQ ID NO: 57) |
| SAR 38 | FFRFRR (SEQ ID NO: 58) |
| SAR 39 | FFRRFR (SEQ ID NO: 59) |
| SAR 40 | FRRFFR (SEQ ID NO: 60) |
| SAR 41 | FRRFRF (SEQ ID NO: 61) |
| SAR 42 | FRFRFR (SEQ ID NO: 62) |
| SAR 43 | RFFRFR (SEQ ID NO: 63) |
| SAR 44 | GΦRRRR (SEQ ID NO: 64) |
| SAR 45 | FFFFRRR (SEQ ID NO: 65) |
| SAR 46 | RFFRRRR (SEQ ID NO: 66) |
| SAR 47 | RRFFRRR (SEQ ID NO: 67) |
| SAR 48 | RFFFRRR (SEQ ID NO: 68) |
| SAR 49 | RRFFFRR (SEQ ID NO: 69) |
| SAR 50 | FFRRFRR (SEQ ID NO: 70) |
| SAR 51 | FFRRRRF (SEQ ID NO: 71) |
| SAR 52 | FRRFFRR (SEQ ID NO: 72) |
| SAR 53 | FFFRRRRR (SEQ ID NO: 73) |
| SAR 54 | FFFRRRRRR (SEQ ID NO: 74) |
| SAR 55 | FΦRrRr (SEQ ID NO: 75) |
| SAR 56 | XXRRRR (SEQ ID NO: 76) |
| SAR 57 | FfFRrR (SEQ ID NO: 77) |
| SAR 58 | fFfrRr (SEQ ID NO: 78) |
| SAR 59 | fFfRrR (SEQ ID NO: 79) |
| SAR 60 | FfFrRr (SEQ ID NO: 80) |
| SAR 61 | fFΦrRr (SEQ ID NO: 81) |
| SAR 62 | fΦfrRr (SEQ ID NO: 82) |
| SAR 63 | ΦFfrRr (SEQ ID NO: 83) |
| SAR 64 | FΦrRr (SEQ ID NO: 84) |
| SAR 65 | fΦrRr (SEQ ID NO: 85) |
| SAR 66 | Ac-(Lys-fFRrRrD) (SEQ ID NO: 86) |
| SAR 67 | Ac-(Dap-fFRrRrD) (SEQ ID NO: 87) |
| SAR 68 | CWWRRRRC (disulfide S—S) (SEQ NO: 88) |
| SAR 69 | CWWVRRRC (disulfide S—S) (SEQ NO: 89) |
| SAR 70 | CFWRRRRC (disulfide S—S) (SEQ NO: 90) |
| SAR 71 | CWWWRRRC (disulfide S—S) (SEQ NO: 91) |
| Pin1 15 | Pip-Nal-Arg-Glu-arg-arg-glu (SEQ ID NO: 92) |
| Pin1 16 | Pip-Nal-Arg-Arg-arg-arg-glu (SEQ ID NO: 93) |
| Pin1 17 | Pip-Nal-Nal-Arg-arg-arg-glu (SEQ ID NO: 94) |
| Pin1 18 | Pip-Nal-Nal-Arg-arg-arg-Glu (SEQ ID NO: 95) |
| Pin1 19 | Pip-Nal-Phe-Arg-arg-arg-glu (SEQ ID NO: 96) |
| Pin1 20 | Pip-Nal-Phe-Arg-arg-arg-Glu (SEQ ID NO: 97) |
| Pin1 21 | Pip-Nal-phe-Arg-arg-arg-glu (SEQ ID NO: 98) |
| Pin1 22 | Pip-Nal-phe-Arg-arg-arg-Glu (SEQ ID NO: 99) |
| Pin1 23 | Pip-Nal-nal-Arg-arg-arg-Giu (SEQ ID NO: 100) |
| Pin1 24 | Pip-Nal-nal-Arg-arg-arg-glu (SEQ ID NO: 101) |
| Rev-13 | [Pim-RQRR-Nlys]GRRR[b] (SEQ ID NO: 102) |
| hLF | KCFQWQRNMRKVRGPPVSC (SEQ ID NO: 103) |
| cTat | [KrRrGrKkRrE][c] (SEQ ID NO: 104) |
| cR10 | [KrRrRrRrRrRE][c] (SEQ ID NO: 105) |
| L-50 | [RVRTRGKRRIRRpP] (SEQ ID NO: 106) |
| L-51 | [RTRTRGKRRIRVpP] (SEQ ID NO: 107) |
| [WR]4 | [WRWRWRWR] (SEQ ID NO: 108) |
| MCoTI-II | [GGVCPKILKKCRRDSDCPGACICRGNGYCGSGSD] (SEQ ID NO: 109) |
| Rotstein et at. Chem. Eur J. 2011 | [P-Cha-r-Cha-r-Cha-r-Cha-r-G][d] (SEQ ID NO: 110) |
| Lian et al. J Am. Chew. Soc. 2014 | Tm(SvP-F2Pmp-H)-Dap-(FΦRRRR-Dap)][f] (SEQ ID NO: 111) |
| Lian et al. J. Am. Chem. Soc. 2014 | [Tm(a-Sar-D-pThr-Pip-ΦRAa)-Dap-(FΦRRRR-Dap)][f] (SEQ ID NO: 112) |
| IA8b | [CRRSRRGCGRRSRRCG][g] (SEQ ID NO: 113) |
| Dod-[R5] | [K(Dod)RRRR] (SEQ ID NO: 114) |
| LK-3 | LKKLCKLLKKLCKLAG (SEQ ID NO: 115) |
|  | LKKLCKLLKKLCKLAG (SEQ ID NO: 115) |
|  | RRRR-[KRRRE][e] (SEQ ID NO: 116) |
|  | RRR-[KRRRRE][e] (SEQ ID NO: 117) |
|  | RR-[KRRRRRE][e] (SEQ ID NO: 118) |
|  | R-[KRRRRRE][e] (SEQ ID NO: 119) |
| [CR]4 | [CRCRCRCR] (SEQ ID NO: 120) |
| cyc3 | [Pra-LRKRLRKFRN-AzK][h] (SEQ ID NO: 121) |
| PMB | T-Dap-[Dap-Dap-f-L-Dap-Dap-T] (SEQ ID NO: 122) |
| GPMB | T-Agp-[Dap-Agp-f-L-Agp-Agp-T] (SEQ ID NO: 123) |
| cCPP1 | FΦRRRR (SEQ ID NO: 19) |
| cCPP12 | FfΦRrRr (SEQ ID NO: 27) |
| cCPP9 | fΦRrRr (SEQ ID NO: 21) |
| cCPP11 | fΦRrRrR (SEQ ID NO: 124) |
| cCPP18 | FΦrRrR (SEQ ID NO: 20) |
| cCPP13 | FΦrRrR (SEQ ID NO: 20) |
| cCPP6 | FΦRRRRR (SEQ ID NO: 125) |
| cCPP3 | RRFRΦRQ (SEQ ID NO: 126) |
| cCPP7 | FFΦRRRR (SEQ ID NO: 28) |
| cCPP8 | RFRFRΦR (SEQ ID NO: 127) |
| cCPP5 | FΦRRR (SEQ ID NO: 14) |
| cCPP4 | FRRRRΦ (SEQ ID NO: 23) |
| cCPP10 | rRFRΦR (SEQ ID NO: 24) |
| cCPP2 | RRΦFRR (SEQ ID NO: 25) |
| cCPP62 | fΦfrRr (SEQ ID NO: 82) |

Φ, L-2-naphthylalanine;
Pim, pimelic acid;
Nlys, lysine peptoid residue;
D-pThr, D-phosphothreonine;
Pip, L-piperidine-2-carboxylic acid;
Cha, L-3-cyclohexyl-alanine;
Tm, trimesic acid;
Dap, L-2,3-diaminopropionic acid;
Sar, sarcosine;
F2Pmp, L-difluorophosphonomethyl phenylalanine;
Dod, dodecanoyl;
Pra, L-propargylglycine;
AzK, L-6-Azido-2-amino-hexanoic;
Agp, L-2-amino-3-guanidinylpropionic acid;
[b]Cyclization between Pim and Nlys;
[c]Cyclization between Lys and Glu;
[d]Macrocyclization by multicomponent reaction with aziridine aldehyde and isocyanide;
[e]Cyclization between the main-chain of Gln residue;
[f]N-terminal amine and side chains of two Dap residues bicyclized with Tm;
[g]Three Cys side chains bicyclized with tris(bromomethyl)benzene;
[h]Cyclization by the click reaction between Pra and Azk.

Additionally, the cCPP used in the compounds and methods described herein can include any sequence disclosed in: U.S. application Ser. No. 15/312,878; U.S. application Ser. No. 15/360,719; International PCT Application Publication No. WO/2018/089648 (including the corresponding US publication), and International PCT Application Publication No. WO 2018/098231, each of which is incorporated by reference in its entirety for all purposes.

Thymidine Phosphorylase

As discussed above, the compounds described herein include a wild type (wt) thymidine phosphorylase protein, or an active fragment or analog thereof (collectively referred to herein as "TP"). Thus, "TP" is used throughout the disclosure and the claims to refer to the wild type protein, or an active fragment or analog of wild type protein.

As used herein, an "active fragment" refers to a portion of human or non-human wild type thymidine phosphorylase that exhibits an activity, such as one or more activities of a full-length thymidine phosphorylase or possesses another activity. In particular embodiments, a portion of wild type thymidine phosphorylase that shares at least one biological activity of wild type thymidine phosphorylase is considered to be an active fragment of thymidine phosphorylase. In some embodiments, the active fragment also includes at least one modification disclosed herein. Activity can be any percentage of activity (i.e., more or less) of the full-length thymidine phosphorylase, including but not limited to, about 1% of the activity, about 2%, about 3%, about 4%, about 5%, about 10%, about 20%, about 30%, about 40%, about 50%, about 60%, about 70%, about 80%, about 90%, about 95%, about 96%, about 97%, about 98%, about 99%, about 100%, about 200%, about 300%, about 400%, about 500%, or more activity compared to the full-length thymidine phosphorylase. Thus, in some embodiments, the active fragment may be substituted for native thymidine phosphorylase and retain at least a portion of one or more biological activities of wild type thymidine phosphorylase. In other embodiments, the active fragment may be substituted for native thymidine phosphorylase and enhance one or more biological activities of wild type thymidine phosphorylase.

The TP used in the present disclosure can be derived from any eukaryotic cell, e.g., mammalian cells. In some embodiments, the mammal is a mouse, human, bovine, rat, pig, horse, chicken, sheep, and the like. In particular embodiments, TP in human thymidine phosphorylase or derived from human thymidine phosphorylase. In some embodiments, TP is derived from E. coli.

In some embodiments, TP for use in the compounds is full length human thymidine phosphorylase protein (SEQ ID NO. 1) or truncated protein (i.e., fragment), e.g., 1-10 propeptide-cleaved, (TP11; SEQ ID NO. 2), 1-15 peptide-cleaved (TP16; SEQ ID NO. 3) 1-21 peptide cleaved (TP21; SEQ ID NO 4), and 1-34 peptide cleaved (TP34; SEQ ID NO 5). In some embodiments, a suitable TP moiety may be a homologue or an analogue of truncated human thymidine phosphorylase or full-length human thymidine phosphorylase. For example, a homologue or an analogue of truncated or full-length human thymidine phosphorylase protein may be a modified thymidine phosphorylase protein containing one or more amino acid substitutions, deletions, and/or insertions as compared to a wild-type or naturally-occurring protein (e.g., SEQ ID NO. 1, NO. 2, NO. 3, NO. 4, or NO 5), while retaining substantial thymidine phosphorylase protein activity.

TABLE 5

| Human Thymidine phosphorylase (TP) (P19971) | |
| --- | --- |
| Full-Length (1-482) | MAALMTPGTGAPPAPGDFSGEGSQGLPDPSPEPKQLPELIRMKRDGGR LSEADIRGFVAAVVNGSAQGAQIGAMLMAIRLRGMDLEETSVLTQAL AQSGQQLEWPEAWRQQLVDKHSTGGVGDKVSLVLAPALAACGCKV PMISGRGLGHTGGTLDKLESIPGFNVIQSPEQMQVLLDQAGCCIVGQS EQLVPADGILYAARDVTATVDSLPLITASILSKKLVEGLSALVVDVKF GGAAVFPNQEQARELAKTLVGVGASLGLRVAAALTAMDKPLGRCVG HALEVEEALLCMDGAGPPDLRDLVTTLGGALLWLSGHAGTQAQGAA RVAAALDDGSALGRFERMLAAQGVDPGLARALCSGSPAERRQLLPR AREQEELLAPADGTVELVRALPLALVLHELGAGRSRAGEPLRLGVGA ELLVDVGQRLRRGTPWLRVHRDGPALSGPQSRALQEALVLSDRAPFA APSPFAELVEPPQQ (SEQ ID NO. 1) |
| Truncated (11-482) "TP11" (cleavage of 1-10 propeptide) | APPAPGDFSGEGSQGLPDPSPEPKQLPELIRMKRDGGRLSEADIRGFVA AVVNGSAQGAQIGAMLMAIRLRGMDLEETSVLTQALAQSGQQLEWP EAWRQQLVDKHSTGGVGDKVSLVLAPALAACGCKVPMISGRGLGHT GGTLDKLESIPGFNVIQSPEQMQVLLDQAGCCIVGQSEQLVPADGILY AARDVTATVDSLPLITASILSKKLVEGLSALVVDVKFGGAAVFPNQEQ ARELAKTLVGVGASLGLRVAAALTAMDKPLGRCVGHALEVEEALLC MDGAGPPDLRDLVTTLGGALLWLSGHAGTQAQGAARVAAALDDGS ALGRFERMLAAQGVDPGLARALCSGSPAERRQLLPRAREQEELLAPA DGTVELVRALPLALVLHELGAGRSRAGEPLRLGVGAELLVDVGQR LRRGTPWLRVHRDGPALSGPQSRALQEALVLSDRAPFAAPSPFAELVL PPQQ (SEQ ID NO. 2) |
| Truncated (16-482) "TP16" (cleavage of 1-15 peptide) | GDFSGEGSQGLPDPSPEPKQLPELIRMKRDGGRLSEADIRGFVAAVVN GSAQGAQIGAMLMAIRLRGMDLEETSVLTQALAQSGQQLEWPEAWR QQLVDKHSTGGVGDKVSLVLAPALAACGCKVPMISGRGLGHTGGTL DKLESIPGFNVIQSPEQMQVLLDQAGCCIVGQSEQLVPADGILYAARD VTATVDSLPLITASILSKKLVEGLSALVVDVKFGGAAVFPNQEQAREL AKTLVGVGASLGLRVAAALTAMDKPLGRCVGHALEVEEALLCMDG AGPPDLRDLVTTLGGALLWLSGHAGTQAQGAARVAAALDDGSALGR FERMLAAQGVDPGLARALCSGSPAERRQLLPRAREQEELLAPADGTV ELVRALPLALVLHELGAGRSRAGEPLRLGVGAELLVDVGQRLRRGTP WLRVHRDGPALSGPQSRALQEALVLSDRAPFAAPSPFAELVLPPQQ (SEQ ID NO. 3) |
| Truncated (22-482) "TP22" (cleavage of 1-21 peptide) | GSQGLPDPSPEPKQLPELIRMKRDGGRLSEADIRGFVAAVVNGSAQGA QIGAMLMAIRLRGMDLEETSVLTQALAQSGQQLEWPEAWRQQLVDK HSTGGVGDKVSLVLAPALAACGCKVPMISGRGLGHTGGTLDKLESIP GFNVIQSPEQMQVLLDQAGCCIVGQSEQLVPADGILYAARDVTATVD SLPLITASILSKKLVEGLSALVVDVKFGGAAVFPNQEQARELAKTLVG VGASLGLRVAAALTAMDKPLGRCVGHALEVEEALLCMDGAGPPDLR DLVTTLGGALLWLSGHAGTQAQGAARVAAALDDGSALGRFERMLA AQGVDPGLARALCSGSPAERRQLLPRAREQEELLAPADGTVELVRAL |

TABLE 5-continued

Human Thymidine phosphorylase (TP) (P19971)

| | |
|---|---|
| | PLALVLHELGAGRSRAGEPLRLGVGAELLVDVGQR<br>LRRGTPWLRVHRDGPALSGPQSRALQEALVLSDRAPFAAPSPFAELVL<br>PPQQ (SEQ ID NO. 4) |
| Truncated<br>(35-482)<br>"TP35"<br>(cleavage of<br>1-34 peptide) | QLPELIRMKRDGGRLSEADIRGFVAAVVNGSAQGAQIGAMLMAIRLR<br>GMDLEETSVLTQALAQSGQQLEWPEAWRQQLVDKHSTGGVGDKVS<br>LVLAPALAACGCKVPMISGRGLGHTGGTLDKLESIPGFNVIQSPEQMQ<br>VLLDQAGCCIVGQSEQLVPADGILYAARDVTATVDSLPLITASILSKKL<br>VEGLSALVVDVKFGGAAVFPNQEQARELAKTLVGVGASLGLRVAAA<br>LTAMDKPLGRCVGHALEVEEALLCMDGAGPPDLRDLVTTLGGALLW<br>LSGHAGTQAQGAARVAAALDDGSALGRFERMLAAQGVDPGLARAL<br>CSGSPAERRQLLPRAREQEELLAPADGTVELVRALPLALVLHELGAGR<br>SRAGEPLRLGVGAELLVDVGQR<br>LRRGTPWLRVHRDGPALSGPQSRALQEALVLSDRAPFAAPSPFAELVL<br>PPQQ (SEQ ID NO. 5) |

Thus, in some embodiments, TP suitable for the compounds and methods described herein is substantially homologous to full-length human thymidine phosphorylase protein (SEQ ID NO. 1). In some embodiments, the TP suitable for the present compounds and methods has an amino acid sequence that is at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more homologous to SEQ ID NO. 1. In some embodiments, the TP suitable for the compounds and methods described herein has an amino acid sequence 95% or more homologous to SEQ ID NO:1.

In some embodiments, TP suitable for the compounds and methods described herein is substantially homologous to truncated (e.g., 1-10, 1-15, 1-21, or 1-34 propeptide-cleaved) thymidine phosphorylase protein (SEQ ID NO: 2, 3, 4, or 5). In some embodiments, TP suitable for the present compounds and methods has an amino acid sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more homologous to SEQ ID NO. 2, 3, 4, 5 or 5. In some embodiments, the TP suitable for the compounds and methods described herein has an amino acid sequence 95% or more homologous to SEQ ID NO: 2, 3, 4, or 5.

Thus, in some embodiments, TP suitable for the compounds and methods described herein is substantially identical to full-length human TP protein (SEQ ID NO. 1). In some embodiments, TP suitable for the present compounds and methods herein has an amino acid sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more identical to SEQ ID NO:1. In some embodiments, the TP suitable for the compounds and methods described herein has an amino acid sequence 95% or more identical to SEQ ID NO:1.

Thus, in some embodiments, TP suitable for the compounds and methods described herein is substantially identical to truncated (1-10 propeptide-cleaved) human TP protein (SEQ ID NO. 2). In some embodiments, TP suitable for the present compounds and methods has an amino acid sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more identical to SEQ ID NO: 2, 3, 4, or 5. In some embodiments, the TP suitable for the compounds and methods described herein has an amino acid sequence 95% or more identical to SEQ ID NO: 2, 3, 4, or 5.

In some embodiments, the TP suitable for the compounds and methods described herein contains a fragment of full-length human TP protein (SEQ ID NO. 1) or a fragment of truncated (1-10, 1-15, 1-21, or 1-34 propeptide-cleaved) thymidine phosphorylase protein (SEQ ID NO: 2, 3, 4, or 5).

As discussed above, TP can be the wild-type human protein or an active fragment of wild type human protein which can be substituted for native thymidine phosphorylase. In some embodiments, an active fragment of thymidine phosphorylase can rescue one or more phenotypes or symptoms associated with MNGIE or symptoms associated with thymidine phosphorylase-deficiency once located to the cytosol. An active fragment of the wild-type sequence is a sequence which functions in a substantially similar manner to the wild-type protein. Thus, the active fragment includes any amino acid sequence of the wild-type protein that, when located in the cytosol, allows the cell to function substantially similar to a similar cell which otherwise includes wild-type TP. In some embodiments, the active fragment includes an amino acid sequence which results in an insignificant decrease in function after cytosol entry compared to the wild-type TP but still exhibits the desired therapeutic effect, e.g., about 1%, about 2%, about 3%, about 4%, about 5%, about 6%, about 7%, about 8%, about 9%, about 10%, about 15%, about 205, about 25%, about 30%, about 35%, about 40%, about 45%, or about 50%.

In some embodiments, the active fragment of the wild-type protein may have amino acid sequence that is reduced by about 1 or more amino acids, e.g., about 5, about 10, about 15, about 20, about 25, about 30, about 35, about 40, about 45, about 50, about 55, about 60, about 65, about 70, about 75, about 80, about 90, about 95, about 100, about 105, about 110, about 115, about 120, about 125, about 130, about 135, about 140, about 145, about 150, about 155, about 160, about 165, about 170, about 175, or about 180 or more amino acids.

As used herein, an "analog" refers to a variant of TP which has phosphorylase activity, but one or more properties of the variant are improved relative to wild-type TP. For example, the phosphorylase activity can be improved to enhancing binding and/or enzymatic activity through protein engineering, or stability may be enhanced, either through protein engineering or conjugation of a water-soluble polymer, e.g., as described herein. In other embodiments, one or more properties (other than the phosphorylase activity) of the wild-type TP are either not present (eliminated) or are reduced in the "analog." Non-limiting examples of properties that may be reduced or eliminated include immunogenic, angiogenic, thrombogenic, and SRC homology 3 domain (SH3 domain) binding activity. For example, the interaction between a PXXP sequence and the SH3 domain on certain proteins, such as between the PXXP sequence on Fyn and the SH3 domain on Lyn, is believed to increase the risk of thrombosis (Circ Res. 2014, 115(12): 997-1006). Amino acids 12-15 of SEQ ID NO: 1 (PPAP) in wild-type human TP have this sequence. Thus truncated TP sequences (SEQ. NO. 3, NO. 4, or NO. 5) with this PPAP sequence removed were designed.

In some such embodiments, TP may be fused or conjugated to a moiety that improves half-life or stability. Non-limiting examples of such moieties include proteins and water-soluble polymers. In some embodiments, TP may be fused or conjugated to Fc or human serum albumin (HSA). Without being bound by theory, Fc and HSA interact with FCRn receptor, and this activity allows for Fc and/or HSA fusions with TP to increase the circulating half-life of TP. In some embodiments, Fc or HSA is located on the N-terminal of TP, with or without the PPAP sequence (amino acids 12-15). In other embodiments, Fc or HSA is located on the C-terminal of TP, with or without the PPAP sequence (amino acids 12-15). In some embodiments, a linker can be used to connect TP (with or with PPAP) to Fc or HSA. Non-limiting examples of such constructs are provided below in Table 6. The present disclosure contemplates sequences having a sequence identity of at least about 85% of those provided in Table 6

TABLE 6

| Example TP and Fc Conjugates | |
|---|---|
| IgG1Fc-TP (16-482) N-terminal fusion | EPKSCDKTHTCPPCPAPELLGGPSVFLFPPKPKDTLMISRTPEVTTCVVV DVSHEDPEVKFNWYVDGVEVHNAKTKPREEQYNSTYRVVSVLTVLH QDWLNGKEYKCKVSNKALPAPIEKTISKAKGQPREPQVYTLPPSREE MTKNQVSLTCLVKGFYPSDIAVEWESNGQPENNYKTTPPVLDSDGSF FLYSKLTVDKSRWQQGNVFSCSVMHEALHNHYTQKSLSLSPGKGDFS GEGSQGLPDDSPEPKQLPELIRMKRDGGRLSEADIRGFVAAVVNGSAQ GAQIGAMLMAIRLRGMDLEETSVLTQALAQSGQQLEWPEAWRQQLV DKHSTGGVGDKVSLVLAPALAACGCKVPMISGRGLGHTGGTLDKLES IPGFNVIQSPEQMQVLLDQAGCCIVGQSEQLVPADGILYAARDVTATV DSLPLITASILSKKLVEGLSALVVDVKFGGAAVFPNQEQARELAKTLV GVGASLGLRVAAALTAMDKPLGRCVGHALEVEEALLCMDGAGPPDL RDLVTTLGGALLWLSGHAGTQAQGAARVAAALDDGSALGRFERML AAQGVDPGLARALCSGSPAERRQLLPRAREQEELLAPADGTVELVRA LPLALVLHELGAGRSRAGEPLRLGVGAELLVDVGQRLRRGTPWLRVH RDGPALSGPQSRALQEALVLSDRAPFAAPSPFAELVLPPQQ (SEQ ID NO. 6) |
| IgG1Fc-TP (16-482) N-terminal fusion with GGGGS linker "Fc-TP16" | EPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLH QDWLNGKEYKCKVSNKALPAPIEKTISKAKGQPREPQVYTLPPSREE MTKNQVSLTCLVKGFYPSDIAVEWESNGQPENNYKTTPPVLDSDGSF FLYSKLTVDKSRWQQGNVFSCSVMHEALHNHYTQKSLSLSPGKGGG GSGDFSGEGSQGLPDPSPEPKQLPELIRMKRDGGRLSEADIRGFVAAV VNGSAQGAQIGAMLMAIRLRGMDLEETSVLTQALAQSGQQLEWPEA WRQQLVDKHSTGGVGDKVSLVLAPALAACGCKVPMISGRGLGHTGG TLDKLESIPGFNVIQSPEQMQVLLDQAGCCIVGQSEQLVPADGILYAA RDVTATVDSLPLITASILSKKLVEGLSALVVDVKFGGAAVFPNQEQAR ELAKTLVGVGASLGLRVAAALTAMDKPLGRCVHALEVEEALLCMD GAGPPDLRDLVTTLGGALLWLSGHAGTQAQGAARVAAALDDGSALG RFERMLAAQGVDPGLARALCSGSPAERRQLLPRAREQEELLAPADGT VELVRALPLALVLHELGAGRSRAGEPLRLGVGAELLVDVGQRLRRGT PWLRVHRDGPALSGPQSRALQEALVLSDRAPFAAPSPFAELVLPPQQ (SEQ ID NO. 7) |
| TP (16-482)- IgG1Fc C-terminal fusion | GDFSGEGSQGLPDPSPEPKQLPELIRMKRDGGRLSEADIRGFVAAVVN GSAQGAQIGAMLMAIRLRGMDLEETSVLTQALAQSGQQLEWPEAWR QQLVDKHSTGGVGDKVSLVLAPALAACGCKVPMISGRGLGHTGGTL DKLESIPGFNVIQSPEQMQVLLDQAGCCIVGQSEQLVPADGILYAARD VTATVDSLPLITASILSKKLVEGLSALVVDVKFGGAAVFPNQEQAREL AKTLVGVGASLGLRVAAALTAMDKPLGRCVGHALEVEEALLCMDG AGPPDLRDLVTTLGGALLWLSGHAGTQAQGAARVAAALDDGSALGR FERMLAAQGVDPGLARALCSGSPAERRQLLPRAREQEELLAPADGTV ELVRALPLALVLHELGAGRSRAGEPLRLGVGAELLVDVGQRLRRGTP WLRVHRDGPALSGPQSRALQEALVLSDRAPFAAPSPFAELVLPPQQEP KSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSREEMTK NQVSLTCLVKGFYPSDIAVEWESNGQPENNYKTTPPVLDSDGSFFLYS KLTVDKSRWQQGNVFSCSVMHEALHNHYTQKSLSLSPGK (SEQ ID NO. 8) |

TABLE 6-continued

Example TP and Fc Conjugates

TP (16-482)-
IgG1Fc
C-terminal
fusion with
GGGGS
linker
"TP16-Fc"

GDFSGEGSQGLPDPSPEPKQLPELIRMKRDGGRLSEADIRGFVAAVVN
GSAQGAQIGAMLMAIRLRGMDLEETSVLTQALAQSGQQLEWPEAWR
QQLVDKHSTGGVGDKVSLVLAPALAACGCKVPMISGRGLGHTGGTL
DKLESIPGFNVIQSPEQMVLLDQAGCCIVGQSEQLVPADGILYAARD
VTATVDSLPLITASILSKKLVEGLSALVVDVKFGGAAVFPNQEQAREL
AKTLVGVGASLGLRVAAALTAMDKPLGRCVGHALEVEEALLCMDG
AGPPDLRDLVTTLGGALLWLSGHAGTQAQGAARVAAALDDGSALGR
FERMLAAQGVDPGLARALCSGSPAERRQLLPRAREQEELLAPADGTV
ELVRALPLALVLHELGAGRSRAGEPLRLGVGAELLVDVGQRLRRGTP
WLRVHRDGPALSGPQSRALQEALVLSDRAPFAAPSPFAELVLPPQQG
GGGSEPKSCDKTHTCPPCPAPELLGGPSVFLFPPKPKDTLMISRTPEVT
CVVVDVSHEDPEVKFNWYVDGVEVHNAKTKPREEQYNSTYRVVSVL
TVLHQDWLNGKEYKCKVSNKALPAPIEKTISKAKGQPREPQVYTLPPS
REEMTKNQVSLTCLVKGFYPSDIAVEWESNGQPENNYKTTPPVLDSD
GSFFLYSKLTVDKSRWQQGNVFSCSVMHEALHNHYTQKSLSLSPGK
(SEQ ID NO. 9)

TP (16-482)-
IgG1Fc_R435
C-terminal
fusion with
GGGGS
linker

GDFSGEGSQGLPDPSPEPKQLPELIRMKRDGGRLSEADIRGFVAAVVN
GSAQGAQIGAMLMAIRLRGMDLEETSVLTQALAQSGQQLEWPEAWR
QQLVDKHSTGGVGDKVSLVLAPALAACGCKVPMISGRGLGHTGGTL
DKLESIPGFNVIQSPEQMVLLDQAGCCIVGQSEQLVPADGILYAARD
VTATVDSLPLITASILSKKLVEGLSALVVDVKFGGAAVFPNQEQAREL
AKTLVGVGASLGLRVAAALTAMDKPLGRCVGHALEVEEALLCMDG
AGPPDLRDLVTTLGGALLWLSGHAGTQAQGAARVAAALDDGSALGR
FERMLAAQGVDPGLARALCSGSPAERRQLLPRAREQEELLAPADGTV
ELVRALPLALVLHELGAGRSRAGEPLRLGVGAELLVDVGQRLRRGTP
WLRVHRDGPALSGPQSRALQEALVLSDRAPFAAPSPFAELVLPPQQG
GGGSEPKSCDKTHTCPPCPAPELLGGPSVFLFPPKPKDTLMISRTPEVT
CVVVDVSHEDPEVKFNWYVDGVEVHNAKTKPREEQYNSTYRVVSVL
TVLHQDWLNGKEYKCKVSNKALPAPIEKTISKAKGQPREPQVYTLPPS
REEMTKNQVSLTCLVKGFYPSDIAVEWESNGQPENNYKTTPPVLDSD
GSFFLYSKLTVDKSRWQQGNVFSCSVMHEALHNRYTQKSLSLSPGK
(SEQ ID NO. 10)

IgG1Fc(R435)-
TP (16-482)
N-terminal
fusion with
GGGGS
linker

EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLH
QDWLNGKEYKCKVSNKALPAPIEKTISKAKGQPREPQVYTLPPSREE
MTKNQVSLTCLVKGFYPSDIAVEWESNGQPENNYKTTPPVLDSDGSF
FLYSKLTVDKSRWQQGNVFSCSVMHEALHNRYTQKSLSLSPGKGGG
GSGDFSGEGSQGLPDPSPEPKQLPELIRMKRDGGRLSEADIRGFVAAV
VNGSAQGAQIGAMLMAIRLRGMDLEETSVLTQALAQSGQQLEWPEA
WRQQLVDKHSTGGVGDKVSLVLAPALAACGCKVPMISGRGLGHTGG
TLDKLESIPGFNVIQSPEQMVLLDQAGCCIVGQSEQLVPADGILYAA
RDVTATVDSLPLITASILSKKLVEGLSALVVDVKFGGAAVFPNQEQAR
ELAKTLVGVGASLGLRVAAALTAMDKPLGRCVGHALEVEEALLCMD
GAGPPDLRDLVTTLGGALLWLSGHAGTQAQGAARVAAALDDGSALG
RFERMLAAQGVDPGLARALCSGSPAERRQLLPRAREQEELLAPADGT
VELVRALPLALVLHELGAGRSRAGEPLRLGVGAELLVDVGQRLRRGT
PWLRVHRDGPALSGPQSRALQEALVLSDRAPFAAPSPFAELVLPPQQ
(SEQ ID NO. 11)

IgG1Fc-
TP_R435
(16-482)
N-terminal
fusion

EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLH
QDWLNGKEYKCKVSNKALPAPIEKTISKAKGQPREPQVYTEPPSREE
MTKNQVSLTCLVKGFYPSDIAVEWESNGQPENNYKTTPPVLDSDGSF
FLYSKLTVDKSRWQQGNVFSCSVMHEALHNRYTQKSLSLSPGKGDFS
GEGSQGLPDPSPEPKQLPELIRMKRDGGRLSEADIRGFVAAVVNGSAQ
GAQIGAMLMAIRLRGMDLEETSVLTQALAQSGQQLEWPEAWRQQLV
DKHSTGGVGDKVSLVLAPALAACGCKVPMISGRGLGHTGGTLDKLES
IPGFNVIQSPEQMVLLDQAGCCIVGQSEQLVPADGILYAARDVTATV
DSLPLITASILSKKLVEGLSALVVDVKFGGAAVFPNQEQARELAKTLV
GVGASLGLRVAAALTAMDKPLGRCVGHALEVEEALLCMDGAGPPDL
RDLVTTLGGALLWLSGHAGTQAQGAARVAAALDDGSALGRFERML
AAQGVDPGLARALCSGSPAERRQLLPRAREQEELLAPADGTVELVRA
LPLALVLHELGAGRSRAGEPLRLGVGAELLVDVGQRLRRGTPWLRVH
RDGPALSGPQSRALQEALVLSDRAPFAAPSPFAELVLPPQQ
(SEQ ID NO. 12)

TP (16-482)
IgG1Fc_R435
C-terminal
fusion

GDFSGEGSQGLPDPSPEPKQLPELIRMKRDGGRLSEADIRGFVAAVVN
GSAQGAQIGAMLMAIRLRGMDLEETSVLTQALAQSGQQLEWPEAWR
QQLVDKHSTGGVGDKVSLVLAPALAACGCKVPMISGRGLGHTGGTL
DKLESIPGFNVIQSPEQMVLLDQAGCCIVGQSEQLVPADGILYAARD
VTATVDSLPLITASILSKKLVEGLSALVVDVKFGGAAVFPNQEQAREL
AKTLVGVGASLGLRVAAALTAMDKPLGRCVGHALEVEEALLCMDG
AGPPDLRDLVTTLGGALLWLSGHAGTQAQGAARVAAALDDGSALGR
FERMLAAQGVDPGLARALCSGSPAERRQLLPRAREQEELLAPADGTV
ELVRALPLALVLHELGAGRSRAGEPLRLGVGAELLVDVGQRLRRGTP
WLRVHRDGPALSGPQSRALQEALVLSDRAPFAAPSPFAELVLPPQQEP

TABLE 6-continued

Example TP and Fc Conjugates

```
KSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQD
WLNGKEYKCKVSNKALPAPIEKTISKAKGQPREPQVYTLPPSREEMTK
NQVSLTCLVKGFYPSDIAVEWESNGQPENNYKTTPPVLDSDGSFFLYS
KLTVDKSRWQQGNVFSCSVMHEALHNRYTQKSLSLSPGK
(SEQ ID NO. 13)
```

In some embodiments, TP in the present compounds and methods has an amino acid sequence at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more identical to SEQ ID NO.; 6, 7, 8, 9, 10, 11, 12, or 13. In some embodiments, the TP suitable for the compounds and methods described herein has an amino acid sequence 95% or more identical to SEQ ID NO: 6, 7, 8, 9, 10, 11, 12, or 13.

In some embodiments, the TP analog contains one or more amino acid substitutions. Skilled persons can use molecular modeling to select mutations that are likely to be structurally tolerated, e.g. deletion in loops, insertion in loops, deletion of domains, C-terminal truncations, and N-terminal truncations. Homology modeling against TP variants from other organisms may be used to identify amino-acid residues as tolerant of mutations. Modeling is also used to select mutations that alter the function of the enzyme, such as mutations in and near the active site of the enzyme. In some embodiments, the substitutions may be conservative substitutions or non-conservative substitutions.

Examples of conservative amino acid substitutions include substitution of one amino acid for another amino acid within one from one of the following groups: basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). In some embodiments, structurally similar amino acids are substituted to reverse the charge of a residue (e.g., glutamine for glutamic acid or vice-versa, aspartic acid for asparagine or vice-versa). In some embodiments, tyrosine is substituted for phenylalanine or vice-versa. Other non-limiting examples of amino acid substitutions are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In some embodiments, the TP may be conjugated to a pharmaceutically acceptable water soluble polymer. Non-limiting examples of pharmaceutically acceptable water soluble polymers include polyethylene glycol (PEG), dextran or poly(n-vinyl pyrrolidone)polyethylene glycol, propropylene glycol homopolymers, prolypropylene oxide/ethylene oxide co-polymers, polyoxyethylated polyols, polyvinyl alcohol, polyoxyethylated polyols, polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly(β-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or and mixtures thereof. In particular embodiments, the TP is a PEGylated. As used herein "PEGylation" refers to the coupling of TP to one or more polyethylene glycol (PEG) residues. In some embodiments, the molecular weight of the PEG is from about 0.1 kDa to about 100 kDa, e.g., about 0.1 kDa, about 1 kDa, about 10 kDa, about 20 kDa, about 30 kDa, about 40 kDa, about 50 kDa, about 60 kDa, about 70 kDa, about 80 kDa, about 90 kDa, and about 100 kDa. In particular embodiments, the PEG is about 1, 2, 3, 4, 5, 6, 7, 8, 9, 10, 15, 20, 25, 30, 35, 40, 45, or 50 kDa, including 2 kDa or about 5 kDa. The polymer can be linear or branched. The attachment of the such polymers (e.g. PEG) adds molecular weight to the TP and may lead to an increased half-life by improving stability, and/or reducing degradation and/or excretion. Conjugation of the polymers may also improve the solubility and stability in aqueous solutions at physiological pH while retaining biological activity of TP. PEG, and any other biological polymers, can be attached to HPPD at any suitable site, e.g., the N- or C-termini, or the side chain of any amino acid which has a functional group suitable for conjugate or which can be synthetically modified.

The above polymers, such as PEG groups, can be attached to the TP under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the TP (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., α-iodo acetic acid, α-bromoacetic acid, α-chloroacetic acid). If attached to the TP by reductive alkylation, the polymer selected should have a single reactive aldehyde so that the degree of polymerization is controlled. See, for example, Kinstler et al., Adv. Drug. Delivery Rev. 54: 477-485 (2002); Roberts et al., Adv. Drug Delivery Rev. 54: 459-476 (2002); and Zalipsky et al., Adv. Drug Delivery Rev. 16: 157-182 (1995).

The TP can be linked to the above polymers via direct covalent linkage by reacting targeted amino acid residues of the peptide with an organic derivatizing agent that is capable of reacting with selected side chains or the N- or C-terminal residues of these targeted amino acids. Reactive groups on the peptide or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the TP indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

In embodiments, a thiol moiety within a TP is modified with a water-soluble polymer, such as PEG. In some embodiments, the thiol is modified with maleimide-activated PEG in a Michael addition reaction to result in a PEGylated peptide comprising the thioether linkage. In alternative embodiments, a thiol is modified with a haloacetyl-activated PEG in a nucleophilic substitution reaction to result in a PEGylated peptide comprising the thioether linkage. Cysteinyl residues are most commonly reacted with α-haloacetates (and corresponding amines), such as chloroacetic acid and chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins. Structure and Molecular Properties, W.H. Freeman & Co., San Francisco, pp. 79-86 (1983)), deamidation of asparagine or glutamine, acetylation of the N-terminal amine, and/or amidation or esterification of the C-terminal carboxylic acid group.

In another embodiment, the present invention relates to variants of the polypeptide of SEQ ID NO. 1, 2, 3, 4, 5, 6, 7, 8, 9, 10, 11, 12, or 13, or any other sequence disclosed herein, comprising a substitution, deletion, and/or insertion at one or more (e.g., several) positions. In an embodiment, the number of amino acid substitutions, deletions and/or insertions introduced into the mature polypeptide of SEQ ID NO. 1, 2, 3, 4, 5, 6, 7, 8, 9, 10, 11, 12, or 13, is not more than 50, or not more than 40, or not more than 30, or not more than 20, or not more than 10, e.g., 1, 2, 3, 4, 5, 6, 7, 8, 9, or 10. The, amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Alternatively, the amino acid changes may be of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for activity comparable to native thymidine phosphorylase to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312: Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-

10837; U.S. Pat. No. 5,223,409; WO 92/06204), and region-directed mutagenesis (Derbyshire et al., 1986, *Gene* 46: 145; Ner et al., 1988, *DNA* 7:127).

Non-limiting examples of the peptide conjugates disclosed herein are provided in the following table.

| cCPP | Linker (L) | TP | Water-soluble polymer |
|---|---|---|---|
| cCPP9 | PEG-12 | TP | PEG10K |
| | PEG-8 | TP | PEG5K |
| | PEG-24 | TP | PEG40K |
| | PEG-4 | TP | PEG10K |
| | PEG-12 | TP11 | PEG10K |
| | PEG-8 | TP11 | PEG5K |
| | PEG-24 | TP11 | PEG40K |
| | PEG-4 | TP11 | PEG10K |
| | PEG-12 | TP16 | PEG10K |
| | PEG-8 | TP16 | PEG5K |
| | PEG-24 | TP16 | PEG40K |
| | PEG-4 | TP16 | PEG10K |
| | PEG-12 | TP35 | PEG10K |
| | PEG-8 | TP35 | PEG5K |
| | PEG-24 | TP35 | PEG40K |
| cCPP11 | PEG-12 | TP | PEG10K |
| | PEG-8 | TP | PEG5K |
| | PEG-24 | TP | PEG40K |
| | PEG-4 | TP | PEG10K |
| | PEG-12 | TP11 | PEG10K |
| | PEG-8 | TP11 | PEG5K |
| | PEG-24 | TP11 | PEG40K |
| | PEG-4 | TP11 | PEG10K |
| | PEG-12 | TP16 | PEG10K |
| | PEG-8 | TP16 | PEG5K |
| | PEG-24 | TP16 | PEG40K |
| | PEG-4 | TP16 | PEG10K |
| | PEG-12 | TP35 | PEG10K |
| | PEG-8 | TP35 | PEG5K |
| | PEG-24 | TP35 | PEG40K |
| cCPP12 | PEG-12 | TP | PEG10K |
| | PEG-8 | TP | PEG5K |
| | PEG-24 | TP | PEG40K |
| | PEG-4 | TP | PEG10K |
| | PEG-12 | TP11 | PEG10K |
| | PEG-8 | TP11 | PEG5K |
| | PEG-24 | TP11 | PEG40K |
| | PEG-4 | TP11 | PEG10K |
| | PEG-12 | TP16 | PEG10K |
| | PEG-8 | TP16 | PEG5K |
| | PEG-24 | TP16 | PEG40K |
| | PEG-4 | TP16 | PEG10K |
| | PEG-12 | TP35 | PEG10K |
| | PEG-8 | TP35 | PEG5K |
| | PEG-24 | TP35 | PEG40K |
| | PEG-4 | TP35 | PEG10K |

In some embodiments, cCPP may be conjugated, via the linker, to the N or C terminus of the TP. In some embodiments, the linker further comprises an amino acid (e.g., lysine), which to facilitate chemical conjugation of the TP to a side chain of an amino acid on the cCCP In some embodiments, the water-soluble polymer can be conjugated to any suitable amino acid side chain in TP, e.g., lysine, glutamine, glutamic acid, asparagine, aspartic acid, and the like.

Methods of Treatment

In embodiments of the present disclosure, a method of treating Mitochondrial Neurogastrointestinal Encephalopathy in a patient in need thereof, comprising administering a compound disclosed herein is provided.

MNGIE impacts both the digestive systems and nervous system of patients afflicted with this disease. In various embodiments, treatment therefore refers to partial or complete alleviation, amelioration, relief, inhibition, delaying onset, reducing severity and/or incidence of digestive and nervous system impairment of a patient. In other embodiments, treatment therefore refers to partial or complete alleviation, amelioration, relief, inhibition, delaying onset, reducing severity and/or incidence of digestive system impairment of a patient. As used herein, the term "digestive system impairment" includes various symptoms associated with impairment of the gastrointestinal system Symptoms of digestive system impairment may include, for example, gastrointestinal dysmotility in which the muscles and nerves of the digestive system do not move food through the digestive tract efficiently. The resulting digestive problems include feelings of fullness (satiety) after eating only a small amount, trouble swallowing (dysphagia), nausea and vomiting after eating, episodes of abdominal pain, diarrhea, and intestinal blockage. These gastrointestinal conditions lead to extreme weight loss and reduced muscle mass (cachexia). In some embodiments, treatment refers to partial or complete alleviation, relief, inhibition, delaying onset, reducing severity and/or incidence of gastrointestinal dysmotility and the accompanying conditions.

MNGIE disease is also characterized by abnormalities of the nervous system. Affected individuals can experience tingling, numbness, and weakness in their limbs (peripheral neuropathy), particularly in the hands and feet. Additional neurological signs and symptoms can include droopy eyelids (ptosis), weakness of the muscles that control eye movement (ophthalmoplegia), and hearing loss. Leukoencephalopathy, which is the deterioration of a type of brain tissue known as white matter, is a hallmark of MNGIE disease. In various embodiments, treatment therefore refers to partial or complete alleviation, amelioration, relief, inhibition, delaying onset, reducing severity and/or incidence of nervous system impairment of a patient, including but not limited to conditions such as ptosis, ophthalmoplegia, and hearing loss. In related embodiments, the methods of treatment provide partial or complete alleviation, amelioration, relief, inhibition, delaying onset, reducing severity and/or incidence of the peripheral neuropathy that can be a neurological symptom of MNGIE.

In some embodiments, a method is provided for reducing extracellular and intracellular levels of thymidine in a patient in need thereof, comprising administering a compound disclosed herein. That is, not only does intracellular delivery of TP as described here reduce intracellular levels of thymidine, but it also reduces extracellular levels of thymidine in circulation. Mutations in TYMP, the gene that provides instructions for making TP, are believed to cause MNGIE disease by reducing or eliminating appropriate levels of enzymatic activity of this protein. Excess levels of thymidine that can result from these mutations are toxic to the body, leading to the disruption of the usual maintenance and repair of mitochondrial DNA. Without being bound by theory, the resulting genetic changes can impair the normal function of mitochondria, leading to the digestive and neurological problems associated with MNGIE. In some embodiments, treatment according to the present invention results in decreased intracellular and/or extracellular levels of thymidine in a patient by more than about 5%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as compared to the average level of thymidine in the patient before the treatment or of one or more control individuals with similar disease without treatment. In various embodiments of the present disclosure, the method of reducing extracellular and intracellular levels of thymidine in a patient in need thereof, comprises administering a compound disclosed herein is effective for treating MNGIE.

The terms, "improve," "increase," "reduce," "decrease," and the like, as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with MNGIE, who is about the same age and/or gender as the individual being treated (to ensure that the stages of the disease in the treated individual and the control individual(s) are comparable).

The individual (also referred to as "patient") being treated is an individual (fetus, infant, child, adolescent, or adult human) having MNGIE or having the potential to develop MNGIE. The individual can have residual endogenous thymidine phosphorylase expression and/or activity, or no measurable activity. In various embodiments, the individual having MNGIE may have thymidine phosphorylase expression or activity levels that are less than about 1-99% of normal thymidine phosphorylase expression or activity levels in an individual not afflicted with MNGIE. In some embodiments, the range includes, but is not limited to less than about 80-99%, less than about 65-80%, less than about 50-65%, less than about 30-50%, less than about 25-30%, less than about 20-25%, less than about 15-20%, less than about 10-15%, less than about 5-10%, less than about 1-5% of normal thymidine phosphorylase expression or activity levels.

In some embodiments, the individual is an individual who has been recently diagnosed with the disease. Typically, early treatment (treatment commencing as soon as possible after diagnosis) is important to minimize the effects of the disease and to maximize the benefits of treatment.

Methods of Making

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, WI), Acros Organics (Morris Plains, NJ), Fisher Scientific (Pittsburgh, PA), Sigma (St. Louis, MO), Pfizer (New York, NY), GlaxoSmithKline (Raleigh, NC), Merck (Whitehouse Station, NJ), Johnson & Johnson (New Brunswick, NJ), Aventis (Bridgewater, NJ), AstraZeneca (Wilmington, DE), Novartis (Basel, Switzerland), Wyeth (Madison, NJ), Bristol-Myers-Squibb (New York, NY), Roche (Basel, Switzerland), Lilly (Indianapolis, IN), Abbott (Abbott Park, IL), Schering Plough (Kenilworth, NJ), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopentyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for aspartic acid and glutamic acid, benzyl and t-butyl and for cysteine, triphenylmethyl (trityl). In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N, N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thioanisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivatized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

The above polymers, such as PEG groups, can be attached to the TP under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the TP (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., α-iodo acetic acid, α-bromoacetic acid, (α-chloroacetic acid). If attached to the TP by reductive alkylation, the polymer selected should have a single reactive aldehyde so that the degree of polymerization is controlled. See, for example, Kinstler et al., Adv. Drug. Delivery Rev. 54: 477-485 (2002); Roberts et al., Adv. Drug Delivery Rev. 54: 459-476 (2002); and Zalipsky et al., Adv. Drug Delivery Rev. 16: 157-182 (1995).

In order direct covalently link the TP to the CPP, appropriate amino acid residues of CPP may be reacted with an organic derivatizing agent that is capable of reacting with a selected side chain or the N- or C-termini of an amino acids. Reactive groups on the peptide or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art.

The present disclosure also provides for recombinant fusion protein wherein a linear CPP is fused to the N-terminus and/or C-terminus of the TP. When prepared as recombinant fusions, the compounds can be prepared by known recombinant expression techniques. For example, to recombinantly produce the compound, a nucleic acid sequence encoding the chimeric gene is operatively linked to a suitable promoter sequence such that the nucleic acid sequence encoding such fusion protein will be transcribed and/or translated into the desired fusion protein in the host cells. Preferred promoters are those useful for expression in *E. coli*, such as the T7 promoter. Any commonly used expression system may be used, including eukaryotic or prokaryotic systems. Specific examples include yeast (e.g., *Saccharomyces* spp., *Pichia* spp.), baculovirus, mammalian, and bacterial systems, such as *E. coli*, and *Caulobacter*.

Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.10% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

EXAMPLES

Example 1. Synthesis of Compounds

Thymidine Phosphorylase.

The gene coding for the mature thymidine phosphorylase protein (11-482) was prepared by de novo gene synthesis, and the resulting DNA fragment was subcloned in a prokaryotic expression vector pET-30a(+) at EcoRV-EcoRI sites. E. coli Lemo21(DE3) competent cells transformed with the plasmid encoding the thymidine phosphorylase was incubated at 37° C. in a LB containing 50 µg/mL kanamycin. The culture was grown at 37° C. until an OD600 between 0.4-0.6. The protein expression was induced at 25° C. overnight in the presence of 0.25 mM isopropyl-beta-D-thiogalactopyranoside (IPTG). After overnight culture, bacteria cells were harvested by centrifugation (4000 g for 15 min at 4° C.). Cell pellets were stored at −20° C. until further purification.

The gene coding for truncated active thymidine phosphorylase protein (TP16, TP22, or TP35) were prepared by de novo gene synthesis, and the resulting DNA fragment was subcloned in a prokaryotic expression vector pET-24a(+) at NdeI-XhoI sites. EMD Millipore™ Novagen™ Rosetta™ 2 (DE3) Singles Competent Cells transformed with the plasmid encoding the thymidine phosphorylase was incubated at 37° C. in a LB containing 50 µg/mL kanamycin in the shaking flask. The culture was grown at 37° C. until an OD600 between 0.4-0.6. The protein expression was induced at 30° C. overnight in the presence of 0.25 mM isopropyl-beta-D-thiogalactopyranoside (IPTG). After overnight culture, bacteria cells were harvested by centrifugation (4000 g for 15 min at 4° C.). Cell pellets were stored at −20° C. until further purification.

To prepare human IgG1-Fc fusion of TP proteins, the gene coding for human IgG1Fc fused TP conjugates (SEQ ID NO. 6-13, Table 6) were prepared by de novo gene synthesis, and the resulting DNA fragment was subcloned in a prokaryotic expression vector pET-21a(+) at NdeI-XhoI sites. EMD Millipore™ Novagen™ Rosetta™ 2 (DE3) Singles Competent Cells transformed with the plasmid encoding SEQ ID NO 7 (Fc-TP16) was incubated at 37° C. in a LB containing 50 µg/mL Ampicillin in the shaking flask. The culture was grown at 37° C. until an OD600 between 0.4-0.6. The protein expression was induced at 30° C. overnight in the presence of 0.25 mM isopropyl-beta-D-thiogalactopyranoside (IPTG). After overnight culture, bacteria cells were harvested by centrifugation (4000 g for 15 min at 4° C.). Cell pellets were stored at −20° C. until further purification.

Process of preparing recombinant TP protein using bioreactor: a glycerol stock seed (1 mL) was thawed and used to inoculate the initial culture (5 ml growth medium composed of 10 g/L soyton, 5 g/L yeast extract, 10 g/L NaCl, pH 7.5, 50 mg/L1 Kanamycin) at 37° C., 250 rpm for 4 hour. Then the culture was used to inoculate 100 mL medium and grown additional 5 hours. When the culture achieved an optical density ($OD_{600\ nm}$) around 2-3, it was used to inoculate a 2 L minimum medium in the bioreactor. The composition of the minimum medium per liter is as follows: 2 g $(NH_4)_2SO_4$, 6.75 g $KH_2PO_4$, 0.35 g $MgSO_4$, 0.85 g citric acid, 20 g/L glucose. After inoculation, the culture was grown for 10 hours at 37° C. with the temperature controlled by a PID loop. Dissolved oxygen (DO) was set at 30% and was also controlled by a PID loop control and with stirring-first-oxygen priority in that order, the minimum/maximum stirring was set at 400/800 rpm. The pH was adjusted to 7.2 and controlled by a PID loop, using 28-30% (m/v) $NH_4OH$ through the alkali pump. After 10 hours, the $OD_{600\ nm}$ reached about 9-10, a glucose feeding solution was set up through the acid pump and under the same pH PID loop control, and this was maintained until the end of the fermentation process. The composition of the glucose feeding solution is as follows: 50% (w/v) glucose, 9.8 g/L $(NH_4)_2SO_4$ and 1× trace metal solution. Additionally, a yeast extract solution was constantly fed through an external pump at 10-15 mL per hour per liter of culture. The composition of this solution was 10 g/L yeast extract and 20 g/L $NaH_2PO_4$. The culture was induced with 0.5 mM IPTG at $OD_{600\ nm}$ around 20 at 30 degree Celsius. The culture was induced two more times with the same IPTG concentration every 2.5 hours. The biomass was harvested 8-9 hours post-first-induction by centrifugation, the achieved biomass production was ~50 g/L of culture, and the pellet was stored at −80° C. till further purification.

For the purification of TP11, bacteria pellets from 1 L cell culture were resuspended in 50 mL lysis buffer (20 mM sodium phosphate, pH 7.4, 200 mM sodium chloride, 5% (v/v) glycerol, 20 mM imidazole). Once the pellet was resuspended, 5 mg of pre-dissolved lysozyme and 500 µl of protease inhibitor cocktail (protease inhibitor cocktail, Sigma, P8849) were added. The solution was stirred on ice for approximately 15 min and the cells were sonicated on ice (pulsed six times for 20 sec with 40 sec resting periods in between, level 100; Sonic Dismembrator, Model 100, Fisher Scientific). The suspension was cleared by centrifugation at 20,000 g for 30 min at 4° C. The supernatant was harvested and applied to a 5 ml His-tag affinity column (HisTrap, fast flow, 5 ml, GE) at 1 mL/min before washed with 100 mL of washing buffer A (20 mM sodium phosphate, pH 7.4, 200 mM sodium chloride, 5% (v/v) glycerol, 20 mM imidazole). To remove endotoxin, the column was then washed with 20 column volume of Triton X-114 buffer (buffer A supplemented with 0.1% (v/v) Triton X-114 detergent) followed by 20 column volume of CHAPS buffer (buffer A supplemented with 1% (w/v) CHAPS detergent). Afterwards, the column was washed with 10 CV of buffer A before His-tagged thymidine phosphorylase was eluted with buffer A supplemented with 100-500 mM imidazole in 10 column volume (FIG. 1A).

Figure 1B:
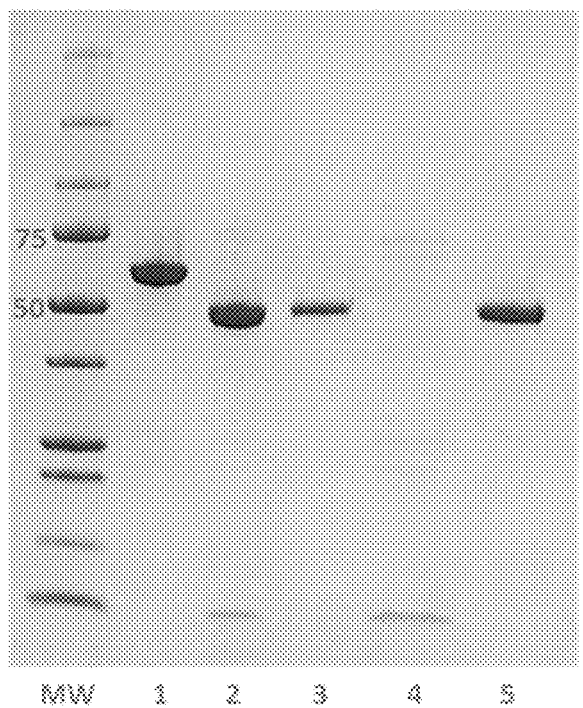
FIG. 1B is the SDS-PAGE analysis showing the cleavage of His-tag from His-TP11 by Enterokinase Protease. From left to right: molecular weight marker (MW), before cleavage (lane 1), protease cleavage reaction (lane 2), flow through from His-Trap column (lane 3), elution from His-Trap column (lane 4), and concentrated tag-free TP product (lane 5).

The purity of TP was determined by SDS-PAGE and fractions of high purity were combined. Endotoxin level was typically lower than 50 EU per mg quantified by the Pierce™ LAL Chromogenic Endotoxin Quantitation Kit. Purified His-tagged TP11 were pooled and dialyzed against 4 liter of EK cleavage buffer (20 mM Tris-HCl, pH 7.4, 50 mM NaCl, 2 mM $CaCl_2$, 5% glycerol). To remove the affinity tag, 100 mg of His-tagged protein at a concentration of 2 mg/mL was mixed with 1:100 (w/w) recombinant bovine Enterokinase (His-tagged) (GeneScript) at 4° C. overnight. The cleavage mixture were then loaded to 5 mL HisTrap column. The flow-through and 5 CV of washing solution typically contain tag-free thymidine phosphorylase, which were dialyzed against phosphate buffer saline for the bioconjugation step (FIG. 1B).

Figure 17A:
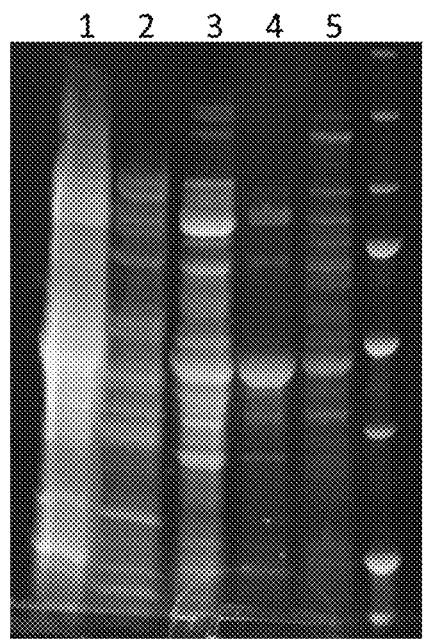
FIG. 17A is an SDS-PAGE analysis showing the expression and purification of tag-free thymidine phosphorylase TP16 was expressed from E. coli culture using minimal medium as batch medium and yeast extract as fed-batch medium in a PDI loop controlled bioreactor. From left to right are 1. Supernatant of cell lysate, 2. Flow through from the first Phenyl Sepharose chromatograph capture step, 3. Elution with 50% buffer B from Phenyl Sepharose chromatograph, 4. Elution with 75% buffer B from hydrophobicity interaction chromatograph, 5. Elution with 100% buffer B from hydrophobicity interaction chromatograph.
Figure 17B:
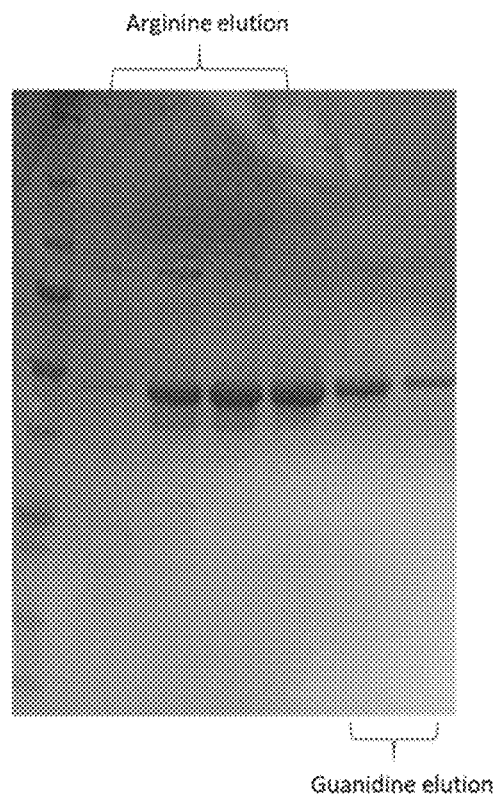
FIG. 17B is an SDS-PAGE analysis showing the elution profile from the purification of TP16 using Capto adhere multimodal chromatography.

For the purification of tag free TP16 harvested from bioreactor process described above. The pellet in lysis buffer (5 mL per gram of biomass). The composition of the lysis buffer is 50 mM Tris-HCl pH 7.5, 5 mM EDTA, 1 ml of 1× protease inhibitory cocktail per 20 grams of pellet. Homogenization of the biomass was performed by sonication in a Branson instrument, four rounds of 10-cycles sonication were required to fully release soluble TP enzyme. Sonication cycles were 30 s On/30 s Off at 30% intensity. Clarification of the crude solution was done by centrifugation for 30 min at 18000 G and 4° C. Purification of TP16 from the crude supernatant was achieved in two chromatography steps using phenyl (hs) and capto adhere prepacked resins. First, the crude supernatant containing the soluble TP16 was loaded on a HiTrap® Phenyl Fast Flow (HS) in the presence of 0.7 M $(NH_4)_2SO_4$ with a proportion of 20 mg total protein per ml of resin. The phenyl column was pre-equilibrated with buffer A, 50 mM Tris-HCl 0.7 M $(NH_4)_2SO_4$ adjusted to pH 7.5. The bound protein was washed with 10 column volume (CV) of buffer A. The target enzyme was eluted with a three-steps gradient (50%, 75% and 100%) of increasing concentration of buffer B, 10 mM TrisHCl pH 8.0 (FIG. 17A). The fraction that eluted at 75% of buffer B was directly loaded into capto adhere prepacked column with a proportion of 10 mg/ml of resin. The capto adhere column was pre-equilibrated with buffer B. Bound protein was washed with 20 CV of buffer B, followed by 20 CV of 50 mM citrate buffer washing, then 1 M NaCl pH 4.5, 20 CV of PBS buffer washing, 0.250 M arginine pH 7.4 washing, and 20 CV of 0.5% CHAPS 5 mM EDTA in TrisHCl buffer pH 7.5 washing. Most of the target protein was eluted with 30 CV of 0.500 M arginine in PBS buffer pH 7.4, while the rest was eluted with 20 CV of 0.75 M guanidine-HCl. The purity of this pool was more than 90% (determined by SDS-PAGE) (FIG. 17B). The final TP16 production was buffer exchanged into PBS for storage or protein modifications.

The tag free TP can also be produced with high efficiency using an inclusion body based refolding process. In this case, a glycerol stock seed (1 mL) was thawed and used to inoculate the initial culture (5 ml terrific broth growth medium, composed of 10 g/L soyton, 5 g/L yeast extract, 10 g/L NaCl, pH 7.5, 50 mg/L1 Kanamycin) at 28° C., 250 rpm for overnight. When the culture achieved an optical density ($OD_{600\ nm}$) around 2-3, it was used to inoculate a 2 L terrific broth growth medium in the bioreactor. After inoculation, the culture was grown at 37° C. with the temperature controlled by a PID loop. Dissolved oxygen (DO) was set at 20% and was also controlled by a PID loop control and with stirring-first-oxygen priority in that order, the minimum/maximum stirring was set at 400/800 rpm. The pH was adjusted to 7.2 and controlled by a PID loop, using 28-30% (m/v) $NH_4OH$ through the alkali pump. A glucose feeding solution was setup through the acid pump and under the same pH PID loop control, and this was maintained until the end of the fermentation process. The culture was induced with 1 mM IPTG at $OD_{600\ nm}$ around 15 at 37 degree Celsius. The culture was induced one more time with the same IPTG concentration after 2.5 hours. The biomass was harvested 5-6 hours post-first-induction by centrifugation, the achieved biomass production was ~25 g/L of culture, and the pellet was stored at −80° C. till further purification.

The cell pellet was resuspended in 50 mM Tris buffer pH 8.0, 200 mM NaCl, 5 mM DTT and homogenized by sonication (10 mL lysis buffer per gram pellet). The lysate was centrifuged at 12000 rpm for 30 min and the pellet containing inclusion bodies were collected. The inclusion bodies were washed with a buffer containing 50 mM Tris, pH 8.0, 200 mM NaCl, 5 mM DTT and 1% Triton X-100, resuspended by a short cycle of sonication and centrifuged at 12000 rpm at 4° C. Four washing steps were needed to remove most of impure proteins and membrane components. A buffer without Triton but with 1M NaCl was used for the last step washing to remove residual Triton X-100 and host genomic DNA. The purified inclusion bodies can be stored at −20° C. till further purification.

Figure 35:
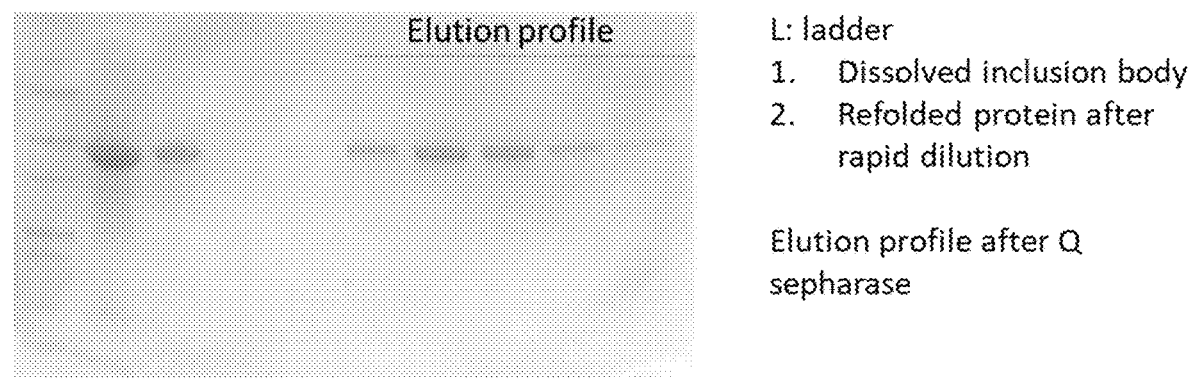
FIG. 35 is the SDS-PAGE analysis showing the refolding process of TP16. From left to right, molecular weight marker (lane 1), dissolved inclusion body (lane 2), refolded protein after rapid dilution (lane 3), flow through from Q sepharase chromatography.
Figure 36:
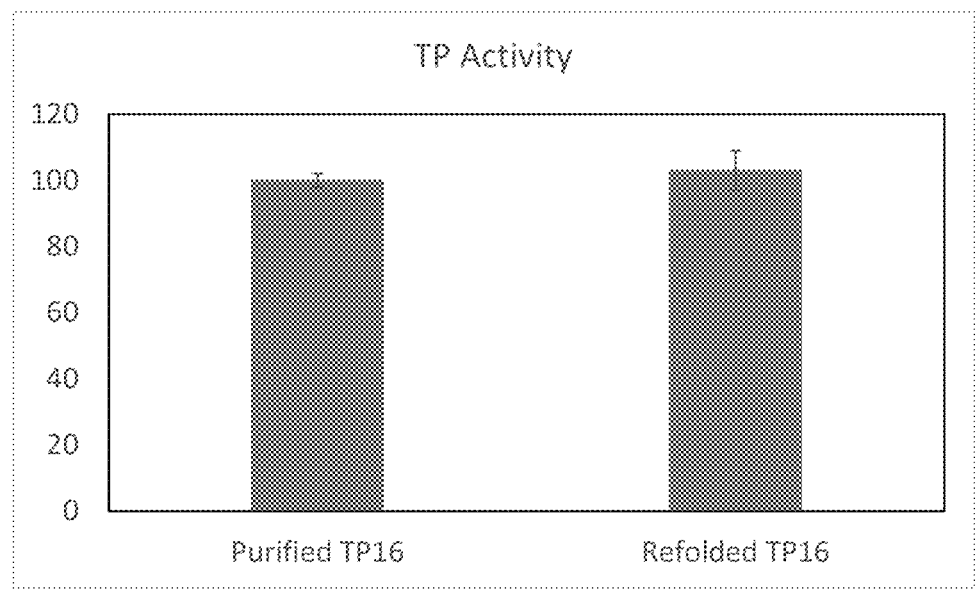
FIG. 36 is a graph comparing the enzymatic activity of TP16 purified from soluble fraction (left) and TP16 obtained from refolding process (right).

The inclusion body was gently dissolved with 50 mM Tris, pH 8.0, 200 mM NaCl, 8 M Urea, and 10 mM DTT to 20 mg/mL of protein solution at room temperature. The dissolved inclusion body solution was harvested as the soluble solution after centrifuge at 12000 rpm for 30 min at 4° C. Afterwards, urea-free buffer was added to bring down the urea concentration to 6M. To remove the bioburden and DNA contents, the inclusion body solution was applied on Q sepharose column on an AKTA purifier and the flow through was collected. To refold the protein, the inclusion body solution was rapidly diluted by 20 fold into 50 mM Tris, pH 8.0, 200 mM NaCl, and 5 mM DTT at 4° C. The resulting solution was kept at 4° C. for overnight before it was further diluted another six fold with into 50 mM Tris, pH 8.0 and 1 mM DTT. The resulting solution was loaded on Q sepharase column and the target protein was eluted with increasing sodium chloride concentration to obtain the refolded protein with desired specific TP activity (FIGS. 35 and 36).

Figure 30:
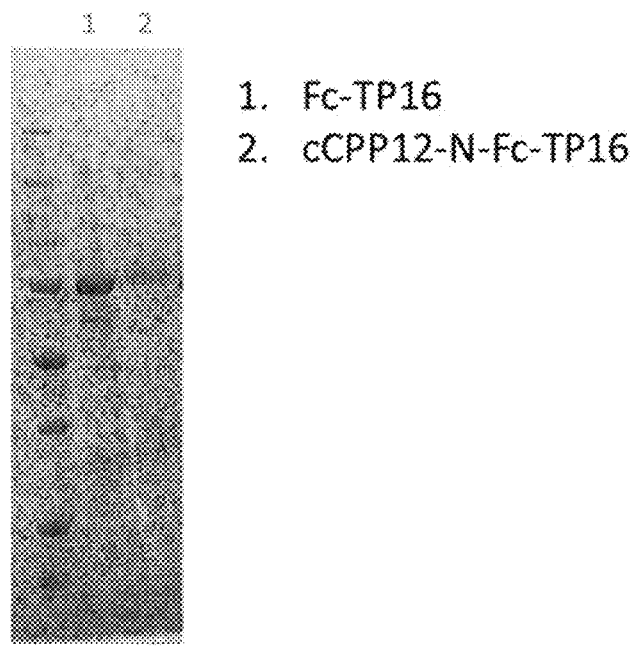
FIG. 30 is an SDS-PAGE analysis showing the Fc-TP16 and CPP conjugated Fc-TP16. Lane 1 Purified Fc-TP16 (SEQ ID NO. 7 in Table 6), and lane 2. cCPP12-N-Fc-TP16 conjugated protein.

For the purification of human IgG1Fc fusion TP16 (e.g. Fc-TP16), bacteria pellets from 1 L cell culture were resuspended in 10 mL lysis buffer (20 mM sodium phosphate, pH 7.4, 1 mM EDTA). Once the pellet was resuspended, 2 mg of pre-dissolved lysozyme and 100 μl of protease inhibitor cocktail (protease inhibitor cocktail, Sigma, P8849) were added. The solution was stirred on ice for approximately 15 min and the cells were sonicated on ice. The suspension was cleared by centrifugation at 20,000 g for 30 min at 4° C. The supernatant was harvested and applied to a 1 ml Protein A column (Protein A, fast flow, 1 ml, GE) at 1 mL/min before washed with 20 mL of washing buffer A (20 mM sodium phosphate, pH 7.4). To remove endotoxin, the column was then washed with 50 column volume of Triton X-114 buffer and CHAPS buffer (buffer A supplemented with 0.1% Triton X-114 (v/v) and 1% (w/v) CHAPS detergent). Afterwards, the column was washed with 20 CV of buffer A before elution with elution buffer (0.1M sodium citrate, pH 3.0) in 10 column volume (FIG. 30).

Cyclic Cell Penetrating Peptides (cCPPs).

cCPPs were synthesized by solid phase peptide synthesis using Fmoc-chemistry, deprotected and released from the solid support, triturated, and purified using RP-HPLC. Conjugation of between cCPP12 with a C-terminal Lysine and 4-formyl-benzamido-dPEG$_{12}$-TFP ester (Product #10081, Quanta Biodesign) was performed in pH 7.4 phosphate buffer at 1:1 ratio for 2 h. The product, cCPP12-PEG$_{12}$-FBA, was again purified by RP-HPLC and lyophilized for storage prior to use.

Amine-Based TP-cCPP Conjugation.

Figure 3:
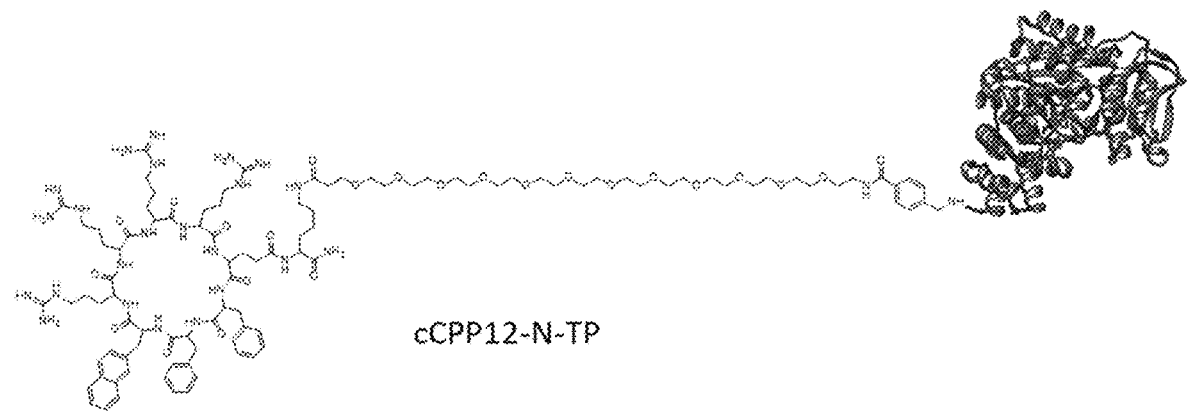
FIG. 3 is a structural scheme of cCPP12-N-TP produced by reductive amination reaction between TP and cCPP12-PEG$_2$-FBA.
Figure 19:
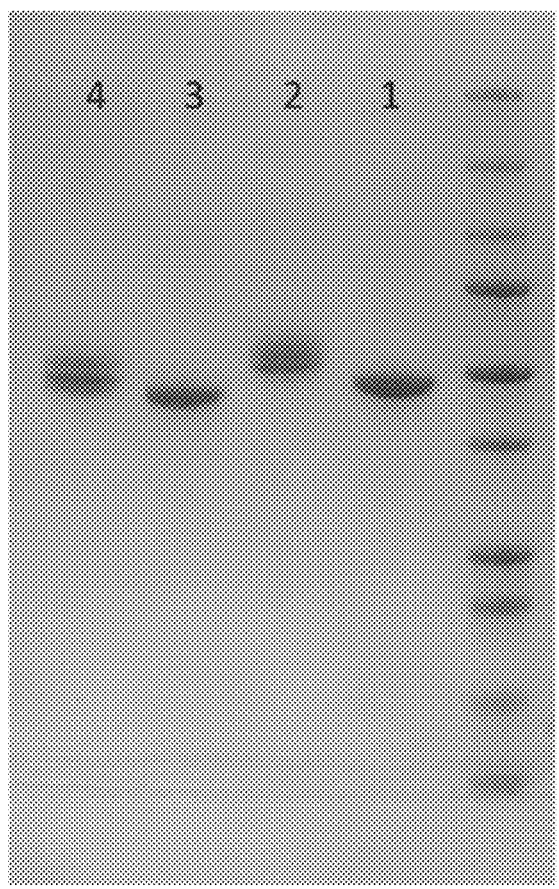
FIG. 19 is an SDS-PAGE analysis showing the cCPP-conjugated TP proteins. 1. TP11 protein, 2. cCPP12-N-TP11 protein, 3. TP16 protein, 4. cCPP12-N-TP16 protein.

To prepare the cCPP-TP conjugates through reductive amination reactions on amine groups of TP protein, freshly purified TP11 or TP16 (0.5 mg/mL, 10 µM) was mixed with the cCPP-linker conjugate, e.g., cCPP12-PEG$_{12}$-FBA (80 µM) in pH 6.0 2-(N-morpholino)ethanesulfonic acid buffer (0.1 M), followed by the addition of 10 mM freshly prepared sodium cyaonoborohydride. The reaction was gently mixed for 36 h before analyzed by SDS-PAGE to confirm the completion of bioconjugation. Reaction was then quenched with glycine, and small molecules as well as extra peptides were removed by dialysis against phosphate buffer saline (pH 7.4) for 16 h twice. The resulting conjugates are represented as "CPP-N-TP", with N referring to the N-terminal of TP as the site of conjugation. Alternatively, cCPP12-N-TP11 or cCPP12-N-TP16 were prepared by mixing TP (2 mg/mL, 40 µM) with cCPP12-PEG$_{12}$-FBA (320 µM) and 10 mM freshly prepared sodium cyanoborohydride in phosphate buffer saline (pH 7.4) for 36 h, and then the reaction mixture was purified by filtration to remove extra peptide and other chemical reagents. Conjugated protein (e.g. cCPP12-N-TP11, see FIG. 3 or FIG. 19; e.g. cCPP12-N-TP16, see FIG. 19) was then temporally stored in 4° C. for immediate usage or formulated in the presence of 2% mannitol for long-term storage at −20° C.

To prepare the CPP-conjugated Fc-TP16 through reductive amination reactions on amine groups of TP protein, freshly purified FcTP16 (1.65 mg/mL, 22 micromolar) was mixed with the cCPP-linker conjugate, e.g., cCPP-PEG12-FBA (220 micromolar) in pH 8.0, 4-(2-hydroxyethyl)-1-piperazineethanesulfonic acid (HEPES) buffer (0.1 M), followed by the addition of 10 mM freshly prepared sodium cyaonoborohydride. The reaction was gently mixed for 48 h before analyzed by SDS-PAGE to confirm the completion of bioconjugation (e.g. cCPP12-N-Fc-TP16, see FIG. 30).

PEGylated Conjugates.

To prepare PEGylated products, freshly purified cCPP12-N-TP11 or cCPP12-N-TP16 (4 mg/mL, 80 µM) was mixed with the PEG5K/10K/40K linear/40K branched-NHS ester (NHS, N-hydroxyl succinimide) or PEG12-NHS ester (around 2 kDa molecular weight). The reaction was gently mixed for 2 h at room temperature in phosphate buffer (50 mM sodium phosphate, pH 7.4, 150 mM sodium chloride) or sodium bicarbonate buffer before analyzed by SDS-PAGE to confirm the completion of PEGylation. PEGylated proteins (CPP12-N-TP-PEG5K, CPP12-N-TP-PEG10K, CPP12-N-TP-PEG40K linear, CPP12-N-TP-PEG40K branched, or CPP12-N-TP-PEG12) were then diluted with 20 mM Tris, pH 8.0 to 0.4 mg/mL protein concentration before applied on Q-Sepharose column at the flow rate of 1 ml/min. Additional PEGylation reagents were washed with 20 mM Tris, pH 8.0. PEGylated proteins were eluted with 20 mM Tris, pH 8.0 with 1 M sodium chloride. Combined fractions with desired product were dialyzed with phosphate buffer saline (pH 7.4) twice and sterile filtered and stored at 4 mg/mL at −20° C. Final products including cCPP12-N-TP-PEG5K, cCPP12-N-TP-PEG10K, cCPP12-N-TP-PEG40K linear, or cCPP12-N-TP-PEG40K branch were further characterized in biological assays.

To facilitate the detection of TP and conjugated TP in vitro and in vivo. Alexa568 fluorophore was used to label the protein on random lysine residues. Briefly, 2.0 mg/mL of protein was mixed with 7.5-15 equivalent of Alexa Fluor 568 NHS Ester (ThermoFisher Scientific) at room temperature. The reaction was quenched by glycine solution after 2 h. Fluorescently labeled material was isolated by size exclusion chromatography.

Disulfide-Based TP-cCPP Conjugation ("CPP-S-S-TP").

Figure 18:
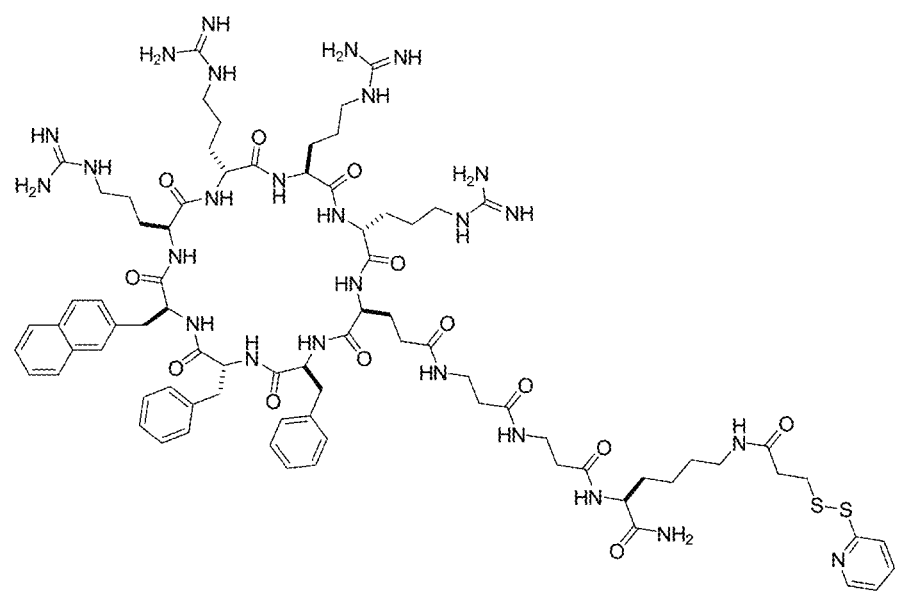
FIG. 18 is the structure of cCPP12-SS-SPDP.

To conjugate the TP protein through Cys residues, cyclic CPP with an activated disulfide modality (SPDP) was designed and synthesized on solid phase. The product, cCPP12-S—S-SPDP was purified by RP-HPLC and lyophilized for storage prior to conjugation. The structure is shown in FIG. 18.

Preparation of cCPP12-SS-TP-PEG10K.

Figure 20:
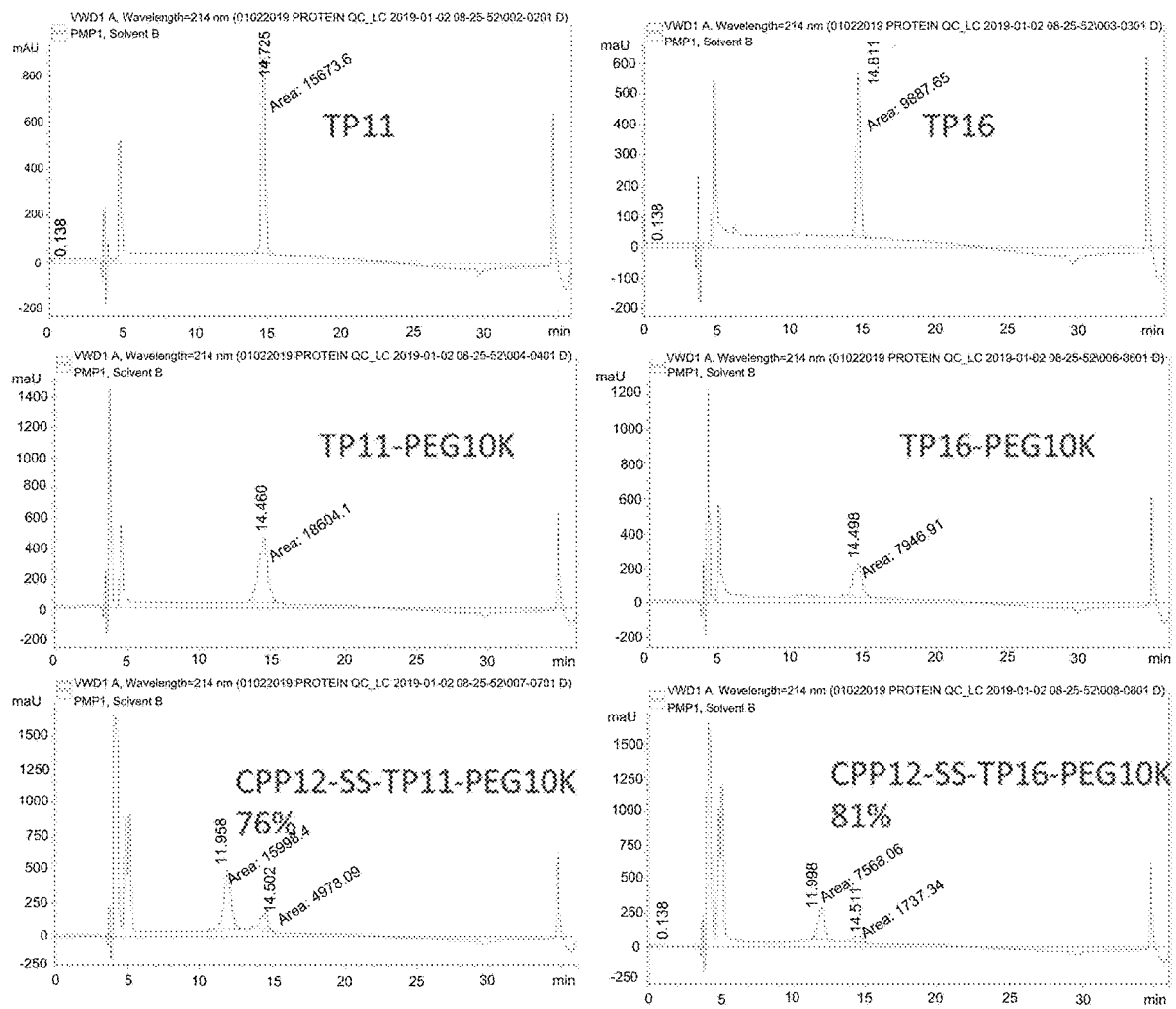
FIG. 20 is the RP-HPLC analysis of TP11, TP16, PEG10K-modified TP11, PEG10K modified TP16, cCPP12-SS-TP11-PEG10K, or cCPP12-SS-TP16-PEG10K.

Freshly purified TP11 or TP16 (2 mg/mL, 40 µM) was mixed with the PEG10K-NHS ester (NHS, N-hydroxyl succinimide, 1:20 molar ratio) in PBS buffer. The reaction was gently mixed for 30 min at room temperature followed by another treatment of 1:20 molar ratio PEG10K-NHS ester for 1 h at room temperature in PBS before analyzed by SDS-PAGE to confirm the completion of PEGylation. PEGylated proteins (PEG10K-TP11 or PEG10K-TP16) were then diluted with PBS to 0.5 mg/mL protein concentration before cCPP conjugation. Diluted PEGylated proteins were pre-treated at 48° C. for 30 min. cCPP12-B-B-SPDP was immediately added to the protein solution (1:30 molar ratio) and react at 48° C. for another 1 h. Excess PEG10K and peptides were removed by Amicon Ultra-15 centrifugal filter units (30K MWCO). The conjugation reactions were monitored by RP-HPLC equipped with C4 column using 0.1% TFA (v/v) supplemented water as buffer A and 0.1% TFA (v/v) supplemented acetonitrile as buffer B as shown in FIG. 20. The products, CPP12-SS-TP11-PEG10K and CPP12-SS-TP16-PEG10K, were further evaluated in biological assays.

Example 2. Characterization of TP and TP Conjugates

Figure 21:
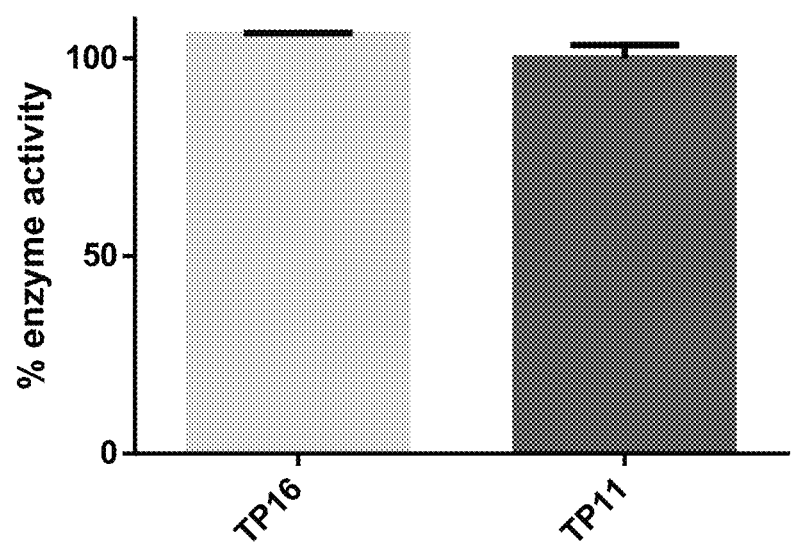
FIG. 21 is graph comparing the enzymatic activity of TP11 (right) and TP16 (left).

A biochemical TP enzyme activity assay was developed. The enzyme activities of purified TP or conjugated TP were performed by measuring the change of absorbance at 290 nm during enzymatic phosphorylation of thymidine. Basically, 200 microliter of nanomolar concentrations of the enzyme in phosphate buffer saline was mixed with 2 mM thymidine at 37° C. Progress of reactions were monitored at 290 nm, indicating the conversion of thymidine to thymine by TP. Coeffeciency of 2000 $M^{-1}$ $cm^{-1}$ was used to calculate the turnover rate in the unit of $s^{-1}$, which is the number of thymidine molecule converted to thymine every second by one enzyme. TP16 is functionally similar to TP11 at a concentration of 100 nM in the enzymatic assay (see FIG. 21, y axis represent the normalized enzyme activity, error bars represent the technical triplicates for the data).

Figure 2A:
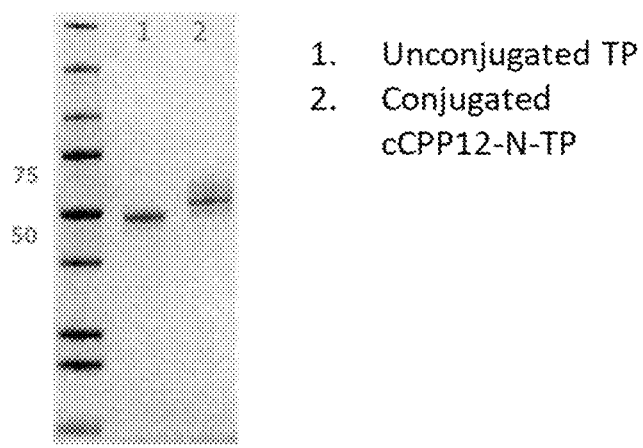
FIG. 2A is the SDS-PAGE analysis showing the conjugation and production of CPP12-N-TP11.
Figure 2B:
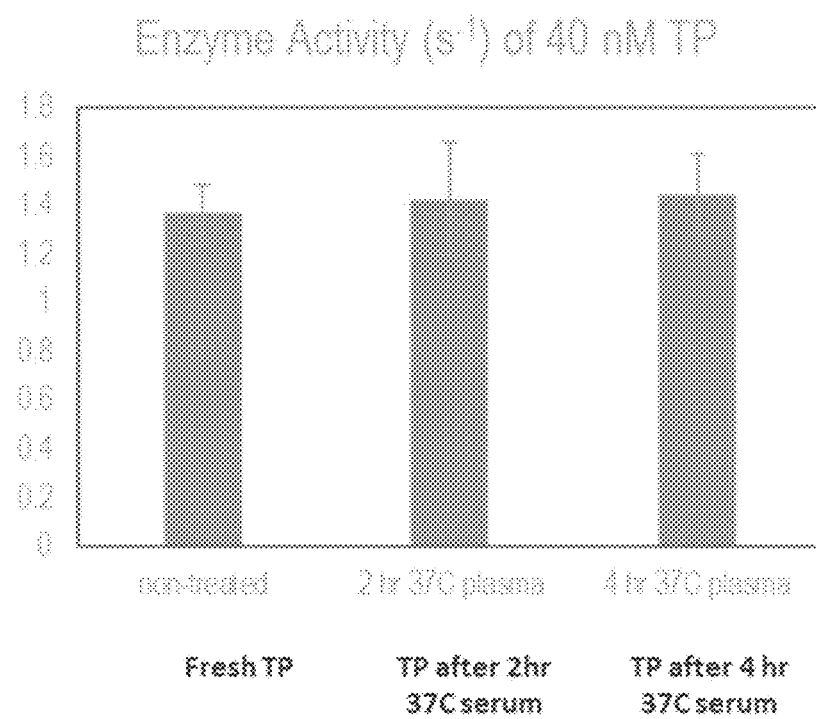
FIG. 2B is a graph showing the maintenance of enzymatic activity (i.e. enzymatic stability) of TP11 in mouse serum after 2 h and 4 h treatments.

Enzyme stability of TP11 in serum was evaluated and the data is presented in FIG. 2B. The data in the graph indicates that enzymatic activity (i.e. enzymatic stability) of TP in mouse serum was maintained after both 2 h and 4 h incubation at 37° C.

Figure 4A:
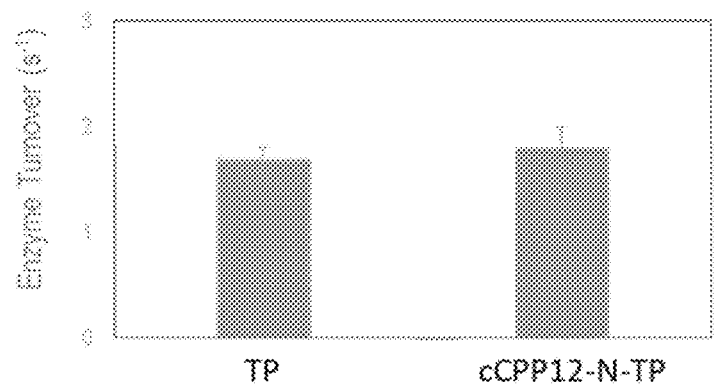
FIG. 4A is a graph comparing the enzymatic activity of unconjugated human TP11 (40 nM) with the enzymatic activity of cCPP12-N-TP11 (40 nM).
Figure 22:
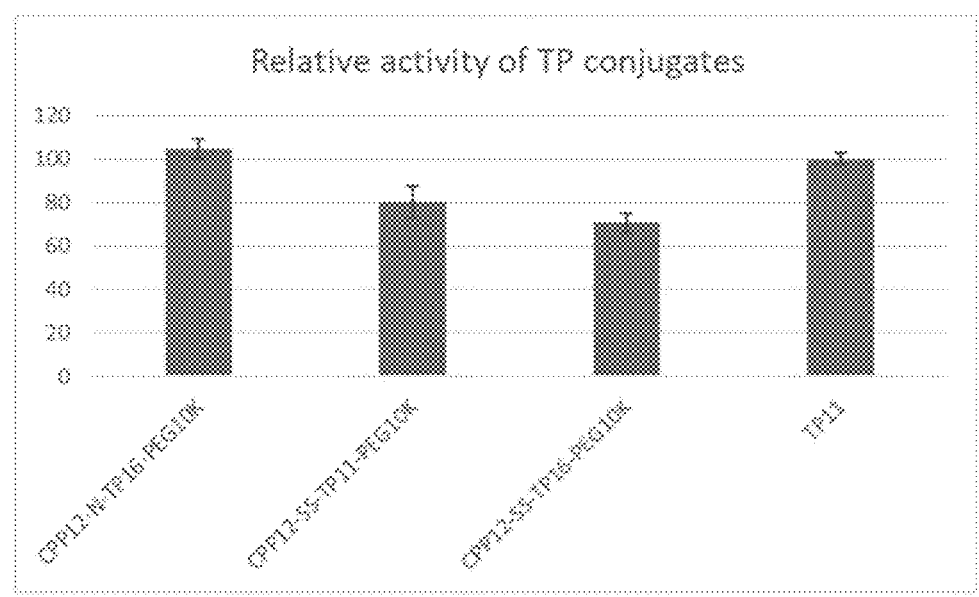
FIG. 22 is graph comparing the enzymatic activity of (from right to left) TP11, cCPP12-SS-TP16-PEG10K, cCPP12-SS-TP11-PEG10K, and cCPP12-N-TP16-PEG10K.
Figure 31:
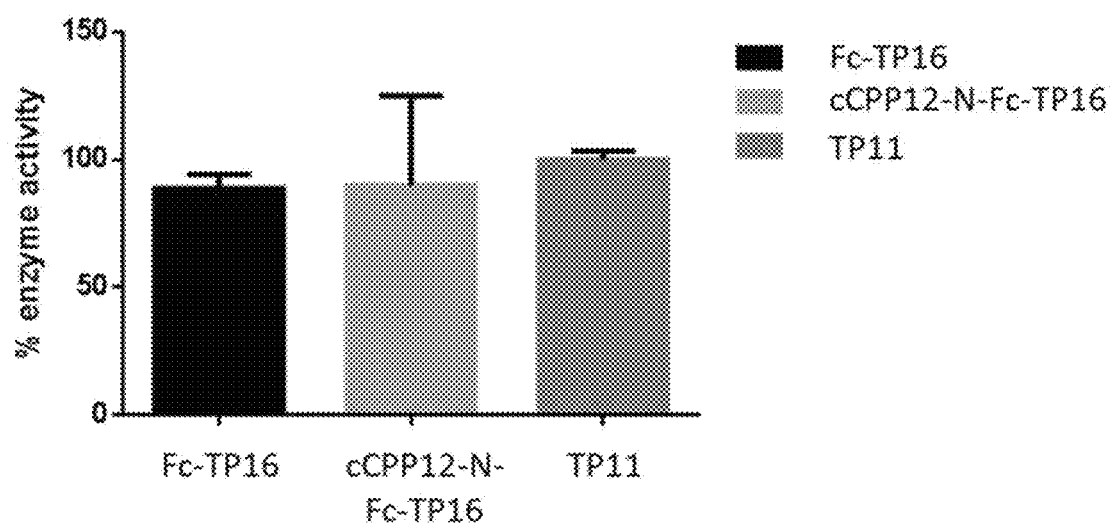
FIG. 31 is a is graph comparing the enzymatic activity of Fc-TP16 (left), cCPP12-N-FcTP16 (middle), and unconjugated TP11 (right).

CPP12 was conjugated to N-terminus of TP11 according to the procedures described in Example 1. The enzymatic activity of the resulting product CPP12-N-TP11 (see FIG. 3) was compared to unconjugated TP11 (FIG. 4A) at a concentration of 40 nM. Measuring enzyme turnover rate showed that CPP12-N-TP11 is functionally equivalent to unconjugated TP1 (similar observations for TP16 and CPP12-N-TP16). All PEGylated TP disulfide linked or N-terminus labeled CPP conjugates (CPP12-SS-TP11-PEG10K and CPP12-SS-TP16-PEG10K and CPP12-N-TP11-PEG10K and CPP12-N-TP16-PEG10K) possess similar activity to unconjugated TP11 at a concentration of 100 nM in enzymatic assay (FIG. 22). And Fc fused TP16 (e.g. Fc-TP16) and the CPP conjugated Fc-TP16 also show similar enzyme activity compared to unconjugated TP11 at a concentration of 100 nM in enzymatic assay (FIG. 31).

Figure 4B:
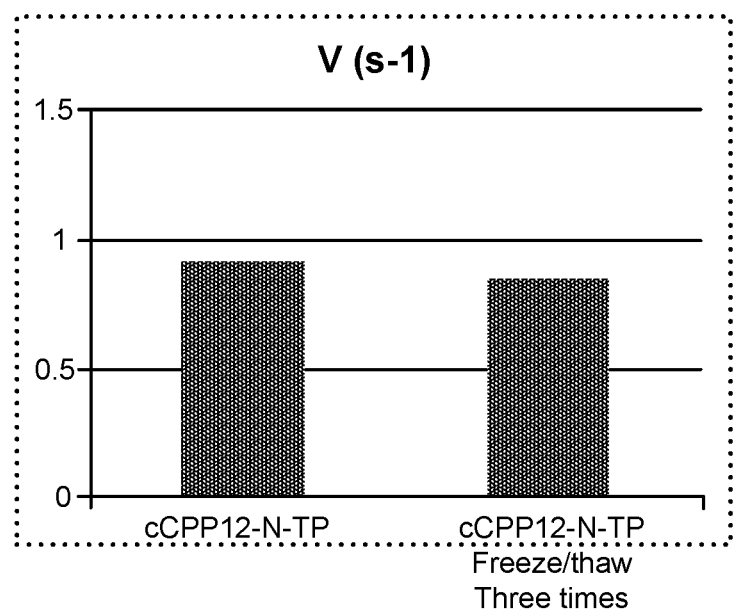
FIG. 4B is a graph comparing the enzymatic activity of CPP12-N-TP11 (40 nM) before (left) and after (right) three cycles of freeze and thaw.
Figure 4C:
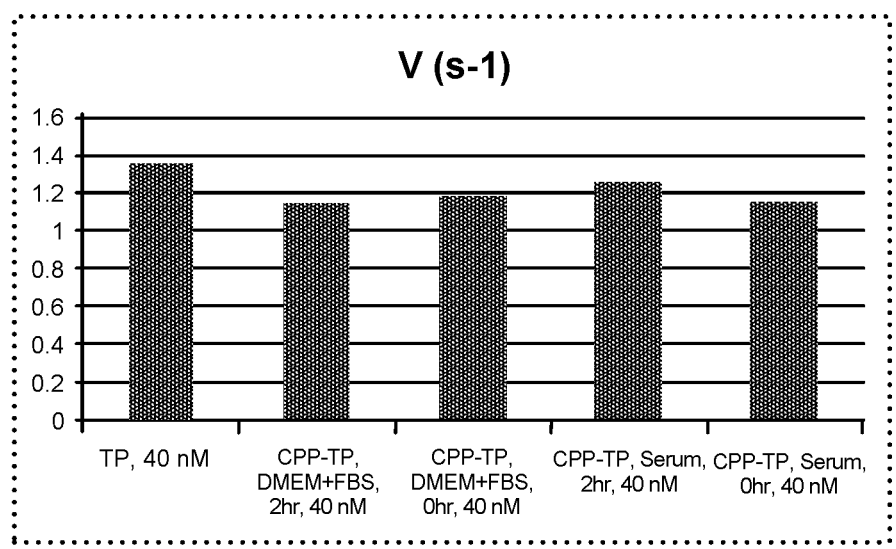
FIG. 4C is a graph showing the maintenance of enzymatic activity (i.e. enzymatic stability) of 40 nM cCPP12-N-TP11 in mouse serum or cell growth medium (DMEM+FBS) after 2 h treatment.
Figure 5:
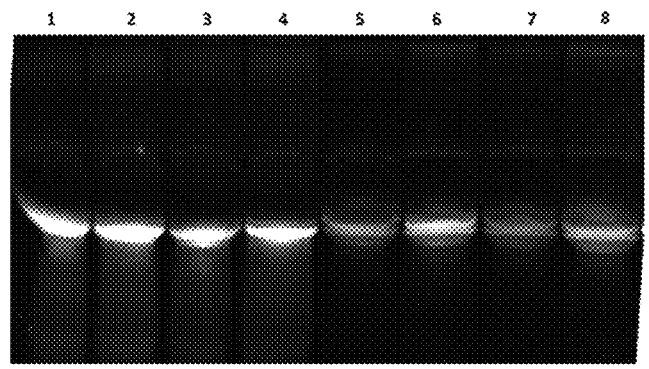
FIG. 5 shows the serum stability of Alexa568-labeled TP11 and Alexa568-labeled cCPP12-N-TP11 in mouse serum after treatments of 0, 2 h, 12 h, or 24 h at 37° C. No degradation is observed.

Further characterization of CPP12-N-TP11 showed that the conjugated compound is stable after freezing and thawing (FIG. 4B). It also remains enzymatically stable after incubation with full growth medium (DMEM+FBS) as well as mouse serum (FIG. 4C). In addition, no degradation was observed for either Alexa568-labeled TP11 or CPP12-N-TP11 in mouse serum at 37° C. for 2 h, 12 h, and 24 h (FIG. 5).

Example 3. Cellular Delivery of TP

Figure 6A:
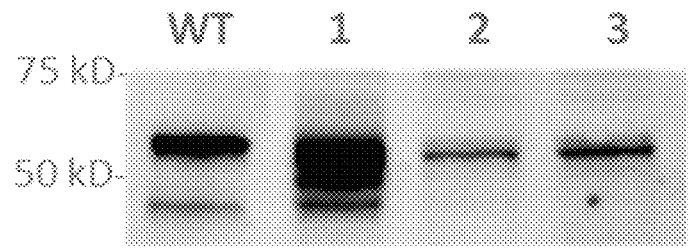
FIG. 6A shows a Western Blotting analysis comparing the amount of intracellular TP in Hela cells (WT with normal TP levels) to LS174T cells (TP-deficient) pretreated for 6 h with 1) 1 µM cCPP12-N-TP11; 2) 1 µM TP11; or 3) control medium. cCPP12-N-TP11 efficiently enters the cell and is enzymatically active.

Studies showed that CPP12-N-TP efficiently enters cells and is enzymatically active. LS174T cells ($1.5 \times 10^6$ per well) were seeded on a 6-well plate in McCoy 5A modified medium containing 10% FBS and 1% penicillin/streptomycin, and cultured for 16 h to reach approximately 80% confluency. Then the growth medium for each well was replaced by 1.5 mL of fresh medium with or without designated amount of TP or CPP12-N-TP. After 6 h treatment, the medium was removed and each well was washed by 4 ml phosphate buffer saline four times. The cells were harvested by trypsinization, and pelleted at 250 G for 5 min. Resuspended cells again were washed with phosphate buffer saline and pelleted for storage at −80° C. till further analysis. Different cell pellets were resuspended on ice with 100 microliter of lysis buffer to extract either cytosolic proteins using cytosolic lysis buffer (50 mg/mL digitonin, 75 mM sodium chloride, 10 mM sodium phosphate, pH 7.4, 250 mM sucrose supplemented with protease inhibitors) or whole-cell proteins using whole cell lysis buffer (1% Triton X-100, 150 mM sodium chloride, 50 mM Tris-HCl, pH 8.0). After lysis, cellular contents were then centrifuged at 16,000 G for 10 min. Supernatants were collected for western blotting analysis or enzyme activity analysis. Western Blotting analysis (FIG. 6A) was used to compare intracellular levels of TP in Hela Cells (WT) with intracellular levels of TP in LS174T (TP-deficient) cells treated under three sets of conditions. Lane 1 showed a high concentration of transduced TP inside of LS174T cells after treatment of 6 h with 1 μM CPP12-N-TP, yielding more abundant TP protein than that of WT cells. Minimum amount of TP entered LS174T cells that were treated with 1 μM unconjugated TP. This level is in line with what was established with control medium. The Western Blotting analysis demonstrated that the CPP modification is necessary and efficient to deliver TP into mammalian cells.

Figure 6B:
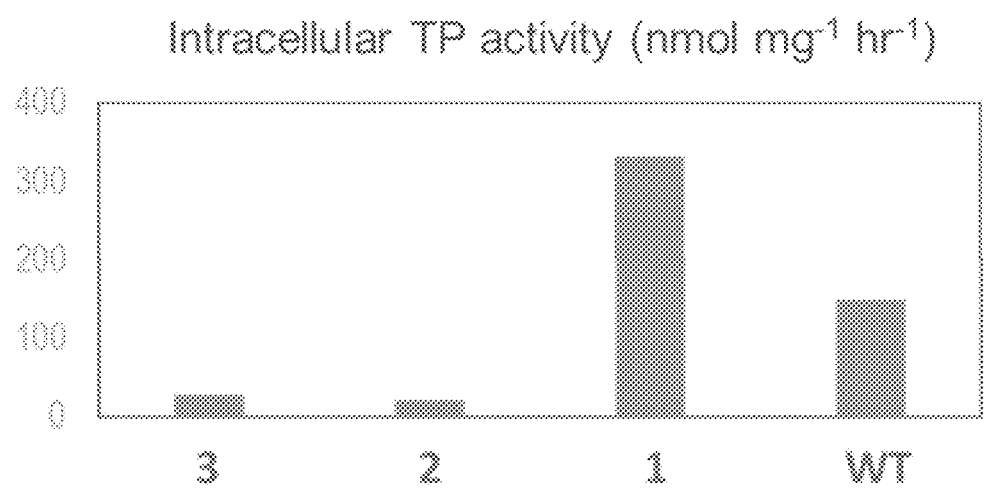
FIG. 6B shows a graph of intracellular TP activity in Hela cells (WT with normal TP levels) to LS174T cells (TP-deficient) pretreated for 6 h with 1) 1 µM cCPP12-N-TP11; 2) 1 µM TP11, or 3) control medium cCPP12-N-TP11 efficiently enters the cell and is enzymatically active.

Intracellular TP activity of cell lysates is expressed as the thymidine to thymine conversion (in nanomole) per hour per mg of cell lysate protein. Briefly, 10 microliter of 10× phosphate buffer saline, pH 7.4, and 12.5 microliter of 80 mM thymidine were added into 77.5 microliter of cell lysate proteins of approximately 2 mg/mL concentration. The reaction mixtures were incubated at 37° C. for different time periods: 0 hr, 1 hr, 4 hr or overnight. After desired reaction time, 20 microliter of reaction mixture was mixed with 180 microliter of 0.3 M sodium hydroxide in water to terminate the reaction. The absorbance at 300 nm was measured, and thymidine to thymine conversion was calculated using absorption coefficient of 3,400 $M^{-1}$ $cm^{-1}$. Comparison of intracellular TP activity (FIG. 6B) between Hela cells (WT) and TP deficient cells (LS174T) under various treatment demonstrated efficient and functional intracellular delivery of TP after 6 h treatment with 1 μM CPP12-N-TP. The enzyme activity of CPP12-N-TP treated LS174T cells is over 300 nmol $hr^{-1}$ $mg^{-1}$, which is considerably stronger than that of WT cells. TP treated and medium treated deficient cells only have background level of TP activity which is between 20-40 nmol $hr^{-1}$ $mg^{-1}$. Thus, CPP12-N-TP not only enters cells, but exhibits high levels of enzymatic activity.

Figure 7:
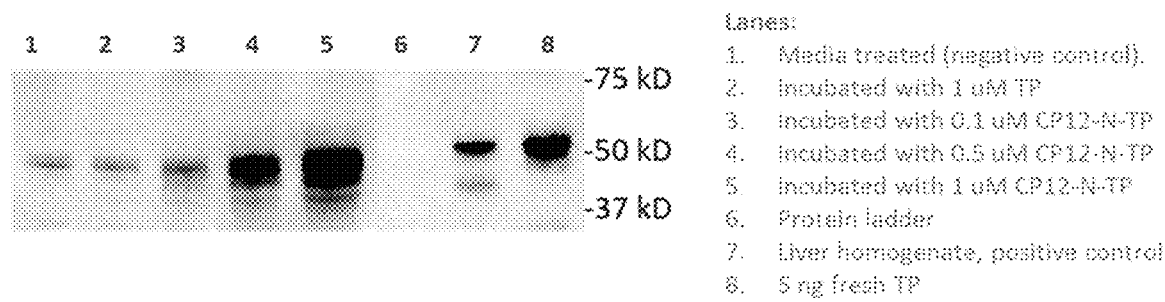
FIG. 7 is a Western Blotting analysis showing the dose dependent delivery of TP11 into LS174T cells: 1) LS174T cells treated with media (negative control), 2) LS174T cells incubated with 1 µM TP11; 3) LS174T cells incubated with 0.1 µM CPP12-TP11; 4) LS174T cells incubated with 0.5 µM CPP12-N-TP11; 5) LS174T cells incubated with 1 µM CPP12-N-TP11; 6) protein ladder, 7) human liver homogenate (positive control); and 8) 5 ng of fresh TP11.

Dose dependent delivery of TP into LS174 cells was analyzed by Western Blot (FIG. 7). Modifying the amount of CPP12-N-TP used to incubate the cells from 0.1 to 0.5 to 1 μM CPP12-N-TP showed a dose-dependent increase in the level of TP delivered into the cultured cells. A substantial increase of intracellular TP contents s observed with 0.5 or 1 μM CPP12-N-TP compared to cells incubated with 1 μM TP, which was essentially equivalent to media treated cells (negative control).

Figure 8:
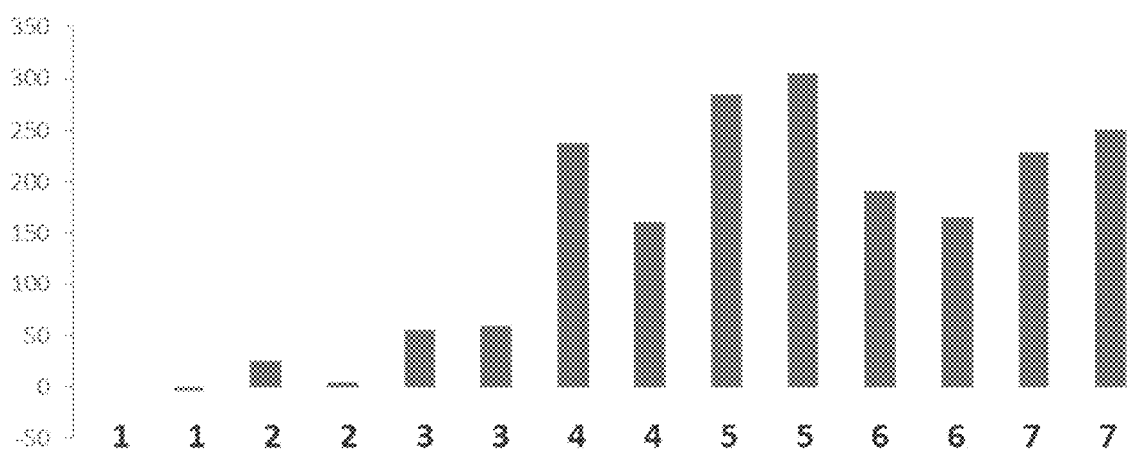
FIG. 8 is a graph showing whole cell or cytosolic TP activity delivered into TP-deficient LS174 cells analyzed by TP enzyme activity: 1) LS174T cells treated with media (negative control); 2) LS174T cells incubated with 1 µM TP11; 3) LS174T cells incubated with 0.1 µM cCPP12-N-TP11; 4) LS174T cells incubated with 0.5 µM cCPP12-N-TP11; 5) LS174T cells incubated with 1 µM CPP12-N-TP11; 6) LS174T cells incubated with 1 µM cCPP12-N-TP11 and lysed with cytosolic lysis buffer; and 7) 20 nM of fresh cCPP12-N-TP11. The data shown in FIG. 8 is from duplicate experiments.

Whole cell and cytosolic TP activity delivered into TP-deficient LS174T cells were analyzed by a TP enzyme activity assay (FIG. 8). LS174T cells were treated for 6 h with different concentrations of CPP12-N-TP (0.1, 0.5, or 1 μM). 1 μM TP and medium treatment were used as controls. The whole cell lysate samples were collected and characterized by enzyme activity assay. Dose-dependency was verified by the data presented in columns 3, 4, and 5, which showed the intracellular TP activity of LS174T cells after treatment with 0.1, 0.5, or 1 μM of CPP12-N-TP, respectively. Cellular uptake and intracellular TP activity was highest at 1 μM CPP12-N-TP, as expected based on the WB results. Moreover, for 1 micromolar CPP12-N-TP treated cells, its cytosolic fraction was also collected. The cytosolic TP activity (column 6) was comparable to the TP activity from WT cells. Comparing TP activity from columns 5, and 6, more than 50% delivered enzyme activity entered cytosol. The result further confirmed that CPP12-N-TP not only successfully internalized into the cells, but also efficiently escaped from the endosome and entered into cytosol.

Figure 34:
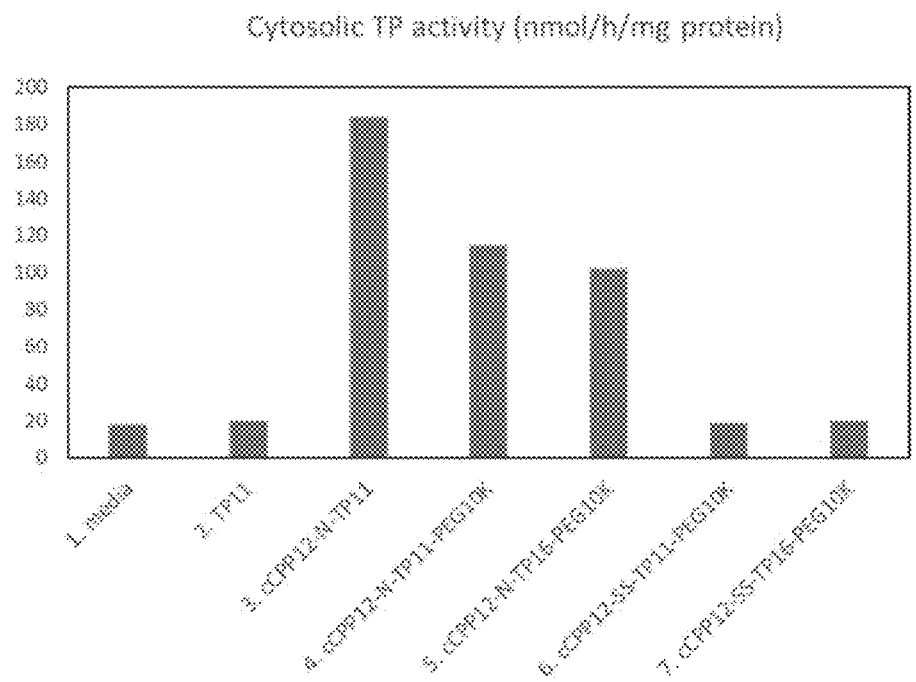
FIG. 34 is a graph showing cytosolic TP activity delivered into TP-deficient LS174 cells as analyzed by TP enzyme activity: 1) LS174T cells treated with media (negative control); 2) LS174T cells incubated with 1 micromolar TP11; 3) LS174T cells incubated with 1 micromolar cCPP12-N-TP11; 4) LS174T cells incubated with 1 micromolar cCPP12-N-TP11-PEG10K, 5) LS174T cells incubated with 1 micromolar cCPP12-N-TP16-PEG10K; (6) LS174T cells incubated with 1 micromolar cCPP12-SS-TP11-PEG10K; and (7) LS174T cells incubated with 1 micromolar cCPP12-SS-TP16-PEG10K.

To evaluate the uptake efficiency of various CPP-TP-conjugates, whole cell and cytosolic TP activity delivered into TP-deficient LS174T cells were analyzed by a similar TP enzyme activity assay. LS174T cells were treated for 6 h with 1 micromolar of cCPP12-N-TP11, cCPP12-N-TP11-PEG10K, cCPP12-N-TP16-PEG10K, cCPP12-SS-TP11-PEG10K, or cCPP12-SS-PEG16-PEG10K. 1 μM TP and medium treatment were used as controls. The cytosolic fraction of incubated cells were collected and characterized by enzyme activity assay (FIG. 34). Cellular uptake and intracellular TP activity were highest at 1 μM CPP12-N-TP treated cells. cCPP12-N-TP11-PEG10K as well as cCPP12-N-TP16-PEG10K also showed significant uptake as expected. Surprisingly, the disulfide based conjugated cCPP12-SS-TP11-PEG10K and cCPP12-SS-TP16-PEG10K showed minimal cellular uptake similar to the level of tag free TP. The result demonstrated that the choice of conjugation chemistry and the site of conjugation are critical for successful cellular delivery and endosomal escape into cytosol.

Example 4. In Vivo Assay

12691 To determine the half-life and biodistribution of CPP-conjugated TP proteins, Alexa568-labeled proteins will be injected through subcutaneous (s.c.), intradermal (i.d.), intravenous (i.v.), or intraperitoneal (i.p.) routes into CD1 mouse or C57BL/6 mouse at 0.1, 1, 2, 5, 10, or 20 mpk per injection. Control group will be injected with PBS or Alexa568-labeled TP protein. Plasma, blood cells, PBMC, various organs (heart, lung, liver, spleen, pancreas, kidney, muscle, intestine, and brain) will be harvested at various time points post injection (0.5, 4, 8, 24, 48, or 96 h). TP enzyme activities from various tissues samples were quantified. Tissue samples were properly reserved for further immunohistology analysis as well as histopathology analysis. Fluorescence in various tissues were quantified. Biodistribution of fluorescently-labeled TP proteins were further examined by SDS-PAGE analysis of tissue homogenates followed by in-gel fluorescence scanning.

To demonstrate the in vivo efficacy of CPP-conjugated TP as a potential treatment of MNGIE, a murine model was leveraged: Tymp/Upp1 double KO mice (reference: Hum Mol Genet 18: 714-722.). Tymp/Upp1 double KO mice were injected with CPP-conjugated TP, TP, or solvent cohorts by i.p., i.v., or s.c. method at once, twice, or thrice weekly with dose up to 20 mpk per injection. Blood samples were collected weekly. Thymidine and deoxyuridine levels in blood were tested by LC-MS assay throughout the study. Thymidine phosphorylase activity in blood were also tested by the TP enzyme activity assay throughout the study. By the end of the treatment (4-12 weeks), mice were sacrificed and the thymidine and level in liver, brain, skeletal muscle, small intestine, and kidney were quantified by LC-MS assay. From the same tissue samples, TP enzyme activity was also quantified following literature method (ref. FEBS Lett 581: 3410-3414.). The abundance of delivered TP in various tissues was also analyzed by western blotting as well as by immunofluorescence assays.

After administration of conjugated TP, plasma thymidine concentrations in most study samples drop from relatively high level (around 10 µM in MNGIE mouse model) to wild-type level (1-3 micromolar). Two to eight months after treatment (end of the study), nucleotides levels in tissues harvested also drop significantly. For example, in liver, thymidine level will decrease from 40-120 pmol/mg protein to lower than 20 pmol/mg protein. Substantial increases of TP protein in various tissues are detected by both an enzyme activity assay as well as Western Blot analysis.

Example 5. Quantification of Serum Thymidine Level in MNGIE Mouse Model

MNGIE mouse models (Mol Cell Biol. 2002; 22: 5212-5221) were used to evaluate thymidine reduction in serum by administrations of CPP-TP conjugates disclosed herein. MNGIE mice have aberrantly high levels (around 10 µM) of thymidine due to the absence of functional TYMP and UPP1 genes thus cannot metabolize thymidine into thymine effectively. Delivery of TP via CPP is therefore expected to reduce thymidine levels.

To quantify the thymidine level in serum, approximately 25 microliter of freshly isolated serum sample were mixed with 46.8 microliter of distilled water and 3.2 microliter of concentrated perchloric acid (initial concentration 11.7 M, final concentration of 0.55 M). Samples were then vortexed for 10 s and kept on ice for 10 min to help with protein precipitation. Afterwards, precipitates were removed by centrifuge at 17,000 G at 4° C. for 10 min. Clear supernatants were collected and analyzed on an Agilent 1100 analytical HPLC equipped with a C18 5 µm, 4.6×250 mm column using gradient elution and UV detection (268 nm). Elution gradient can be referenced to Methods Mol. Biol. 2012; 837: 121-133. Concentration of thymidine, deoxyuridine, and other nucleotides were calculated using area under curve (AUC) and the calibration curves.

Figure 9:
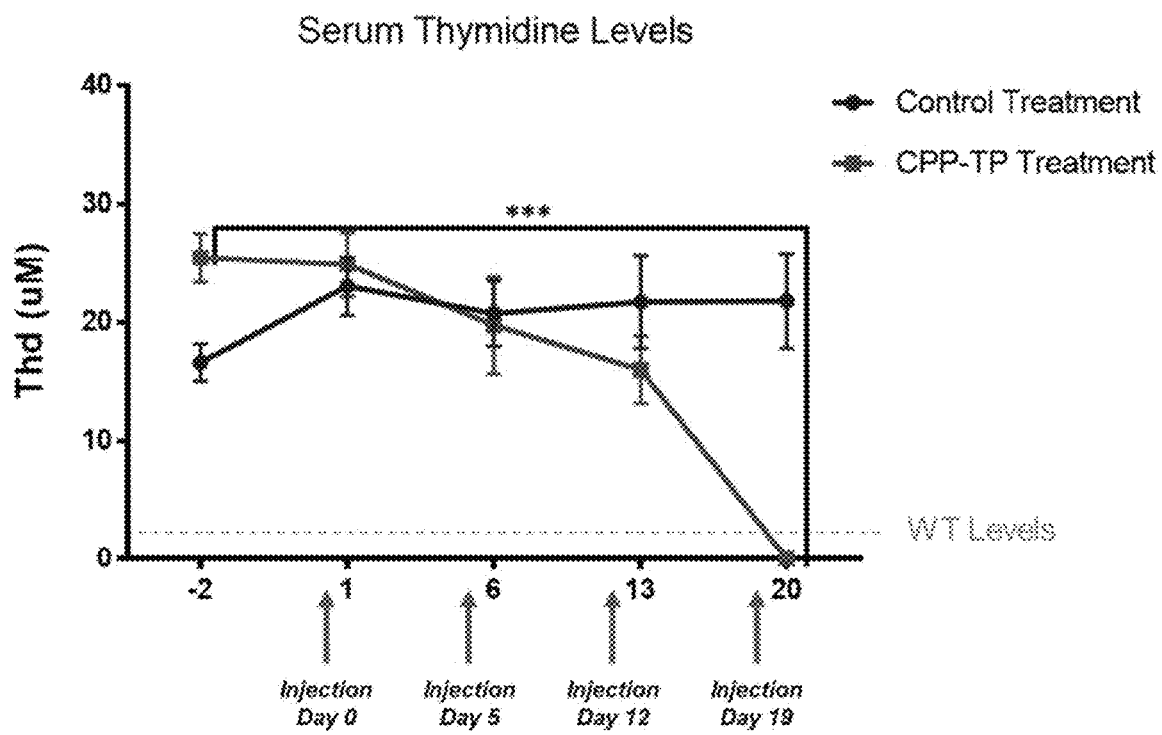
FIG. 9 is a graph showing serum thymidine levels in MNGIE mice treated with a CPP12-N-TP11 conjugate disclosed herein compared to a control.

To test the ability of CPP-TP conjugates to reduce thymidine levels, MINGE mice were treated with a CPP-TP conjugate via tail-vein intravenous injection. Treatment occurred on four days: day 0; day 5; day 12 and day 19 at 7.5, 7.5, 20, and 20 mpk respectively. Serum thymidine levels of the MNGIE mice were measured two days prior to treatment (day −2), and the day after each treatment (day 1, after the first injection; day 6, after the second injection; day 12, after the third injection; and day 20, after the fourth injection). Thymidine levels were compared to untreated MNGIE mice. Statistical analysis was performed using a one-way ANOVA with Geisser-Greenhouse correction (*** indicates a p-value <0.0001). The results are provided in FIG. 9.

The results show that the CPP-TP conjugates reduce serum thymidine levels to healthy levels measured for wild-type mice (comparing day−2 levels to day20 level) whereas thymidine levels in control (phosphate buffer saline) treated group remained elevated.

Figure 10A:
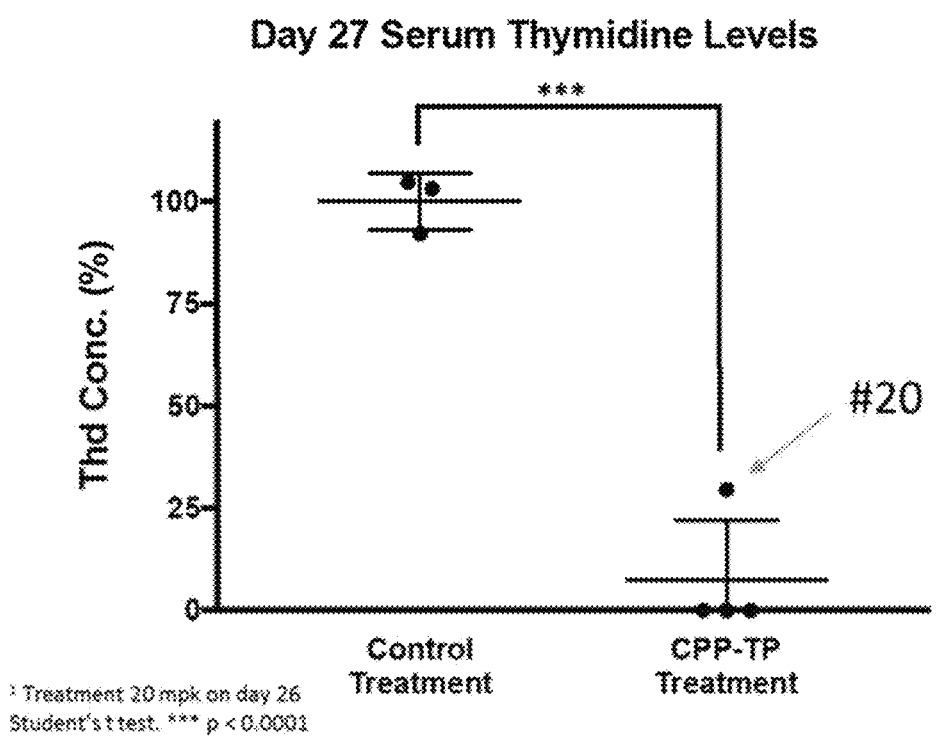
FIG. 10A is a graph showing the percent reduction of thymidine concentration in serum on day 27 in MNGIE mice after administration of a cCPP12-N-TP11 conjugate on day 26.

To confirm results obtained on day 20, the same groups of MNGIE mice were injected again with 20 mpk CPP-TP or vehicle control on day 26, and their thymidine levels were measured on day 27 as described above. Interestingly, three out of four (other than mouse T20) treated MNGIE mice showed depleted thymidine levels in serum, which further confirmed the in vivo efficacy of CPP-TP treatments (FIG. 10A).

Figure 10B:
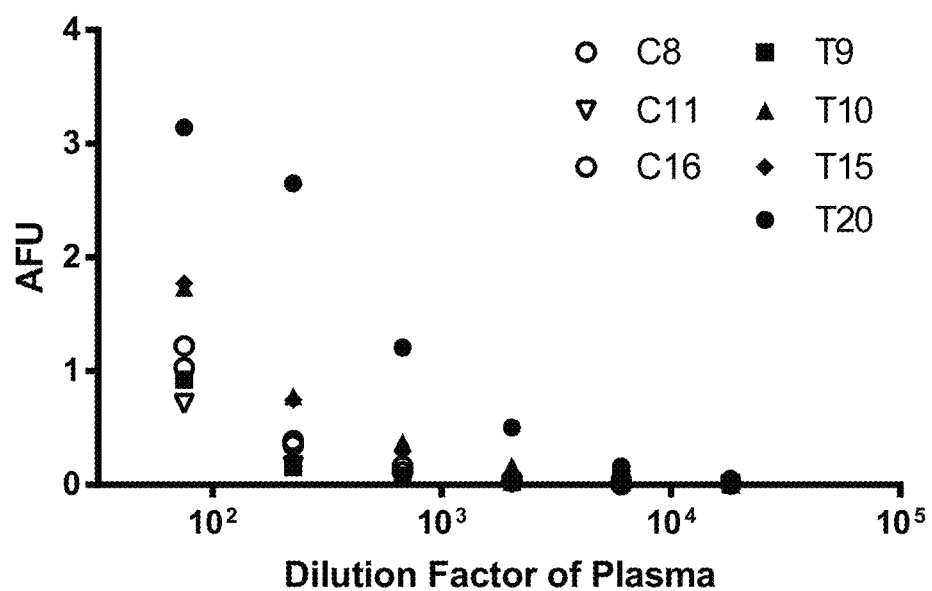
FIG. 10B is graph showing the detection of an anti-CPP-TP antibody by ELISA in MNGIE mice serum on week four, after once-weekly administration for four weeks. Statistical analysis was performed using a Student's t-test (*** indicates a p-value <0.0001).

To investigate the incomplete depletion of thymidine level in the serum of MNGIE mouse T20 (FIG. 10A), potential immunogenicity properties of CPP-human TP were investigated by detecting the formation of anti-drug antibody using an ELISA assay. Briefly, wells in 96-well polystyrene plate were coated with 1 µg/mL of CPP-TP at 37° C. for 1 hour. Wells were then washed three times with washing buffer (phosphate buffer saline and 0.05% tween 20) and incubated with blocking buffer (phosphate buffer saline and 2% bovine serum albumin) at 37° C. for 0.5 hour. Wells were then washed once with washing buffer before incubated with serially diluted serum samples from treated (T9, T10, T15, or T20) or control (C8, C11, or C16) mice at 37° C. for 1 hour. After the incubation, wells were washed thrice and then incubated with 1 µg/mL HRP-labeled goat-anti-mouse IgG (H+L) at 4° C. Afterwards, wells were washed thrice and incubated with TMB substrate solution at room temperature in the dark for 30 min before quenched with 0.1 mL of 1 M hydrogen chloride solution. The absorption at 450 nm were recorded by a plate reader, and the values were plotted against the dilution factor of plasma (FIG. 10B). In this ELISA assay, stronger AFU (i.e. absorption at 450 nm) is positively correlated with increased anti-CPP-TP mouse IgG antibody. Interestingly, serum from mouse T20 is showed significantly elevated level of anti-drug mouse IgG levels which could be the reason for insufficient depletion of thymidine for T20 as shown in FIG. 10A.

Example 6. MNGIE Mouse Model Assay—Duration of Action

To investigate the duration of action by the disclosed CPP-TP conjugates on MNGIE mice, a new group of MNGIE mice were treated with 20 mpk of the CPP-TP conjugate by intravenous injection once weekly for four weeks. Serum thymidine levels were measured on weeks one and two, 24 hours after treatment (W1-24 hr and W2-24 hr, respectively), on week three, 32 hours after treatment (W3-32 hr), and on week four, 36 hours after treatment (W3-36 hr). 50 microliter of serum were harvested at designated time points and their levels of nucleotides were analyzed by HPLC-UV assay as described in EXAMPLE 4.

Figure 11:
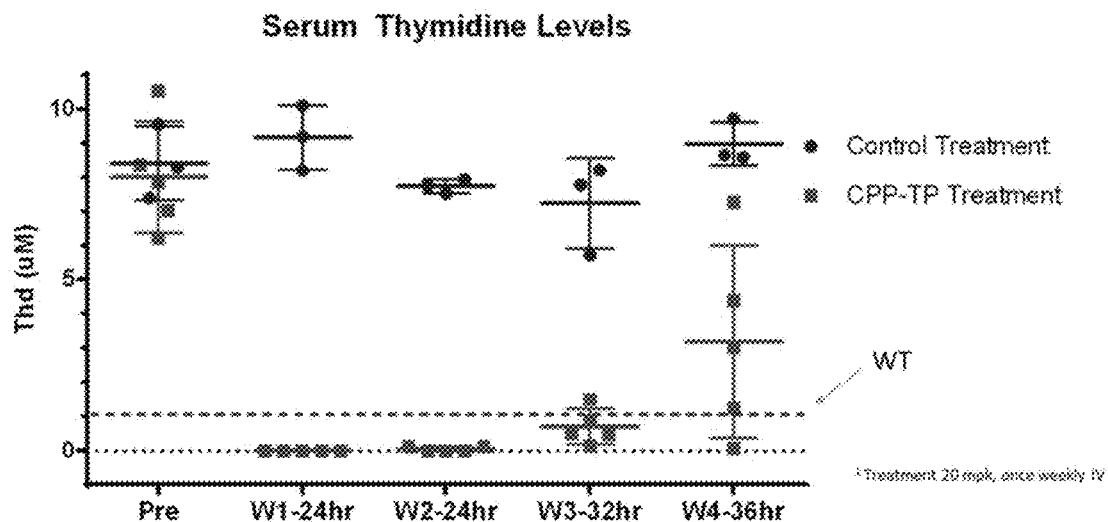
FIG. 11 shows thymidine levels measured after intravenous injection of cCPP12-N-TP11 conjugates at the following time points: weeks one and two 24 hours after treatment (W1-24 hr and W2-24 hr, respectively); week three 32 hours after treatment (W3-32 hr); and week four 36 hours after treatment (W3-36 hr).

The results of this assay are provided in FIG. 11. These results indicate that CPP-TP can reduce and maintain serum thymidine levels in MNGIE mice to that of healthy levels (measured for mice which do not have a mutated TYMP gene) for at least 32 hr.

Example 7. In Vivo Assays with PEGylated CPP-TP Conjugate

Conjugation of water-soluble polymers to proteins has been reported to improve stability of the protein. Disclosed CPP-TP was PEGylated (polyethylene glycol was conjugated on CPP-TP) to investigate whether such a modification would increase cellular stability and thus increase the duration of action. PEGs having a molecular weight of 5 kDa (PEG5K), 2 kDa (PEG12), 10 kDa (PEG10K), 40 kDa with different structures (40K linear and 40K branched) were conjugated to CPP12-N-TP11, respectively, according to the following procedure.

Figure 13:
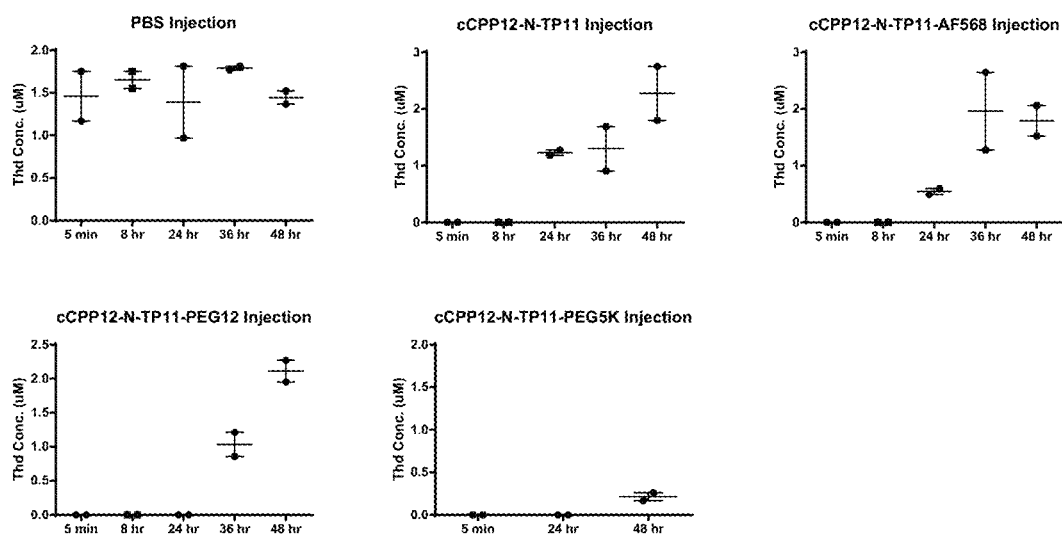
FIG. 13. shows thymidine concentrations (µM) measured at various time points after intravenous injection of non-PEGylated cCPP-TP conjugate (cCPP12-N-TP11) and a fluorescently labeled cCPP-TP conjugate (cCPP12-N-TP11-AF568) compared to two PEGylated cCPP-TP conjugates (cCPP12-N-TP11-PEG12 and cCPP12-N-TP11-PEG5K).

To investigate the duration of action of pegylated CPP-TP conjugates over a 48 hour period following intravenous injection, PBS control, CPP12-N-TP11, CPP12-N-TP11-AF658, CPP12-N-TP11-PEG5K or CPP12-N-TP11-PEG12 were administered to wild type CD1 mice at 8 mpk. Thymidine concentration (µM) in serum was measured at the following time points after tail-vein intravenous administration: 5 min; 8 hr; 24 hr; 36 hr; and 48 hr as described in EXAMPLE 4 (FIG. 13). These results showed that PEGylated CPP-TP conjugates maintain reduced thymidine levels for elongated amount of time compared to non PEGylated analogues. Notably, the PEGylated conjugates (e.g., cCPP12-N-TP11-PEG5K) which significantly reduced the thymidine levels for at least 48 hours following intravenous injection, whereas thymidine levels return to control levels after about 24 hours in the cases of are non-PEGylated TP.

Figure 12:
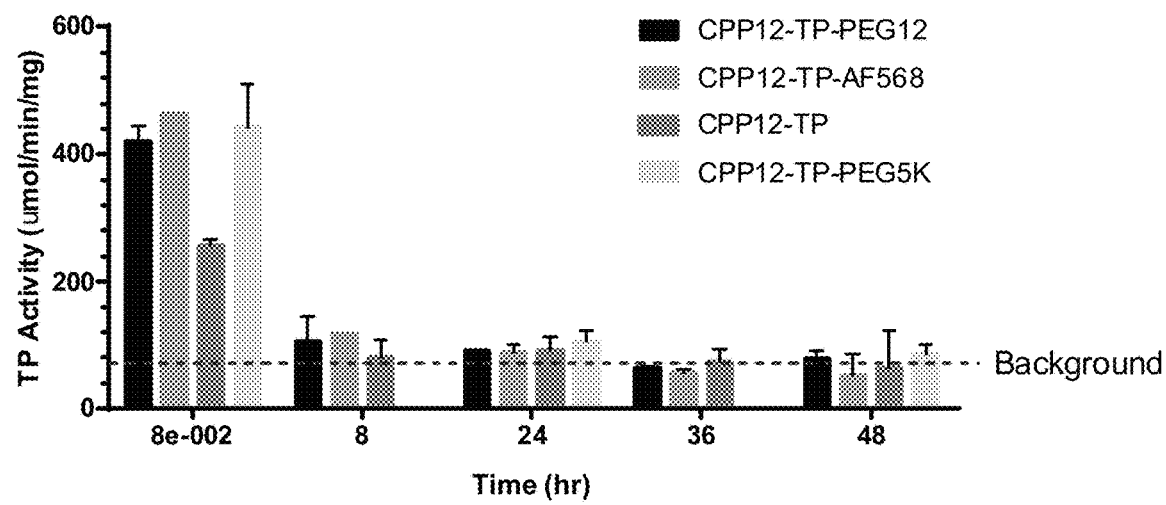
FIG. 12 is a graph showing thymidine phosphorylase levels in the serum of MNGIE mice 24, 32, or 36 hours after treatment with a control, a non-PEGylated cCPP12-N-TP11 conjugate (cCPP12-TP), a fluorescently labeled cCPP-TP conjugate (cCPP12-N-TP11-AF568), and two PEGylated cCPP-TP conjugates (cCPP12-N-TP11-PEG12 and cCPP12-N-TP11-PEG5K).
Figure 14:
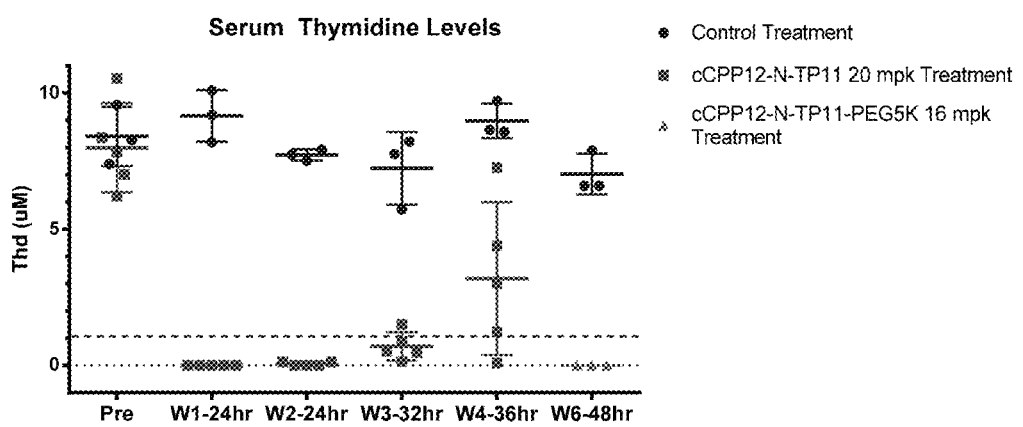
FIG. 14 is a graph showing serum thymidine concentrations (µM) in MNGIE mice after treatment with a PEGylated cCPP-TP conjugate (cCPP12-N-TP11-PEG5K at 16 mpk) compared to a non-PEGylated cCPP-TP conjugate (cCPP12-N-TP11 20 mpk) and a control.
Figure 23:
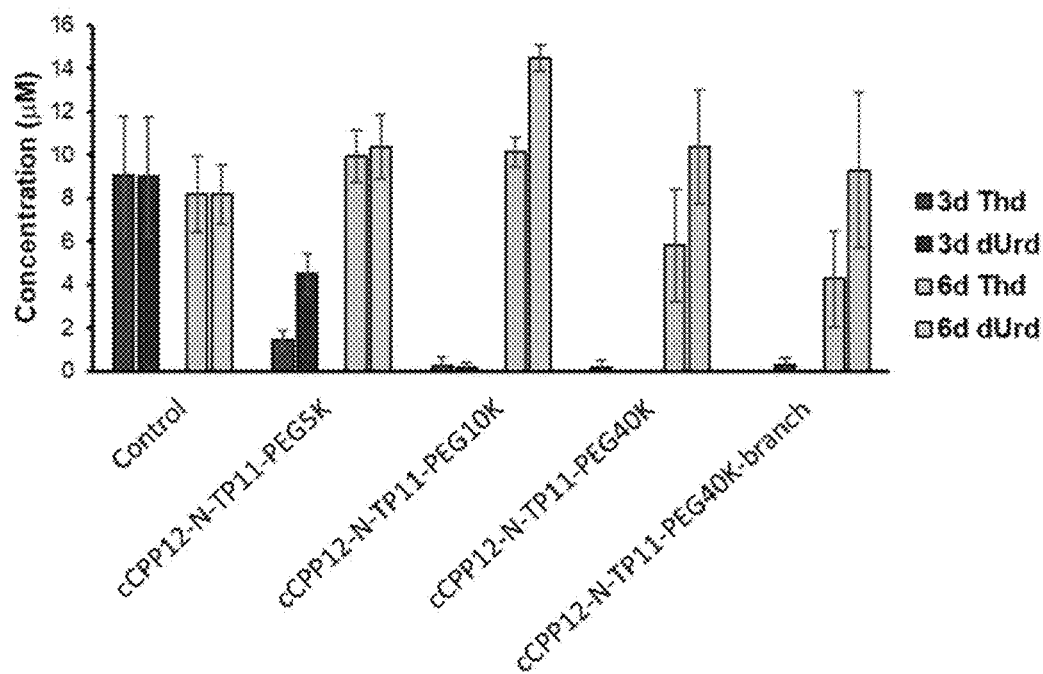
FIG. 23 is a graph shows thymidine (Thd) concentrations (μM) and deoxyuridine (dUrd) concentrations (μM) in the serum measured at 3 or 6 days post intravenous injection of 10 mpk of PEGylated cCPP-TP conjugates: cCPP12-N-TP11-PEG5K, cCPP12-N-TP11-PEG10K, cCPP12-N-TP11-PEG40K linear, or cCPP12-N-TP11-PEG40K branch (W1 data).
Figure 24A:
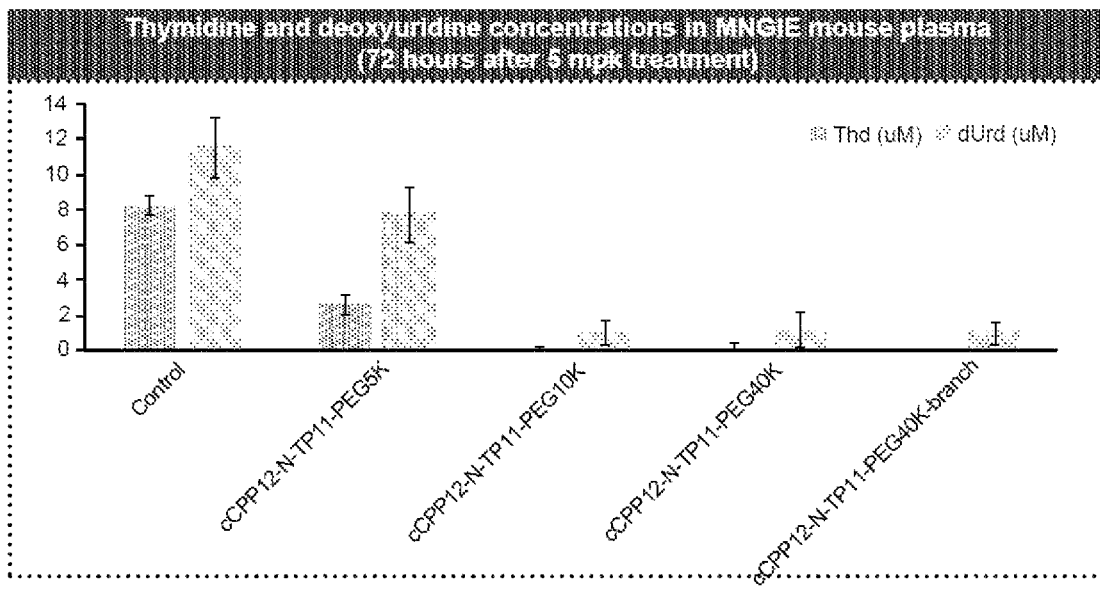
FIG. 24A is a graph shows thymidine (Thd) concentrations (μM) and deoxyuridine (dUrd) concentrations (μM) in the serum measured at 3 days post intravenous injection of 5 mpk of PEGylated cCPP-TP conjugates: cCPP12-N-TP11-PEG5K, cCPP12-N-TP11-PEG10K, cCPP12-N-TP11-PEG40K linear, or cCPP12-N-TP11-PEG40K branch (W3 data).
Figure 24B:
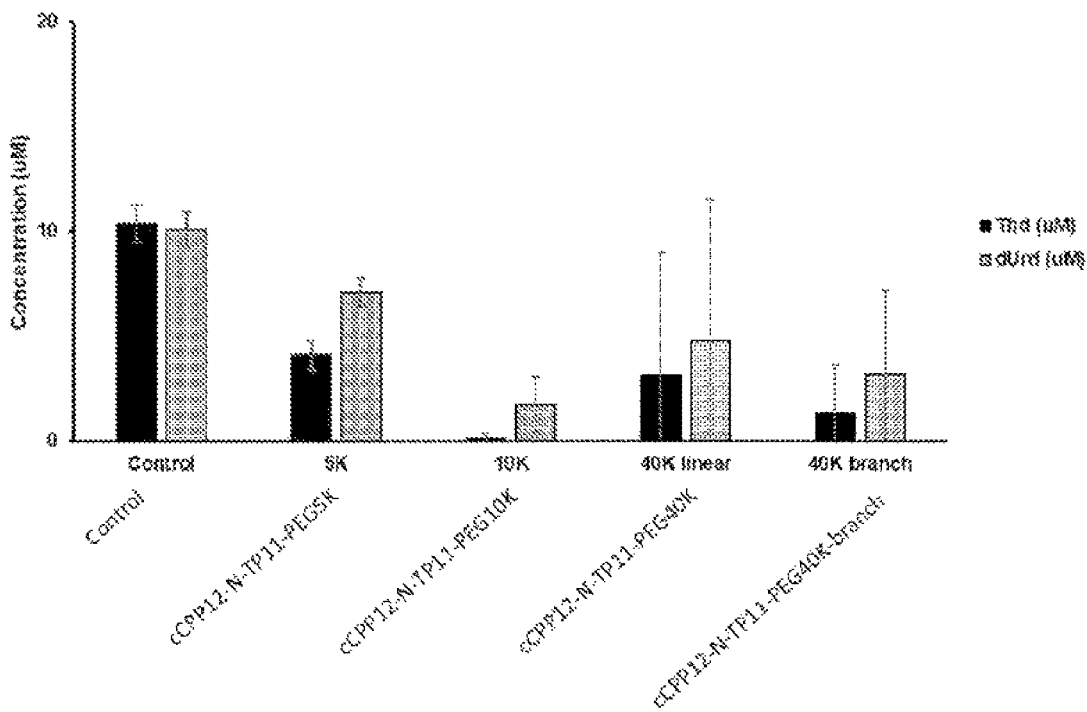
FIG. 24B is a graph shows thymidine (Thd) concentrations (μM) and deoxyuridine (dUrd) concentrations (μM) in the serum measured at 3 days post intravenous injection of 5 mpk of PEGylated CPP-TP conjugates: cCPP12-N-TP11-PEG5K, cCPP12-N-TP11-PEG10K, cCPP12-N-TP11-PEG40K linear, or cCPP12-N-TP11-PEG40K branch (W4 data).
Figure 25:
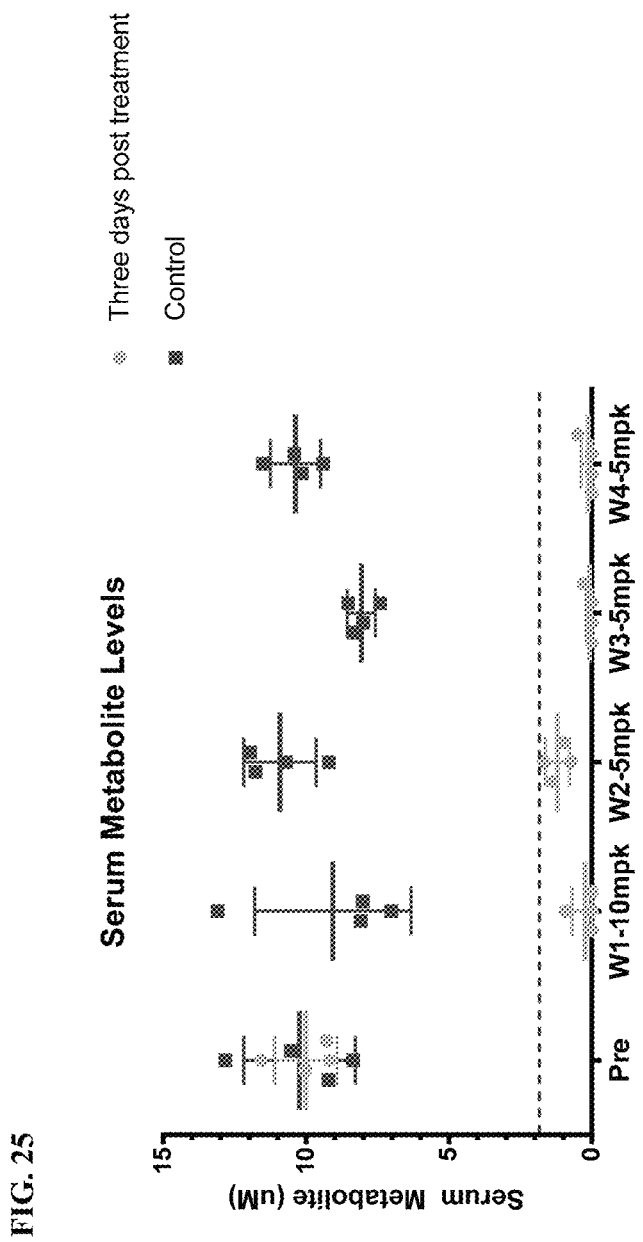
FIG. 25 is a graph shows the depletion of thymidine (Thd) concentrations (μM) in the serum measured at 3 days post intravenous injection of 10 mpk (W1) or 5 mpk (W2, W3, and W4) of CPP12-N-TP11-PEG10K over weekly injections in a month.
Figure 26A:
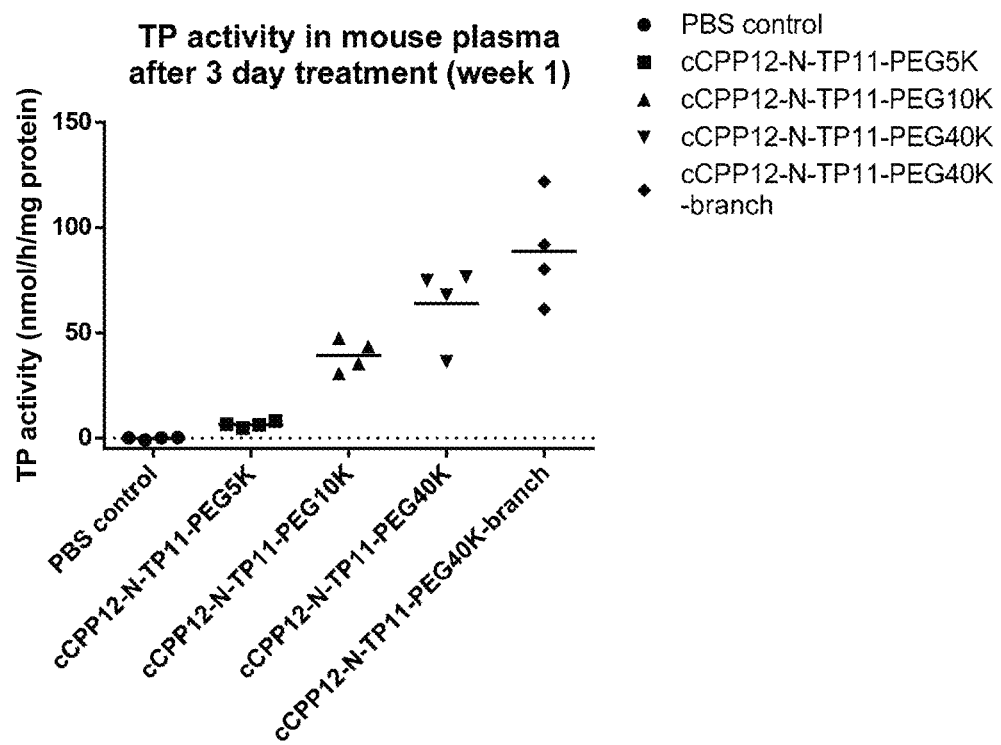
FIG. 26A is a graph shows specific TP activity in the serum measured at 3 days post intravenous injection of 10 mpk of PEGylated CPP-TP conjugates: cCPP12-N-TP11-PEG5K, cCPP12-N-TP11-PEG10K, cCPP12-N-TP11-PEG40K linear, or cCPP12-N-TP11-PEG40K branch (W1 data).
Figure 26B:
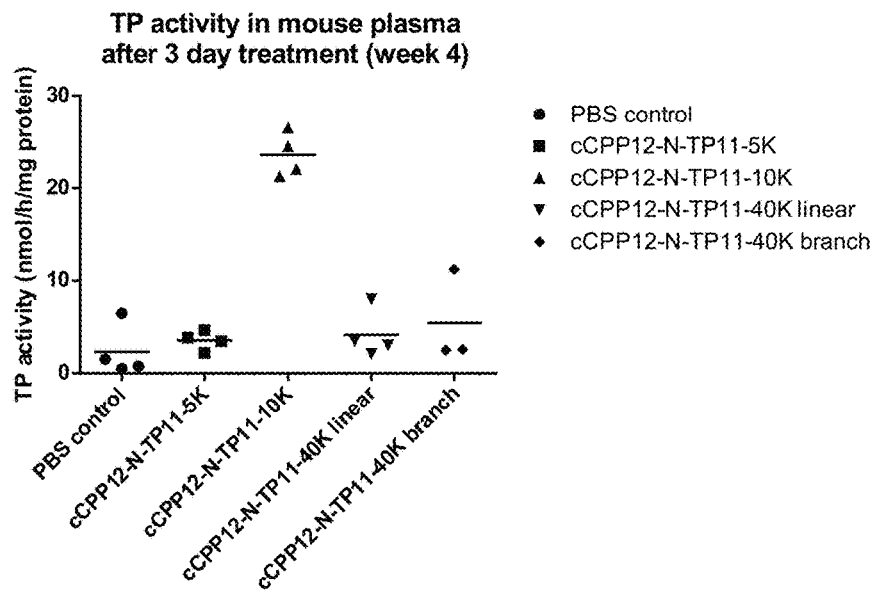
FIG. 26B is a graph shows specific TP activity in the serum measured at 3 days post intravenous injection of 5 mpk of PEGylated CPP-TP conjugates: cCPP12-N-TP11-PEG5K, cCPP12-N-TP11-PEG10K, cCPP12-N-TP11-PEG40K linear, or cCPP12-N-TP11-PEG40K branch (W4 data).

To compare the pharmacokinetic profiles of PEGylated and non-PEGylated CPP12-N-TP11, specific TP enzyme activities of serum samples collected at 5 min; 8 hr; 24 hr; 36 hr; and 48 hr were tested. These results are provided in FIG. 12. The pharmacokinetic profiles of PEGylated and non-PEGylated cCPP12-N-TP11 did not show significant difference, as all cCPP12-N-TP11 variants showed minimal TP enzyme activity in serum 24 hr post administration. The duration of action of cCPP12-N-TP11-PEG5K was further investigated using MNGIE mice. In this case, MNGIE mice from EXAMPLE 6 were subjected to intravenous administration of cCPP12-N-TP11-PEG5K at 16 mpk. Thymidine levels in serum were measured for the treated MNGIE mice and compared to untreated MNGIE mice. The assay was conducted according to Example 6 and additional study day on week six was added. Specifically, serum thymidine concentrations were measured on week six 48 hours after treatment (W6-48 hr). The results of cCPP12-N-TP11-PEG5K are included in FIG. 14. Compared to cCPP12-N-TP11, which can reduce and maintain serum thymidine levels in MNGIE mice for approximately 36 hr (W4-36 hr, FIG. 14), PEGylated cCPP-TP conjugates (e.g., cCPP12-N-TP11-5K) are able to deplete serum thymidine levels for at least 48 hours after treatment (W6-48 hr, FIG. 14). To compare the efficacy of different PEGylated cCPP12-N-TP11, cCPP12-N-TP11-PEG5K, cCPP12-N-TP11-PEG10K, cCPP12-N-TP11-PEG40K linear or cCPP12-N-TP11PEG40K branched were administered to MNGIE mice from EXAMPLE 6. MNGIE mice were treated once per week for 4 weeks. The first injection was done at 10 mpk and followed by 3 more injections at 5 mpk. Thymidine concentration (µM) and TP enzyme activity in serum was measured at the following time points after tail-vein intravenous administration: 3 days and 6 days for each week after one injection as described in EXAMPLE 6. Three days post injection, cCPP12-N-TP1 1-PEG10K, cCPP12-N-TP11-PEG40K linear and cCPP12-N-TP11-PEG40K branched treated mice showed significantly decreased Thymidine concentration at 10 mpk injections during week 1 (FIG. 23). Over four-week period, the efficacy were quantified by Thymidine or deoxyuridine level three days post injection. And the efficacy of cCPP12-N-TP11-PEG40K linear and cCPP12-N-TP11-PEG40K treatments were decreasing over multiple injections (see FIGS. 24A and 24B). On the other hand, cCPP12-N-TP11-PEG10K significant decreased the metabolite (Thymidine) level for over four weeks (FIG. 25). In addition to the metabolite level, we also quantified the TP enzyme activity in the serum. From the samples collected during week 1, we found TP activity in the serum especially from cCPP12-N-TP-PEG40K injected mice (FIG. 26A). From the samples collected during week 4, however, the circulating TP activity from serum samples collected from cCPP12-N-TP-PEG40K injected mice dropped significantly to background level (FIG. 26B). This indicates the presence of anti-drug antibody against PEG40K modified protein over repetitive injections possibly due to its elongated half-life in the circulation.

Example 8. Pharmacokinetics of cCPP12-TP and TP Proteins

Figure 15A:
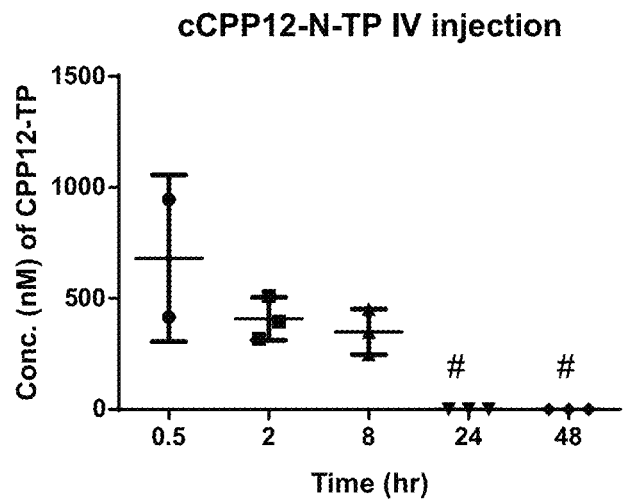
FIG. 15A is a graph showing the concentration of cCPP12-N-TP11 (nM) at 0.5 hr, 2 hr, 8 hr, 24 hr, or 48 hr after 20 mpk intravenous injection determined by Western Blotting
Figure 15B:
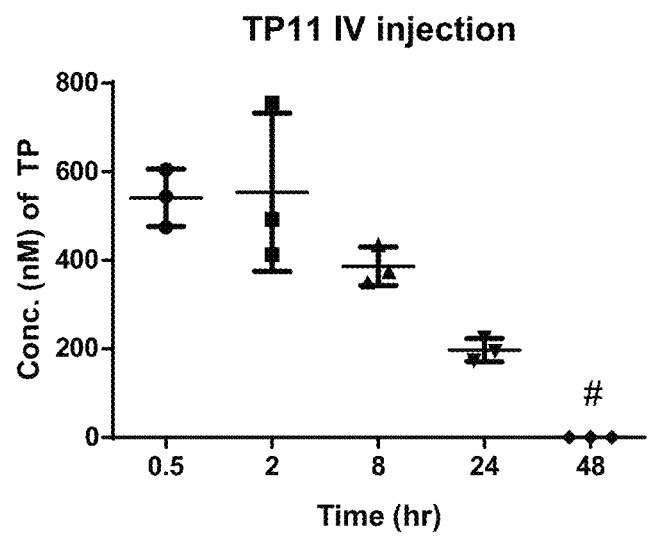
FIG. 15B is a graph showing the concentration of TP (nM) at 0.5 hr, 2 hr, 8 hr, 24 hr, or 48 hr after 20 mpk intravenous injection as determined by a western blot. # indicates that protein levels were below the limits of detection.

The pharmacokinetics of the cCPP12-TP11 conjugates of the present disclosure or TP were investigated using mouse models. The cCPP12-TP11 conjugate (20 mpk) was intravenously injected into wild-type CD1 mice, and serum samples were collected at the following time points after administration: 0.5 hour; 2 hours; 8 hours; 24 hours; and 48 hours (FIG. 15A). As a comparator, 20 mpk intravenous injection of free TP (not conjugated to CPP) was also injected into wild-type mice, and serum samples were collected at the same time points (FIG. 15B). Samples were analyzed and quantified using a western blot assay.

The data shows that cCPP-TP11 disappear from the circulation by 12 hour post IV injection, which indicates that the half life of cCPP-TPs are significantly shorter than that of the free TP, indicating depletion from circulation and intracellular delivery of the cargo TP protein in a cCPP-dependent manner.

Figure 27A:
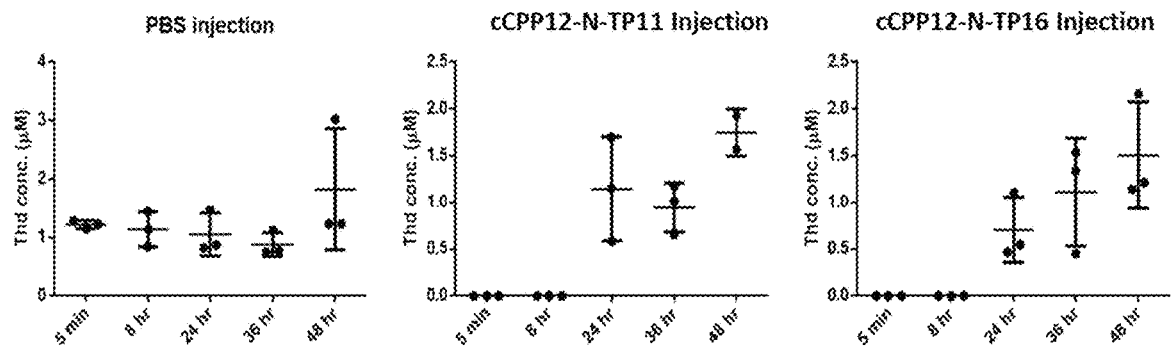
FIG. 27A is a graph shows thymidine (Thd) concentrations in the serum measured at 5 min, 8 hr, 24 hr, 36 hr, or 48 hr post intravenous injection of 5 mpk of cCPP12-N-TP11, cCPP12-N-TP16, or PBS control.
Figure 27B:
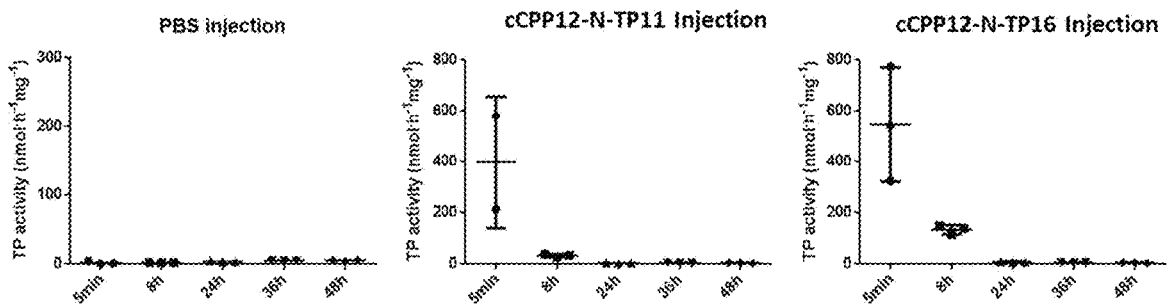
FIG. 27B is a graph shows specific TP activity in the serum measured at 5 min, 8 hr, 24 hr, 36 hr, or 48 hr post intravenous injection of 5 mpk of cCPP12-N-TP11, cCPP12-N-TP16, or PBS control.

To compare the pharmacokinetic and pharmacodynamic profiles of the cCPP12-N-TP11 and cCPP12-N-TP16, wild type mice were injected with 5 mpk cCPP12-N-TP11 or cCPP12-N-TP16, or PBS control, and serum samples were collected 5 min, 8 hr, 24 hr, 36 hr, or 48 hr post injection. Specific TP enzyme activities of serum samples were measured by enzyme activity assay described above and thymidine level of serum samples were also tested. These results are provided in FIGS. 27A and 27B.

The data showed that the pharmacokinetic profiles of cCP12-N-TP11 and cCPP12-N-TP16 did not show significant difference. And both cCPP12-N-TP11 and cCPP12-N-TP16 variants showed comparable efficacy in reducing the thymidine levels in vivo.

Figure 28A:
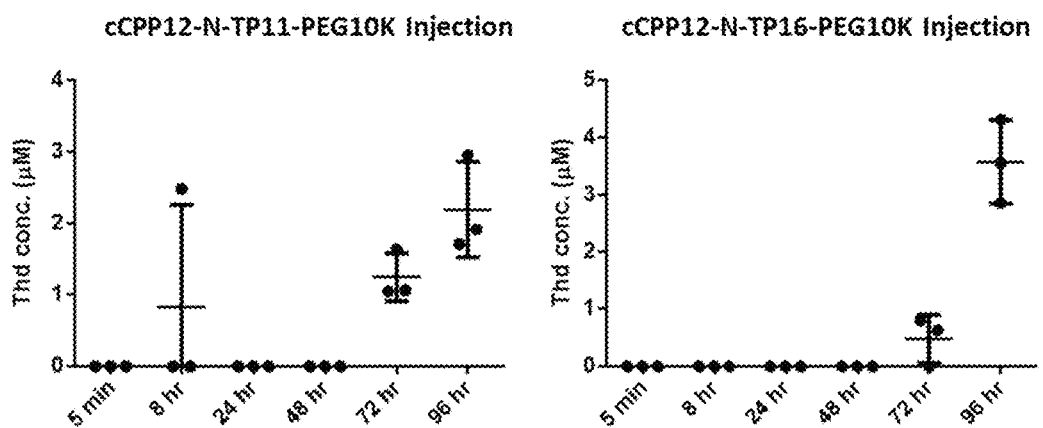
FIG. 28A is a graph shows thymidine (Thd) concentrations in the serum measured at 5 min, 8 hr, 24 hr, 48 hr, 72 hr, or 96 hr post intravenous injection of 5 mpk of cCPP12-N-TP11-PEG10K, cCPP12-N-TP16-PEG10K, or PBS control.
Figure 28B:
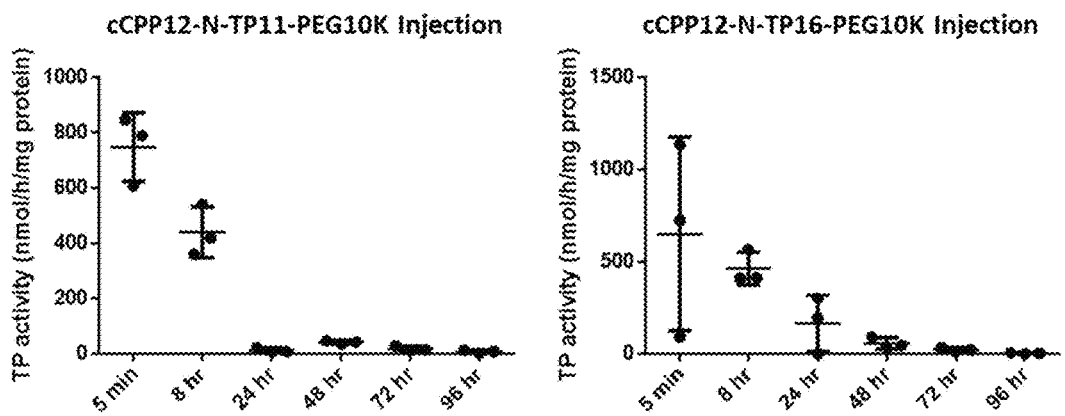
FIG. 28B is a graph shows specific TP activity in the serum measured at 5 min, 8 hr, 24 hr, 48 hr, 72 hr, or 96 hr post intravenous injection of 5 mpk of cCPP12-N-TP11-PEG10K, cCPP12-N-TP16-PEG10K, or PBS control

To compare the pharmacokinetic and pharmacodynamic profiles of cCPP12-N-TP11-PEG10K and cCPP12-N-TP16-PEG10K, wild type mice were injected with 5 mpk cCPP12-N-TP11-PEG10K or cCPP12-N-TP16-PEG10K. Serum samples were collected at 5 min, 8 hr, 24 hr, 48 hr, 72 hr or 96 hr post injection. Specific TP enzyme activities of serum samples were measured by enzyme activity assay described above, and thymidine level of serum samples were also tested as described above. The results were provided in FIGS. 28A and 28B.

The data showed that similar to the non-PEGylated protein, PEGylated cCPP-TP11 and cCPP-TP16 did not show significant difference for the pharmacokinetic profiles. And both cCPP12-N-TP11-PEG10K and cCPP12-N-TP16-PEG10K showed effects for the depletion of thymidine level in vivo.

Figure 29A:
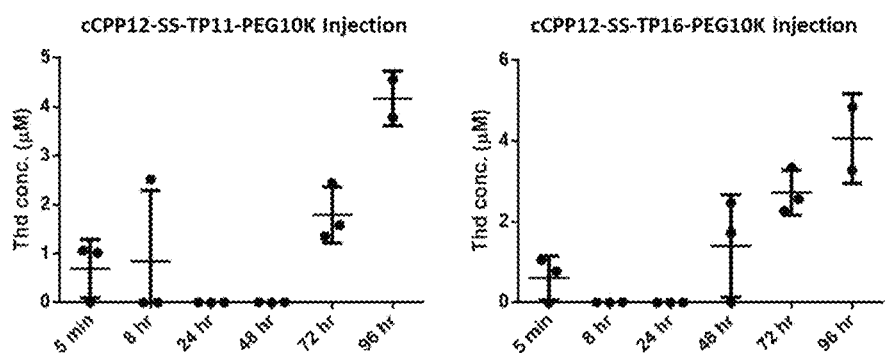
FIG. 29A is a graph shows thymidine (Thd) concentrations in the serum measured at 5 min, 8 hr, 24 hr, 48 hr, 72 hr, or 96 hr post intravenous injection of 5 mpk of cCPP12-SS-TP11-PEG10K, or cCPP12-SS-TP16-PEG10K.
Figure 29B:
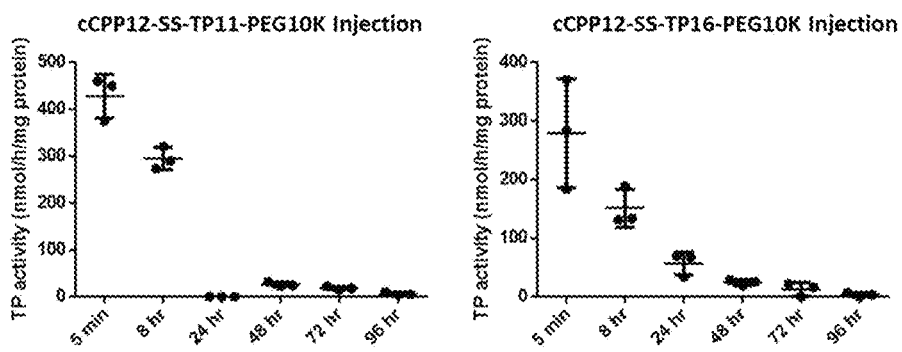
FIG. 29B is a graph shows specific TP activity in the serum at 5 min, 8 hr, 24 hr, 48 hr, 72 hr, or % hr post intravenous injection of 5 mpk of cCPP12-SS-TP11-PEG10K, or cCPP12-SS-TP16-PEG10K.

To compare the pharmacokinetic and pharmacodynamic profiles of cCPP12-SS-TP11-PEG10K and cCPP12-SS-TP16-PEG10K, wild type mice were injected with 5 mpk cCPP12-SS-TP11-PEG10K or cCPP12-SS-TP16-PEG10K, and serum samples were collected 5 min, 8 hr, 24 hr, 48 hr, 72 hr or 96 hr post injection. Specific TP enzyme activities of serum samples were measured by enzyme activity assay described above, and thymidine level of serum samples were also tested as described above. The results are provided in FIGS. 29A and 29B.

The data showed that cCPP12-SS-TP11-PEG10K showed similar pharmacokinetic profiles compared to cCPP12-SS-TP16-PEK10K. Both TP derivatives showed effects for the depletion of thymidine level in vivo.

Figure 32:
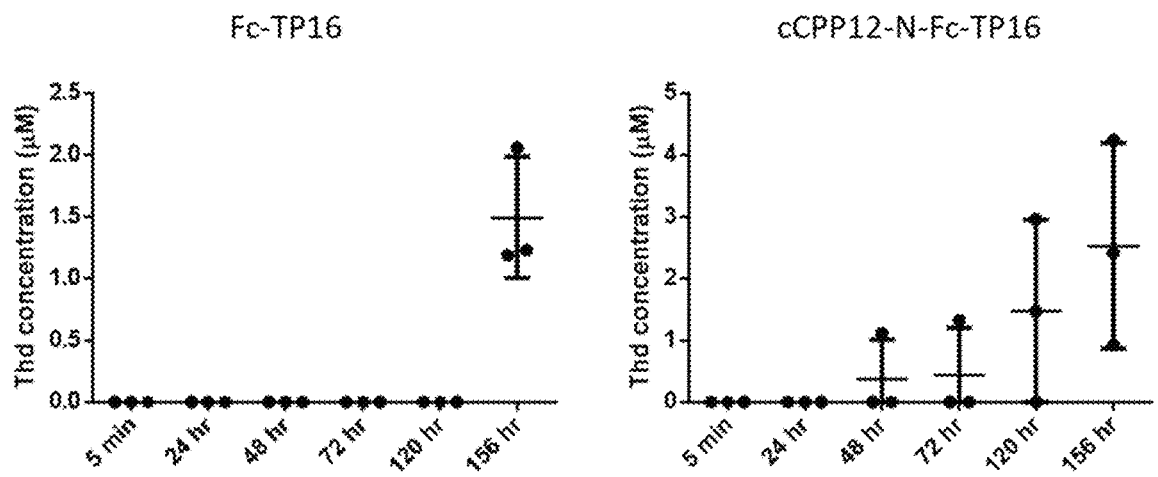
FIG. 32 is a graph shows thymidine (Thd) concentrations in the serum measured at 5 min, 24 hr, 48 hr, 72 hr, 120 hr, or 156 hr post intravenous injection of 5 mpk of Fc-TP16, or cCPP12-N-Fc-TP16.
Figure 33:
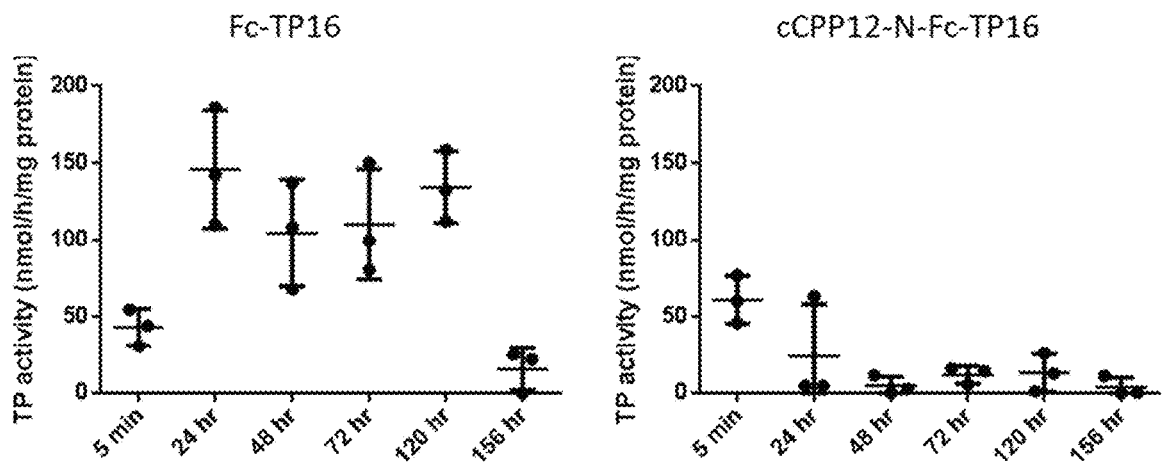
FIG. 33 is a graph shows specific TP activity in the serum at 5 min, 24 hr, 48 hr, 72 hr, 120 hr, or 156 hr post intravenous injection of 5 mpk of Fc-TP16, or cCPP12-N-Fc-TP16.

To compare the pharmacokinetic and pharmacodynamic profiles of Fc_-P16 and cCPP12-N-Fc-TP16, wild type mice were injected with Fc-TP16 and cCPP12-N-Fc-TP16 at 5 mpk, and serum samples were collected at 5 min, 24 hr, 48 hr, 72 hr, 120 hr or 156 hr post injection. Specific TP enzyme activities of serum samples were measured by enzyme activity assay described above, and thymidine level of serum samples were also tested as described above. The results are provided in FIGS. 32 and 33.

Example 9. Biodistribution

The biodistribution of the CPP-TP conjugates in the wild type CD1 mice 4 h, 8 h, or 24 h after intravenous administration was investigated using a fluorescently labeled CPP-TP. The CPP-TP was fluorescently labeled with Alexa-Flour568 (AF568) and yielded the CPP-TP-AF568 used in this study. Briefly, CPP12-N-TP (2 mg/mL, 40 µM) was mixed with the AlexaFluoro568-NHS ester (NHS, N-hydroxyl succinimide, ThermoFisher) at 1:8 molar ratio in phosphate buffer saline (pH 7.4). To separate extra fluorophore, PD-10 columns were applied according manufacturer's protocol and CPP-TP-AF568 were obtained. Combined fractions with desired product were sterile filtered, concentrated, and stored at 2 mg/mL at −20° C.

Figure 16A:
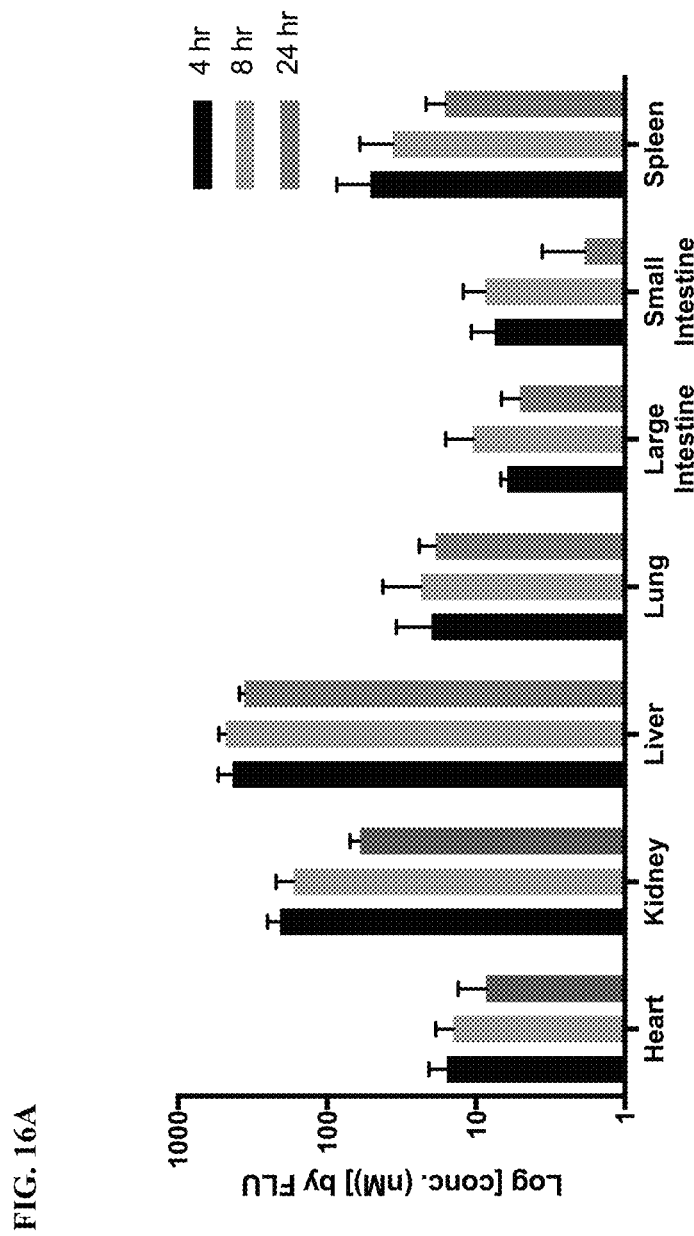
FIG. 16A is a bar graph showing the biodistribution of fluorescently labeled cCPP-TP (cCPP12-N-TP11-AF568) 24 hours after intravenous administration as measured by fluorescence in tissue homogenates
Figure 16B:
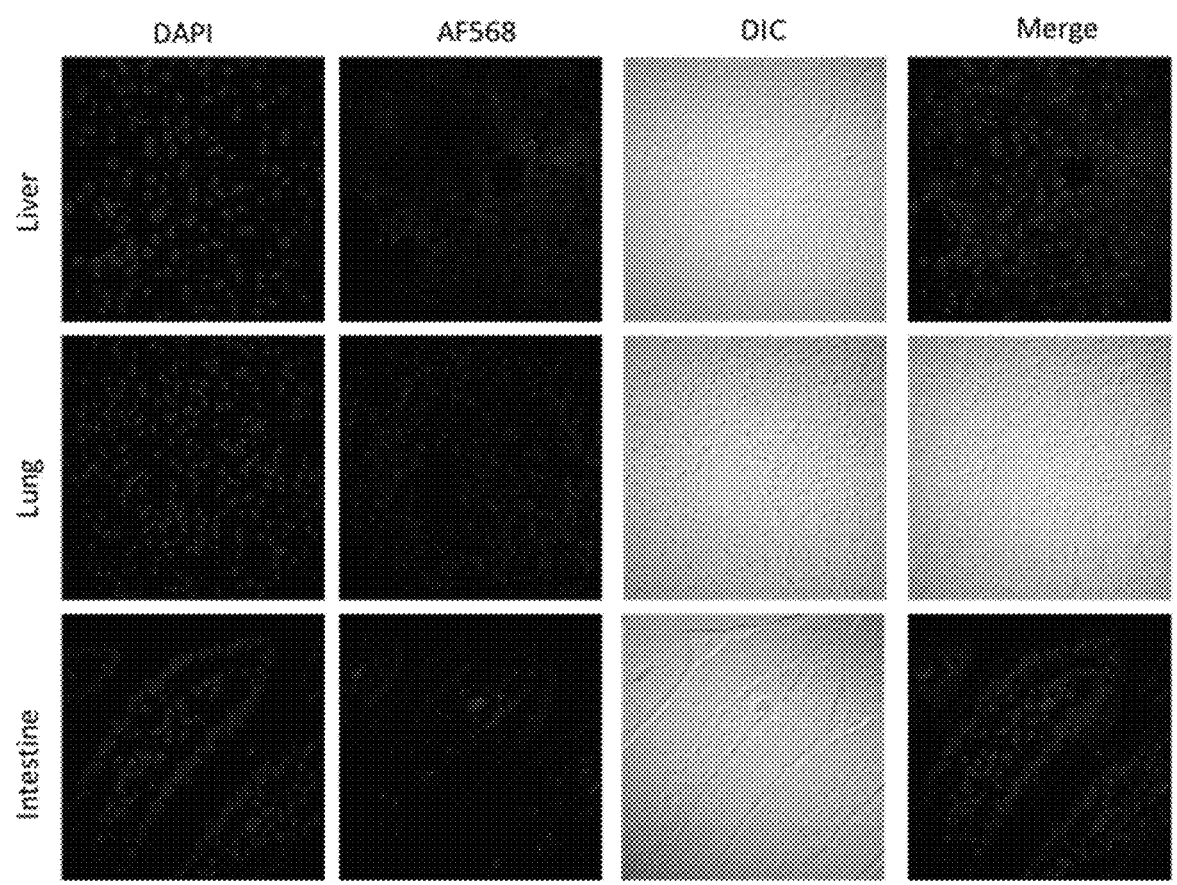
FIG. 16B is a graph showing the localization of fluorescently labeled cCPP-TP (cCPP12-N-TP11-AF568) in the liver, lungs, and intestines 24 hours after intravenous administration as measured by confocal fluorescence imaging.

To study the tissue distribution of CPP-TP, mice were injected intravenously at 5 mpk with CPP-TP-AF568. Then, mice were anesthetized, bled, euthanized, and dissected 4 h, 8 h, or 24 h after injection. Heart, kidney, liver, lung, large intestine, small intestine, and spleen were harvested; each piece was weighed, and several organs were halved for cryosection and tissue homogenization. For fluorescence quantification, organs were homogenized with a Tissue Lyser II system in pre-chilled tubes, stainless steel beads, and RIPA buffer supplemented with 1× protease inhibitor. Supernatant after centrifuge were obtained and transferred for fluorescence quantification. Tissues harvested from uninjected mice were used as blank and were also spiked with known concentration of CPP-TP-AF568 to generate a standard curve. The intensity of the fluorescence of samples and standard probe was detected at fluorescence plate reader. The concentrations of the homogenates were extrapolated from the calibration curves made for each organ. The tissue concentration were back-calculated with the dilution factor of tissue homogenization and homogenate concentrations. The results of the biodistribution studies are presented in FIG. 16A. These results indicate that CPP-TP can internalize into wide range of cells and is predominately localized in the liver, kidney and spleen (FIG. 16A). Confocal images of the distribution of CPP-TP in the liver, lung, and intestine were obtained using confocal imaging (FIG. 16B).

The invention claimed is:

1. A compound having a structure according to Formula I-A:

CPP-L-TP    (I-A), wherein:
CPP is a cyclic cell-penetrating peptide (cCPP);
TP is thymidine phosphorylase, or an active fragment or analog thereof; and has an amino acid sequence that is at least 95% identical to SEQ ID NO. 1, 2, 3, 4, 5, 6, 7, 8, 9, 10, 11, 12, or 13;
L is a linker; and
wherein L is a covalently bound to the side chain of an amino acid on the CPP and to the N-terminus of the TP;
the cCPP has a sequence comprising any of Formula IV-A-D:

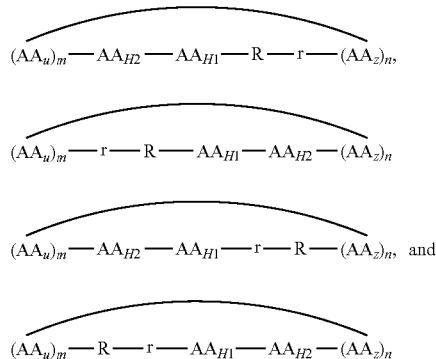

wherein:
each of $AA_{H1}$ and $AA_{H2}$ are independently a D or L hydrophobic aromatic amino acid;
at each instance and when present, each of $AA_U$ and $AA_Z$ are independently a D or L amino acid;
m and n are independently selected from a number from 0 to 6; and
wherein Formula IV-A-D comprise at least three consecutive arginine, and at least three-consecutive hydrophobic aromatic amino acids.

2. The compound of claim 1, wherein L is: (a) one or more D or L amino acids, each of which is optionally substituted; (b) alkylene, alkenylene, alkynylene, carbocyclyl, or heterocyclyl, each of which is optionally substituted; or (c) —($R^1$—X—$R^2$)z-, wherein each of $R^1$ and $R^2$, at each instance, are independently selected from alkylene, alkenylene, alkynylene, carbocyclyl, and heterocyclyl, each X is independently $NR^3$, —$NR^3C(O)$—, S, and O, wherein $R^3$ is independently selected from H, alkyl, alkenyl, alkynyl, carbocyclyl, and heterocyclyl, wherein each alkylene, alkenylene, alkynylene, carbocyclyl, and heterocyclyl is optionally substituted, and wherein z is an integer from 1 to 20; or combinations thereof.

3. The compound of claim 1, wherein L has a structure according to Formula II-A' or II-B':

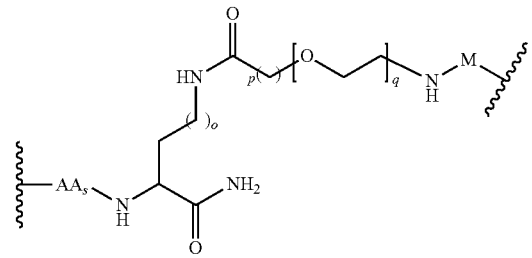

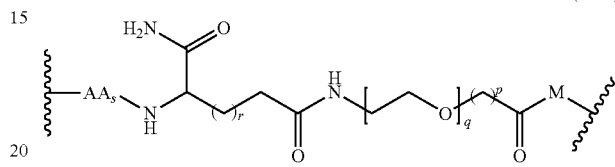

and wherein
M is absent or a group bound to TP;
$AA_s$ is a side chain or terminus of an amino acid on the CPP;
o is an integer from 0 to 10;
p is an integer from 0 to 10;
q is an integer from 1 to 50; and
r is 0 or 1.

4. The compound of claim 3, wherein M is present and comprises an alkylene, alkenylene, alkynylene, carbocyclyl, or heterocyclyl, each of which is optionally substituted.

5. The compound of claim 4, wherein M is present and selected from the group consisting of:

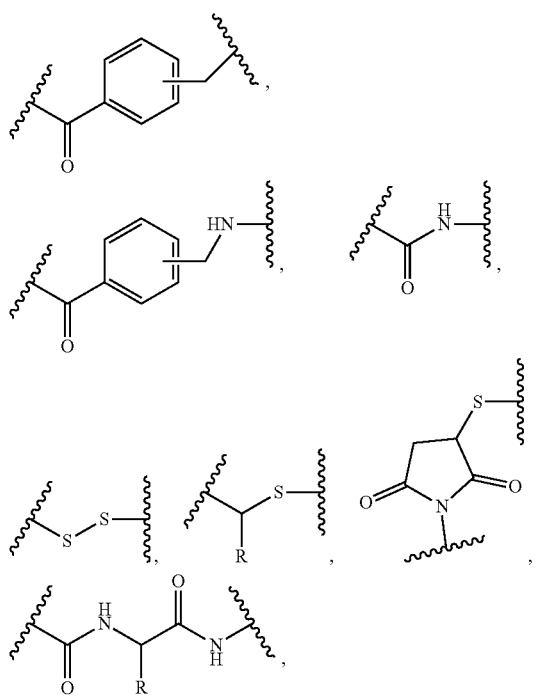

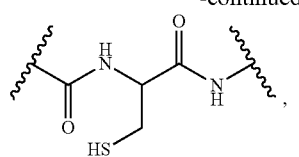
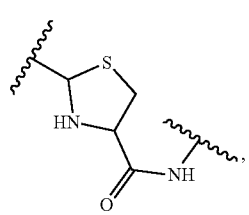
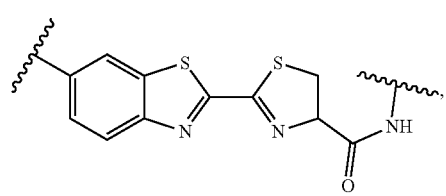 and
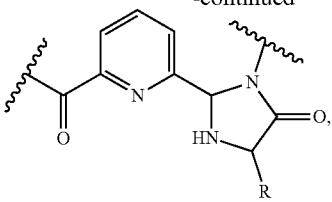
wherein each R is independently an alkyl, alkenyl, alkynyl, carbocyclyl, or heterocyclyl.
6. The compound of claim 3, wherein M is
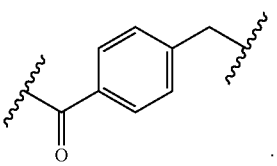 [SMILES: *Cc1ccc(C(*)=O)cc1].
7. The compound of claim 4, wherein M is present and is covalently bound to the N-terminus TP.
8. The compound of claim 1, wherein the compound has a structure according to Formula V-A1, V-A2, or V-A3:
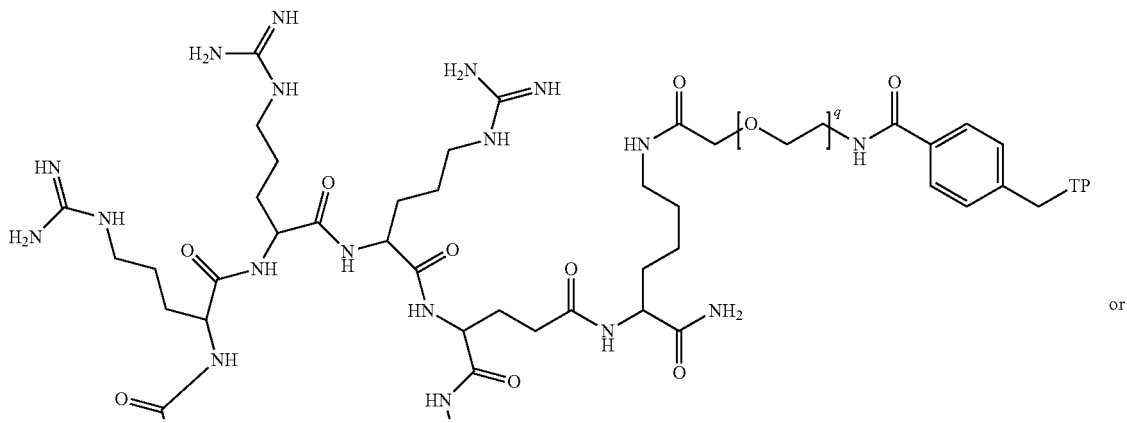
(V-A1)
or
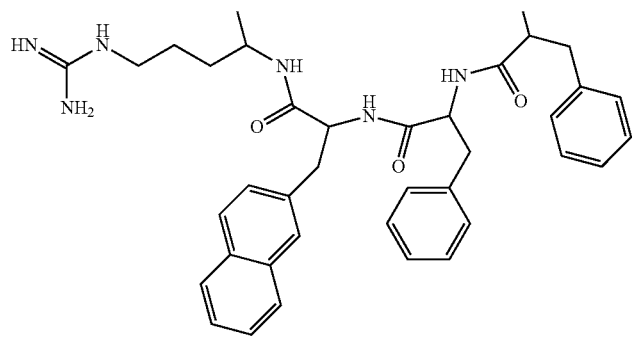

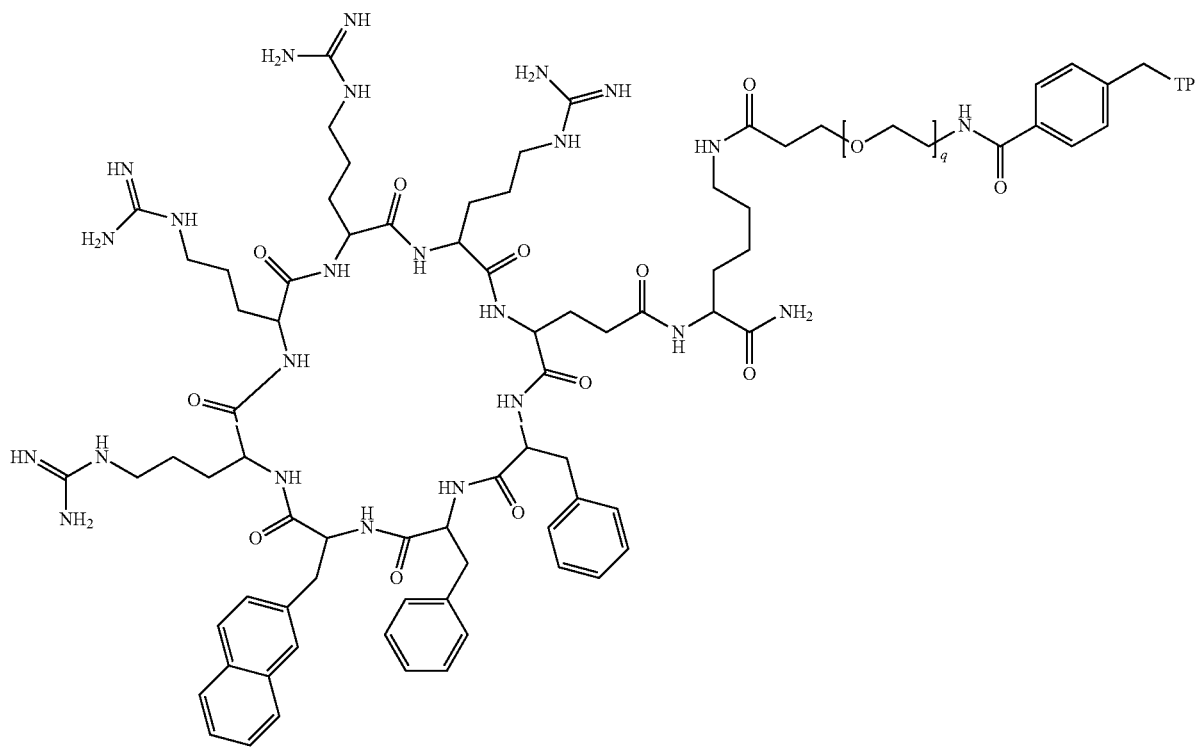
(V-A2)
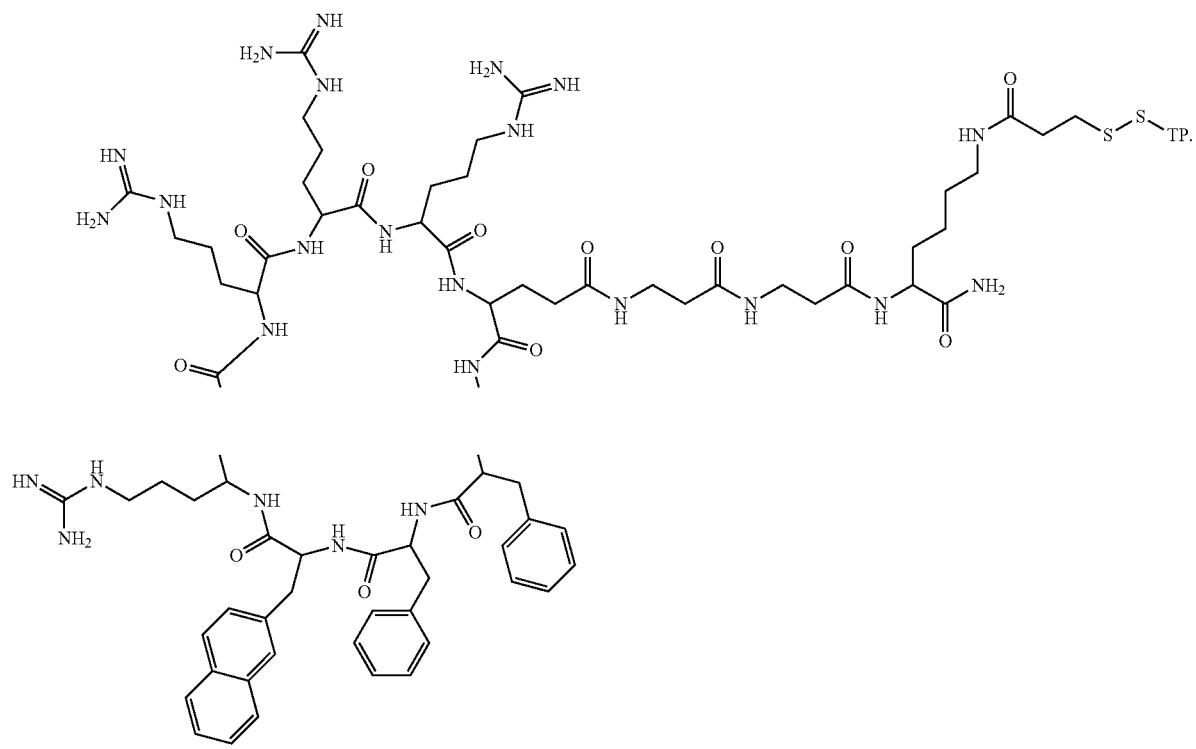
(V-A3)
wherein q is an integer from 10-15.
9. The compound of claim 1, wherein the TP has the amino acid sequence of SEQ ID NO. 1.
10. The compound of claim 1, wherein the TP has the amino acid sequence of SEQ ID NO. 2.
11. The compound of claim 1, wherein the TP has the amino acid sequence of SEQ ID NO. 3, 4, 5, 6, 7, 8, 9, 10, 11, 12, or 13.
12. The compound of claim 1, wherein the TP has the amino acid sequence of SEQ ID NO, 3.

13. The compound of claim 1, further comprising a water-soluble polymer conjugated to the TP.

14. The compound of claim 13, wherein the water-soluble polymer comprises a polyethylene glycol (PEG) residue.

15. The compound of claim 14, wherein the PEG residue has a molecular weight ranging from about 1 kDa to about 20 kDa.

16. The compound of claim 1, wherein the hydrophobic aromatic amino acid are independently, selected from piperidine-2-carboxylic acid, naphthylalanine, tryptophan, and phenylalanine, each of which is optionally substituted with one or more substituents.

17. The compound of claim 1, wherein the sum of m and n is from 2 to 6; and Formula IV-A-D comprise at least four consecutive arginine, at least three consecutive hydrophobic aromatic amino acids and at least three adjacent amino acids having alternating chirality.

18. The compound of claim 1, wherein the cCPP has the amino acid sequence selected from SEQ ID NO. 21, 27 or 124.

\* \* \* \* \*

UNITED STATES PATENT AND TRADEMARK OFFICE
CERTIFICATE OF CORRECTION

Page 1 of 2

PATENT NO. : 11,987,821 B2
APPLICATION NO. : 17/495238
DATED : May 21, 2024
INVENTOR(S) : Sethuraman et al.

It is certified that error appears in the above-identified patent and that said Letters Patent is hereby corrected as shown below:

In the Claims

In Column 191, in Claim 1, Line 2, delete "stricture" and insert -- structure --, therefor.

In Columns 193-194, in Claim 8, the structure of "(V-A1)" should read:

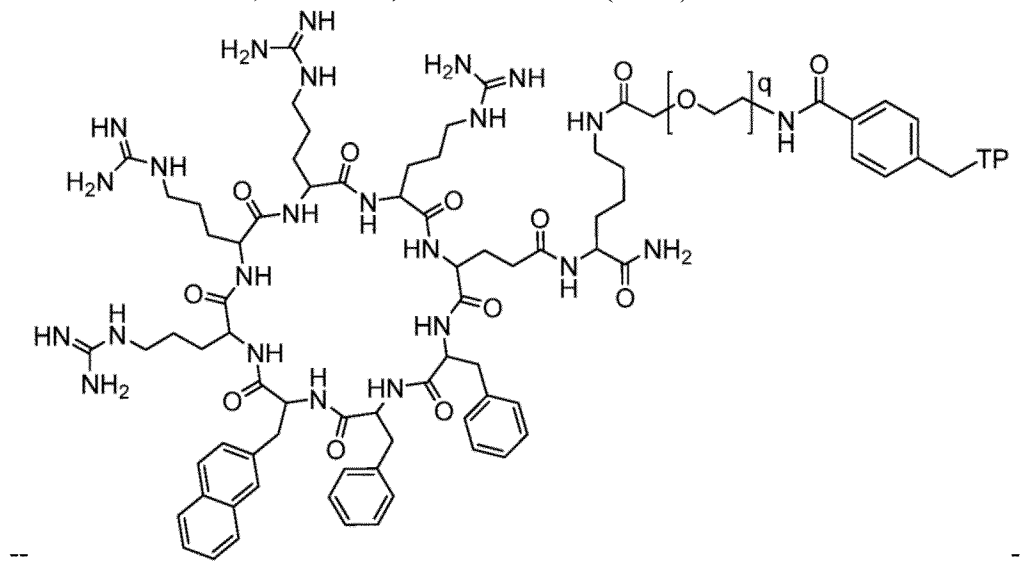

--, therefor.

Signed and Sealed this
Tenth Day of June, 2025

Coke Morgan Stewart
*Acting Director of the United States Patent and Trademark Office*

CERTIFICATE OF CORRECTION (continued)
U.S. Pat. No. 11,987,821 B2

In Columns 195-196, in Claim 8, the structure of "(V-A2)" should read:

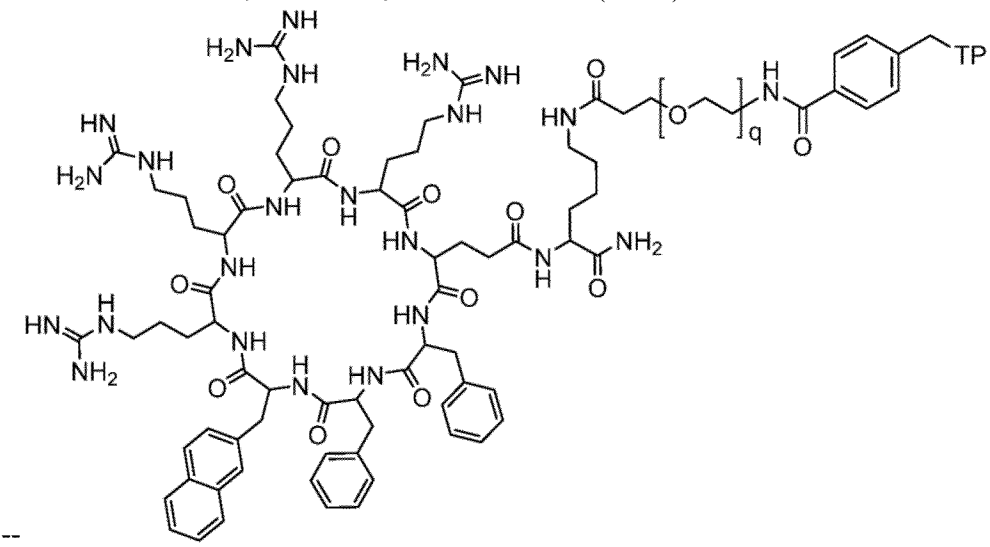

-- , therefor.

In Columns 195-196, in Claim 8, the structure of "(V-A3)" should read:

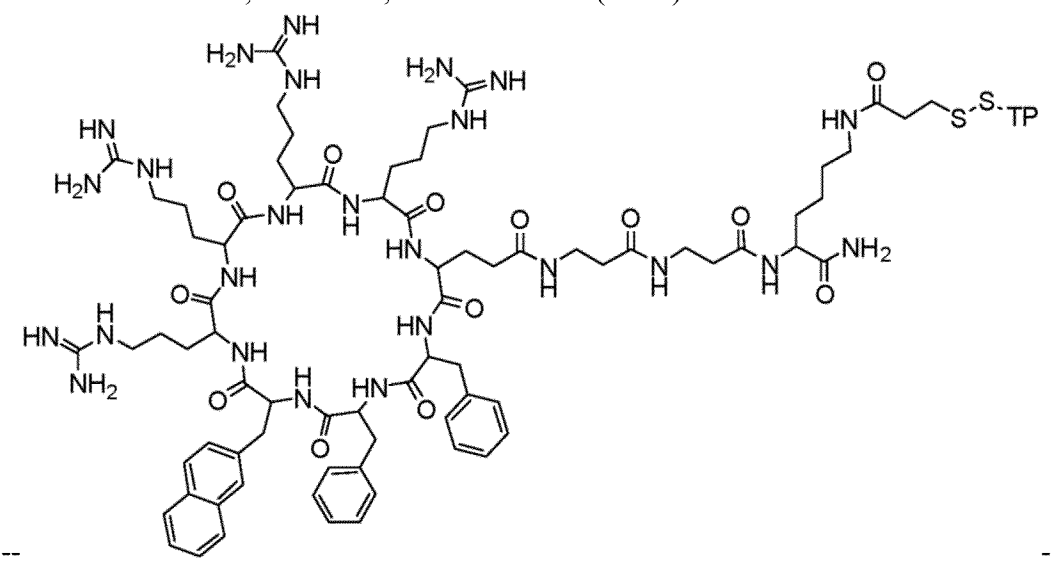

-- , therefor.

In Column 196, in Claim 12, Line 67, delete "NO," and insert -- NO. --, therefor.